(12) United States Patent
Leimbach et al.

(10) Patent No.: US 12,285,168 B2
(45) Date of Patent: Apr. 29, 2025

(54) SURGICAL INSTRUMENT WITH FIRING STROKE TARGET SPEED ADJUSTMENT

(71) Applicant: CILAG GMBH INTERNATIONAL, Zug (CH)

(72) Inventors: Richard L. Leimbach, Cincinnati, OH (US); Michael J. Stokes, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

(21) Appl. No.: 18/442,396

(22) Filed: Feb. 15, 2024

(65) Prior Publication Data

US 2024/0180555 A1 Jun. 6, 2024

Related U.S. Application Data

(63) Continuation of application No. 16/846,303, filed on Apr. 11, 2020, now Pat. No. 11,903,581.
(Continued)

(51) Int. Cl.
*A61B 17/072* (2006.01)
*A61B 17/00* (2006.01)
(Continued)

(52) U.S. Cl.
CPC .... *A61B 17/07207* (2013.01); *A61B 18/1445* (2013.01); *A61B 2017/00039* (2013.01);
(Continued)

(58) Field of Classification Search
CPC .......... A61B 17/07207; A61B 18/1445; A61B 2017/00039; A61B 2017/0019;
(Continued)

(56) References Cited

U.S. PATENT DOCUMENTS 6,120,462 A * 9/2000 Hibner ............... A61B 10/0275
600/568
11,931,037 B1 * 3/2024 Shelton, IV ......... A61B 17/072
(Continued)

OTHER PUBLICATIONS

USPTO, Final Office Action issued Sep. 26, 2022 in related U.S. Appl. No. 16/846,310.
(Continued)

*Primary Examiner* — Dariush Seif
(74) *Attorney, Agent, or Firm* — TROUTMAN PEPPER LOCKE LLP

(57) ABSTRACT

A surgical instrument having a shaft, an end effector, a firing system, and a control system is disclosed herein. The firing member is configured to translate an electric motor through a firing stroke. The control system includes a pulse width modulation circuit configured to adjust a duty cycle of voltage pulses to drive the firing system to a target speed. The control system includes a control circuit configured to evaluate the duty cycle of pulses at a predetermined adjustment point and set the target speed based at least in part on the comparison (maintain or new speed). The controls system may be configured to set the target speed at two or more adjustment points during the firing stroke and/or evaluate the duty cycle of pulses at an adjustment point more than half way through the firing stroke.

19 Claims, 84 Drawing Sheets

Related U.S. Application Data

(60) Provisional application No. 62/840,715, filed on Apr. 30, 2019.

(51) Int. Cl.
*A61B 18/00* (2006.01)
*A61B 18/14* (2006.01)

(52) U.S. Cl.
CPC .............. *A61B 2017/0019* (2013.01); *A61B 2017/00398* (2013.01); *A61B 2017/00734* (2013.01); *A61B 2017/07228* (2013.01); *A61B 2017/07257* (2013.01); *A61B 2017/07271* (2013.01); *A61B 2017/07285* (2013.01); *A61B 2018/0063* (2013.01)

(58) Field of Classification Search
CPC ........... A61B 2017/00398; A61B 2017/00734; A61B 2017/07228; A61B 2017/07257; A61B 2017/07271; A61B 2017/07285; A61B 2018/0063
USPC .............. 227/175.1–182.1; 606/75, 219, 220
See application file for complete search history.

(56) References Cited

U.S. PATENT DOCUMENTS

| | | | |
|---|---|---|---|
| 2002/0134811 A1* | 9/2002 | Napier | B24B 23/04 227/134 |
| 2006/0278680 A1* | 12/2006 | Viola | A61B 17/068 227/176.1 |
| 2009/0039820 A1* | 2/2009 | Milano | H02P 29/60 318/590 |
| 2009/0057369 A1* | 3/2009 | Smith | A61B 17/07207 227/175.1 |
| 2009/0090763 A1* | 4/2009 | Zemlok | A61B 17/07207 227/175.2 |
| 2011/0204119 A1* | 8/2011 | McCuen | A61B 17/068 227/175.1 |
| 2013/0175322 A1* | 7/2013 | Yates | A61B 17/3205 227/180.1 |
| 2014/0148803 A1* | 5/2014 | Taylor | A61B 18/1445 606/49 |
| 2015/0054753 A1 | 2/2015 | Morgan et al. | |
| 2016/0099601 A1* | 4/2016 | Leabman | H02J 50/90 307/104 |
| 2016/0174977 A1* | 6/2016 | Lytle, IV | A61B 17/068 227/180.1 |
| 2016/0256184 A1* | 9/2016 | Shelton, IV | A61B 17/295 |
| 2016/0374716 A1* | 12/2016 | Kessler | A61B 17/320758 606/159 |
| 2017/0000549 A1* | 1/2017 | Gilbert | A61B 18/1233 |
| 2017/0079644 A1* | 3/2017 | Overmyer | A61B 17/068 |
| 2017/0238991 A1* | 8/2017 | Worrell | H05K 1/034 |
| 2017/0245854 A1* | 8/2017 | Zemlok | A61B 17/07207 |
| 2017/0249431 A1* | 8/2017 | Shelton, IV | H01M 10/425 |
| 2017/0296169 A1* | 10/2017 | Yates | A61B 17/07207 |
| 2017/0296213 A1* | 10/2017 | Swensgard | A61B 17/32 |
| 2018/0125590 A1* | 5/2018 | Giordano | A61B 17/320092 |
| 2018/0132850 A1* | 5/2018 | Leimbach | A61B 17/07207 |
| 2018/0360445 A1* | 12/2018 | Shelton, IV | A61B 17/1114 |
| 2018/0360449 A1* | 12/2018 | Shelton, IV | A61B 17/068 |
| 2018/0360452 A1* | 12/2018 | Shelton, IV | A61B 17/0686 |
| 2018/0360456 A1* | 12/2018 | Shelton, IV | A61B 17/295 |
| 2019/0183503 A1* | 6/2019 | Shelton, IV | A61B 90/06 |
| 2019/0200977 A1* | 7/2019 | Shelton, IV | A61B 34/35 |
| 2019/0201029 A1* | 7/2019 | Shelton, IV | A61B 17/07207 |
| 2019/0201082 A1* | 7/2019 | Shelton, IV | A61M 1/74 |
| 2019/0201594 A1* | 7/2019 | Shelton, IV | G06K 19/07749 |
| 2019/0261984 A1* | 8/2019 | Nelson | A61B 17/07207 |
| 2020/0345353 A1* | 11/2020 | Leimbach | A61B 18/1445 |
| 2020/0345356 A1* | 11/2020 | Leimbach | A61B 17/07207 |
| 2020/0345357 A1* | 11/2020 | Leimbach | A61B 17/07207 |
| 2022/0133310 A1* | 5/2022 | Ross | A61B 17/072 227/176.1 |
| 2022/0133428 A1* | 5/2022 | Leimbach | A61B 17/072 227/176.1 |

OTHER PUBLICATIONS

USPTO, Non-Final Offic Action issued Aug. 9, 2021 in related U.S. Appl. No. 16/846,310.
USPTO, Final Office Action Issued Dec. 11, 2023 In Related U.S. Appl. No. 16/846,310.
USPTO, Non-Final Office Action Issued Aug. 22, 2023, In Related U.S. Appl. No. 16/846,310.
USPTO, Non-Final Office Action Issued May 5, 2023 In Related U.S. Appl. No. 16/846,310.
USPTO, Non-Final Office Action Issued Apr. 13, 2022 In Related U.S. Appl. No. 16/846,310.
USPTO, Final Office Action Issued Nov. 19, 2021 In Related U.S. Appl. No. 16/846,310.
USPTO, Final Office Action Issued Sep. 26, 2022 In Related U.S. Appl. No. 16/846,309.
USPTO, Final Office Action Issued Dec. 8, 2023 In Related U.S. Appl. No. 16/846,309.
USPTO, Non-Final Office Action Issued Aug. 22, 2023 In Related U.S. Appl. No. 16/846,309.
USPTO, Non-Final Office Action Issued May 5, 202 In Related U.S. Appl. No. 16/846,309.
USPTO, Non-Final Office Action Issued Apr. 13, 2022 In Related U.S. Appl. No. 16/846,309.
USPTO, Final Office Action Issued Nov. 19, 2021 In Related U.S. Appl. No. 16/846,309.
USPTO, Non-Final Office Action Issued Aug. 9, 2021 In Related U.S. Appl. No. 16/846,309.

* cited by examiner

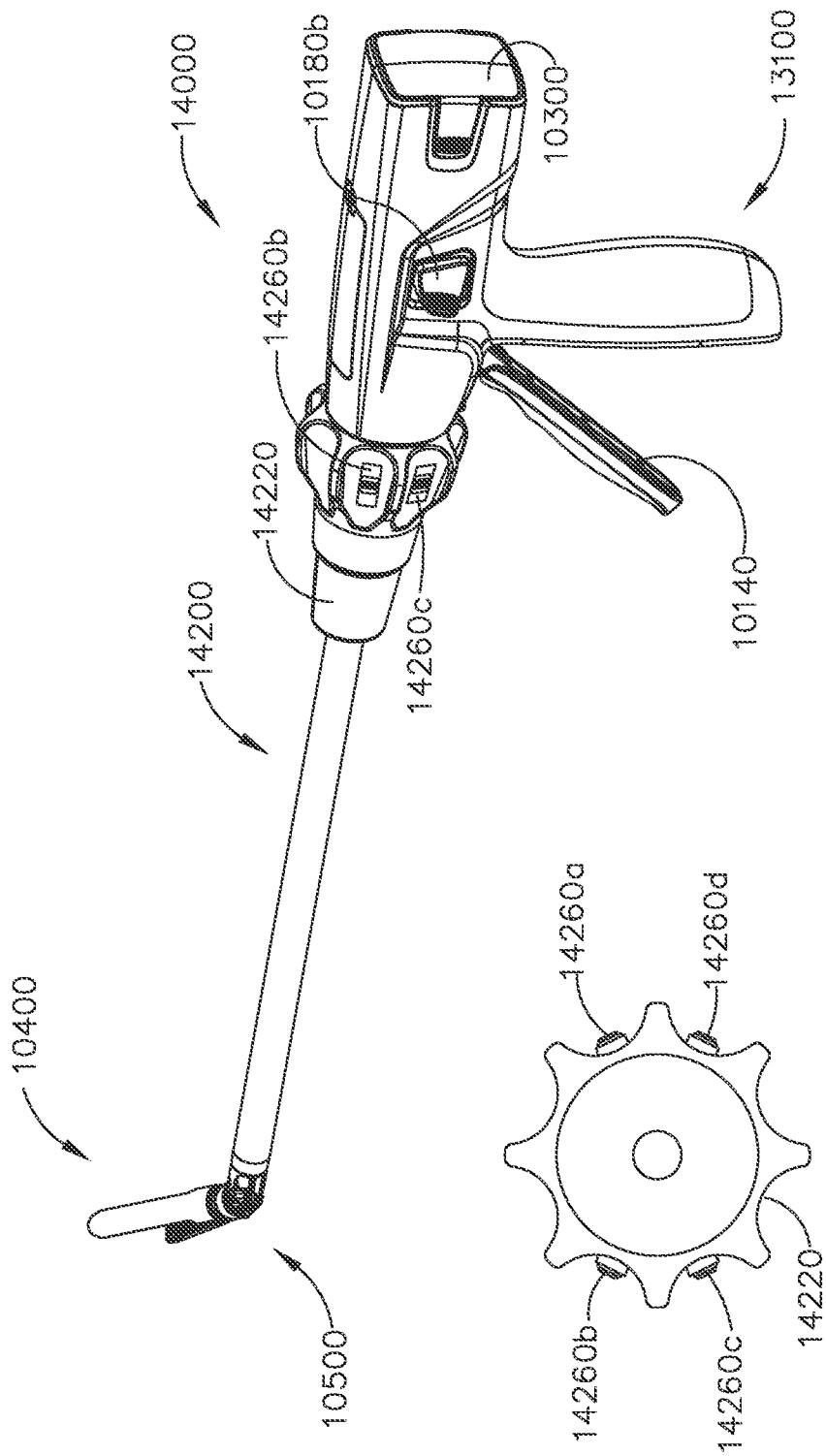

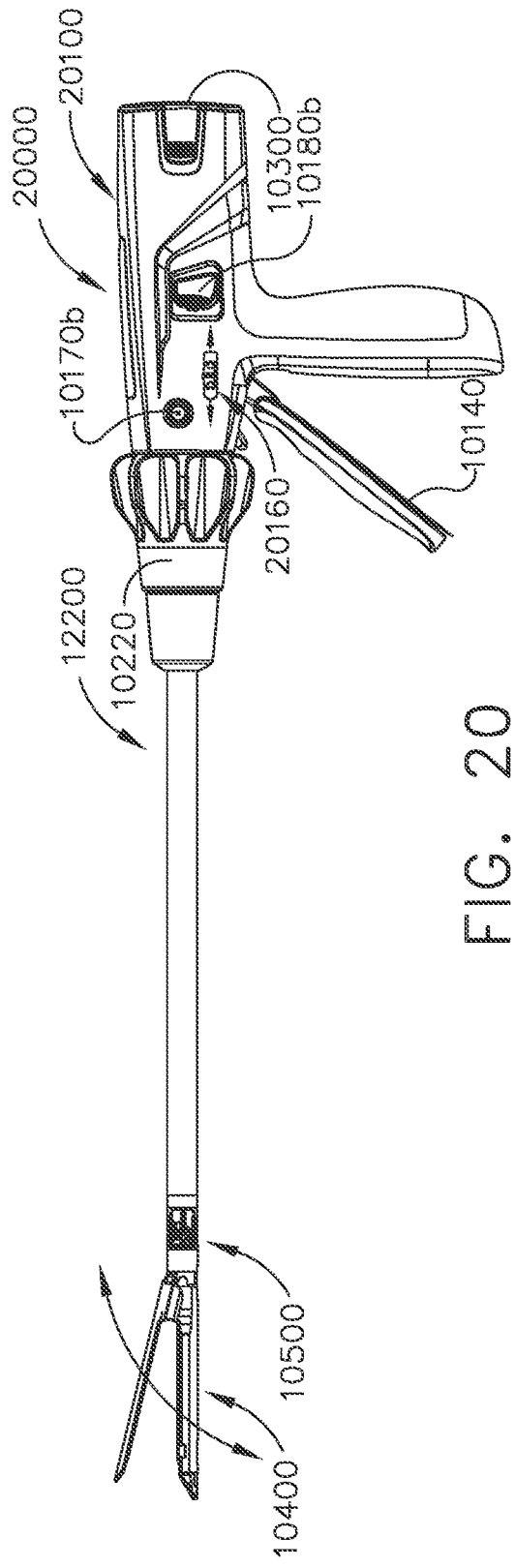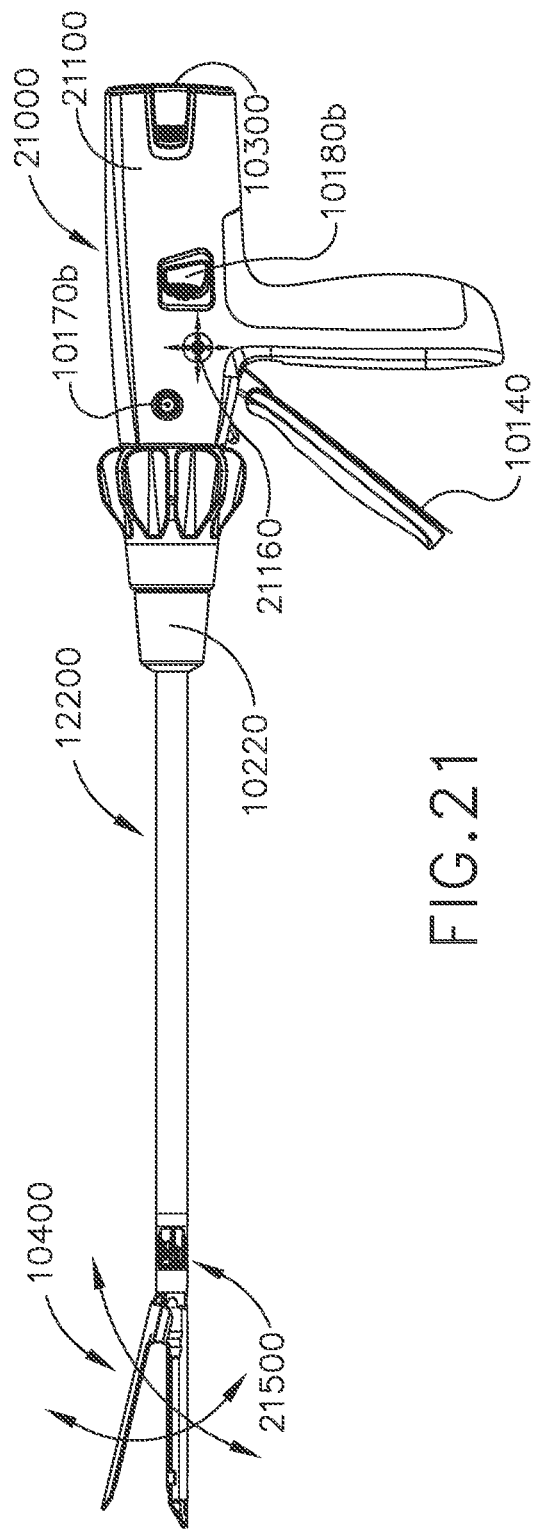

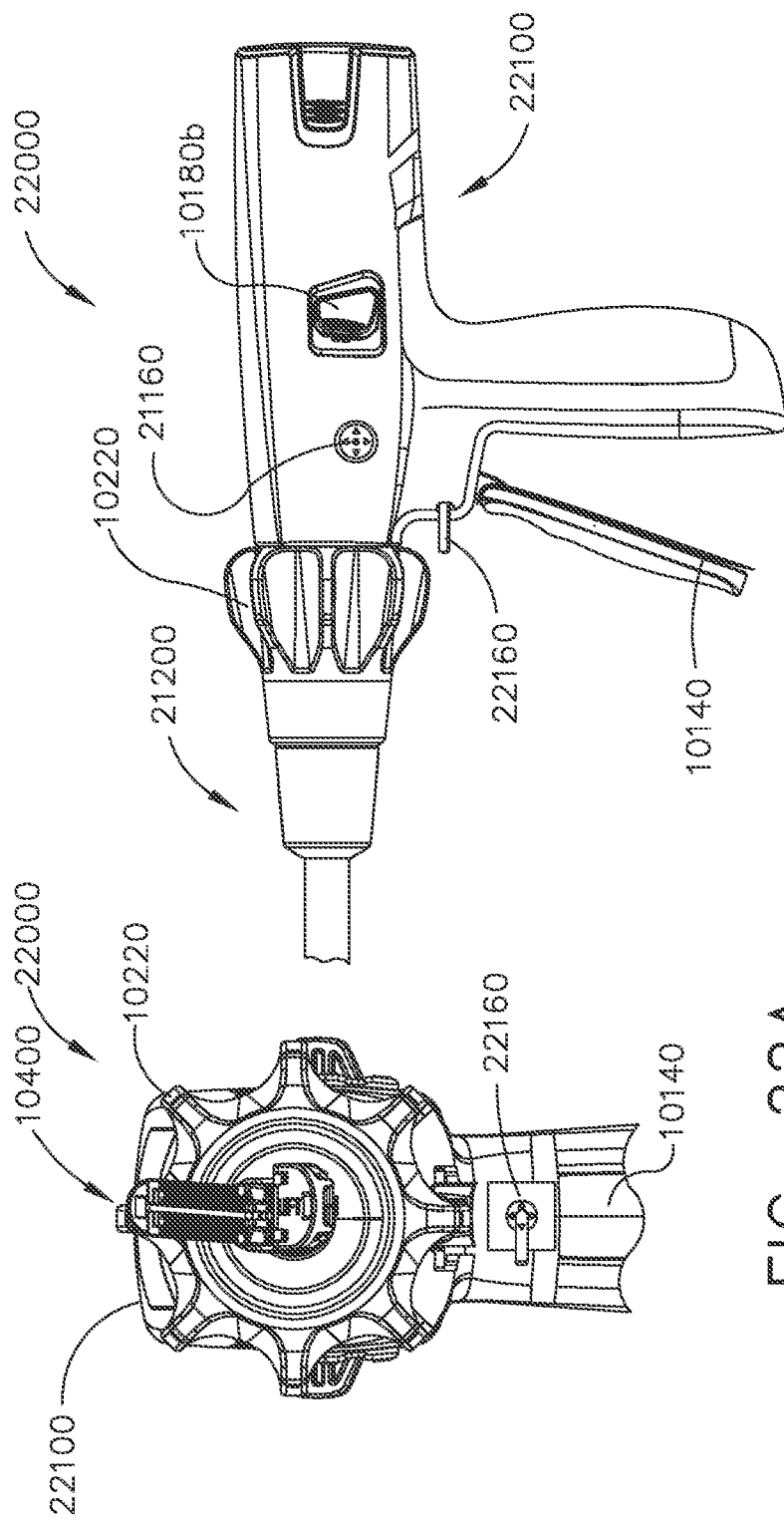

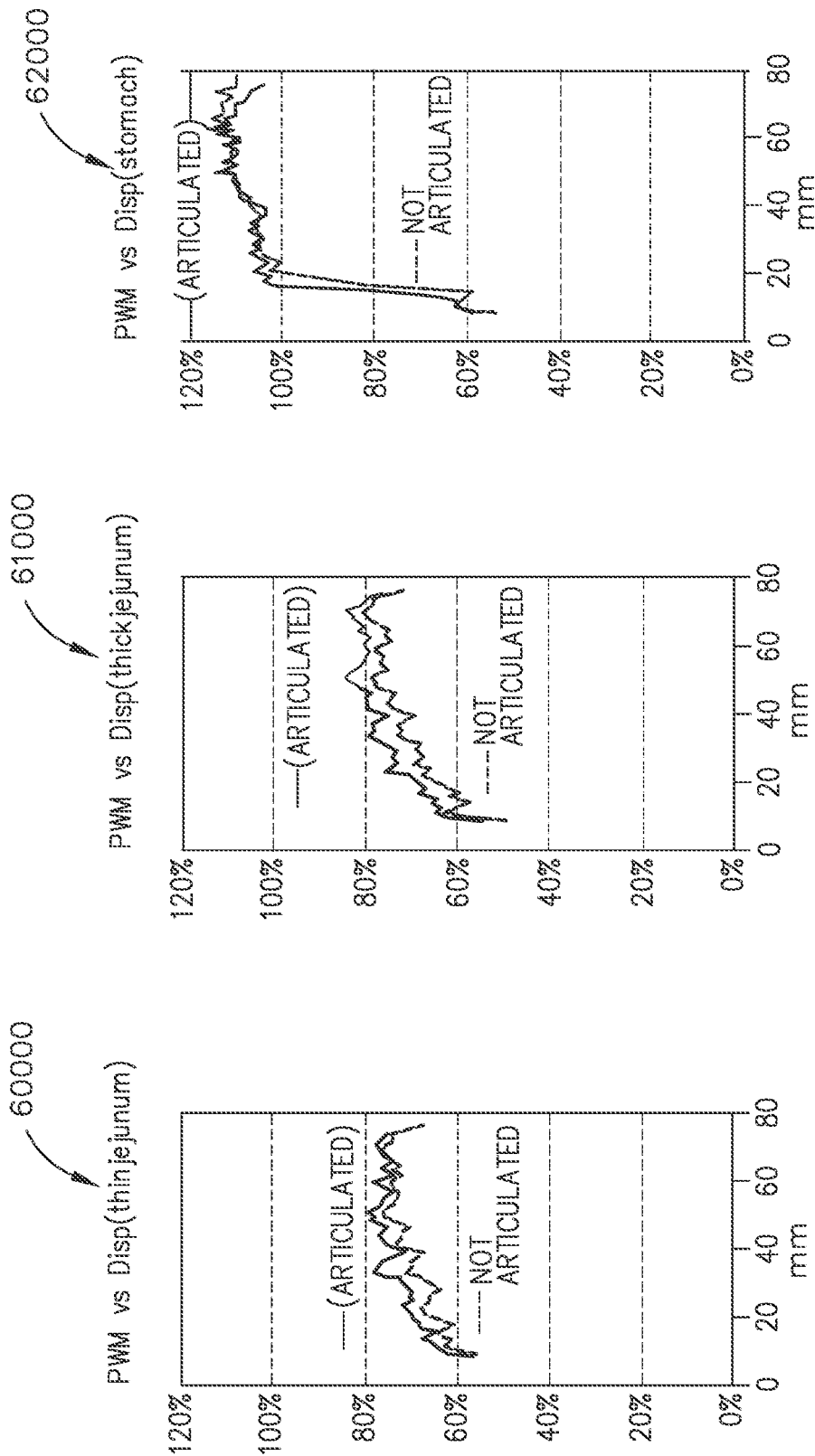

SURGICAL INSTRUMENT WITH FIRING STROKE TARGET SPEED ADJUSTMENT

CROSS-REFERENCE TO RELATED APPLICATIONS

This application is a continuation of U.S. patent application Ser. No. 16/846,303, entitled METHODS FOR STAPLING TISSUE USING A SURGICAL INSTRUMENT filed Apr. 11, 2020, which claims the benefit of U.S. Provisional Patent Application Ser. No. 62/840,715, entitled SURGICAL INSTRUMENT COMPRISING AN ADAPTIVE CONTROL SYSTEM, filed Apr. 30, 2019, the entire disclosures of each of which are hereby incorporated by reference herein.

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows:

FIG. 11 is a perspective view of a surgical instrument in accordance with at least one embodiment comprising a handle and a rotatable shaft including two articulation actuators on opposing sides of the shaft;

FIG. 12 is an end view of the shaft of FIG. 11;

FIG. 20 is an elevational view of a surgical instrument in accordance with at least one embodiment including an articulation joystick actuatable along a longitudinal axis;

FIG. 21 is an elevational view of a surgical instrument in accordance with at least one embodiment including an end effector and an articulation joystick actuatable to articulate the end effector about more than one axis;

FIG. 22A is a front elevational view of a surgical instrument in accordance with at least one embodiment including a plurality of articulation controls;

FIG. 22B is a partial side elevational view of the surgical instrument of FIG. 22A;

FIG. 86A depicts a graph of the duty cycle of the staple firing system of the surgical instrument of FIG. 1 during staple firing strokes through thin jejunum tissue;

FIG. 86B depicts a graph of the duty cycle of the staple firing system of the surgical instrument of FIG. 1 during staple firing strokes through thick jejunum tissue;

FIG. 86C depicts a graph of the duty cycle of the staple firing system of the surgical instrument of FIG. 1 during staple firing strokes through stomach tissue;

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
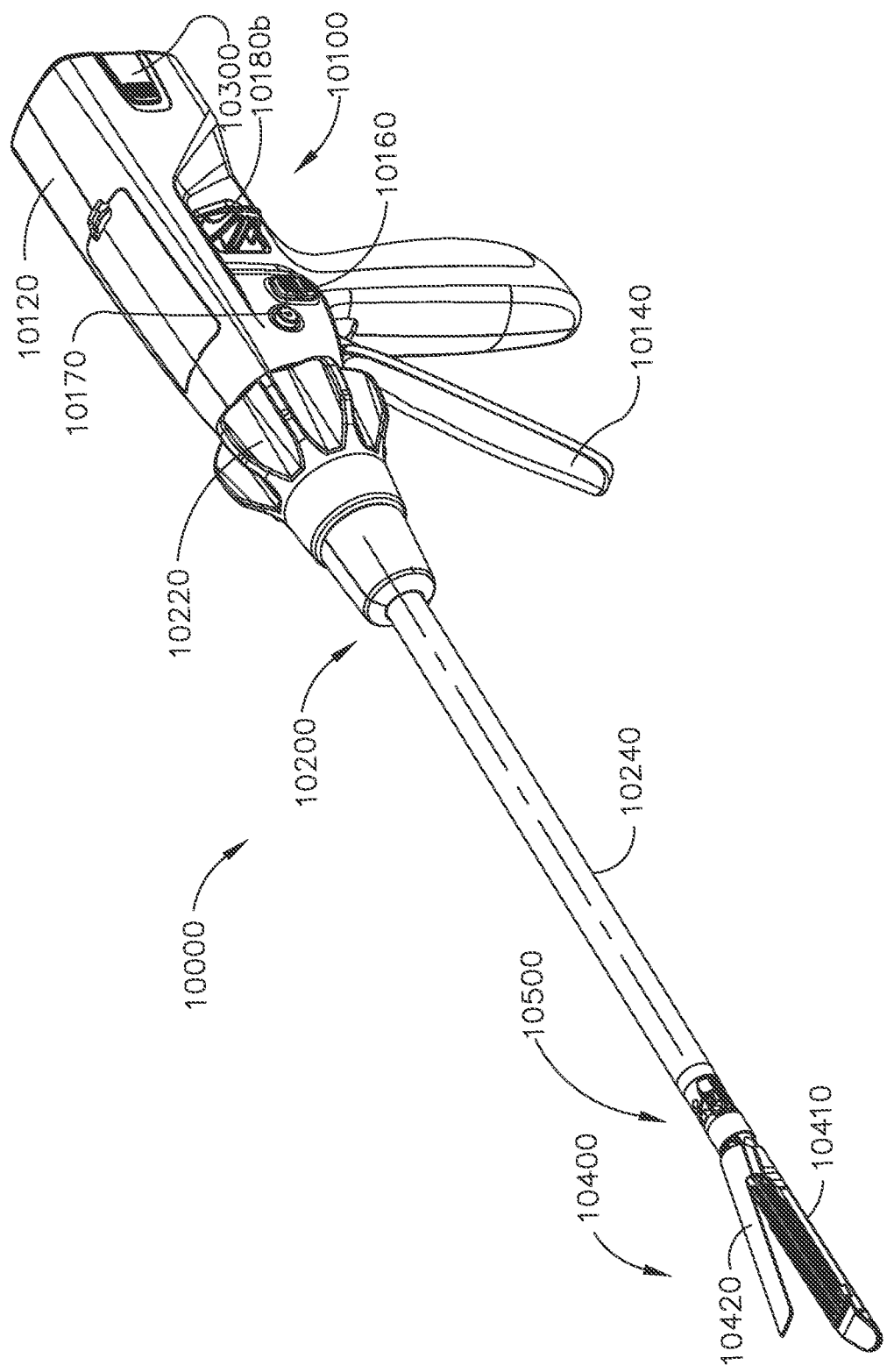
FIG. 1 is a perspective view of a surgical instrument in accordance with at least one embodiment.
Figure 1B:
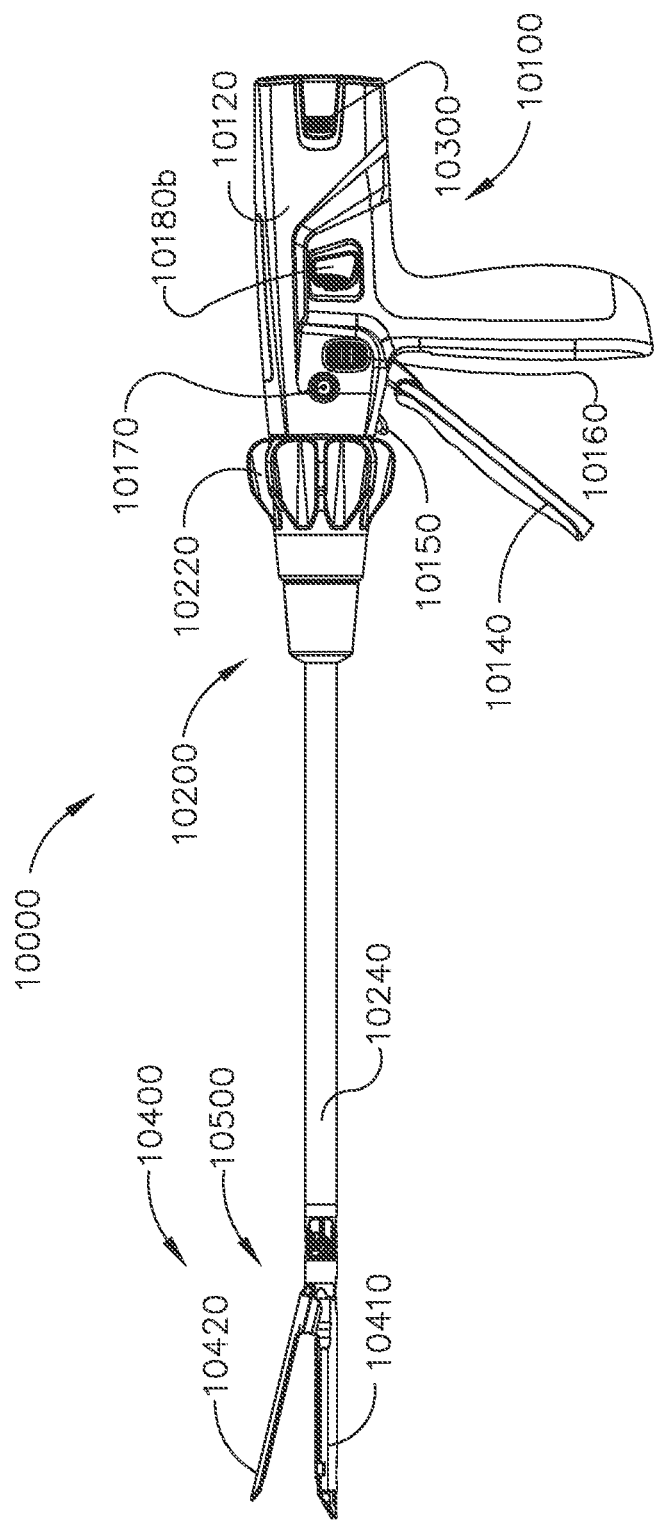
FIG. 1B is a left side elevation view of the surgical instrument of FIG. 1.
Figure 1C:
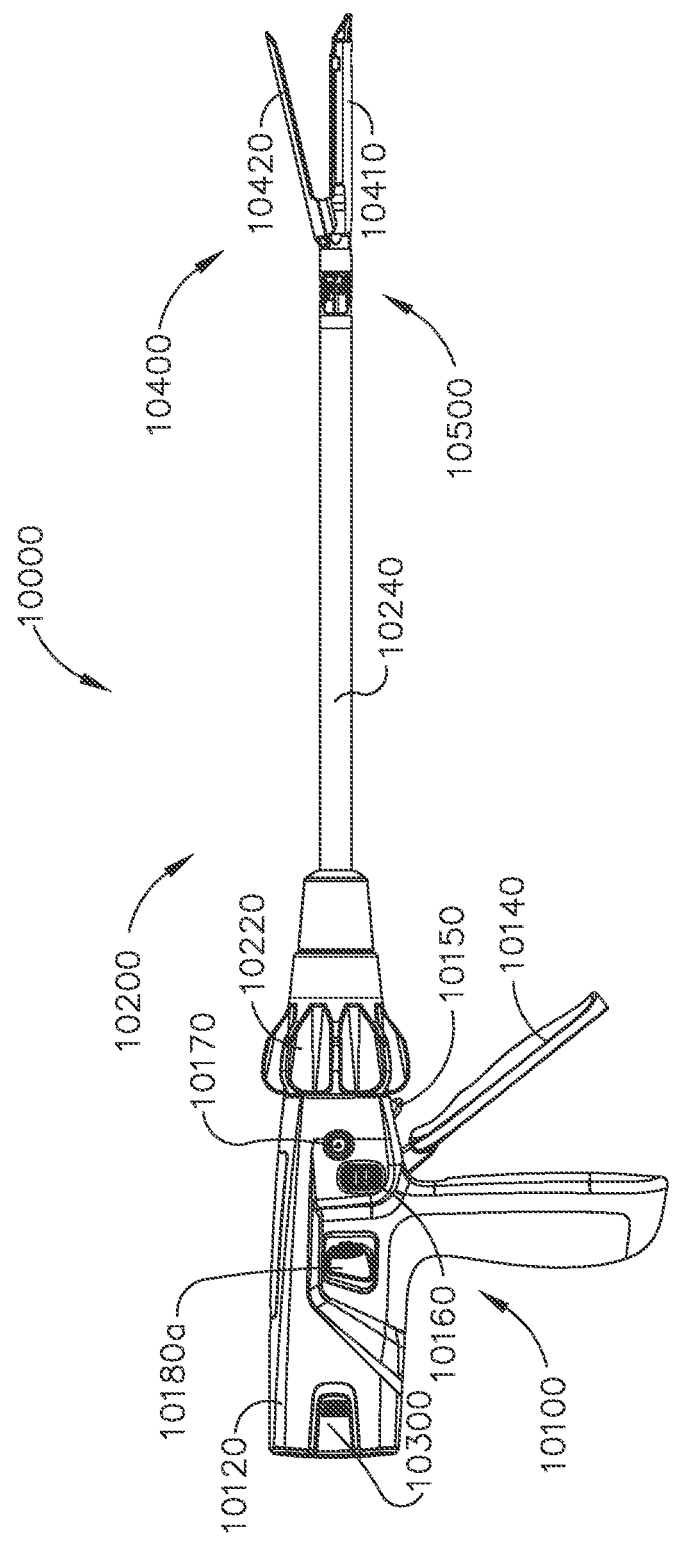
FIG. 1C is a right side elevation view of the surgical instrument of FIG. 1.
Figure 1D:
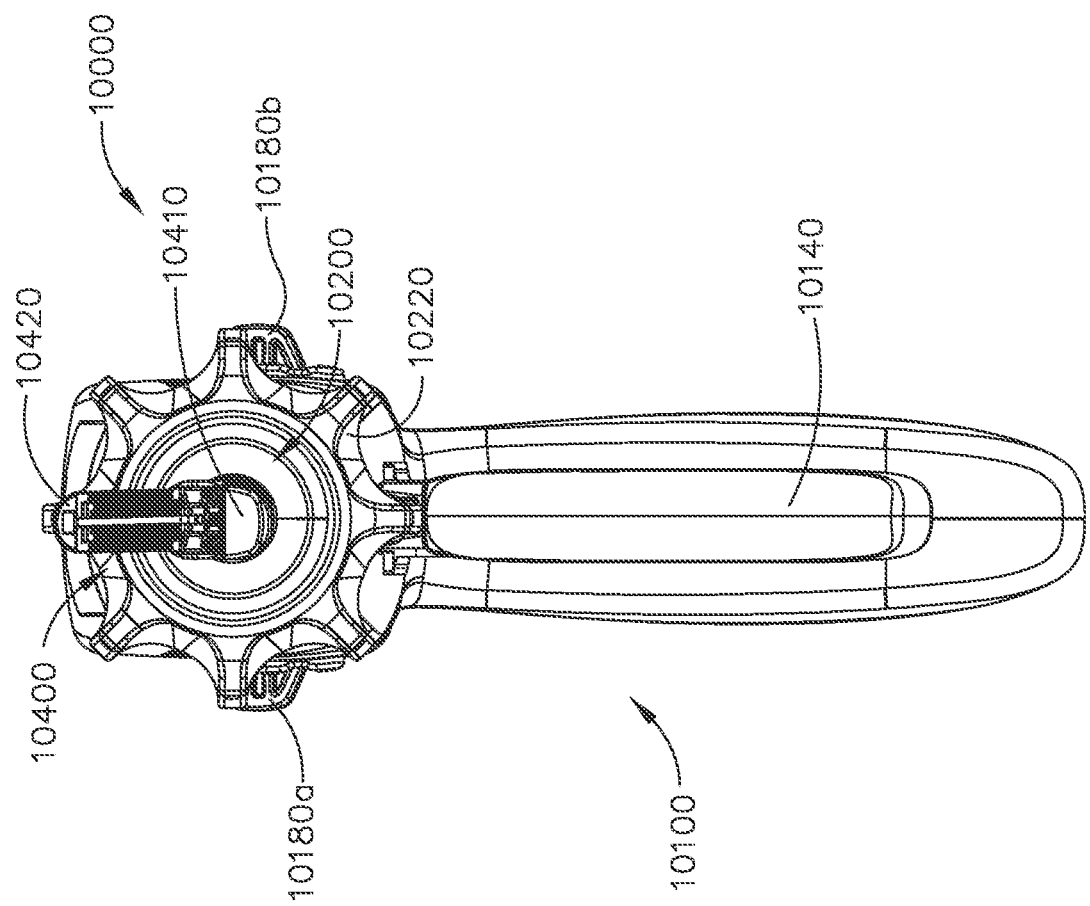
FIG. 1D is a front elevation view of the surgical instrument of FIG. 1.
Figure 1E:
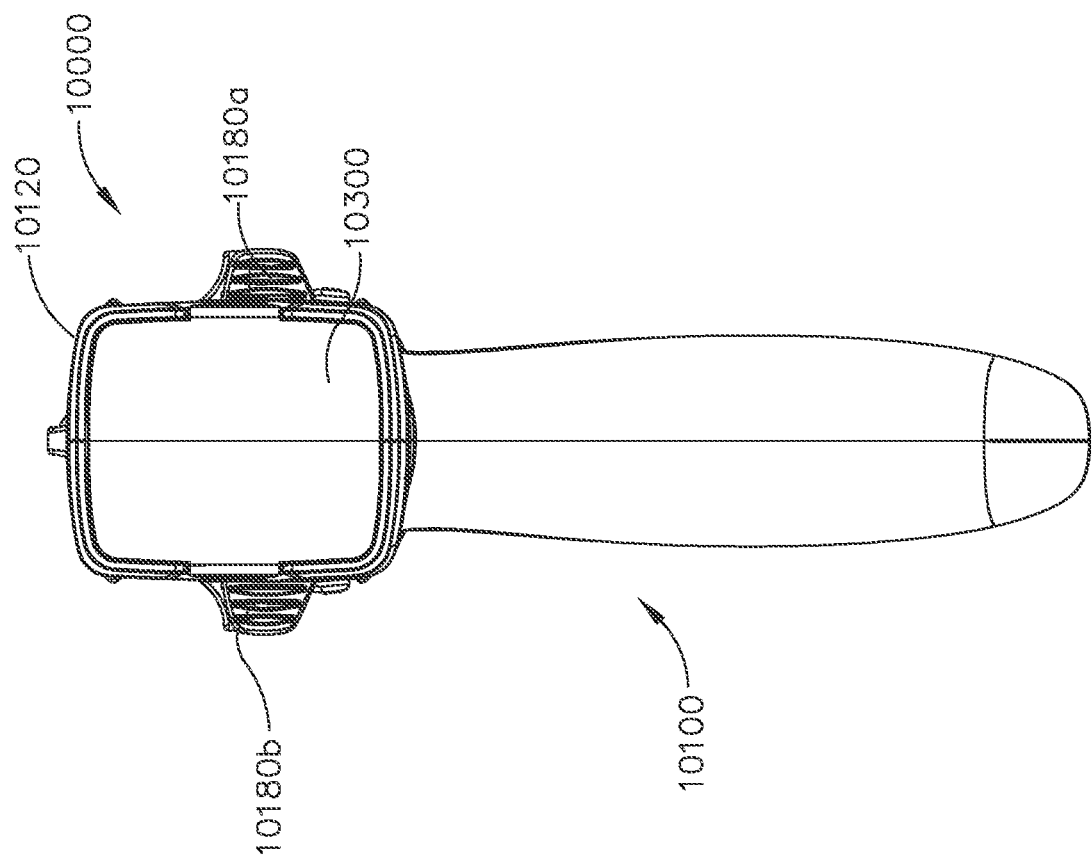
FIG. 1E is a back elevation view of the surgical instrument of FIG. 1.
Figure 1F:
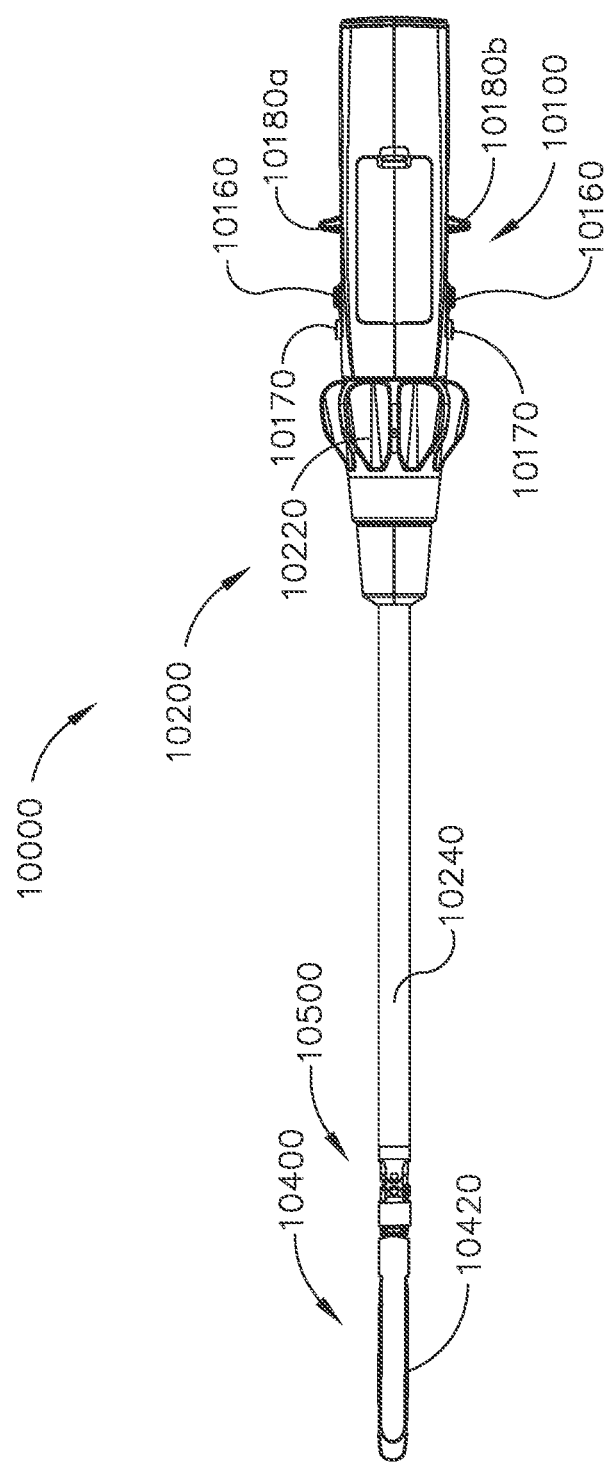
FIG. 1F is a plan view of the surgical instrument of FIG. 1.
Figure 1G:
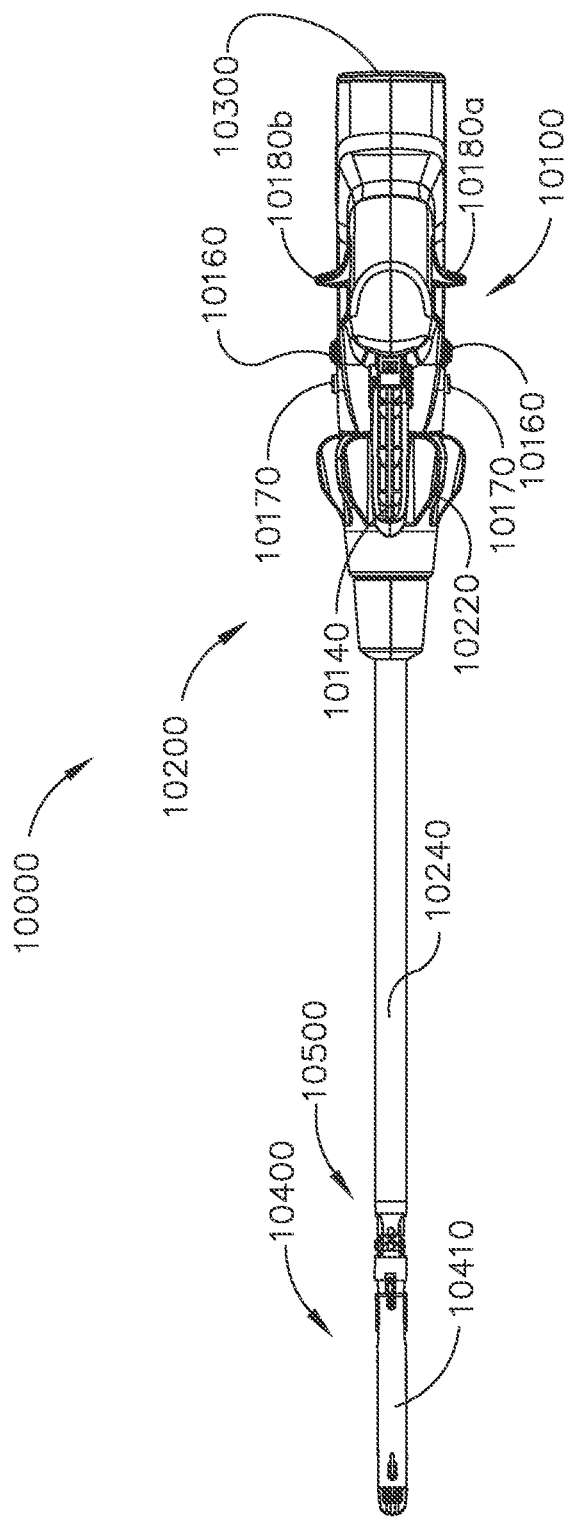
FIG. 1G is a bottom view of the surgical instrument of FIG. 1.

Applicant of the present application also owns the following U.S. patent applications that were filed on Apr. 11, 2020 and which are each herein incorporated by reference in their respective entireties:

U.S. patent application Ser. No. 16/846,304, entitled ARTICULATION ACTUATORS FOR A SURGICAL INSTRUMENT; patented as U.S. Pat. No. 11,452,528;

U.S. patent application Ser. No. 16/846,305, entitled ARTICULATION DIRECTIONAL LIGHTS ON A SURGICAL INSTRUMENT; patented as U.S. Pat. No. 11,426,251;

U.S. patent application Ser. No. 16/846,307, entitled SHAFT ROTATION ACTUATOR ON A SURGICAL INSTRUMENT; patented as U.S. Pat. No. 11,253,254;

U.S. patent application Ser. No. 16/846,308, entitled ARTICULATION CONTROL MAPPING FOR A SURGICAL INSTRUMENT; patented as U.S. Pat. No. 11,471,157;

U.S. patent application Ser. No. 16/846,309, entitled INTELLIGENT FIRING ASSOCIATED WITH A SURGICAL INSTRUMENT; published as US2020/0345356;

U.S. patent application Ser. No. 16/846,310, entitled INTELLIGENT FIRING ASSOCIATED WITH A SURGICAL INSTRUMENT; published as US2020/03455357;

U.S. patent application Ser. No. 16/846,311, entitled ROTATABLE JAW TIP FOR A SURGICAL INSTRUMENT; patented as U.S. Pat. No. 11,648,009;

U.S. patent application Ser. No. 16/846,312, entitled TISSUE STOP FOR A SURGICAL INSTRUMENT; published as US2020/0345359; and U.S. patent application Ser. No. 16/846,313, entitled ARTICULATION PIN FOR A SURGICAL INSTRUMENT; patented as U.S. Pat. No. 11,432,816.

Applicant of the present application owns the following U.S. Patent Applications that were filed on Feb. 21, 2019 and which are each herein incorporated by reference in their respective entireties:

U.S. patent application Ser. No. 16/281,658, entitled METHODS FOR CONTROLLING A POWERED SURGICAL STAPLER THAT HAS SEPARATE ROTARY CLOSURE AND FIRING SYSTEMS;

U.S. patent application Ser. No. 16/281,670, entitled STAPLE CARTRIDGE COMPRISING A LOCKOUT KEY CONFIGURED TO LIFT A FIRING MEMBER;

U.S. patent application Ser. No. 16/281,675, entitled SURGICAL STAPLERS WITH ARRANGEMENTS FOR MAINTAINING A FIRING MEMBER THEREOF IN A LOCKED CONFIGURATION UNLESS A COMPATIBLE CARTRIDGE HAS BEEN INSTALLED THEREIN;

U.S. patent application Ser. No. 16/281,685, entitled SURGICAL INSTRUMENT COMPRISING CO-OPERATING LOCKOUT FEATURES;

U.S. patent application Ser. No. 16/281,693, entitled SURGICAL STAPLING ASSEMBLY COMPRISING A LOCKOUT AND AN EXTERIOR ACCESS ORIFICE TO PERMIT ARTIFICIAL UNLOCKING OF THE LOCKOUT;

U.S. patent application Ser. No. 16/281,704, entitled SURGICAL STAPLING DEVICES WITH FEATURES FOR BLOCKING ADVANCEMENT OF A CAMMING ASSEMBLY OF AN INCOMPATIBLE CARTRIDGE INSTALLED THEREIN;

U.S. patent application Ser. No. 16/281,707, entitled STAPLING INSTRUMENT COMPRISING A DEACTIVATABLE LOCKOUT;

U.S. patent application Ser. No. 16/281,741, entitled SURGICAL INSTRUMENT COMPRISING A JAW CLOSURE LOCKOUT;

U.S. patent application Ser. No. 16/281,762, entitled SURGICAL STAPLING DEVICES WITH CARTRIDGE COMPATIBLE CLOSURE AND FIRING LOCKOUT ARRANGEMENTS;

U.S. patent application Ser. No. 16/281,666, entitled SURGICAL STAPLING DEVICES WITH IMPROVED ROTARY DRIVEN CLOSURE SYSTEMS;

U.S. patent application Ser. No. 16/281,672, entitled SURGICAL STAPLING DEVICES WITH ASYMMETRIC CLOSURE FEATURES;

U.S. patent application Ser. No. 16/281,678, entitled ROTARY DRIVEN FIRING MEMBERS WITH DIFFERENT ANVIL AND CHANNEL ENGAGEMENT FEATURES; and U.S. patent application Ser. No. 16/281,682, entitled SURGICAL STAPLING DEVICE WITH SEPARATE ROTARY DRIVEN CLOSURE AND FIRING SYSTEMS AND FIRING MEMBER THAT ENGAGES BOTH JAWS WHILE FIRING.

Applicant of the present application owns the following U.S. Provisional Patent applications that were filed on Feb. 19, 2019 and which are each herein incorporated by reference in their respective entireties:

U.S. Provisional Patent Application Ser. No. 62/807,310, entitled METHODS FOR CONTROLLING A POWERED SURGICAL STAPLER THAT HAS SEPARATE ROTARY CLOSURE AND FIRING SYSTEMS;

U.S. Provisional Patent Application Ser. No. 62/807,319, entitled SURGICAL STAPLING DEVICES WITH IMPROVED LOCKOUT SYSTEMS; and U.S. Provisional Patent Application Ser. No. 62/807,309, entitled SURGICAL STAPLING DEVICES WITH IMPROVED ROTARY DRIVEN CLOSURE SYSTEMS.

Applicant of the present application owns the following U.S. Provisional Patent applications, filed on Mar. 28, 2018, each of which is herein incorporated by reference in its entirety:

U.S. Provisional Patent Application Ser. No. 62/649,302, entitled INTERACTIVE SURGICAL SYSTEMS WITH ENCRYPTED COMMUNICATION CAPABILITIES;

U.S. Provisional Patent Application Ser. No. 62/649,249, entitled DATA STRIPPING METHOD TO INTERROGATE PATIENT RECORDS AND CREATE ANONYMIZED RECORD;

U.S. Provisional Patent Application Ser. No. 62/649,300, entitled SURGICAL HUB SITUATIONAL AWARENESS;

U.S. Provisional Patent Application Ser. No. 62/649,309, entitled SURGICAL HUB SPATIAL AWARENESS TO DETERMINE DEVICES IN OPERATING THEATER;

U.S. Provisional Patent Application Ser. No. 62/649,310, entitled COMPUTER IMPLEMENTED INTERACTIVE SURGICAL SYSTEMS;

U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, entitled ADAPTIVE CONTROL PROGRAM UPDATES FOR SURGICAL DEVICES;

U.S. Provisional Patent Application Ser. No. 62/649,333, entitled CLOUD-BASED MEDICAL ANALYTICS FOR CUSTOMIZATION AND RECOMMENDATIONS TO A USER;

U.S. Provisional Patent Application Ser. No. 62/649,327, entitled CLOUD-BASED MEDICAL ANALYTICS FOR SECURITY AND AUTHENTICATION TRENDS AND REACTIVE MEASURES;

U.S. Provisional Patent Application Ser. No. 62/649,315, entitled DATA HANDLING AND PRIORITIZATION IN A CLOUD ANALYTICS NETWORK;

U.S. Provisional Patent Application Ser. No. 62/649,313, entitled CLOUD INTERFACE FOR COUPLED SURGICAL DEVICES;

U.S. Provisional Patent Application Ser. No. 62/649,320, entitled DRIVE ARRANGEMENTS FOR ROBOT-ASSISTED SURGICAL PLATFORMS;

U.S. Provisional Patent Application Ser. No. 62/649,307, entitled AUTOMATIC TOOL ADJUSTMENTS FOR ROBOT-ASSISTED SURGICAL PLATFORMS; and U.S. Provisional Patent Application Ser. No. 62/649,323, entitled SENSING ARRANGEMENTS FOR ROBOT-ASSISTED SURGICAL PLATFORMS.

Applicant of the present application owns the following U.S. Provisional Patent Application, filed on Mar. 30, 2018, which is herein incorporated by reference in its entirety:

U.S. Provisional Patent Application Ser. No. 62/650,887, entitled SURGICAL SYSTEMS WITH OPTIMIZED SENSING CAPABILITIES.

Applicant of the present application owns the following U.S. Patent Application, filed on Dec. 4, 2018, which is herein incorporated by reference in its entirety:

U.S. patent application Ser. No. 16/209,423, entitled METHOD OF COMPRESSING TISSUE WITHIN A STAPLING DEVICE AND SIMULTANEOUSLY DISPLAYING THE LOCATION OF THE TISSUE WITHIN THE JAWS.

Applicant of the present application owns the following U.S. Patent Applications that were filed on Aug. 20, 2018 and which are each herein incorporated by reference in their respective entireties:

U.S. patent application Ser. No. 16/105,101, entitled METHOD FOR FABRICATING SURGICAL STAPLER ANVILS;

U.S. patent application Ser. No. 16/105,183, entitled REINFORCED DEFORMABLE ANVIL TIP FOR SURGICAL STAPLER ANVIL;

U.S. patent application Ser. No. 16/105,150, entitled SURGICAL STAPLER ANVILS WITH STAPLE DIRECTING PROTRUSIONS AND TISSUE STABILITY FEATURES;

U.S. patent application Ser. No. 16/105,098, entitled FABRICATING TECHNIQUES FOR SURGICAL STAPLER ANVILS;

U.S. patent application Ser. No. 16/105,140, entitled SURGICAL STAPLER ANVILS WITH TISSUE STOP FEATURES CONFIGURED TO AVOID TISSUE PINCH;

U.S. patent application Ser. No. 16/105,081, entitled METHOD FOR OPERATING A POWERED ARTICULATABLE SURGICAL INSTRUMENT;

U.S. patent application Ser. No. 16/105,094, entitled SURGICAL INSTRUMENTS WITH PROGRESSIVE JAW CLOSURE ARRANGEMENTS;

U.S. patent application Ser. No. 16/105,097, entitled POWERED SURGICAL INSTRUMENTS WITH CLUTCHING ARRANGEMENTS TO CONVERT LINEAR DRIVE MOTIONS TO ROTARY DRIVE MOTIONS;

U.S. patent application Ser. No. 16/105,104, entitled POWERED ARTICULATABLE SURGICAL INSTRUMENTS WITH CLUTCHING AND LOCKING ARRANGEMENTS FOR LINKING AN ARTICULATION DRIVE SYSTEM TO A FIRING DRIVE SYSTEM;

U.S. patent application Ser. No. 16/105,119, entitled ARTICULATABLE MOTOR POWERED SURGICAL INSTRUMENTS WITH DEDICATED ARTICULATION MOTOR ARRANGEMENTS;

U.S. patent application Ser. No. 16/105,160, entitled SWITCHING ARRANGEMENTS FOR MOTOR POWERED ARTICULATABLE SURGICAL INSTRUMENTS; and U.S. Design Patent Application Ser. No. 29/660,252, entitled SURGICAL STAPLER ANVILS.

Applicant of the present application owns the following U.S. Patent Applications and U.S. Patents that are each herein incorporated by reference in their respective entireties:

U.S. patent application Ser. No. 15/386,185, entitled SURGICAL STAPLING INSTRUMENTS AND REPLACEABLE TOOL ASSEMBLIES THEREOF, now U.S. Patent Application Publication No. 2018/0168642;

U.S. patent application Ser. No. 15/386,230, entitled ARTICULATABLE SURGICAL STAPLING INSTRUMENTS, now U.S. Patent Application Publication No. 2018/0168649;

U.S. patent application Ser. No. 15/386,221, entitled LOCKOUT ARRANGEMENTS FOR SURGICAL END EFFECTORS, now U.S. Patent Application Publication No. 2018/0168646;

U.S. patent application Ser. No. 15/386,209, entitled SURGICAL END EFFECTORS AND FIRING MEMBERS THEREOF, now U.S. Patent Application Publication No. 2018/0168645;

U.S. patent application Ser. No. 15/386,198, entitled LOCKOUT ARRANGEMENTS FOR SURGICAL END EFFECTORS AND REPLACEABLE TOOL ASSEMBLIES, now U.S. Patent Application Publication No. 2018/0168644;

U.S. patent application Ser. No. 15/386,240, entitled SURGICAL END EFFECTORS AND ADAPTABLE FIRING MEMBERS THEREFOR, now U.S. Patent Application Publication No. 2018/0168651;

U.S. patent application Ser. No. 15/385,939, entitled STAPLE CARTRIDGES AND ARRANGEMENTS OF STAPLES AND STAPLE CAVITIES THEREIN, now U.S. Patent Application Publication No. 2018/0168629;

U.S. patent application Ser. No. 15/385,941, entitled SURGICAL TOOL ASSEMBLIES WITH CLUTCHING ARRANGEMENTS FOR SHIFTING BETWEEN CLOSURE SYSTEMS WITH CLOSURE STROKE REDUCTION FEATURES AND ARTICULATION AND FIRING SYSTEMS, now U.S. Patent Application Publication No. 2018/0168630;

U.S. patent application Ser. No. 15/385,943, entitled SURGICAL STAPLING INSTRUMENTS AND STAPLE-FORMING ANVILS, now U.S. Patent Application Publication No. 2018/0168631;

U.S. patent application Ser. No. 15/385,950, entitled SURGICAL TOOL ASSEMBLIES WITH CLOSURE STROKE REDUCTION FEATURES, now U.S. Patent Application Publication No. 2018/0168635;

U.S. patent application Ser. No. 15/385,945, entitled STAPLE CARTRIDGES AND ARRANGEMENTS OF STAPLES AND STAPLE CAVITIES THEREIN, now U.S. Patent Application Publication No. 2018/0168632;

U.S. patent application Ser. No. 15/385,946, entitled SURGICAL STAPLING INSTRUMENTS AND STAPLE-FORMING ANVILS, now U.S. Patent Application Publication No. 2018/0168633;

U.S. patent application Ser. No. 15/385,951, entitled SURGICAL INSTRUMENTS WITH JAW OPENING FEATURES FOR INCREASING A JAW OPENING DISTANCE, now U.S. Patent Application Publication No. 2018/0168636;

U.S. patent application Ser. No. 15/385,953, entitled METHODS OF STAPLING TISSUE, now U.S. Patent Application Publication No. 2018/0168637;

U.S. patent application Ser. No. 15/385,954, entitled FIRING MEMBERS WITH NON-PARALLEL JAW ENGAGEMENT FEATURES FOR SURGICAL END EFFECTORS, now U.S. Patent Application Publication No. 2018/0168638;

U.S. patent application Ser. No. 15/385,955, entitled SURGICAL END EFFECTORS WITH EXPANDABLE TISSUE STOP ARRANGEMENTS, now U.S. Patent Application Publication No. 2018/0168639;

U.S. patent application Ser. No. 15/385,948, entitled SURGICAL STAPLING INSTRUMENTS AND STAPLE-FORMING ANVILS, now U.S. Patent Application Publication No. 2018/0168584;

U.S. patent application Ser. No. 15/385,956, entitled SURGICAL INSTRUMENTS WITH POSITIVE JAW OPENING FEATURES, now U.S. Patent Application Publication No. 2018/0168640;

U.S. patent application Ser. No. 15/385,958, entitled SURGICAL INSTRUMENTS WITH LOCKOUT ARRANGEMENTS FOR PREVENTING FIRING SYSTEM ACTUATION UNLESS AN UNSPENT STAPLE CARTRIDGE IS PRESENT, now U.S. Patent Application Publication No. 2018/0168641;

U.S. patent application Ser. No. 15/385,947, entitled STAPLE CARTRIDGES AND ARRANGEMENTS OF STAPLES AND STAPLE CAVITIES THEREIN, now U.S. Patent Application Publication No. 2018/0168634;

U.S. patent application Ser. No. 15/385,896, entitled METHOD FOR RESETTING A FUSE OF A SURGICAL INSTRUMENT SHAFT, now U.S. Patent Application Publication No. 2018/0168597;

U.S. patent application Ser. No. 15/385,898, entitled STAPLE-FORMING POCKET ARRANGEMENT TO ACCOMMODATE DIFFERENT TYPES OF STAPLES, now U.S. Patent Application Publication No. 2018/0168599;

U.S. patent application Ser. No. 15/385,899, entitled SURGICAL INSTRUMENT COMPRISING IMPROVED JAW CONTROL, now U.S. Patent Application Publication No. 2018/0168600;

U.S. patent application Ser. No. 15/385,901, entitled STAPLE CARTRIDGE AND STAPLE CARTRIDGE CHANNEL COMPRISING WINDOWS DEFINED THEREIN, now U.S. Patent Application Publication No. 2018/0168602;

U.S. patent application Ser. No. 15/385,902, entitled SURGICAL INSTRUMENT COMPRISING A CUTTING MEMBER, now U.S. Patent Application Publication No. 2018/0168603;

U.S. patent application Ser. No. 15/385,904, entitled STAPLE FIRING MEMBER COMPRISING A MISSING CARTRIDGE AND/OR SPENT CARTRIDGE LOCKOUT, now U.S. Patent Application Publication No. 2018/0168605;

U.S. patent application Ser. No. 15/385,905, entitled FIRING ASSEMBLY COMPRISING A LOCKOUT, now U.S. Patent Application Publication No. 2018/0168606;

U.S. patent application Ser. No. 15/385,907, entitled SURGICAL INSTRUMENT SYSTEM COMPRISING AN END EFFECTOR LOCKOUT AND A FIRING ASSEMBLY LOCKOUT, now U.S. Patent Application Publication No. 2018/0168608;

U.S. patent application Ser. No. 15/385,908, entitled FIRING ASSEMBLY COMPRISING A FUSE, now U.S. Patent Application Publication No. 2018/0168609;

U.S. patent application Ser. No. 15/385,909, entitled FIRING ASSEMBLY COMPRISING A MULTIPLE FAILED-STATE FUSE, now U.S. Patent Application Publication No. 2018/0168610;

U.S. patent application Ser. No. 15/385,920, entitled STAPLE-FORMING POCKET ARRANGEMENTS, now U.S. Patent Application Publication No. 2018/0168620;

U.S. patent application Ser. No. 15/385,913, entitled ANVIL ARRANGEMENTS FOR SURGICAL STAPLERS, now U.S. Patent Application Publication No. 2018/0168614;

U.S. patent application Ser. No. 15/385,914, entitled METHOD OF DEFORMING STAPLES FROM TWO DIFFERENT TYPES OF STAPLE CARTRIDGES WITH THE SAME SURGICAL STAPLING INSTRUMENT, now U.S. Patent Application Publication No. 2018/0168615;

U.S. patent application Ser. No. 15/385,893, entitled BILATERALLY ASYMMETRIC STAPLE-FORMING POCKET PAIRS, now U.S. Patent Application Publication No. 2018/0168594;

U.S. patent application Ser. No. 15/385,929, entitled CLOSURE MEMBERS WITH CAM SURFACE ARRANGEMENTS FOR SURGICAL INSTRUMENTS WITH SEPARATE AND DISTINCT CLOSURE AND FIRING SYSTEMS, now U.S. Patent Application Publication No. 2018/0168626;

U.S. patent application Ser. No. 15/385,911, entitled SURGICAL STAPLERS WITH INDEPENDENTLY ACTUATABLE CLOSING AND FIRING SYSTEMS, now U.S. Patent Application Publication No. 2018/0168612;

U.S. patent application Ser. No. 15/385,927, entitled SURGICAL STAPLING INSTRUMENTS WITH SMART STAPLE CARTRIDGES, now U.S. Patent Application Publication No. 2018/0168625;

U.S. patent application Ser. No. 15/385,917, entitled STAPLE CARTRIDGE COMPRISING STAPLES WITH DIFFERENT CLAMPING BREADTHS, now U.S. Patent Application Publication No. 2018/0168617;

U.S. patent application Ser. No. 15/385,900, entitled STAPLE-FORMING POCKET ARRANGEMENTS COMPRISING PRIMARY SIDEWALLS AND POCKET SIDEWALLS, now U.S. Patent Application Publication No. 2018/0168601;

U.S. patent application Ser. No. 15/385,931, entitled NO-CARTRIDGE AND SPENT CARTRIDGE LOCKOUT ARRANGEMENTS FOR SURGICAL STAPLERS, now U.S. Patent Application Publication No. 2018/0168627;

U.S. patent application Ser. No. 15/385,915, entitled FIRING MEMBER PIN ANGLE, now U.S. Patent Application Publication No. 2018/0168616;

U.S. patent application Ser. No. 15/385,897, entitled STAPLE-FORMING POCKET ARRANGEMENTS COMPRISING ZONED FORMING SURFACE GROOVES, now U.S. Patent Application Publication No. 2018/0168598;

U.S. patent application Ser. No. 15/385,922, entitled SURGICAL INSTRUMENT WITH MULTIPLE FAILURE RESPONSE MODES, now U.S. Patent Application Publication No. 2018/0168622;

U.S. patent application Ser. No. 15/385,924, entitled SURGICAL INSTRUMENT WITH PRIMARY AND SAFETY PROCESSORS, now U.S. Patent Application Publication No. 2018/0168624;

U.S. patent application Ser. No. 15/385,910, entitled ANVIL HAVING A KNIFE SLOT WIDTH, now U.S. Patent Application Publication No. 2018/0168611;

U.S. patent application Ser. No. 15/385,903, entitled CLOSURE MEMBER ARRANGEMENTS FOR SURGICAL INSTRUMENTS, now U.S. Patent Application Publication No. 2018/0168604;

U.S. patent application Ser. No. 15/385,906, entitled FIRING MEMBER PIN CONFIGURATIONS, now U.S. Patent Application Publication No. 2018/0168607;

U.S. patent application Ser. No. 15/386,188, entitled STEPPED STAPLE CARTRIDGE WITH ASYMMETRICAL STAPLES, now U.S. Patent Application Publication No. 2018/0168585;

U.S. patent application Ser. No. 15/386,192, entitled STEPPED STAPLE CARTRIDGE WITH TISSUE RETENTION AND GAP SETTING FEATURES, now U.S. Patent Application Publication No. 2018/0168643;

U.S. patent application Ser. No. 15/386,206, entitled STAPLE CARTRIDGE WITH DEFORMABLE DRIVER RETENTION FEATURES, now U.S. Patent Application Publication No. 2018/0168586;

U.S. patent application Ser. No. 15/386,226, entitled DURABILITY FEATURES FOR END EFFECTORS AND FIRING ASSEMBLIES OF SURGICAL STAPLING INSTRUMENTS, now U.S. Patent Application Publication No. 2018/0168648;

U.S. patent application Ser. No. 15/386,222, entitled SURGICAL STAPLING INSTRUMENTS HAVING END EFFECTORS WITH POSITIVE OPENING FEATURES, now U.S. Patent Application Publication No. 2018/0168647;

U.S. patent application Ser. No. 15/386,236, entitled CONNECTION PORTIONS FOR DEPOSABLE LOADING UNITS FOR SURGICAL STAPLING INSTRUMENTS, now U.S. Patent Application Publication No. 2018/0168650;

U.S. patent application Ser. No. 15/385,887, entitled METHOD FOR ATTACHING A SHAFT ASSEMBLY TO A SURGICAL INSTRUMENT AND, ALTERNATIVELY, TO A SURGICAL ROBOT, now U.S. Patent Application Publication No. 2018/0168589;

U.S. patent application Ser. No. 15/385,889, entitled SHAFT ASSEMBLY COMPRISING A MANUALLY-OPERABLE RETRACTION SYSTEM FOR USE WITH A MOTORIZED SURGICAL INSTRUMENT SYSTEM, now U.S. Patent Application Publication No. 2018/0168590;

U.S. patent application Ser. No. 15/385,890, entitled SHAFT ASSEMBLY COMPRISING SEPARATELY ACTUATABLE AND RETRACTABLE SYSTEMS, now U.S. Patent Application Publication No. 2018/0168591;

U.S. patent application Ser. No. 15/385,891, entitled SHAFT ASSEMBLY COMPRISING A CLUTCH CONFIGURED TO ADAPT THE OUTPUT OF A ROTARY FIRING MEMBER TO TWO DIFFERENT SYSTEMS, now U.S. Patent Application Publication No. 2018/0168592;

U.S. patent application Ser. No. 15/385,892, entitled SURGICAL SYSTEM COMPRISING A FIRING MEMBER ROTATABLE INTO AN ARTICULATION STATE TO ARTICULATE AN END EFFECTOR OF THE SURGICAL SYSTEM, now U.S. Patent Application Publication No. 2018/0168593;

U.S. patent application Ser. No. 15/385,894, entitled SHAFT ASSEMBLY COMPRISING A LOCKOUT, now U.S. Patent Application Publication No. 2018/0168595;

U.S. patent application Ser. No. 15/385,895, entitled SHAFT ASSEMBLY COMPRISING FIRST AND SECOND ARTICULATION LOCKOUTS, now U.S. Patent Application Publication No. 2018/0168596;

U.S. patent application Ser. No. 15/385,916, entitled SURGICAL STAPLING SYSTEMS, now U.S. Patent Application Publication No. 2018/0168575;

U.S. patent application Ser. No. 15/385,918, entitled SURGICAL STAPLING SYSTEMS, now U.S. Patent Application Publication No. 2018/0168618;

U.S. patent application Ser. No. 15/385,919, entitled SURGICAL STAPLING SYSTEMS, now U.S. Patent Application Publication No. 2018/0168619;

U.S. patent application Ser. No. 15/385,921, entitled SURGICAL STAPLE CARTRIDGE WITH MOVABLE CAMMING MEMBER CONFIGURED TO DISENGAGE FIRING MEMBER LOCKOUT FEATURES, now U.S. Patent Application Publication No. 2018/0168621;

U.S. patent application Ser. No. 15/385,923, entitled SURGICAL STAPLING SYSTEMS, now U.S. Patent Application Publication No. 2018/0168623;

U.S. patent application Ser. No. 15/385,925, entitled JAW ACTUATED LOCK ARRANGEMENTS FOR PREVENTING ADVANCEMENT OF A FIRING MEMBER IN A SURGICAL END EFFECTOR UNLESS AN UNFIRED CARTRIDGE IS INSTALLED IN THE END EFFECTOR, now U.S. Patent Application Publication No. 2018/0168576;

U.S. patent application Ser. No. 15/385,926, entitled AXIALLY MOVABLE CLOSURE SYSTEM ARRANGEMENTS FOR APPLYING CLOSURE MOTIONS TO JAWS OF SURGICAL INSTRUMENTS, now U.S. Patent Application Publication No. 2018/0168577;

U.S. patent application Ser. No. 15/385,928, entitled PROTECTIVE COVER ARRANGEMENTS FOR A JOINT INTERFACE BETWEEN A MOVABLE JAW AND ACTUATOR SHAFT OF A SURGICAL INSTRUMENT, now U.S. Patent Application Publication No. 2018/0168578;

U.S. patent application Ser. No. 15/385,930, entitled SURGICAL END EFFECTOR WITH TWO SEPARATE COOPERATING OPENING FEATURES FOR OPENING AND CLOSING END EFFECTOR JAWS, now U.S. Patent Application Publication No. 2018/0168579;

U.S. patent application Ser. No. 15/385,932, entitled ARTICULATABLE SURGICAL END EFFECTOR WITH ASYMMETRIC SHAFT ARRANGEMENT, now U.S. Patent Application Publication No. 2018/0168628;

U.S. patent application Ser. No. 15/385,933, entitled ARTICULATABLE SURGICAL INSTRUMENT WITH INDEPENDENT PIVOTABLE LINKAGE DISTAL OF AN ARTICULATION LOCK, now U.S. Patent Application Publication No. 2018/0168580;

U.S. patent application Ser. No. 15/385,934, entitled ARTICULATION LOCK ARRANGEMENTS FOR LOCKING AN END EFFECTOR IN AN ARTICULATED POSITION IN RESPONSE TO ACTUATION OF A JAW CLOSURE SYSTEM, now U.S. Patent Application Publication No. 2018/0168581;

U.S. patent application Ser. No. 15/385,935, entitled LATERALLY ACTUATABLE ARTICULATION LOCK ARRANGEMENTS FOR LOCKING AN END EFFECTOR OF A SURGICAL INSTRUMENT IN AN ARTICULATED CONFIGURATION, now U.S. Patent Application Publication No. 2018/0168582;

U.S. patent application Ser. No. 15/385,936, entitled ARTICULATABLE SURGICAL INSTRUMENTS WITH ARTICULATION STROKE AMPLIFICATION FEATURES, now U.S. Patent Application Publication No. 2018/0168583;

U.S. patent application Ser. No. 14/318,996, entitled FASTENER CARTRIDGES INCLUDING EXTENSIONS HAVING DIFFERENT CONFIGURATIONS, now U.S. Patent Application Publication No. 2015/0297228;

U.S. patent application Ser. No. 14/319,006, entitled FASTENER CARTRIDGE COMPRISING FASTENER CAVITIES INCLUDING FASTENER CONTROL FEATURES, now U.S. Pat. No. 10,010,324;

U.S. patent application Ser. No. 14/318,991, entitled SURGICAL FASTENER CARTRIDGES WITH DRIVER STABILIZING ARRANGEMENTS, now U.S. Pat. No. 9,833,241;

U.S. patent application Ser. No. 14/319,004, entitled SURGICAL END EFFECTORS WITH FIRING ELEMENT MONITORING ARRANGEMENTS, now U.S. Pat. No. 9,844,369;

U.S. patent application Ser. No. 14/319,008, entitled FASTENER CARTRIDGE COMPRISING NON-UNIFORM FASTENERS, now U.S. Patent Application Publication No. 2015/0297232;

U.S. patent application Ser. No. 14/318,997, entitled FASTENER CARTRIDGE COMPRISING DEPLOYABLE TISSUE ENGAGING MEMBERS, now U.S. Patent Application Publication No. 2015/0297229;

U.S. patent application Ser. No. 14/319,002, entitled FASTENER CARTRIDGE COMPRISING TISSUE CONTROL FEATURES, now U.S. Pat. No. 9,877,721;

U.S. patent application Ser. No. 14/319,013, entitled FASTENER CARTRIDGE ASSEMBLIES AND STAPLE RETAINER COVER ARRANGEMENTS, now U.S. Patent Application Publication No. 2015/0297233; and U.S. patent application Ser. No. 14/319,016, entitled FASTENER CARTRIDGE INCLUDING A LAYER ATTACHED THERETO, now U.S. Patent Application Publication No. 2015/0297235.

Applicant of the present application owns the following U.S. Patent Applications that were filed on Jun. 24, 2016 and which are each herein incorporated by reference in their respective entireties:

U.S. patent application Ser. No. 15/191,775, entitled STAPLE CARTRIDGE COMPRISING WIRE STAPLES AND STAMPED STAPLES, now U.S. Patent Application Publication No. 2017/0367695;

U.S. patent application Ser. No. 15/191,807, entitled STAPLING SYSTEM FOR USE WITH WIRE STAPLES AND STAMPED STAPLES, now U.S. Patent Application Publication No. 2017/0367696;

U.S. patent application Ser. No. 15/191,834, entitled STAMPED STAPLES AND STAPLE CARTRIDGES USING THE SAME, now U.S. Patent Application Publication No. 2017/0367699;

U.S. patent application Ser. No. 15/191,788, entitled STAPLE CARTRIDGE COMPRISING OVER-DRIVEN STAPLES, now U.S. Patent Application Publication No. 2017/0367698; and U.S. patent application Ser. No. 15/191,818, entitled STAPLE CARTRIDGE COMPRISING OFFSET LONGITUDINAL STAPLE ROWS, now U.S. Patent Application Publication No. 2017/0367697.

Applicant of the present application owns the following U.S. Patent Applications that were filed on Jun. 24, 2016 and which are each herein incorporated by reference in their respective entireties:

U.S. Design Patent Application Ser. No. 29/569,218, entitled SURGICAL FASTENER, now U.S. Design Pat. No. D826,405;

U.S. Design Patent Application Ser. No. 29/569,227, entitled SURGICAL FASTENER, now U.S. Design Pat. No. D822,206;

U.S. Design Patent Application Ser. No. 29/569,259, entitled SURGICAL FASTENER CARTRIDGE; and U.S. Design Patent Application Ser. No. 29/569,264, entitled SURGICAL FASTENER CARTRIDGE.

Applicant of the present application owns the following patent applications that were filed on Apr. 1, 2016 and which are each herein incorporated by reference in their respective entirety:

U.S. patent application Ser. No. 15/089,325, entitled METHOD FOR OPERATING A SURGICAL STAPLING SYSTEM, now U.S. Patent Application Publication No. 2017/0281171;

U.S. patent application Ser. No. 15/089,321, entitled MODULAR SURGICAL STAPLING SYSTEM COMPRISING A DISPLAY, now U.S. Pat. No. 10,271,851;

U.S. patent application Ser. No. 15/089,326, entitled SURGICAL STAPLING SYSTEM COMPRISING A DISPLAY INCLUDING A RE-ORIENTABLE DISPLAY FIELD, now U.S. Patent Application Publication No. 2017/0281172;

U.S. patent application Ser. No. 15/089,263, entitled SURGICAL INSTRUMENT HANDLE ASSEMBLY WITH RECONFIGURABLE GRIP PORTION, now U.S. Patent Application Publication No. 2017/0281165;

U.S. patent application Ser. No. 15/089,262, entitled ROTARY POWERED SURGICAL INSTRUMENT WITH MANUALLY ACTUATABLE BAILOUT SYSTEM, now U.S. Patent Application Publication No. 2017/0281161;

U.S. patent application Ser. No. 15/089,277, entitled SURGICAL CUTTING AND STAPLING END EFFECTOR WITH ANVIL CONCENTRIC DRIVE MEMBER, now U.S. Patent Application Publication No. 2017/0281166;

U.S. patent application Ser. No. 15/089,296, entitled INTERCHANGEABLE SURGICAL TOOL ASSEMBLY WITH A SURGICAL END EFFECTOR THAT IS SELECTIVELY ROTATABLE ABOUT A SHAFT AXIS, now U.S. Patent Application Publication No. 2017/0281168;

U.S. patent application Ser. No. 15/089,258, entitled SURGICAL STAPLING SYSTEM COMPRISING A SHIFTABLE TRANSMISSION, now U.S. Patent Application Publication No. 2017/0281178;

U.S. patent application Ser. No. 15/089,278, entitled SURGICAL STAPLING SYSTEM CONFIGURED TO PROVIDE SELECTIVE CUTTING OF TISSUE, now U.S. Patent Application Publication No. 2017/0281162;

U.S. patent application Ser. No. 15/089,284, entitled SURGICAL STAPLING SYSTEM COMPRISING A CONTOURABLE SHAFT, now U.S. Patent Application Publication No. 2017/0281186;

U.S. patent application Ser. No. 15/089,295, entitled SURGICAL STAPLING SYSTEM COMPRISING A TISSUE COMPRESSION LOCKOUT, now U.S. Patent Application Publication No. 2017/0281187;

U.S. patent application Ser. No. 15/089,300, entitled SURGICAL STAPLING SYSTEM COMPRISING AN UNCLAMPING LOCKOUT, now U.S. Patent Application Publication No. 2017/0281179;

U.S. patent application Ser. No. 15/089,196, entitled SURGICAL STAPLING SYSTEM COMPRISING A JAW CLOSURE LOCKOUT, now U.S. Patent Application Publication No. 2017/0281183;

U.S. patent application Ser. No. 15/089,203, entitled SURGICAL STAPLING SYSTEM COMPRISING A JAW ATTACHMENT LOCKOUT, now U.S. Patent Application Publication No. 2017/0281184;

U.S. patent application Ser. No. 15/089,210, entitled SURGICAL STAPLING SYSTEM COMPRISING A SPENT CARTRIDGE LOCKOUT, now U.S. Patent Application Publication No. 2017/0281185;

U.S. patent application Ser. No. 15/089,324, entitled SURGICAL INSTRUMENT COMPRISING A SHIFTING MECHANISM, now U.S. Patent Application Publication No. 2017/0281170;

U.S. patent application Ser. No. 15/089,335, entitled SURGICAL STAPLING INSTRUMENT COMPRISING MULTIPLE LOCKOUTS, now U.S. Patent Application Publication No. 2017/0281155;

U.S. patent application Ser. No. 15/089,339, entitled SURGICAL STAPLING INSTRUMENT, now U.S. Patent Application Publication No. 2017/0281173;

U.S. patent application Ser. No. 15/089,253, entitled SURGICAL STAPLING SYSTEM CONFIGURED TO APPLY ANNULAR ROWS OF STAPLES HAVING DIFFERENT HEIGHTS, now U.S. Patent Application Publication No. 2017/0281177;

U.S. patent application Ser. No. 15/089,304, entitled SURGICAL STAPLING SYSTEM COMPRISING A GROOVED FORMING POCKET, now U.S. Patent Application Publication No. 2017/0281188;

U.S. patent application Ser. No. 15/089,331, entitled ANVIL MODIFICATION MEMBERS FOR SURGICAL STAPLERS, now U.S. Patent Application Publication No. 2017/0281180;

U.S. patent application Ser. No. 15/089,336, entitled STAPLE CARTRIDGES WITH ATRAUMATIC FEATURES, now U.S. Patent Application Publication No. 2017/0281164;

U.S. patent application Ser. No. 15/089,312, entitled CIRCULAR STAPLING SYSTEM COMPRISING AN INCISABLE TISSUE SUPPORT, now U.S. Patent Application Publication No. 2017/0281189;

U.S. patent application Ser. No. 15/089,309, entitled CIRCULAR STAPLING SYSTEM COMPRISING ROTARY FIRING SYSTEM, now U.S. Patent Application Publication No. 2017/0281169; and U.S. patent application Ser. No. 15/089,349, entitled CIRCULAR STAPLING SYSTEM COMPRISING LOAD CONTROL, now U.S. Patent Application Publication No. 2017/0281174.

Applicant of the present application also owns the U.S. Patent Applications identified below which were filed on Dec. 30, 2015 which are each herein incorporated by reference in their respective entirety:

U.S. patent application Ser. No. 14/984,488, entitled MECHANISMS FOR COMPENSATING FOR BATTERY PACK FAILURE IN POWERED SURGICAL INSTRUMENTS, now U.S. Patent Application Publication No. 2017/0189018;

U.S. patent application Ser. No. 14/984,525, entitled MECHANISMS FOR COMPENSATING FOR DRIVETRAIN FAILURE IN POWERED SURGICAL INSTRUMENTS, now U.S. Patent Application Publication No. 2017/0189019; and U.S. patent application Ser. No. 14/984,552, entitled SURGICAL INSTRUMENTS WITH SEPARABLE MOTORS AND MOTOR CONTROL CIRCUITS, now U.S. Pat. No. 10,265,068.

Applicant of the present application also owns the U.S. Patent Applications identified below which were filed on Feb. 9, 2016, which are each herein incorporated by reference in their respective entirety:

U.S. patent application Ser. No. 15/019,220, entitled SURGICAL INSTRUMENT WITH ARTICULATING AND AXIALLY TRANSLATABLE END EFFECTOR, now U.S. Pat. No. 10,245,029;

U.S. patent application Ser. No. 15/019,228, entitled SURGICAL INSTRUMENTS WITH MULTIPLE LINK ARTICULATION ARRANGEMENTS, now U.S. Patent Application Publication No. 2017/0224342;

U.S. patent application Ser. No. 15/019,196, entitled SURGICAL INSTRUMENT ARTICULATION MECHANISM WITH SLOTTED SECONDARY CONSTRAINT, now U.S. Patent Application Publication No. 2017/0224330;

U.S. patent application Ser. No. 15/019,206, entitled SURGICAL INSTRUMENTS WITH AN END EFFECTOR THAT IS HIGHLY ARTICULATABLE RELATIVE TO AN ELONGATE SHAFT ASSEMBLY, now U.S. Patent Application Publication No. 2017/0224331;

U.S. patent application Ser. No. 15/019,215, entitled SURGICAL INSTRUMENTS WITH NON-SYMMETRICAL ARTICULATION ARRANGEMENTS, now U.S. Patent Application Publication No. 2017/0224332;

U.S. patent application Ser. No. 15/019,227, entitled ARTICULATABLE SURGICAL INSTRUMENTS WITH SINGLE ARTICULATION LINK ARRANGEMENTS, now U.S. Patent Application Publication No. 2017/0224334;

U.S. patent application Ser. No. 15/019,235, entitled SURGICAL INSTRUMENTS WITH TENSIONING ARRANGEMENTS FOR CABLE DRIVEN ARTICULATION SYSTEMS, now U.S. Pat. No. 10,245,030;

U.S. patent application Ser. No. 15/019,230, entitled ARTICULATABLE SURGICAL INSTRUMENTS WITH OFF-AXIS FIRING BEAM ARRANGEMENTS, now U.S. Patent Application Publication No. 2017/0224335; and U.S. patent application Ser. No. 15/019,245, entitled SURGICAL INSTRUMENTS WITH CLOSURE STROKE REDUCTION ARRANGEMENTS, now U.S. Patent Application Publication No. 2017/0224343.

Applicant of the present application also owns the U.S. Patent Applications identified below which were filed on Feb. 12, 2016, which are each herein incorporated by reference in their respective entirety:

U.S. patent application Ser. No. 15/043,254, entitled MECHANISMS FOR COMPENSATING FOR DRIVETRAIN FAILURE IN POWERED SURGICAL INSTRUMENTS, now U.S. Pat. No. 10,258,331;

U.S. patent application Ser. No. 15/043,259, entitled MECHANISMS FOR COMPENSATING FOR DRIVETRAIN FAILURE IN POWERED SURGICAL INSTRUMENTS, now U.S. Patent Application Publication No. 2017/0231626;

U.S. patent application Ser. No. 15/043,275, entitled MECHANISMS FOR COMPENSATING FOR DRIVETRAIN FAILURE IN POWERED SURGICAL INSTRUMENTS, now U.S. Patent Application Publication No. 2017/0231627; and U.S. patent application Ser. No. 15/043,289, entitled MECHANISMS FOR COMPENSATING FOR DRIVETRAIN FAILURE IN POWERED SURGICAL INSTRUMENTS, now U.S. Patent Application Publication No. 2017/0231628.

Applicant of the present application owns the following patent applications that were filed on Jun. 18, 2015 and which are each herein incorporated by reference in their respective entirety:

U.S. patent application Ser. No. 14/742,925, entitled SURGICAL END EFFECTORS WITH POSITIVE JAW OPENING ARRANGEMENTS, now U.S. Pat. No. 10,182,818;

U.S. patent application Ser. No. 14/742,941, entitled SURGICAL END EFFECTORS WITH DUAL CAM ACTUATED JAW CLOSING FEATURES, now U.S. Pat. No. 10,052,102;

U.S. patent application Ser. No. 14/742,933, entitled SURGICAL STAPLING INSTRUMENTS WITH LOCKOUT ARRANGEMENTS FOR PREVENTING FIRING SYSTEM ACTUATION WHEN A CARTRIDGE IS SPENT OR MISSING, now U.S. Pat. No. 10,154,841;

U.S. patent application Ser. No. 14/742,914, entitled MOVABLE FIRING BEAM SUPPORT ARRANGEMENTS FOR ARTICULATABLE SURGICAL INSTRUMENTS, now U.S. Patent Application Publication No. 2016/0367255;

U.S. patent application Ser. No. 14/742,900, entitled ARTICULATABLE SURGICAL INSTRUMENTS WITH COMPOSITE FIRING BEAM STRUCTURES WITH CENTER FIRING SUPPORT MEMBER FOR ARTICULATION SUPPORT, now U.S. Patent Application Publication No. 2016/0367254;

U.S. patent application Ser. No. 14/742,885, entitled DUAL ARTICULATION DRIVE SYSTEM ARRANGEMENTS FOR ARTICULATABLE SURGICAL INSTRUMENTS, now U.S. Patent Application Publication No. 2016/0367246; and U.S. patent application Ser. No. 14/742,876, entitled PUSH/PULL ARTICULATION DRIVE SYSTEMS FOR ARTICULATABLE SURGICAL INSTRUMENTS, now U.S. Pat. No. 10,178,992.

Applicant of the present application owns the following patent applications that were filed on Mar. 6, 2015 and which are each herein incorporated by reference in their respective entirety:

U.S. patent application Ser. No. 14/640,746, entitled POWERED SURGICAL INSTRUMENT, now U.S. Pat. No. 9,808,246;

U.S. patent application Ser. No. 14/640,795, entitled MULTIPLE LEVEL THRESHOLDS TO MODIFY OPERATION OF POWERED SURGICAL INSTRUMENTS, now U.S. Patent Application Publication No. 2016/02561185;

U.S. patent application Ser. No. 14/640,832, entitled ADAPTIVE TISSUE COMPRESSION TECHNIQUES TO ADJUST CLOSURE RATES FOR MULTIPLE TISSUE TYPES, now U.S. Patent Application Publication No. 2016/0256154;

U.S. patent application Ser. No. 14/640,935, entitled OVERLAID MULTI SENSOR RADIO FREQUENCY (RF) ELECTRODE SYSTEM TO MEASURE TISSUE COMPRESSION, now U.S. Patent Application Publication No. 2016/0256071;

U.S. patent application Ser. No. 14/640,831, entitled MONITORING SPEED CONTROL AND PRECISION INCREMENTING OF MOTOR FOR POWERED SURGICAL INSTRUMENTS, now U.S. Pat. No. 9,895,148;

U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES, now U.S. Pat. No. 10,052,044;

U.S. patent application Ser. No. 14/640,817, entitled INTERACTIVE FEEDBACK SYSTEM FOR POWERED SURGICAL INSTRUMENTS, now U.S. Pat. No. 9,924,961;

U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE, now U.S. Pat. No. 10,045,776;

U.S. patent application Ser. No. 14/640,837, entitled SMART SENSORS WITH LOCAL SIGNAL PROCESSING, now U.S. Pat. No. 9,993,248;

U.S. patent application Ser. No. 14/640,765, entitled SYSTEM FOR DETECTING THE MIS-INSERTION OF A STAPLE CARTRIDGE INTO A SURGICAL STAPLER, now U.S. Patent Application Publication No. 2016/0256160;

U.S. patent application Ser. No. 14/640,799, entitled SIGNAL AND POWER COMMUNICATION SYSTEM POSITIONED ON A ROTATABLE SHAFT, now U.S. Pat. No. 9,901,342; and U.S. patent application Ser. No. 14/640,780, entitled SURGICAL INSTRUMENT COMPRISING A LOCKABLE BATTERY HOUSING, now U.S. Pat. No. 10,245,033.

Applicant of the present application owns the following patent applications that were filed on Feb. 27, 2015, and which are each herein incorporated by reference in their respective entirety:

U.S. patent application Ser. No. 14/633,576, entitled SURGICAL INSTRUMENT SYSTEM COMPRISING AN INSPECTION STATION, now U.S. Pat. No. 10,045,779;

U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND, now U.S. Pat. No. 10,180,463;

U.S. patent application Ser. No. 14/633,560, entitled SURGICAL CHARGING SYSTEM THAT CHARGES AND/OR CONDITIONS ONE OR MORE BATTERIES, now U.S. Patent Application Publication No. 2016/0249910;

U.S. patent application Ser. No. 14/633,566, entitled CHARGING SYSTEM THAT ENABLES EMERGENCY RESOLUTIONS FOR CHARGING A BATTERY, now U.S. Pat. No. 10,182,816;

U.S. patent application Ser. No. 14/633,555, entitled SYSTEM FOR MONITORING WHETHER A SURGICAL INSTRUMENT NEEDS TO BE SERVICED, now U.S. Patent Application Publication No. 2016/0249916;

U.S. patent application Ser. No. 14/633,542, entitled REINFORCED BATTERY FOR A SURGICAL INSTRUMENT, now U.S. Pat. No. 9,931,118;

U.S. patent application Ser. No. 14/633,548, entitled POWER ADAPTER FOR A SURGICAL INSTRUMENT, now U.S. Pat. No. 10,245,028;

U.S. patent application Ser. No. 14/633,526, entitled ADAPTABLE SURGICAL INSTRUMENT HANDLE, now U.S. Pat. No. 9,993,258;

U.S. patent application Ser. No. 14/633,541, entitled MODULAR STAPLING ASSEMBLY, now U.S. Pat. No. 10,226,250; and U.S. patent application Ser. No. 14/633,562, entitled SURGICAL APPARATUS CONFIGURED TO TRACK AN END-OF-LIFE PARAMETER, now U.S. Pat. No. 10,159,483.

Applicant of the present application owns the following patent applications that were filed on Dec. 18, 2014 and which are each herein incorporated by reference in their respective entirety:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING MEMBER, now U.S. Pat. No. 9,844,374;

U.S. patent application Ser. No. 14/574,483, entitled SURGICAL INSTRUMENT ASSEMBLY COMPRISING LOCKABLE SYSTEMS, now U.S. Pat. No. 10,188,385;

U.S. patent application Ser. No. 14/575,139, entitled DRIVE ARRANGEMENTS FOR ARTICULATABLE SURGICAL INSTRUMENTS, now U.S. Pat. No. 9,844,375;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS, now U.S. Pat. No. 10,085,748;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE, now U.S. Pat. No. 10,245,027;

U.S. patent application Ser. No. 14/575,143, entitled SURGICAL INSTRUMENTS WITH IMPROVED CLOSURE ARRANGEMENTS, now U.S. Pat. No. 10,004,501;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Pat. No. 9,943,309;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS, now U.S. Pat. No. 9,968,355;

U.S. patent application Ser. No. 14/574,493, entitled SURGICAL INSTRUMENT ASSEMBLY COMPRISING A FLEXIBLE ARTICULATION SYSTEM, now U.S. Pat. No. 9,987,000; and U.S. patent application Ser. No. 14/574,500, entitled SURGICAL INSTRUMENT ASSEMBLY COMPRISING A LOCKABLE ARTICULATION SYSTEM, now U.S. Pat. No. 10,117,649.

Applicant of the present application owns the following patent applications that were filed on Mar. 1, 2013 and which are each herein incorporated by reference in their respective entirety:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Pat. No. 9,700,309;

U.S. patent application Ser. No. 13/782,323, entitled ROTARY POWERED ARTICULATION JOINTS FOR SURGICAL INSTRUMENTS, now U.S. Pat. No. 9,782,169;

U.S. patent application Ser. No. 13/782,338, entitled THUMBWHEEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Pat. No. 9,358,003;

U.S. patent application Ser. No. 13/782,460, entitled MULTIPLE PROCESSOR MOTOR CONTROL FOR MODULAR SURGICAL INSTRUMENTS, now U.S. Pat. No. 9,554,794;

U.S. patent application Ser. No. 13/782,358, entitled JOYSTICK SWITCH ASSEMBLIES FOR SURGICAL INSTRUMENTS, now U.S. Pat. No. 9,326,767;

U.S. patent application Ser. No. 13/782,481, entitled SENSOR STRAIGHTENED END EFFECTOR DURING REMOVAL THROUGH TROCAR, now U.S. Pat. No. 9,468,438;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and U.S. patent application Ser. No. 13/782,536, entitled SURGICAL INSTRUMENT SOFT STOP, now U.S. Pat. No. 9,307,986.

Applicant of the present application also owns the following patent applications that were filed on Mar. 14, 2013 and which are each herein incorporated by reference in their respective entirety:

U.S. patent application Ser. No. 13/803,097, entitled ARTICULATABLE SURGICAL INSTRUMENT COMPRISING A FIRING DRIVE, now U.S. Pat. No. 9,687,230;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Pat. No. 9,883,860;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Pat. No. 9,808,244;

U.S. patent application Ser. No. 13/803,148, entitled MULTI-FUNCTION MOTOR FOR A SURGICAL INSTRUMENT, now U.S. Patent Application Publication No. 2014/0263554;

U.S. patent application Ser. No. 13/803,066, entitled DRIVE SYSTEM LOCKOUT ARRANGEMENTS FOR MODULAR SURGICAL INSTRUMENTS, now U.S. Pat. No. 9,629,623;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Pat. No. 9,888,919.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Pat. No. 9,629,629.

Applicant of the present application also owns the following patent applications that were filed on Mar. 26, 2014 and are each herein incorporated by reference in their respective entirety:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Pat. No. 9,826,977;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Pat. No. 10,013,049;

U.S. patent application Ser. No. 14/226,075, entitled MODULAR POWERED SURGICAL INSTRUMENT WITH DETACHABLE SHAFT ASSEMBLIES, now U.S. Pat. No. 9,743,929;

U.S. patent application Ser. No. 14/226,093, entitled FEEDBACK ALGORITHMS FOR MANUAL BAILOUT SYSTEMS FOR SURGICAL INSTRUMENTS, now U.S. Pat. No. 10,028,761;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Pat. No. 9,690,362;

U.S. patent application Ser. No. 14/226,097, entitled SURGICAL INSTRUMENT COMPRISING INTERACTIVE SYSTEMS, now U.S. Pat. No. 9,820,738;

U.S. patent application Ser. No. 14/226,126, entitled INTERFACE SYSTEMS FOR USE WITH SURGICAL INSTRUMENTS, now U.S. Pat. No. 10,004,497;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Pat. No. 9,804,618;

U.S. patent application Ser. No. 14/226,076, entitled POWER MANAGEMENT THROUGH SEGMENTED CIRCUIT AND VARIABLE VOLTAGE PROTECTION, now U.S. Pat. No. 9,733,663;

U.S. patent application Ser. No. 14/226,111, entitled SURGICAL STAPLING INSTRUMENT SYSTEM, now U.S. Pat. No. 9,750,499; and U.S. patent application Ser. No. 14/226,125, entitled SURGICAL INSTRUMENT COMPRISING A ROTATABLE SHAFT, now U.S. Pat. No. 10,201,364.

Applicant of the present application also owns the following patent applications that were filed on Sep. 5, 2014 and which are each herein incorporated by reference in their respective entirety:

U.S. patent application Ser. No. 14/479,103, entitled CIRCUITRY AND SENSORS FOR POWERED MEDICAL DEVICE, now U.S. Pat. No. 10,111,679;

U.S. patent application Ser. No. 14/479,119, entitled ADJUNCT WITH INTEGRATED SENSORS TO QUANTIFY TISSUE COMPRESSION, now U.S. Pat. No. 9,724,094;

U.S. patent application Ser. No. 14/478,908, entitled MONITORING DEVICE DEGRADATION BASED ON COMPONENT EVALUATION, now U.S. Pat. No. 9,737,301;

U.S. patent application Ser. No. 14/478,895, entitled MULTIPLE SENSORS WITH ONE SENSOR AFFECTING A SECOND SENSOR'S OUTPUT OR INTERPRETATION, now U.S. Pat. No. 9,757,128;

U.S. patent application Ser. No. 14/479,110, entitled POLARITY OF HALL MAGNET TO IDENTIFY CARTRIDGE TYPE, now U.S. Pat. No. 10,016,199;

U.S. patent application Ser. No. 14/479,098, entitled SMART CARTRIDGE WAKE UP OPERATION AND DATA RETENTION, now U.S. Pat. No. 10,135,242;

U.S. patent application Ser. No. 14/479,115, entitled MULTIPLE MOTOR CONTROL FOR POWERED MEDICAL DEVICE, now U.S. Pat. No. 9,788,836; and U.S. patent application Ser. No. 14/479,108, entitled LOCAL DISPLAY OF TISSUE PARAMETER STABILIZATION, now U.S. Patent Application Publication No. 2016/0066913.

Applicant of the present application also owns the following patent applications that were filed on Apr. 9, 2014 and which are each herein incorporated by reference in their respective entirety:

U.S. patent application Ser. No. 14/248,590, entitled MOTOR DRIVEN SURGICAL INSTRUMENTS WITH LOCKABLE DUAL DRIVE SHAFTS, now U.S. Pat. No. 9,826,976;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Pat. No. 9,649,110;

U.S. patent application Ser. No. 14/248,595, entitled SURGICAL SYSTEM COMPRISING FIRST AND SECOND DRIVE SYSTEMS, now U.S. Pat. No. 9,844,368;

U.S. patent application Ser. No. 14/248,588, entitled POWERED LINEAR SURGICAL STAPLER, now U.S. Patent Application Publication No. 2014/0309666;

U.S. patent application Ser. No. 14/248,591, entitled SURGICAL INSTRUMENT COMPRISING A GAP SETTING SYSTEM, now U.S. Pat. No. 10,149,680;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Pat. No. 9,801,626;

U.S. patent application Ser. No. 14/248,587, entitled POWERED SURGICAL STAPLER, now U.S. Pat. No. 9,867,612;

U.S. patent application Ser. No. 14/248,586, entitled DRIVE SYSTEM DECOUPLING ARRANGEMENT FOR A SURGICAL INSTRUMENT, now U.S. Pat. No. 10,136,887; and U.S. patent application Ser. No. 14/248,607, entitled MODULAR MOTOR DRIVEN SURGICAL INSTRUMENTS WITH STATUS INDICATION ARRANGEMENTS, now U.S. Pat. No. 9,814,460.

Applicant of the present application also owns the following patent applications that were filed on Apr. 16, 2013 and which are each herein incorporated by reference in their respective entirety:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Applicant of the present application owns the following U.S. Provisional Patent Applications, filed on Dec. 28, 2017, the disclosure of each of which is herein incorporated by reference in its entirety:

U.S. Provisional Patent Application Ser. No. 62/611,341, entitled INTERACTIVE SURGICAL PLATFORM;

U.S. Provisional Patent Application Ser. No. 62/611,340, entitled CLOUD-BASED MEDICAL ANALYTICS; and U.S. Provisional Patent Application Ser. No. 62/611,339, entitled ROBOT ASSISTED SURGICAL PLATFORM.

Applicant of the present application owns the following U.S. Provisional Patent Applications, filed on Mar. 28, 2018, each of which is herein incorporated by reference in its entirety:

U.S. Provisional Patent Application Ser. No. 62/649,302, entitled INTERACTIVE SURGICAL SYSTEMS WITH ENCRYPTED COMMUNICATION CAPABILITIES;

U.S. Provisional Patent Application Ser. No. 62/649,249, entitled DATA STRIPPING METHOD TO INTERROGATE PATIENT RECORDS AND CREATE ANONYMIZED RECORD;

U.S. Provisional Patent Application Ser. No. 62/649,300, entitled SURGICAL HUB SITUATIONAL AWARENESS;

U.S. Provisional Patent Application Ser. No. 62/649,309, entitled SURGICAL HUB SPATIAL AWARENESS TO DETERMINE DEVICES IN OPERATING THEATER;

U.S. Provisional Patent Application Ser. No. 62/649,310, entitled COMPUTER IMPLEMENTED INTERACTIVE SURGICAL SYSTEMS;

U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, entitled ADAPTIVE CONTROL PROGRAM UPDATES FOR SURGICAL DEVICES;

U.S. Provisional Patent Application Ser. No. 62/649,333, entitled CLOUD-BASED MEDICAL ANALYTICS FOR CUSTOMIZATION AND RECOMMENDATIONS TO A USER;

U.S. Provisional Patent Application Ser. No. 62/649,327, entitled CLOUD-BASED MEDICAL ANALYTICS FOR SECURITY AND AUTHENTICATION TRENDS AND REACTIVE MEASURES;

U.S. Provisional Patent Application Ser. No. 62/649,315, entitled DATA HANDLING AND PRIORITIZATION IN A CLOUD ANALYTICS NETWORK;

U.S. Provisional Patent Application Ser. No. 62/649,313, entitled CLOUD INTERFACE FOR COUPLED SURGICAL DEVICES;

U.S. Provisional Patent Application Ser. No. 62/649,320, entitled DRIVE ARRANGEMENTS FOR ROBOT-ASSISTED SURGICAL PLATFORMS;

U.S. Provisional Patent Application Ser. No. 62/649,307, entitled AUTOMATIC TOOL ADJUSTMENTS FOR ROBOT-ASSISTED SURGICAL PLATFORMS; and U.S. Provisional Patent Application Ser. No. 62/649,323, entitled SENSING ARRANGEMENTS FOR ROBOT-ASSISTED SURGICAL PLATFORMS.

Applicant of the present application owns the following U.S. Patent Applications, filed on Mar. 29, 2018, each of which is herein incorporated by reference in its entirety:

U.S. patent application Ser. No. 15/940,641, entitled INTERACTIVE SURGICAL SYSTEMS WITH ENCRYPTED COMMUNICATION CAPABILITIES;

U.S. patent application Ser. No. 15/940,648, entitled INTERACTIVE SURGICAL SYSTEMS WITH CONDITION HANDLING OF DEVICES AND DATA CAPABILITIES;

U.S. patent application Ser. No. 15/940,656, entitled SURGICAL HUB COORDINATION OF CONTROL AND COMMUNICATION OF OPERATING ROOM DEVICES;

U.S. patent application Ser. No. 15/940,666, entitled SPATIAL AWARENESS OF SURGICAL HUBS IN OPERATING ROOMS;

U.S. patent application Ser. No. 15/940,670, entitled COOPERATIVE UTILIZATION OF DATA DERIVED FROM SECONDARY SOURCES BY INTELLIGENT SURGICAL HUBS;

U.S. patent application Ser. No. 15/940,677, entitled SURGICAL HUB CONTROL ARRANGEMENTS;

U.S. patent application Ser. No. 15/940,632, entitled DATA STRIPPING METHOD TO INTERROGATE PATIENT RECORDS AND CREATE ANONYMIZED RECORD;

U.S. patent application Ser. No. 15/940,640, entitled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS;

U.S. patent application Ser. No. 15/940,645, entitled SELF DESCRIBING DATA PACKETS GENERATED AT AN ISSUING INSTRUMENT;

U.S. patent application Ser. No. 15/940,649, entitled DATA PAIRING TO INTERCONNECT A DEVICE MEASURED PARAMETER WITH AN OUTCOME;

U.S. patent application Ser. No. 15/940,654, entitled SURGICAL HUB SITUATIONAL AWARENESS;

U.S. patent application Ser. No. 15/940,663, entitled SURGICAL SYSTEM DISTRIBUTED PROCESSING;

U.S. patent application Ser. No. 15/940,668, entitled AGGREGATION AND REPORTING OF SURGICAL HUB DATA;

U.S. patent application Ser. No. 15/940,671, entitled SURGICAL HUB SPATIAL AWARENESS TO DETERMINE DEVICES IN OPERATING THEATER;

U.S. patent application Ser. No. 15/940,686, entitled DISPLAY OF ALIGNMENT OF STAPLE CARTRIDGE TO PRIOR LINEAR STAPLE LINE;

U.S. patent application Ser. No. 15/940,700, entitled STERILE FIELD INTERACTIVE CONTROL DISPLAYS;

U.S. patent application Ser. No. 15/940,629, entitled COMPUTER IMPLEMENTED INTERACTIVE SURGICAL SYSTEMS;

U.S. patent application Ser. No. 15/940,704, entitled USE OF LASER LIGHT AND RED-GREEN-BLUE COLORATION TO DETERMINE PROPERTIES OF BACK SCATTERED LIGHT;

U.S. patent application Ser. No. 15/940,722, entitled CHARACTERIZATION OF TISSUE IRREGULARITIES THROUGH THE USE OF MONO-CHROMATIC LIGHT REFRACTIVITY; and U.S. patent application Ser. No. 15/940,742, entitled DUAL CMOS ARRAY IMAGING.

Applicant of the present application owns the following U.S. Patent Applications, filed on Mar. 29, 2018, each of which is herein incorporated by reference in its entirety:

U.S. patent application Ser. No. 15/940,636, entitled ADAPTIVE CONTROL PROGRAM UPDATES FOR SURGICAL DEVICES;

U.S. patent application Ser. No. 15/940,653, entitled ADAPTIVE CONTROL PROGRAM UPDATES FOR SURGICAL HUBS;

U.S. patent application Ser. No. 15/940,660, entitled CLOUD-BASED MEDICAL ANALYTICS FOR CUSTOMIZATION AND RECOMMENDATIONS TO A USER;

U.S. patent application Ser. No. 15/940,679, entitled CLOUD-BASED MEDICAL ANALYTICS FOR LINKING OF LOCAL USAGE TRENDS WITH THE RESOURCE ACQUISITION BEHAVIORS OF LARGER DATA SET;

U.S. patent application Ser. No. 15/940,694, entitled CLOUD-BASED MEDICAL ANALYTICS FOR MEDICAL FACILITY SEGMENTED INDIVIDUALIZATION OF INSTRUMENT FUNCTION;

U.S. patent application Ser. No. 15/940,634, entitled CLOUD-BASED MEDICAL ANALYTICS FOR SECURITY AND AUTHENTICATION TRENDS AND REACTIVE MEASURES;

U.S. patent application Ser. No. 15/940,706, entitled DATA HANDLING AND PRIORITIZATION IN A CLOUD ANALYTICS NETWORK; and U.S. patent application Ser. No. 15/940,675, entitled CLOUD INTERFACE FOR COUPLED SURGICAL DEVICES.

Applicant of the present application owns the following U.S. Patent Applications, filed on Mar. 29, 2018, each of which is herein incorporated by reference in its entirety:

U.S. patent application Ser. No. 15/940,627, entitled DRIVE ARRANGEMENTS FOR ROBOT-ASSISTED SURGICAL PLATFORMS;

U.S. patent application Ser. No. 15/940,637, entitled COMMUNICATION ARRANGEMENTS FOR ROBOT-ASSISTED SURGICAL PLATFORMS;

U.S. patent application Ser. No. 15/940,642, entitled CONTROLS FOR ROBOT-ASSISTED SURGICAL PLATFORMS;

U.S. patent application Ser. No. 15/940,676, entitled AUTOMATIC TOOL ADJUSTMENTS FOR ROBOT-ASSISTED SURGICAL PLATFORMS;

U.S. patent application Ser. No. 15/940,680, entitled CONTROLLERS FOR ROBOT-ASSISTED SURGICAL PLATFORMS;

U.S. patent application Ser. No. 15/940,683, entitled COOPERATIVE SURGICAL ACTIONS FOR ROBOT-ASSISTED SURGICAL PLATFORMS;

U.S. patent application Ser. No. 15/940,690, entitled DISPLAY ARRANGEMENTS FOR ROBOT-ASSISTED SURGICAL PLATFORMS; and U.S. patent application Ser. No. 15/940,711, entitled SENSING ARRANGEMENTS FOR ROBOT-ASSISTED SURGICAL PLATFORMS.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Figure 3:
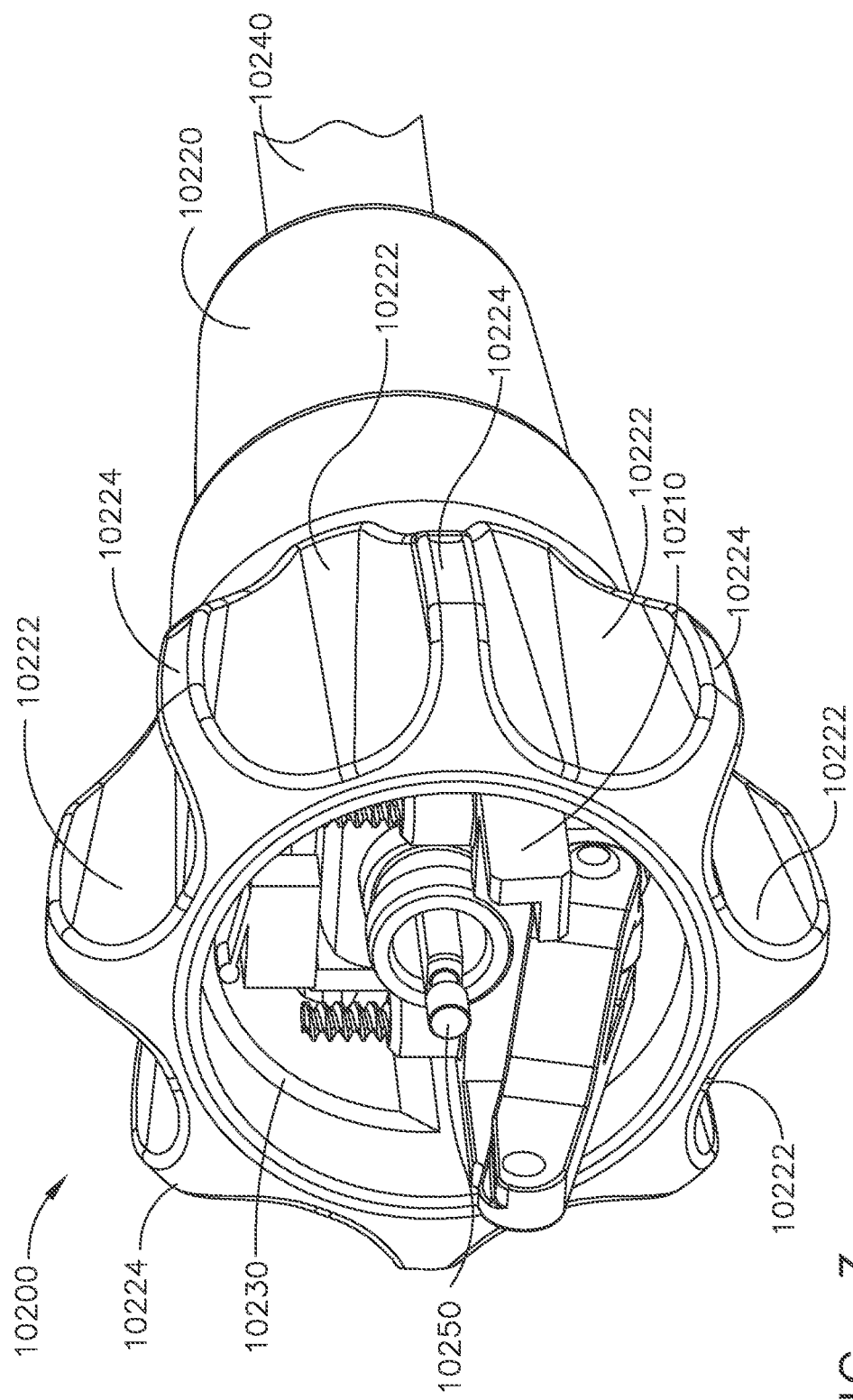
FIG. 3 is a partial perspective view of a shaft of the surgical instrument of FIG. 1.
Figure 4:
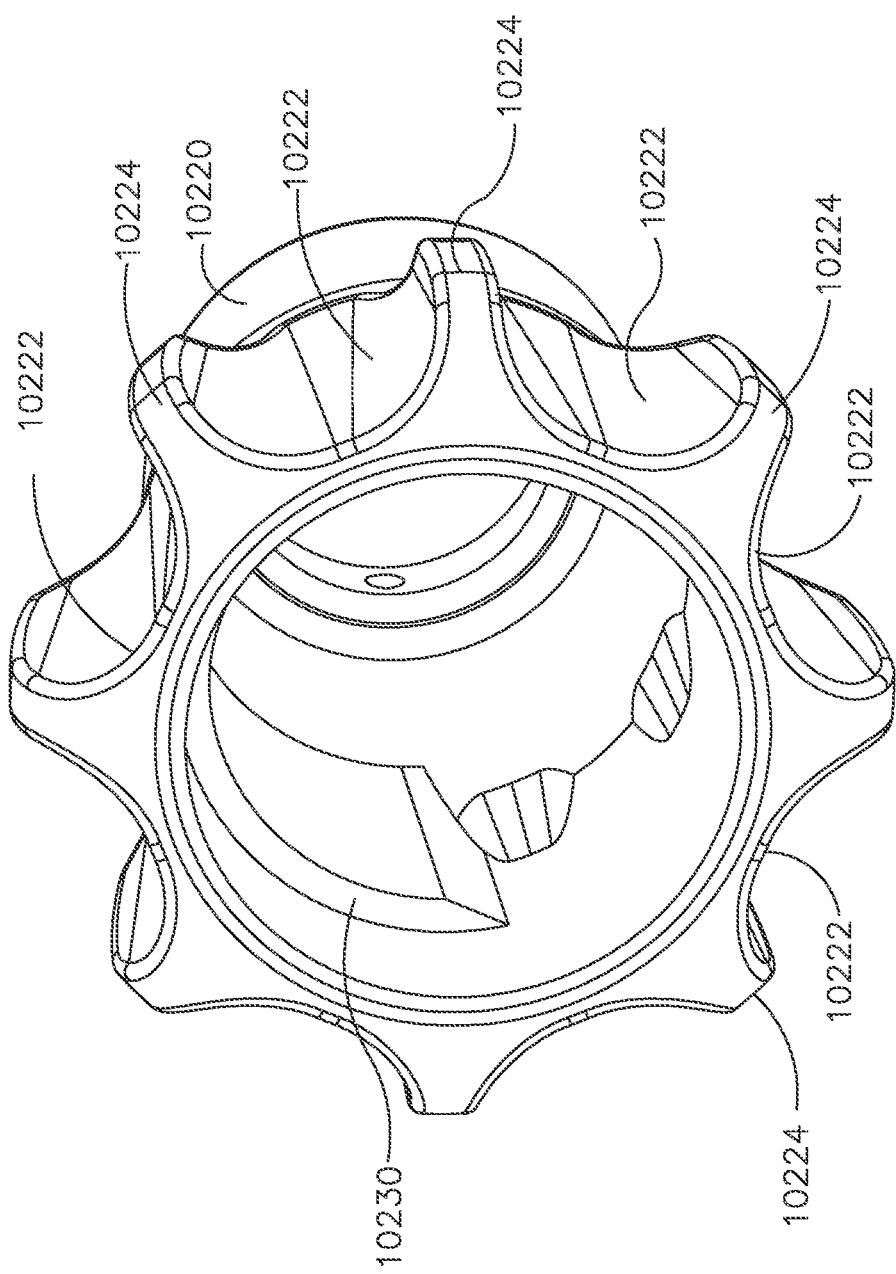
FIG. 4 is a perspective view of a nozzle of the shaft of FIG. 3.
Figure 5:
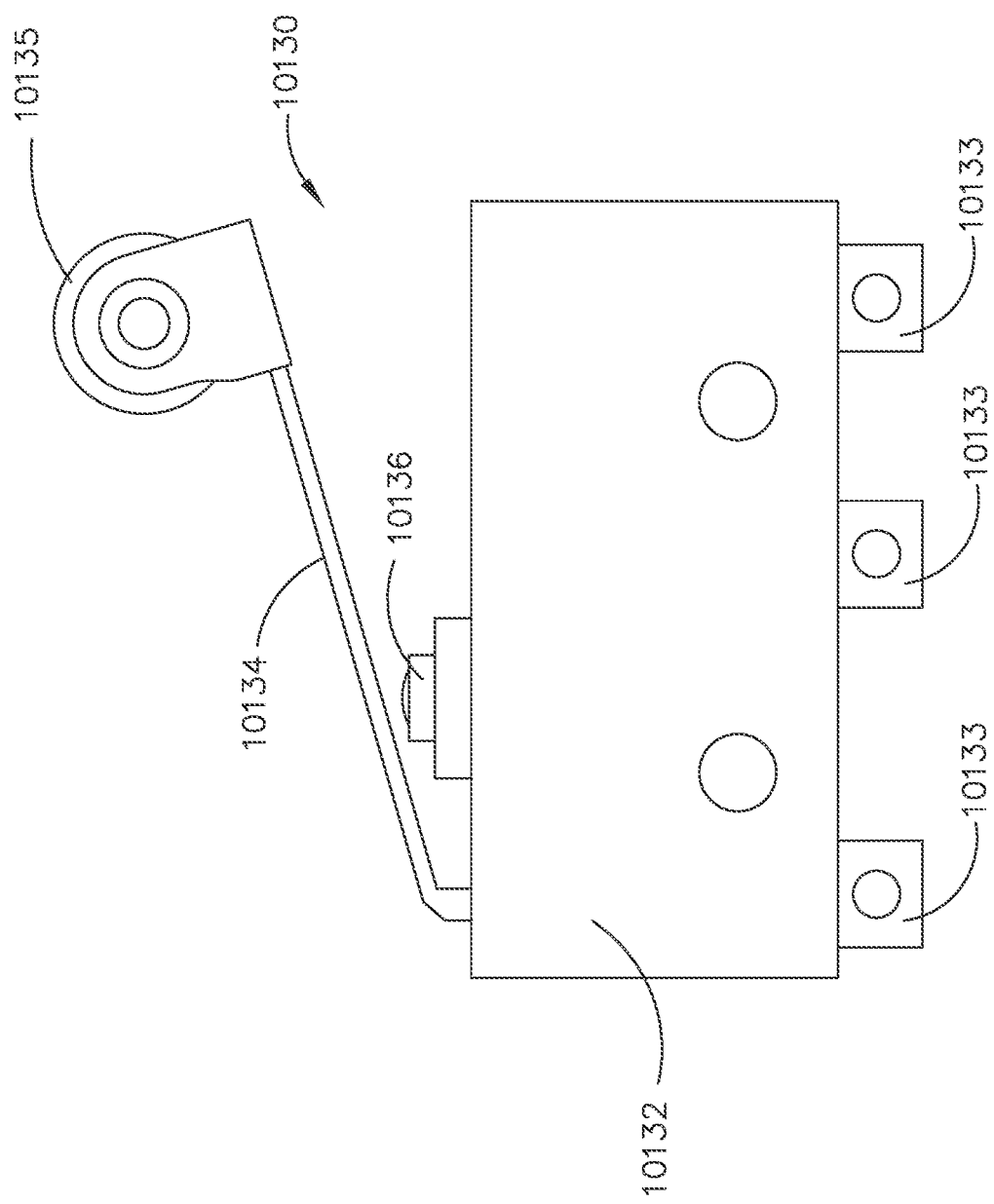
FIG. 5 is an elevational view of an orientation switch of the surgical instrument of FIG. 1.

A surgical instrument 10000 is illustrated in FIG. 1. The surgical instrument 10000 comprises a handle 10100, a shaft 10200 extending from the handle 10100, and an end effector 10400. The end effector 10400 comprises a first jaw 10410 configured to receive a staple cartridge and a second jaw 10420 movable relative to the first jaw 10410. The second jaw 10420 comprises an anvil including staple forming pockets defined therein. The surgical instrument 10000 further comprises a closure actuator 10140 configured to drive a closure system of the surgical instrument 10000 and move the second jaw 10420 between an unclamped position and a clamped position. Referring to FIG. 3, the closure actuator 10140 is operably coupled with a closure tube 10240 that is advanced distally when the closure actuator 10140 is closed. In such instances, the closure tube 10240 contacts the second jaw and cams and/or pushes the second jaw 10420 downwardly into its clamped position. The second jaw 10420 is pivotably coupled to the first jaw about a pivot axis. That said, in alternative embodiments, the second jaw can translate and rotate as it is being moved into its clamped position. Moreover, in various alternative embodiments, a surgical instrument comprises a staple cartridge jaw is movable between an unclamped position and a clamped position relative to an anvil jaw. In any event, the handle 10100 comprises a lock configured to releasably hold the closure actuator 10140 in its clamped position. The handle 10100 further comprises release actuators 10180*a*, 10180*b* which, when either one is actuated, unlock the closure actuator 10140 such that the end effector can be re-opened. In various alternative embodiments, the handle 10100 comprises an electric motor configured to move the closure tube 10240 proximally and/or distally when actuated by the clinician.

The end effector 10400 is attached to the shaft 10200 about an articulation joint 10500 and is rotatable within a plane about an articulation axis. The shaft 10200 defines a longitudinal axis and the end effector 10400 is articulatable between a position in which the end effector 10400 is aligned with the longitudinal axis and positions in which the end effector 10400 extends at a transverse angle relative to the longitudinal axis. The handle 10100 comprises an electric motor and a control system configured to control the operation of the electric motor. The electric motor comprises a brushless DC motor; however, the electric motor can comprise any suitable motor, such as a brushed DC motor, for example. The entire disclosure of U.S. Pat. No. 10,149,683, entitled POWERED SURGICAL CUTTING AND STAPLING APPARATUS WITH MANUALLY RETRACTABLE FIRING SYSTEM, which issued on Dec. 11, 2018, is incorporated by reference herein. The entire disclosure of U.S. Patent Application Publication No. 2018/0125481, entitled MOTOR-DRIVEN SURGICAL CUTTING INSTRUMENT, which published on May 10, 2018, is incorporated by reference herein. The handle 10100 further comprises a replaceable and/or rechargeable battery 10300 attachable to the handle housing which powers the surgical instrument 10000. The entire disclosure of U.S. Pat. No. 8,632,525, entitled POWER CONTROL ARRANGEMENTS FOR SURGICAL INSTRUMENTS AND BATTERIES, which issued on Jan. 21, 2014, is incorporated by reference herein. The electric motor is operably coupled with a firing drive 10250 of the surgical instrument 10000 and is configured to drive a firing member of the firing drive 10250 through a staple firing stroke. The electric motor comprises a rotatable output including a gear engaged with a translatable rack of the firing drive 10250. The electric motor is operated in a first direction to drive the firing member through the staple firing stroke and a second, or opposite, direction to retract the firing member and/or reset the firing drive 10250. The surgical instrument 10000 further comprises an actuator 10150 in communication with the motor control system which, when actuated or rotated, signals to the motor control system to operate the electric motor in the first direction and begin the staple firing stroke. If the actuator 10150 is released, the motor control system stops the electric motor. When the actuator 10150 is re-actuated, the motor control system operates the electric motor in the first direction once again to continue the staple firing stroke. When the firing member reaches the end of the staple firing stroke, the control system stops the electric motor awaiting input from the clinician. When the clinician releases the actuator 10150 at such point, the control system reverses the operation of the electric motor to retract the firing member back into its unfired position. The handle 10100 further comprises a retraction actuator in communication with the motor control system that reverses the direction of the electric motor to retract the firing drive when actuated by the clinician. When the retraction actuator is depressed, the staple firing stroke is terminated regardless of whether the firing member had reached the end of the staple firing stroke.

The electric motor of the surgical instrument 10000 is also used to selectively drive an articulation drive system to articulate the end effector 10400. More specifically, the articulation drive system comprises an articulation driver that is selectively engageable with the firing drive and, when the articulation driver is engaged with the firing drive, the articulation driver is movable proximally and distally by the operation of the electric motor to articulate the end effector 10400. When the electric motor is operated in its first direction, in such instances, the end effector 10400 is articulated in a first direction to push the articulation driver distally. Similarly, the end effector 10400 is articulated in a second direction when the electric motor is operated in its second direction to pull the articulation driver proximally. When the articulation driver is not engaged with the firing drive, the operation of the electric motor does not articulate the end effector 10400. Instead, in such instances, the electric motor only moves the firing drive. That said, it should be appreciated that the movement of the firing drive to articulate the end effector 10400 does not cause the staple firing stroke to be performed. The range of motion needed to articulate the end effector 10400 is small, as compared to the range of motion of the staple firing stroke, and occurs proximal to the beginning of the staple firing stroke such that the staples are not ejected and the tissue is not cut while the end effector 10400 is being articulated. The surgical instrument 10000 further comprises an articulation lock which unlocks when the articulation driver is moved longitudinally by the firing drive and then locks the end effector 10400 in position when the articulation driver is not being driven by the firing drive. The entire disclosure of U.S. Pat. No. 9,629,629, entitled CONTROL SYSTEMS FOR SURGICAL INSTRUMENTS, which issued on Apr. 25, 2017, is incorporated by reference herein. The above being said, a surgical instrument can comprise a separate articulation motor in addition to the firing motor for driving the articulation drive system.

Figure 2:
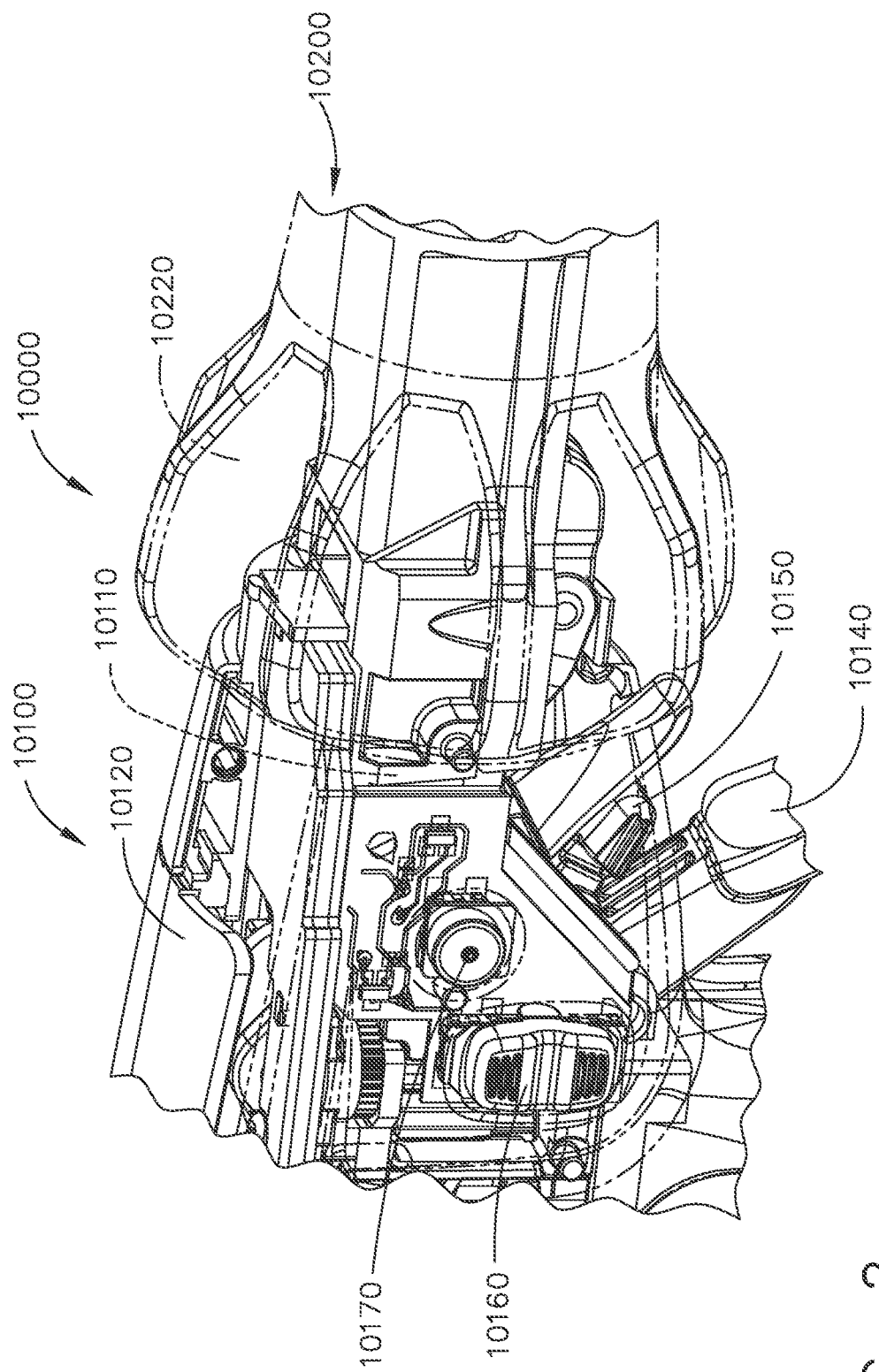
FIG. 2 is a partial perspective view of the surgical instrument of FIG. 1.

Further to the above, referring to FIG. 2, the handle 10100 comprises a frame 10110, a housing 10120, and an articulation actuator 10160. The articulation actuator 10160 comprises a rocker switch, for example, which is oriented vertically on the housing 10120 and is in communication with the motor control system. The rocker switch is rotatable upwardly and downwardly about an axis to articulate the end effector 10400. The upper portion of the articulation actuator 10160 is pushed by the clinician to articulate the end effector 10400 to the left and the lower portion of the articulation actuator 10160 is pushed to articulate the end effector 10400 to the right. Such an arrangement provides an intuitive interface for the clinician; however, any suitable arrangement could be used. The handle 10100 further comprises a home actuator 10170 in communication with the motor control system. When the home actuator 10170 is actuated by the clinician, the motor control system operates the electric motor to re-center the end effector 10400 along the longitudinal axis of the shaft 10200 of the surgical instrument 10000. To this end, the control system is configured to track the position of the end effector such that, when the home actuator 10170 is actuated, the control system operates the electric motor in the correct direction to articulate the end effector 10400 in the correct direction and the correct amount. In various instances, the surgical instrument 10000 comprises a linear encoder configured to track the position of the articulation driver, for example, such that, when the home actuator 10170 is actuated, the control system can properly center the end effector 10400.

Further to the above, the shaft 10200 is rotatable relative to the handle 10100. The shaft 10200 comprises a frame 10210 attached to the frame 10110 of the handle 10100. In embodiments where the shaft 10200 is readily removable from the handle 10100, the shaft frame 10210 can detach from the handle frame 10110. In embodiments where the shaft 10200 is not removable from the handle 10100, the shaft frame 10210 and the handle frame 10110 can be integrally formed. In any event, the shaft 10200 comprises a nozzle, or grip, 10220 fixedly mounted to the closure tube 10240 of the shaft 10200. The grip 10220 comprises finger grooves 10222 defined therein and ridges 10224 extending between the finger grooves 10222 that provide walls against which a clinician can push their finger and assist the clinician in rotating the shaft 10200 about its longitudinal axis.

Notably, further to the above, the end effector 10400 rotates with the shaft 10200 when the shaft 10200 is rotated about its longitudinal axis. Thus, the end effector 10400 rotates clockwise when the shaft 10200 is rotated clockwise by the clinician and counter-clockwise when the shaft 10200 is rotated counter-clockwise by the clinician. In various alternative embodiments, the surgical instrument 10000 comprises an electric motor configured to rotate the shaft 10200 about its longitudinal axis. In either event, the shaft 10200 is rotatable from a top-dead-center (TDC) position in which the anvil 10420 is positioned directly above the staple cartridge jaw 10410 to any other suitable position within a full 360 degree range of positions. For instance, the shaft 10200 is rotatable into a right 90 degree position in which the anvil 10420 is facing to the right of the handle 10100 or a left 90 degree position in which the anvil 10420 is facing to the left of the handle 10100. The shaft 10200 is also rotatable into a bottom-dead-center (BDC) position in which the staple cartridge jaw 10410 is positioned directly above the anvil 10420.

As described above, the end effector 10400 is both articulatable about the articulation joint 10500 and rotatable with the shaft 10200. When the end effector 10400 is rotated in a plane when the end effector 10400 is in its TDC position, as mentioned above, the articulation control 10160 is intuitive to the user—push up to articulate left and push down to articulate right. This arrangement is also intuitive even after the shaft 10200—and end effector 10400—have been rotated 90 degrees to the right or to the left. However, when the shaft 10200 and end effector 10400 have been rotated past 90 degrees in either direction, the articulation control 10160 can become counter-intuitive to the clinician. In fact, the articulation control 10160 can seem backwards. With this in mind, the control system of the surgical instrument 10000 is configured to flip the manner in which the surgical instrument responds to the articulation control 10160 when the shaft 10200 and end effector 10400 have been rotated past 90 degrees in either direction. In such instances, the controls become: push up to articulate right and push down to articulate left. To this end, as described in greater detail below, the surgical instrument 10000 is configured to detect the orientation of the shaft 10200 relative to the handle 10100, i.e., it is configured to detect whether the end effector 10400 is at least partially upside down with respect to the handle 10100 and then enter an alternative operational control mode in which the responsiveness of the surgical instrument 10000 to the articulation control 10160 has been reversed. Such an arrangement can make the surgical instrument 10000 easier to use in various instances.

Referring to FIGS. 2-5, the surgical instrument 10000 comprises a switch 10130 mounted to the handle 10100 in communication with the control system which is configured to detect the rotation of the shaft 10200 relative to the handle 10100. The switch 10130 comprises a switch body 10132 fixedly mounted to the handle frame 10110 and three electrical contacts 10133 which are part of a switch circuit in communication with the control system. The switch 10000 further comprises a switch arm 10134 rotatably connected to the switch body 10132 and an electrical contact 10136 positioned on the switch body 10132. The switch arm 10134 is comprised of an electrically-conductive material, such as brass, for example, and closes the switch circuit when the switch arm 10134 comes into contact with the electrical contact 10136. The switch arm 10134 is rotated between an open position (FIG. 5) and a closed position when the shaft 10200 is rotated past the left or right 90 degree positions. More specifically, the grip, or nozzle, 10220 comprises a cam 10230 defined thereon which pushes the switch arm 10134 into its closed position when the shaft 10200 and the end effector 10400 is at least partially upside down. When the shaft 10200 is rotated upwardly past the 90 degree positions, the cam 10230 permits the switch arm 10134 to resiliently move back into its open position and open the switch circuit. The switch arm 10134 comprises a roller 10135 mounted thereto to facilitate relative rotation between the switch arm 10134 and the grip 10220.

Figure 6:
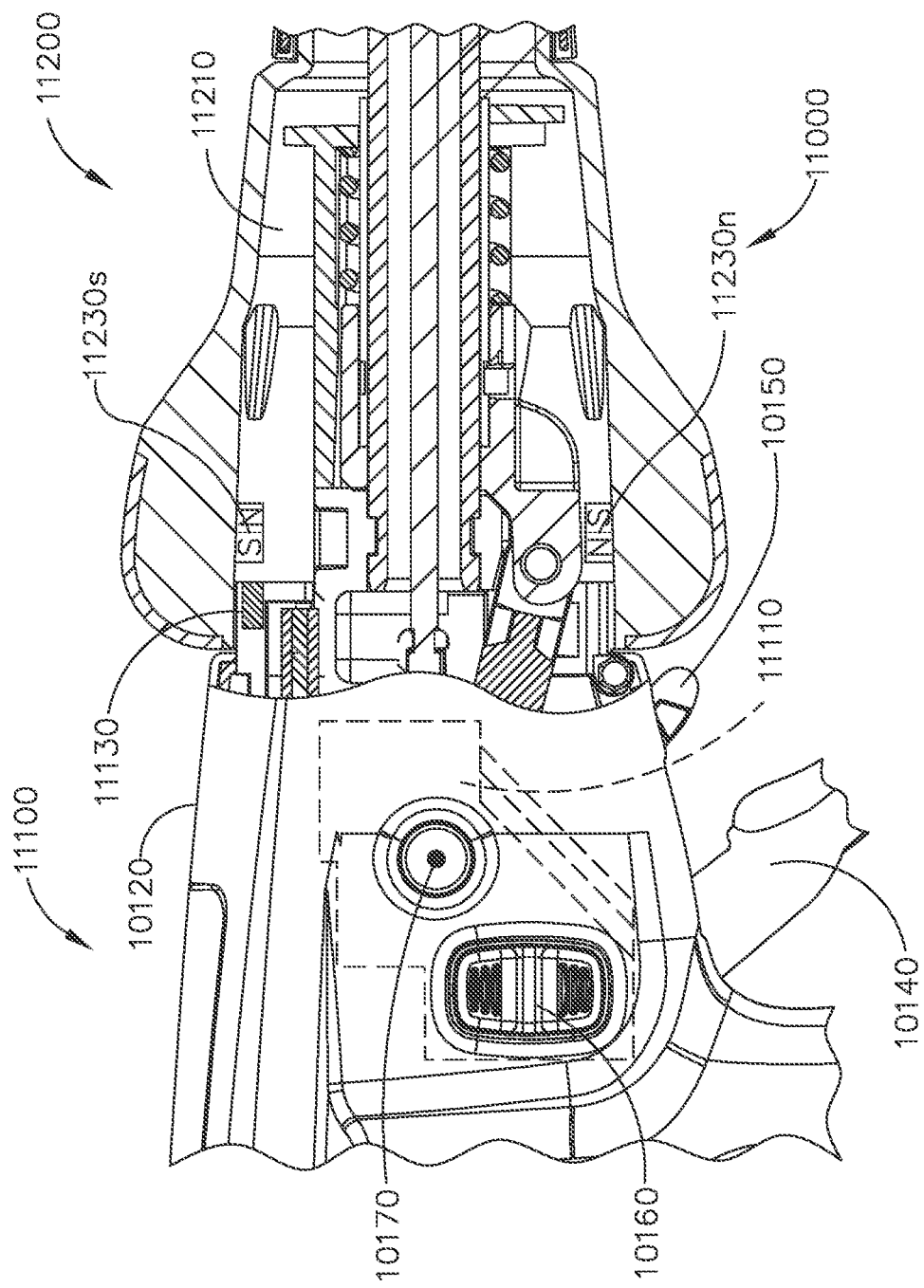
FIG. 6 is a partial perspective view of a surgical instrument in accordance with at least one embodiment comprising a handle including an orientation sensor and a shaft comprising magnetic elements detectable by the orientation sensor.

A surgical instrument 11000 is illustrated in FIG. 6. The surgical instrument 11000 is similar to the surgical instrument 10000 in many respects. The surgical instrument 11000 comprises a handle 11100 and a shaft 11200 extending from the handle 11100. The handle 11100 comprises a frame 11110 and the shaft 11200 comprises a frame 11210 attached to the handle frame 11110. The shaft 11200 comprises a grip, or nozzle, 11220, a first magnetic element 11230s positioned on one side of the grip 11220, and a second magnetic element 11230n positioned on the opposite side of the grip 11220. Stated another way, the first magnetic element 11230s and the second magnetic element 11230n are mounted 180 degrees apart. The handle 11100 further comprises a control system including at least one sensor 11130, such as a Hall Effect sensor, for example, mounted to the handle frame 11110 configured to sense the position of the magnetic elements 11230s and 11230n and, with this information, determine the orientation of the shaft 11200 relative to the handle 11100. Notably, the first magnetic element 11230s comprises a permanent magnet with a south pole facing toward the handle 11100 and a north pole facing away from the handle 11100 and the second magnetic element 11230n comprises a permanent magnet with a north pole facing toward the handle 11100 and a south pole facing away from the handle 11100. The magnetic elements 11230s and 11230n disturb the magnetic field emitted by the Hall Effect sensor and, when the shaft 11200 is at least partially upside down, the disturbance associated with such an orientation of the shaft 11200 is detected by the control system of the surgical instrument 11000 via a sensing circuit including the sensor 11130. In such instances, similar to the above, the control system enters into its second operating mode which flips the responsiveness of the surgical instrument 11000 to the articulation control 10160, as described above.

Figure 8:
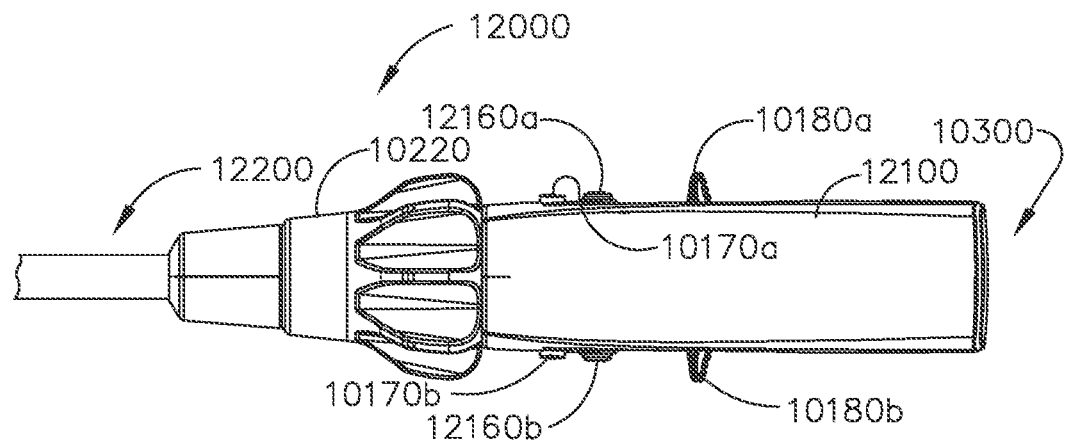
FIG. 8 is a partial plan view of the surgical instrument of FIG. 7.
Figure 7:
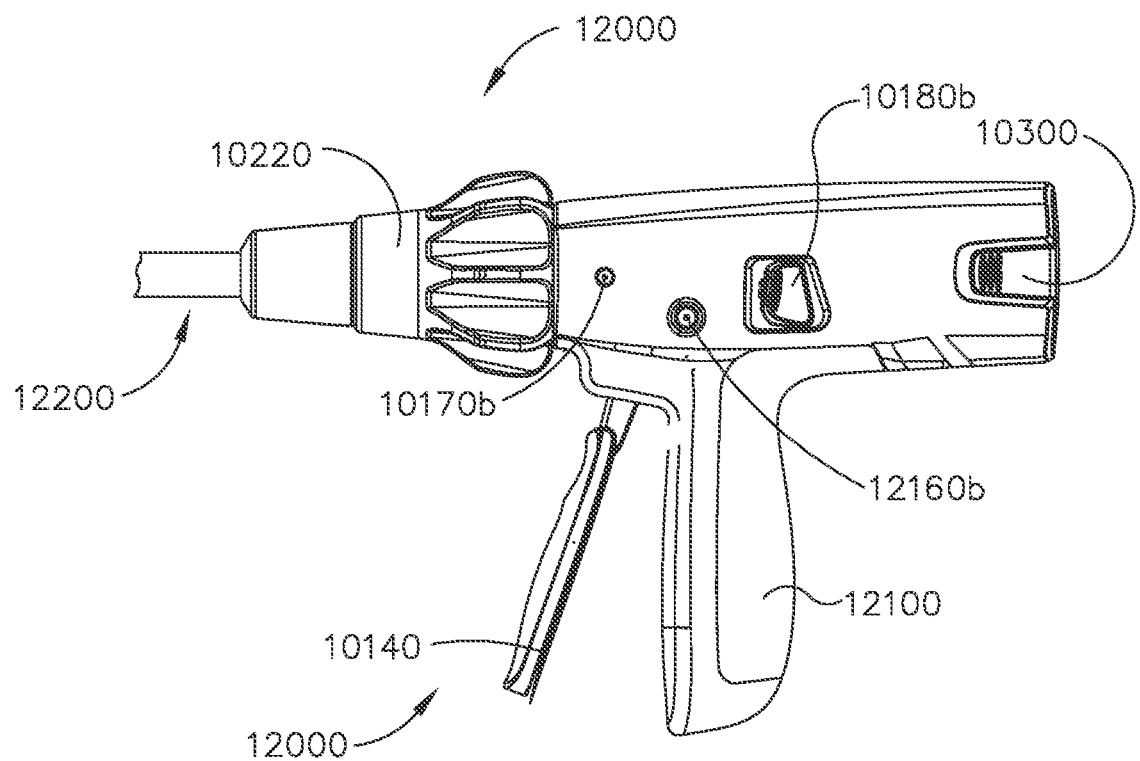
FIG. 7 is a partial elevational view of a surgical instrument in accordance with at least one embodiment comprising a handle and articulation actuators on opposing sides of the handle.

A surgical instrument 12000 is illustrated in FIGS. 7 and 8. The surgical instrument 12000 is similar to the surgical instrument 10000 in many respects. The surgical instrument 12000 comprises a handle 12100 and a shaft 12200 extending from the handle 12100. The handle 12100 comprises a housing, a first articulation control 12160a positioned on a first side of the handle housing, and a second articulation control 12160b positioned on a second, or opposite, side of the handle housing. The first articulation control 12160a is in communication with the control system of the surgical instrument 12000 via a first control circuit and the second articulation control 12160b is in communication with the control system via a second control circuit. The control system is configured to operate the electric motor of the staple firing drive in a first direction to articulate the end effector of the shaft 12200 in a first direction when the first articulation control 12160a is actuated and a second, or opposite, direction to articulate the end effector in a second, or opposite, direction with the second articulate control 12160b is actuated. The handle 12100 further comprises a centering, or home, actuator 10170a positioned on the first side of the handle 12100 and a second centering, or home, actuator 10170b on the second side of the handle 12100. Similar to the above, the actuators 10170a and 10170b are in communication with the control system which is configured such that the actuation of either centering actuator 10170a or 10170b causes the control system to operate the electric motor to re-center the end effector.

Figures 9, 10:
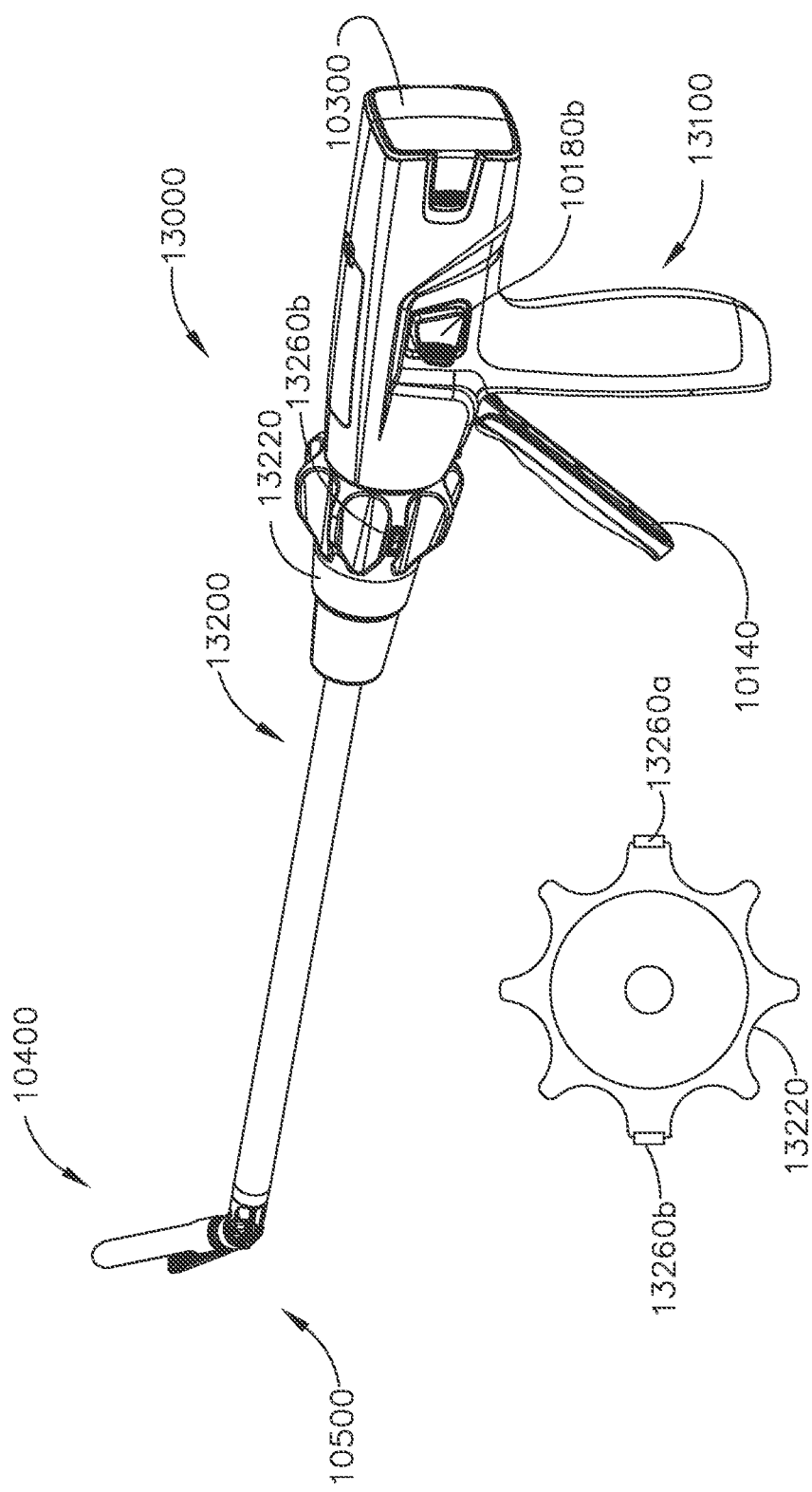
FIG. 9 is a perspective view of a surgical instrument in accordance with at least one embodiment comprising a handle and a rotatable shaft including articulation actuators on opposing sides of the shaft.
FIG. 10 is an end view of the shaft of FIG. 9.

A surgical instrument 13000 is illustrated in FIGS. 9 and 10. The surgical instrument 13000 is similar to the surgical instrument 10000 in many respects. The surgical instrument 13000 comprises a handle 13100 and a shaft 13200 extending from the handle 13100. The shaft 13200 comprises a housing, a first articulation control 13260*a* positioned on a first side of the shaft housing, and a second articulation control 13260*b* positioned on a second, or opposite, side of the shaft housing. The first articulation control 13260*a* is in communication with the control system of the surgical instrument 13000 via a first control circuit and the second articulation control 13260*b* is in communication with the control system via a second control circuit. The control system is configured to operate the electric motor of the staple firing drive in a first direction to articulate the end effector 10400 of the shaft 13200 in a first direction when the first articulation control 13260*a* is actuated and a second, or opposite, direction to articulate the end effector 10400 in a second, or opposite, direction when the second articulation control 13260*b* is actuated. Stated another way, the end effector 10400 articulates in the direction of the articulation control that is actuated. The first articulation control 13260*a* is positioned on a first finger ridge defined on a grip, or nozzle, 13220 of the shaft 13200 and the second articulation control 13260*b* is positioned on a second finger ridge defined on the grip 13220. Notably, the articulation controls 13260*a* and 13260*b* are positioned 180 degrees apart. Alternatively, the articulation controls 13260*a* and 13260*b* can be positioned in the finger grooves defined in the grip 13220, although any suitable arrangement could be used. This arrangement provides an advantage of having the articulation controls in a position which is readily accessible by the hand of the clinician during use and, as a result, they are usable in an intuitive manner as the relative arrangement of the articulation controls 13260*a* and 13260*b* and the articulation directions are fixed.

A surgical instrument 14000 is illustrated in FIGS. 11 and 12. The surgical instrument 14000 is similar to the surgical instrument 13000 in many respects. The surgical instrument 14000 comprises a handle 13100 and a shaft 14200 extending from the handle 13100. The shaft 14200 comprises a housing, a first articulation control 14260*a* positioned on a first side of the shaft housing, and a second articulation control 14260*b* positioned on a second side of the shaft housing. The first articulation control 14260*a* is in communication with the control system of the surgical instrument 14000 via a first control circuit and the second articulation control 14260*b* is in communication with the control system via a second control circuit. The control system is configured to operate the electric motor of the staple firing drive in a first direction to articulate the end effector 10400 of the shaft 14200 in a first direction when the first articulation control 14260*a* is actuated and a second, or opposite, direction to articulate the end effector 10400 in a second, or opposite, direction when the second articulation control 14260*b* is actuated. The first articulation control 14260*a* is positioned in a first finger groove defined in a grip, or nozzle, 14220 of the shaft 14200 and the second articulation control 14260*b* is positioned in a second finger groove defined in the grip 14220, although any suitable arrangement could be used.

In addition to the above, the shaft 14200 further comprises a third articulation control 14260*c* positioned on the second side of the shaft housing and a fourth articulation control 14260*d* positioned on the first side of the shaft housing. The third articulation control 14260*c* is in communication with the control system of the surgical instrument 14000 via a third control circuit and the fourth articulation control 14260*b* is in communication with the control system via a fourth control circuit. The control system is configured to operate the electric motor of the staple firing drive in the second direction to articulate the end effector of the shaft 14200 in the second direction when the third articulation control 14260*c* is actuated and the first direction to articulate the end effector in the first direction when the fourth articulation control 14260*d* is actuated. The third articulation control 14260*c* is positioned in a third finger groove defined in the grip 14220 of the shaft 14200 and the fourth articulation control 14260*d* is positioned in a fourth finger groove defined in the grip 14220, although any suitable arrangement could be used.

Figure 13:
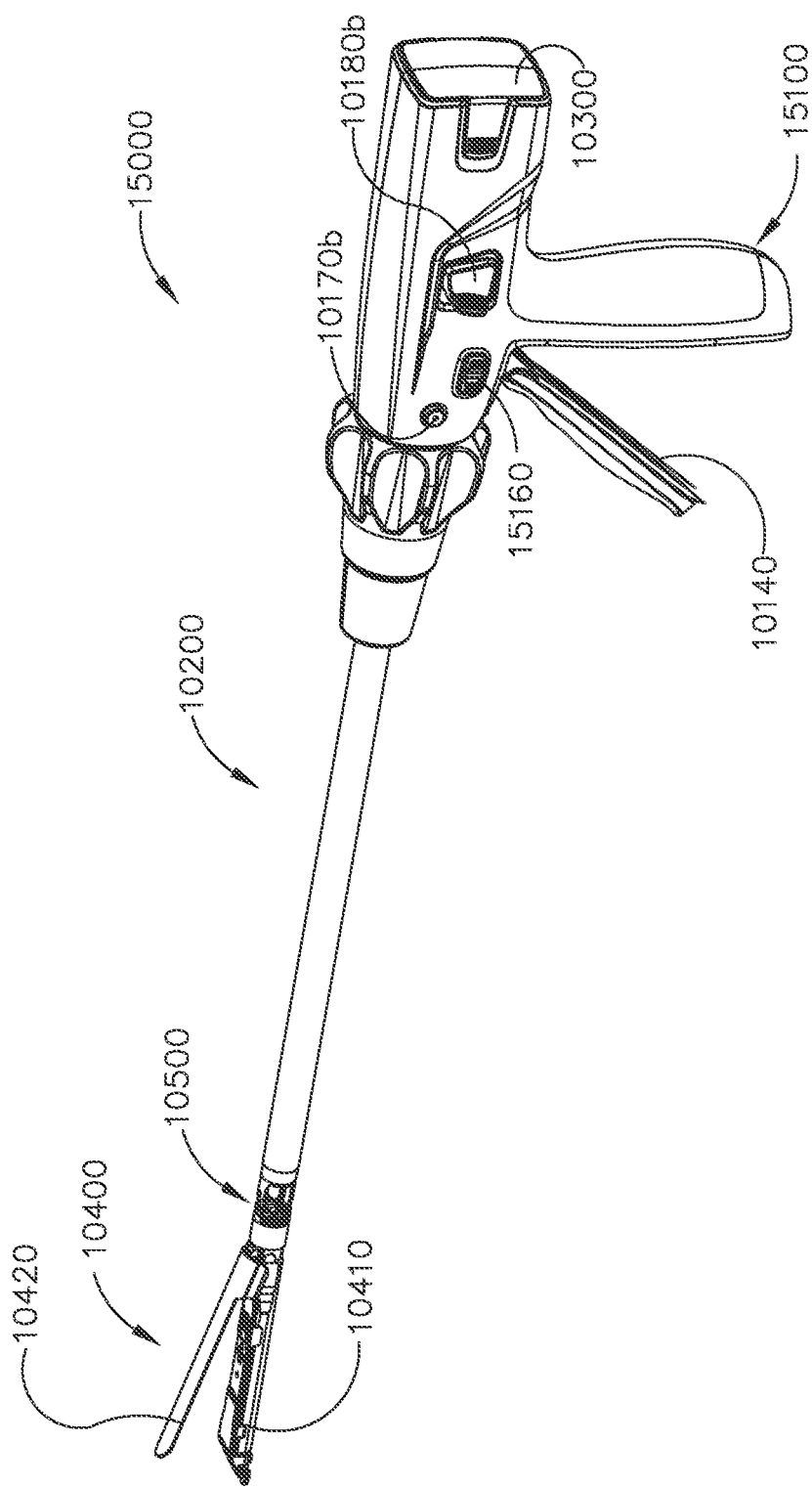
FIG. 13 is a perspective view of a surgical instrument in accordance with at least one embodiment comprising a slideable articulation actuator including two positions and a detent between the two positions.

A surgical instrument 15000 is illustrated in FIG. 13. The surgical instrument 15000 is similar to the surgical instrument 10000 in many respects. The surgical instrument 15000 comprises a handle 15100 and a shaft 10200 extending from the handle 15100. The handle 15100 comprises an articulation actuator 15160 in communication with the control system of the surgical instrument 15000. As opposed to the articulation actuator 10160 which is arranged vertically, the articulation actuator 15160 is arranged horizontally. The articulation actuator 15160 comprises a rotatable element which is rotatable within a plane which is parallel to, or at least substantially parallel to, the longitudinal axis of the shaft 10200. The rotatable element is rotatable distally to articulate the end effector 10400 to the right of the handle 15100 and proximally to articulate the end effector 10400 to the left of the handle 15100. This is true regardless of whether the end effector 10400 is rotated upwardly or downwardly owing to the control responsiveness flipping when the end effector 10400 is rotated past 90 degrees from its TDC position in either direction. That said, the controls of the articulation actuator 15160 can be reversed as outlined above. The articulation actuator 15160 comprises a distal contact which is part of a first articulation control circuit and a proximal contact which is part of a second articulation control circuit. The rotatable element engages the distal contact and closes the first articulation control circuit when the rotatable element is in its distal position. The rotatable element is not in contact with the proximal contact when the rotatable element is in its distal position and, as such, the second articulation control circuit is open. Similarly, the rotatable element engages the proximal contact and closes the second articulation control circuit when the rotatable element is in its proximal position. Correspondingly, the rotatable element is not in contact with the distal contact when the rotatable element is in its proximal position and, as such, the first articulation control circuit is open.

Further to the above, the articulation actuator 15160 comprises a detent in the middle of the range of motion of the rotatable element. The detent is configured to resist the motion of the rotatable element as the rotatable element moves from one side of the articulation actuator 15160 to the other. Such resistance to the motion of the rotatable element can signal to the clinician that they will articulate the end effector 10400 in the opposite direction once they move the rotatable element past that point. Moreover, such a detent provides a place to park the rotatable element such that the end effector 10400 is not being articulated in either direction. The rotatable element comprises a ridge alignable with its center, or parked, position which is pushable and pullable by the clinician to move the rotatable element. Such a ridge provides the clinician with a tactile sensation of the direction in which the rotatable element is rotated and, thus, a sense of the direction in which the end effector 10400 is being articulated.

The above being said, various embodiments are envisioned in which the flipping of the control responsiveness of a surgical instrument can be defeated. In at least one instance, the handle of the surgical instrument comprises an actuator in communication with the control system that, when actuated, causes the control system to not enter into its second, or flipped, operational mode. In at least one such instance, the handle further comprises an indicator, such as a light emitting diode (LED), for example, that is illuminated to indicate the status of the surgical instrument, i.e., whether or not the articulation controls will flip when the end effector is rotated past 90 degrees from its TDC position. In certain instances, the surgical instrument comprises an input screen in communication with a microprocessor of the control system which can receive an input to prevent the control system from entering into its second, or flipped, operational mode. In addition to or in lieu of the above, the flip point in which the surgical instrument enters into its second operation mode can be adjusted. In at least one such embodiment, the clinician can modify the flip point to 85 degrees, for example, in either direction from the TDC position of the end effector. Any suitable number, such as 80 degrees, 95 degrees, or 100 degrees, for example, could be used to suit the preference of the clinician. In at least one embodiment, the surgical instrument comprises an input screen in communication with the microprocessor of the control system which is configured to receive an input from the clinician to adjust the articulation control flip point.

During use, it is desirable for the articulation controls not to flip unexpectedly while the clinician is using the articulation controls. When the clinician starts articulating the end effector, the control system maintains the articulation control mode until the clinician releases the articulation control even if the end effector and shaft are rotated past a flip point during the articulation. Once the articulation has stopped, the control system can re-orient the articulation controls, or switch to the flipped articulation control mode if the end effector and shaft are still in an upside-down position. In certain embodiments, the control system does not immediately flip the articulation controls. Instead, the control system comprises a timer circuit and/or the microprocessor of the control system is programmed to wait a certain amount of time before flipping the controls. In at least one instance, the control system waits 5 seconds, for example, from the last time that the articulation controls were used before flipping the articulation controls. Alternatively, the control system can wait 2 seconds or 10 seconds, for example. Such an arrangement can help prevent confusion with the user of the surgical instrument. In various embodiments, the surgical instrument comprises a haptic feedback generator in communication with the control system which is activated by the control system when the articulation controls are flipped. Motor noise, light, sound, and/or a vibratory feedback, for example, can be used. In some embodiments, the shaft and/or handle comprises a mechanical switch which audibly clicks when the shaft is rotated past its flip point in either direction.

Figure 56:
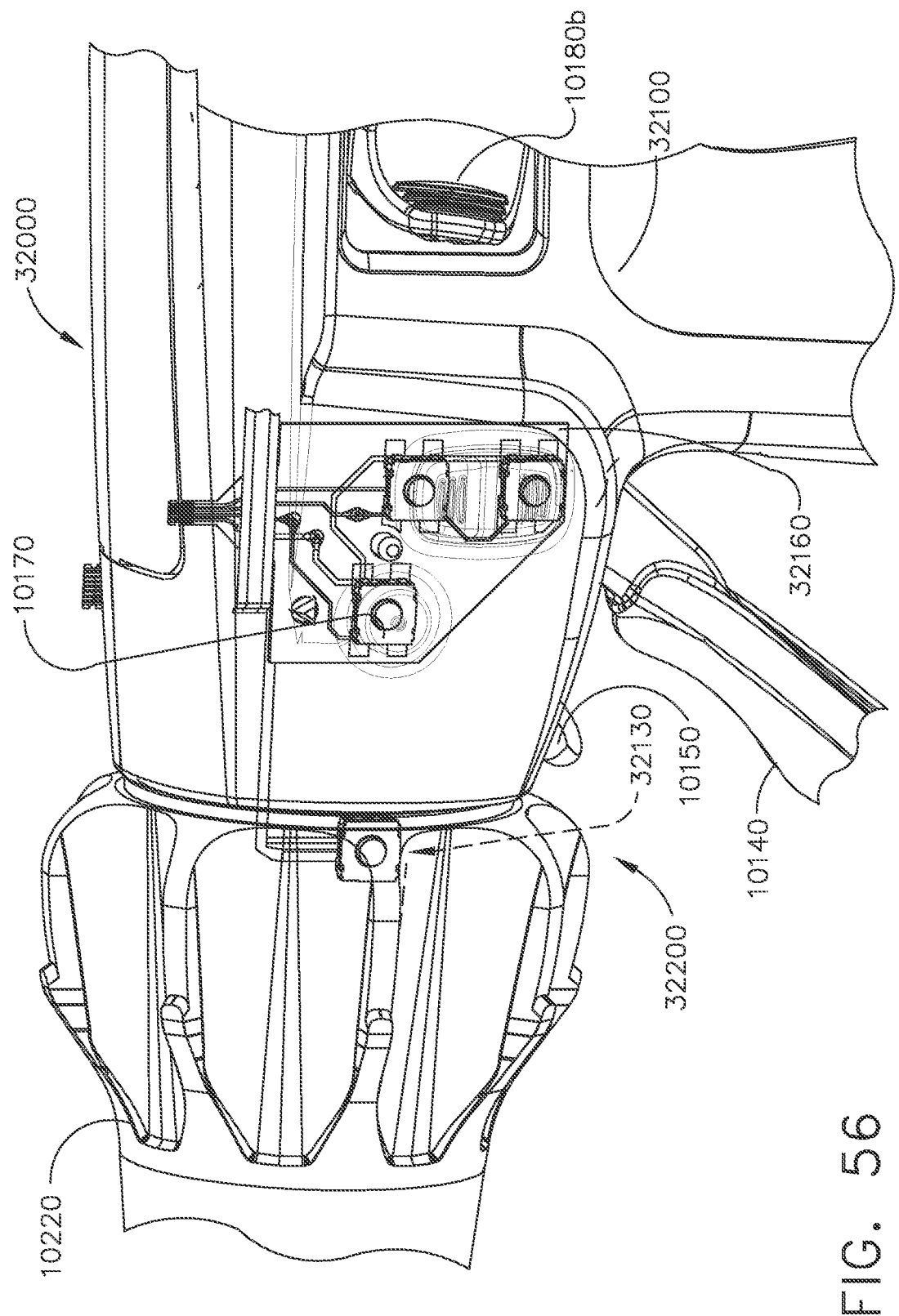
FIG. 56 is a partial perspective view of a surgical instrument in accordance with at least one embodiment.
Figure 57:
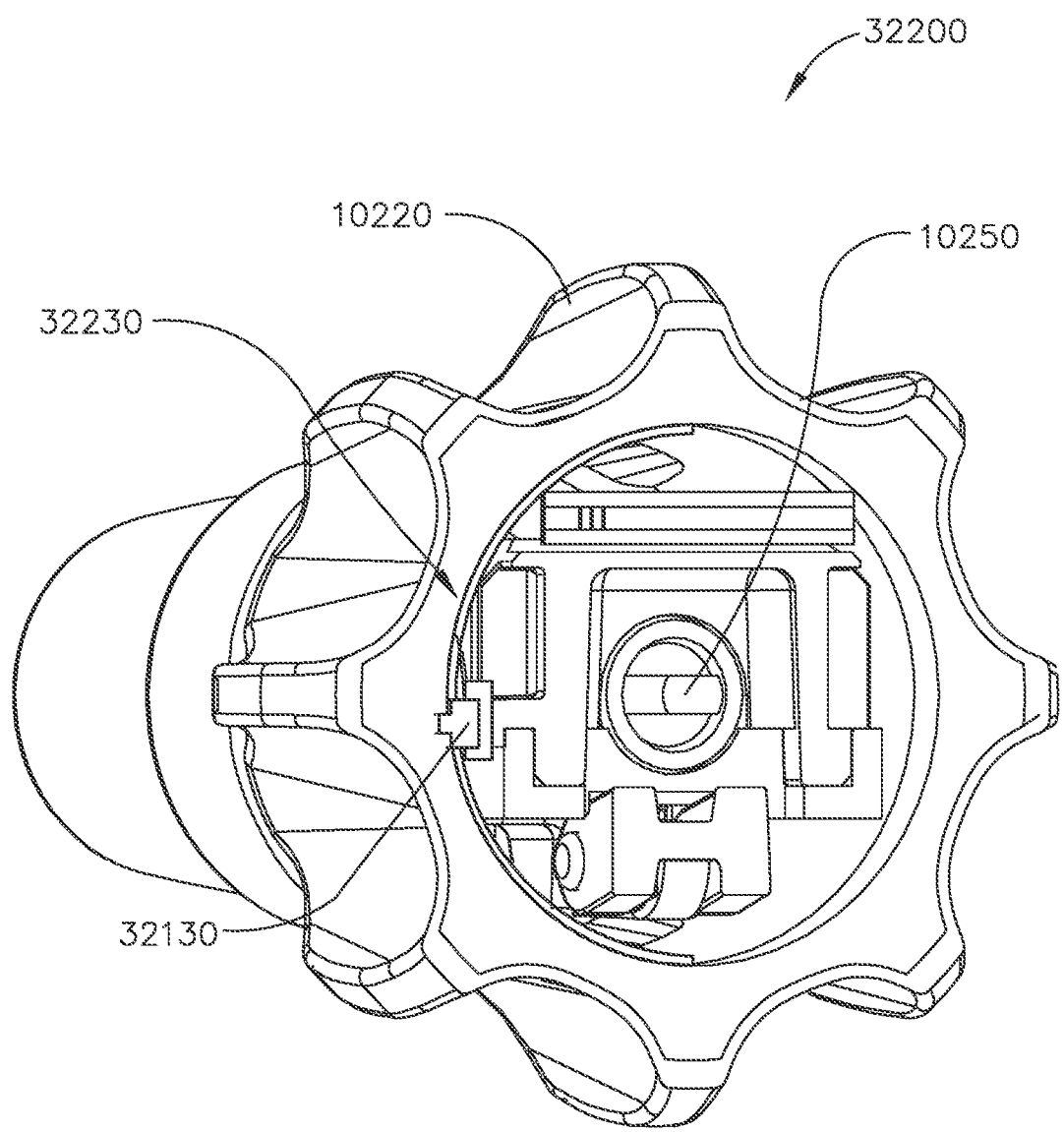
FIG. 57 is a partial perspective view of a shaft of the surgical instrument of FIG. 56.
Figure 58:
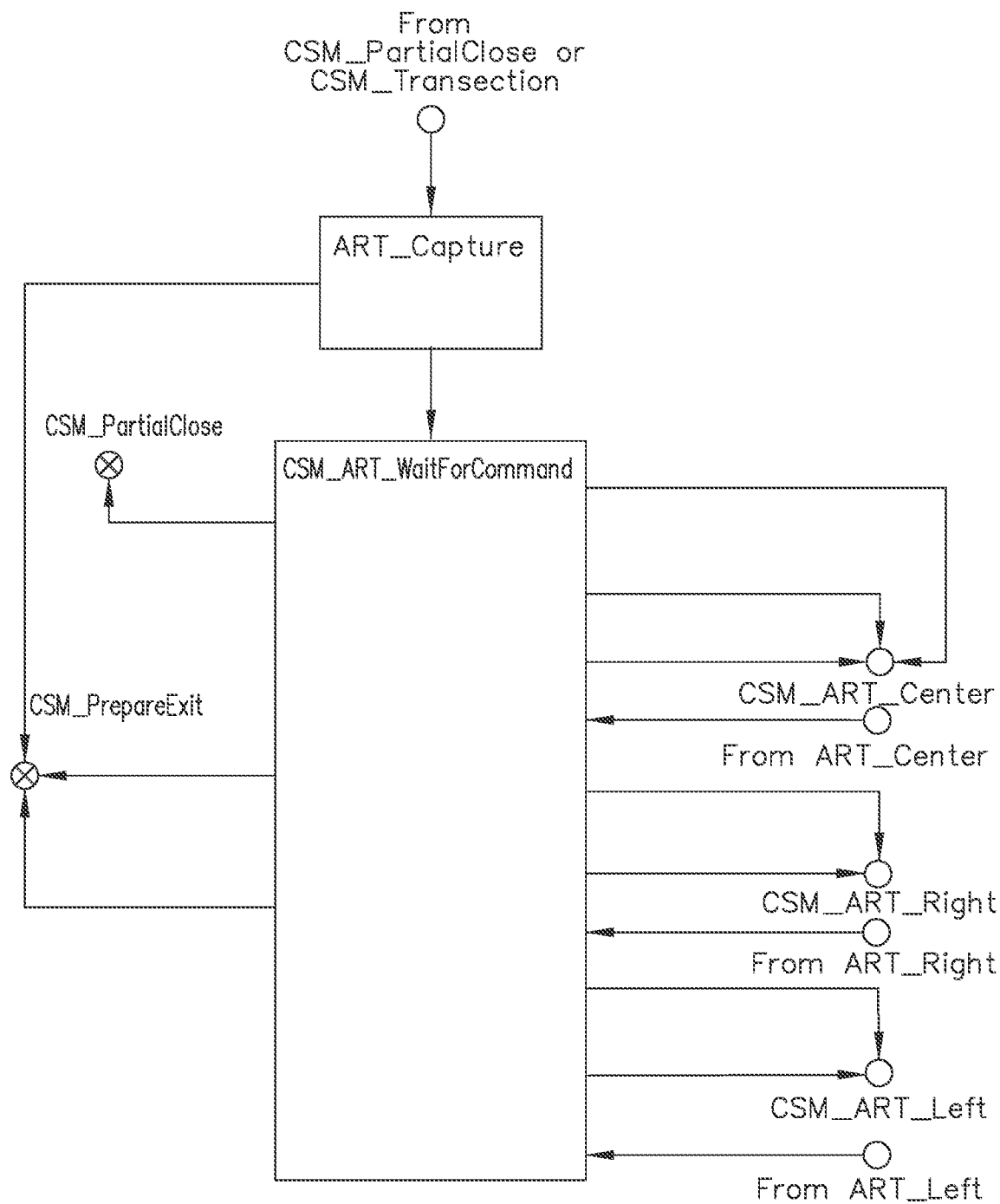
FIG. 58 is a control algorithm implemented by the surgical instrument of FIG. 56.

A surgical instrument 32000 is illustrated in FIGS. 56 and 57, the surgical instrument 32000 comprises a handle 32100 and a shaft 32200. The handle 32100 comprises an articulation control 32160 and an articulation flip switch 32130 in communication with the control system of the surgical instrument 32000. The articulation flip switch 32130 is mounted to a control board, such as a printed control board (PCB), for example, which comprises the hardware and software for the control system of the surgical instrument 32000. When the shaft 32200 is rotated past its 90 degree left or right position, the shaft 32200 contacts the articulation flip switch 32130 which is detected by the control system. At this point, the control system follows an algorithm for deciding when, or if, to the flip the articulation controls. An algorithm 32900 is illustrated in FIG. 58 which can control this, although any suitable algorithm could be used. Similar to the above, the shaft 32200 comprises a cam 32230 configured to contact the articulation flip switch 32130. As a result of the above, the articulation flip switch 32130 is open or "off" for 180 degrees of the rotation of the shaft 32200 and closed or "on" for the other 180 degrees of the rotation of the shaft 32200. The cam 32230 is molded into the shroud of the shaft 32200, but could comprise any suitable arrangement. The above being said, the throw of the cam 32230 is designed such that any lateral float or eccentricity in the rotation of the shaft 32200, or cam 32230, does not accidentally close or open the articulation flip switch 32130. To this end, the shaft 32200 comprises a fixed bearing for controlling the rotation of the shaft 32200 and the cam 32230. Notably, the articulation flip switch 32130 is sealed to prevent fluid ingress.

In various instances, a surgical instrument comprises an input configured to permit a clinician to select whether the articulation controls operate in their ordinary articulation control mode or their flipped articulation control mode. In at least one instance, the handle of the surgical instrument comprises an input switch in communication with the control system of the surgical instrument. When the input switch is open, for instance, the algorithm controls the orientation of the articulation controls according to a predetermined set of criteria. When the input switch is closed by the clinician, the algorithm does not use the predetermined set of criteria to control the orientation of the articulation controls. Instead, the algorithm uses the orientation of the articulation controls selected by the clinician. In at least one instance, the handle comprises three input switches in communication with the control system—a first switch which instructs the control system to use the "anvil up" articulation controls, a second switch which instructs the control system to use the "anvil down" articulation controls, and a third switch which instructs the control system to use the automatic controls. In some embodiments, the surgical instrument does not have the automatic flip controls described herein and can just comprise the first and second switch inputs. Such an arrangement can greatly reduce the cost and/or complexity of a surgical instrument.

Figure 55:
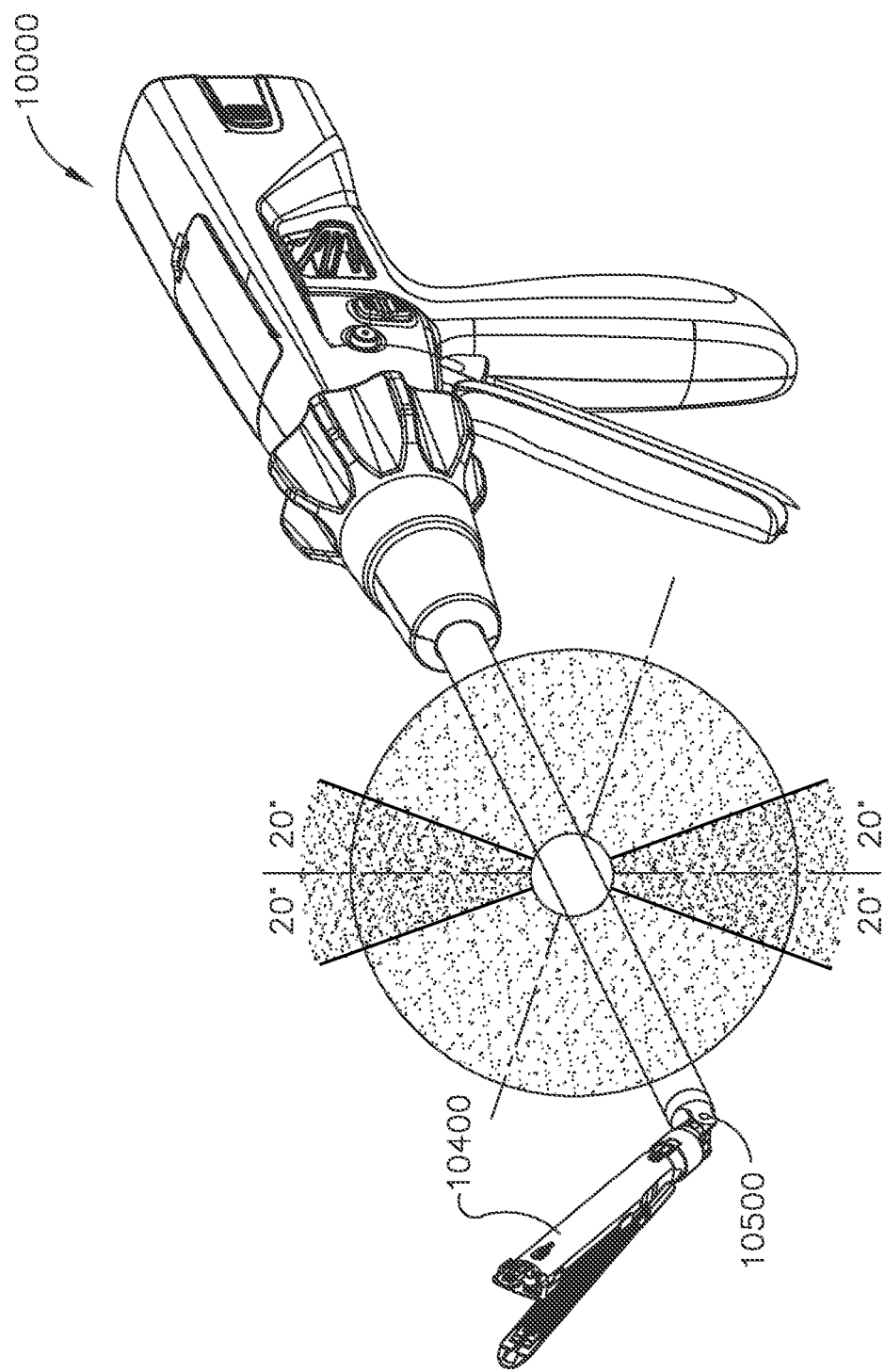
FIG. 55 is a perspective view of the surgical instrument of FIG. 1.

In various instances, further to the above, the flip point can be a specific point in the rotation of the shaft 10200. In certain instances, referring to FIG. 55, a grey zone can exist around the flip point. For instance, the grey zone can include 20 degrees to either side of the flip point, for example. While the shaft 10200 is in the grey zone, the algorithm of the control system is configured to not flip the articulation controls even though the shaft 10200 may have been rotated past the flip point. Such an arrangement allows the shaft 10200 to be rotated back and forth within the grey zone without repeatedly flipping the articulation controls. Once the shaft 10200 is rotated out of the grey zone, however, the control system algorithm flips the articulation controls—subject to any other criteria needed for flipping the articulation controls. In various instances, there is an interface between the range of "anvil up" orientations and the range of "anvil down" orientations. For a shaft that is rotatable 360 degrees, there are two such interfaces—180 degrees apart from another. Each of these interfaces is positioned within a transition range of orientations that extends into the range of "anvil up" orientations and the range of "anvil down" orientations. When the shaft 10200 is rotated from an "anvil up" orientation into a transition range, the control system does not flip the articulation controls—but further rotating the shaft 10200 out of the transition range into an "anvil down" orientation will cause the articulation controls to flip. Similarly, the control system does not flip the articulation controls when the shaft 10200 is rotated from an "anvil down" orientation into a transition range, but further rotating the shaft 10200 out of the transition range in an "anvil up" orientation will cause the articulation controls to flip. In at least one instance, each transition zone includes 5 degrees of orientations from the "anvil up" range and 5 degrees of orientations from the "anvil down" range, for example. In other embodiments, each transition zone includes 10 degrees of orientations from the "anvil up" range and 10 degrees of orientations from the "anvil down" range, for example.

In various embodiments, further to the above, the up and down orientations of the shaft 10200 are measured with respect to the handle and/or a housing rotatably supporting the shaft. In such instances, a handle comprises a top and a bottom—regardless of its gravitational orientation—and the up orientations of the shaft 10200 are associated with the top of the handle while the down orientations of the shaft 10200 are associated with the bottom of the handle. In at least one such embodiment, the shaft 10200 comprises a gravity sensor, such as an accelerometer and/or a gyroscope, for example, and the handle comprises a gravity sensor. In such embodiments, the shaft gravity sensor and the handle gravity sensor are in communication with the control system which is configured to assess the relative orientation between the shaft and the handle using the data from the gravity sensors. In other embodiments, the up and down orientations of the shaft 10200 are measured with respect to gravity regardless of the gravitational orientation of the handle. In at least one such embodiment, the shaft 10200 comprises a gravity sensor in communication with the control system and the up orientations of the shaft 10200 are associated with vertically up positions while the down orientations of the shaft 10200 are associated with vertically down positions.

Figure 14:
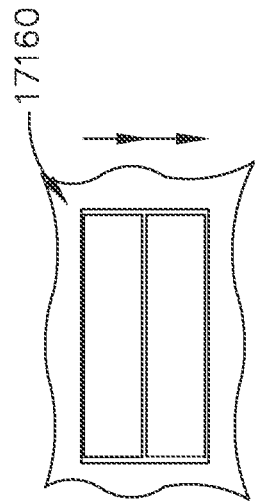
FIG. 14 illustrates a capacitive switch including first and second sides, a first light in the first side which illuminates when the first side is contacted, and a second light in the second side which illuminates when the second side is contacted.

An articulation control 16160 is illustrated in FIG. 14. The articulation control 16160 comprises a first capacitive switch 16162 and a second capacitive switch 16164. The first capacitive switch 16162 and the second capacitive switch 16164 are positioned on opposite sides of an axis 16167. The first capacitive switch 16162 is part of a first articulation control circuit in communication with a control system of a surgical instrument and the second capacitive switch 16164 is part of a second articulation control circuit in communication with the control system. The capacitance of the first capacitive switch 16162 changes when a clinician places their finger on the first capacitive switch 16162 which is detected by the control system and, in response to this change, the control system articulates the end effector of the surgical instrument to the right. The capacitance of the second capacitive switch 16164 changes when a clinician places their finger on the second capacitive switch 16164 which is detected by the control system and, in response to this change, the control system articulates the end effector of the surgical instrument to the left. In various instances, the axis 16167 comprises a dead zone which, if touched by the clinician, does not detectably, or sufficiently, change the capacitance of the first capacitive switch 16162 or the second capacitive switch 16164.

Figure 15:
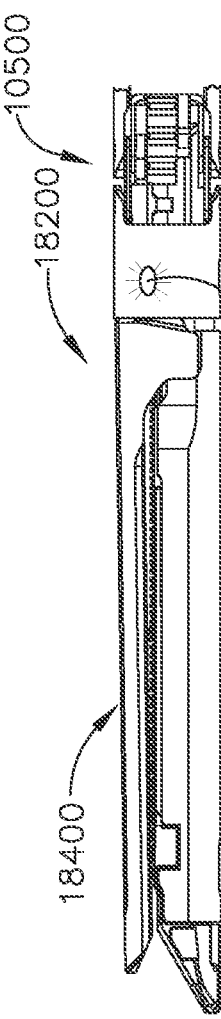
FIG. 15 illustrates a two-stage rocker switch for articulating an end effector of a surgical instrument in accordance with at least one embodiment.

A two-stage switch 17160 is illustrated in FIG. 15. When the switch 17160 is depressed into its first stage, a first articulation control circuit is closed. The first articulation control circuit is in communication with a control system of a surgical instrument. When the control system detects that the first articulation control circuit has been closed, the control system operates an articulation drive motor in a first direction to articulate the end effector of the surgical instrument in a first direction. When the switch 17160 is depressed into its second stage, a second articulation control circuit is closed. In various instances, the first stage comprises a first detent and the second stage comprises a second detent. In at least one such instance, the switch 17160 comprises a dual-detent switch that is depressable to two different depths, for example. In any event, the second articulation control circuit is in communication with the control system of the surgical instrument. When the control system detects that the second articulation control circuit has been closed, the control system operates an articulation drive motor in a second direction to articulate the end effector of the surgical instrument in a second direction. Further to the above, the second articulation control circuit is open when the first articulation control circuit is closed and, likewise, the first articulation control circuit is open when the second articulation control circuit is closed. The above being said, in alternative embodiments, the articulation control circuits can be opened when they are in their respective stages to operate the articulation motor.

Figure 17:
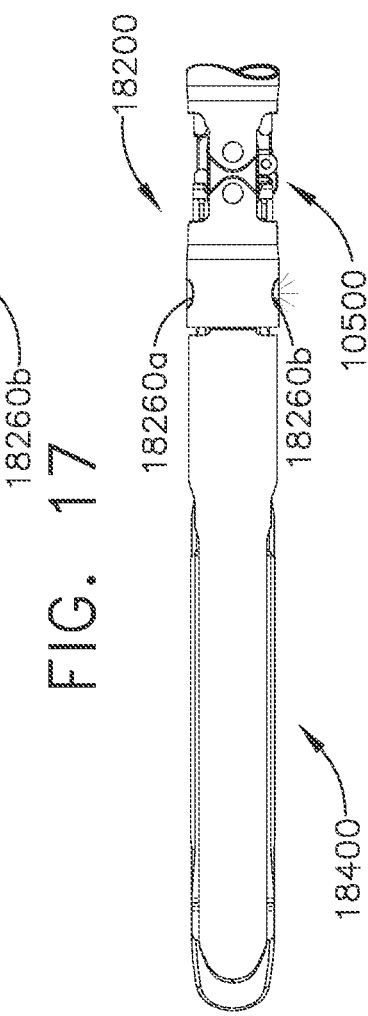
FIG. 17 is a partial elevational view of the surgical instrument of FIG. 16.
Figure 16:
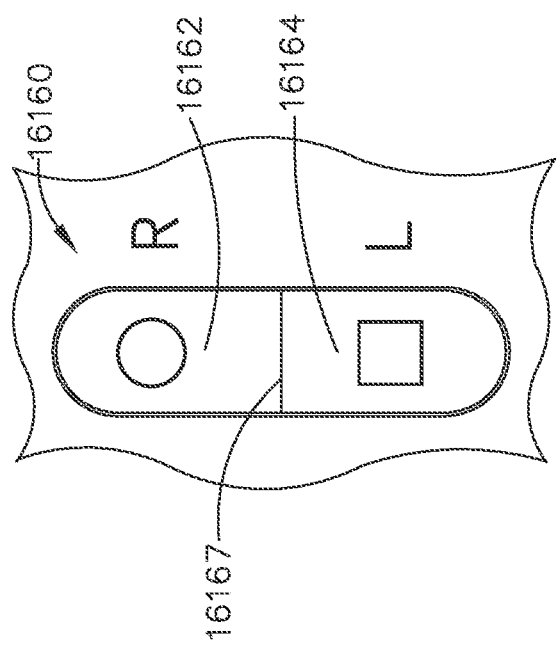
FIG. 16 is a partial top view of a surgical instrument in accordance with at least one embodiment comprising an end effector and lights positioned on opposite sides of the end effector which are illuminated to indicate the direction in which the end effector is being articulated.

Many clinicians, further to the above, prefer to look at the patient when performing an open surgery and/or at an endoscope monitor when performing a laparoscopic surgery. As such, the clinician does not usually look at the surgical instrument that they are holding and, instead, rely on the tactile feel and/or intuitive design of the surgical instrument to operate the surgical instrument. Stated another way, the clinician may not prefer to look down at the handle of the instrument they are holding to verify the direction that they are articulating the instrument. That being said, referring to FIGS. 16 and 17, a surgical instrument can comprise a shaft 18200 comprising indicator lights configured to indicate the direction in which an end effector, such as end effector 18400, for example, is being articulated. The articulation indicator lights are visible to the clinician while they are looking at the end effector 18400 of the surgical instrument—either directly or through an endoscope system monitor. In various instances, an endoscope system comprises an elongate flexible shaft including a camera, a light, and/or any other suitable optical device in communication with a control hub including a control system and/or a video monitor configured to display the output of the camera. In such instances, the end effector 18400 and the indicator lights are visible on the video monitor.

Further to the above, referring again to FIGS. 16 and 17, the shaft 18200 comprises a first indicator light 18260*a* positioned on the right side of the end effector 18400 in communication with the control system of the surgical instrument via a first electrical circuit. When the control system receives an input to articulate the end effector 18400 to the right, the control system operates the articulation drive motor in a direction which articulates the end effector 18400 to the right and, also, illuminates the first indicator light 18260*a*. When the control system no longer receives this input, the control system deactivates the articulation drive motor and the first indicator light 18260*a*. Similarly, the shaft 18200 comprises a second indicator light 18260*b* positioned on the left side of the end effector 18400 in communication with the control system of the surgical instrument via a second electrical circuit. When the control system receives an input to articulate the end effector 18400 to the left, the control system operates the articulation drive motor in a direction which articulates the end effector 18400 to the left and, also, illuminates the second indicator light 18260*b*. When the control system no longer receives this input, the control system deactivates the articulation drive motor and the second indicator light 18260*b*.

Figure 18:
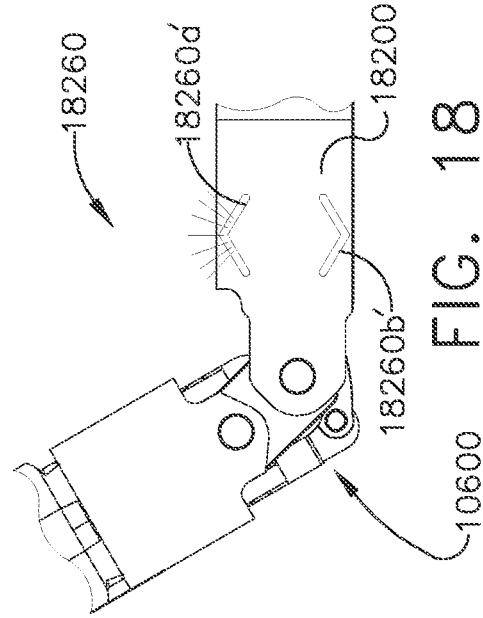
FIG. 18 is a partial elevational view of a surgical instrument in accordance with at least one embodiment comprising directional indicators which are illuminated to indicate which way the end effector is being articulated.

As discussed above, the first and second indicator lights 18260*a* and 18260*b* are positioned on the end effector 18400 in a position which is readily observable by the clinician when they are looking at the end effector 18400. The indicator lights 18260*a* and 18260*b* are positioned distally with respect to the articulation joint 10500; however, in alternative embodiments, the indicator lights 18260*a* and 18260*b* are positioned proximally to the articulation joint 10500. In various embodiments, a surgical instrument comprises more than one set of indicator lights. In at least one such embodiment, a first set of indicator lights 18260*a*, 18260*b* is positioned distally with respect to the articulation joint 10500 and a second set of indicator lights 18260*a*, 18260*b* is positioned proximally with respect to the articulation joint 10500. An alternative embodiment comprising indicator lights 18260*a*' and 18260*b*' on a shaft 18200' is illustrated in FIG. 18. The indicator light 18260*a*' comprises an LED in the shape of a right-facing arrow while the indicator light 18260*b*' comprises an LED in the shape of a left-facing arrow. The right-facing arrow 18260*a*' points to the right of the end effector—but not necessarily to the right of the surgical instrument handle and/or the clinician owing to the possible rotation of the shaft 18200'. Similarly, the left-facing arrow 18260*b*' points to the left of the end effector—but not necessarily to the left of the surgical instrument handle and/or the clinician owing to the possible rotation of the shaft 18200'. Stated another way, the arrows, when illuminated, point in the direction that the end effector is being articulated. Given that the arrows are observable with the end effector on an endoscope monitor, for example, the clinician will develop a sense for the direction that the end effector will move when an arrow is illuminated upon actuating the articulation actuator. If the clinician observes that the illuminated arrow is the opposite of what they expected when they actuate the articulation actuator, the clinician can quickly react and re-actuate the articulation actuator in the correct direction. In various alternative embodiments, the arrows 18260*a*' and 18260*b*' can change colors when they are actuated. For instance, the arrow 18260*a*' is illuminated red when the end effector is not articulated to the right, but is illuminated green when the end effector is articulated to the right. Likewise, the arrow 18260*b*' is illuminated red when the end effector is not articulated to the left, but is illuminated green when the end effector is articulated to the left.

In various embodiments, further to the above, the articulation indicator lights can be embedded in and/or positioned on the outer housing of the shaft. In certain embodiments, the indicator lights are positioned inside the shaft, but are viewable from outside the shaft through windows and/or openings defined in the shaft, for example.

Figure 26:
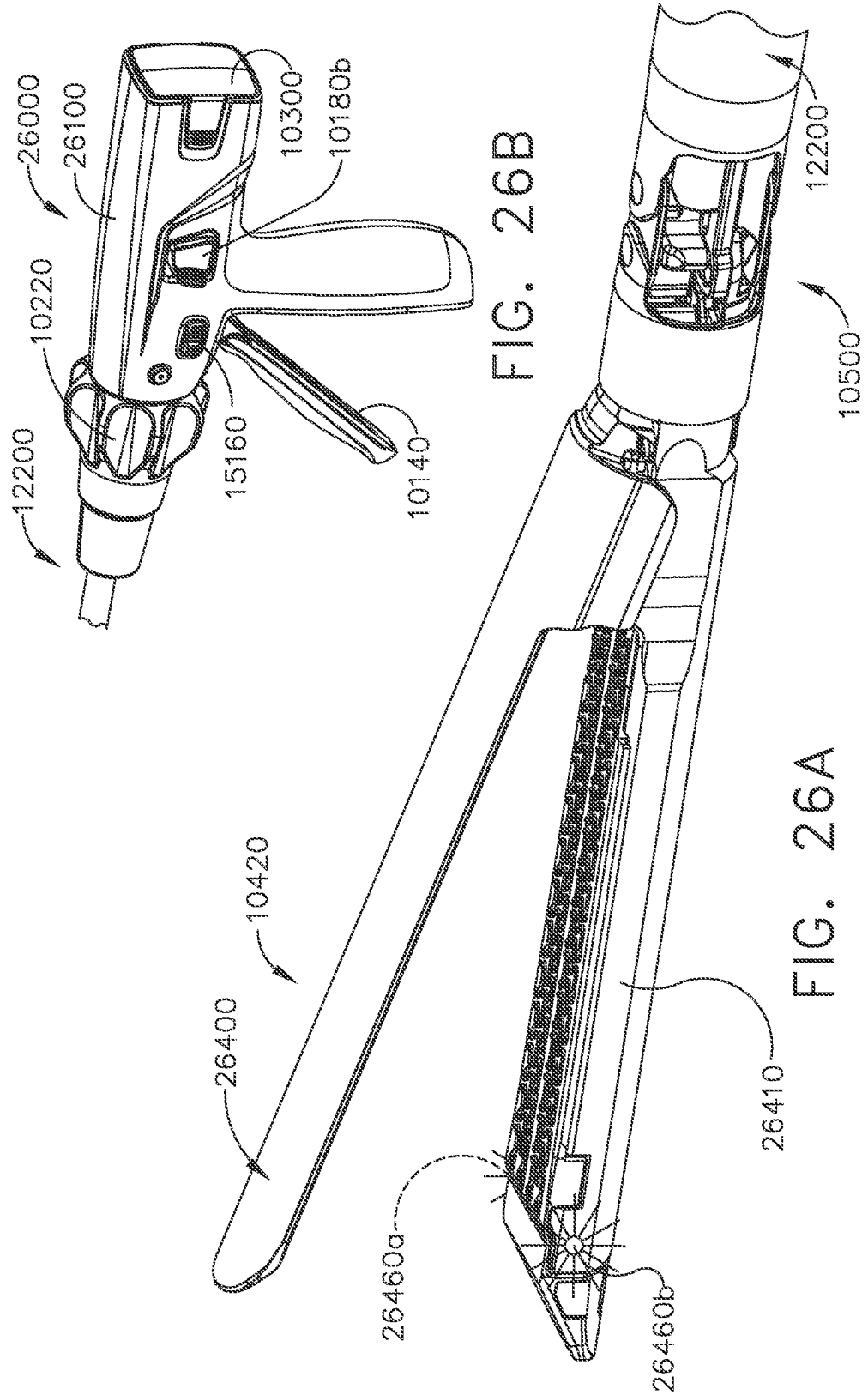
FIG. 26A illustrates a surgical instrument in accordance with at least one embodiment including an end effector and lights positioned on opposite sides of the end effector which are illuminated to indicate the direction in which the end effector is being articulated.
FIG. 26B is a perspective view of the surgical instrument of FIG. 26A.

A surgical instrument 26000 is illustrated in FIGS. 26A and 26B. The surgical instrument 26000 comprises a handle 26100 and a shaft 12200 extending from the handle 26100. The shaft 12200 comprises an end effector 26400 including a staple cartridge jaw 26410 and an anvil jaw 10420. The end effector 26400 further comprises a first articulation indicator light 26460*a* positioned on a first side of the end effector 26400 and a second articulation indicator light 26460*b* positioned on a second side of the end effector 26400. Similar to the above, the control system of the surgical instrument 26000 illuminates the first articulation indicator light 26460*a* when the end effector 26400 is articulated in the first direction. In such instances, the control system does not illuminate the second articulation indicator light 26460*b*. Correspondingly, the control system of the surgical instrument 26000 illuminates the second articulation indicator light 26460*b* when the end effector 26400 is articulated in the second direction. In such instances, the control system does not illuminate the first articulation indicator light 26460*a*. The indicator lights 26460*a* and 26460*b* are mounted to and/or embedded in the frame of the staple cartridge jaw 26410. That said, the indicator lights 26460*a* and 26460*b* can be mounted to and/or embedded in the staple cartridge positioned in the staple cartridge jaw 26410. In such instances, the staple cartridge jaw 26410 comprises an electrical circuit in communication with the control system of the surgical instrument that is placed in communication with an electrical circuit in the staple cartridge when the staple cartridge is seated in the staple cartridge jaw 26410.

Figure 27:
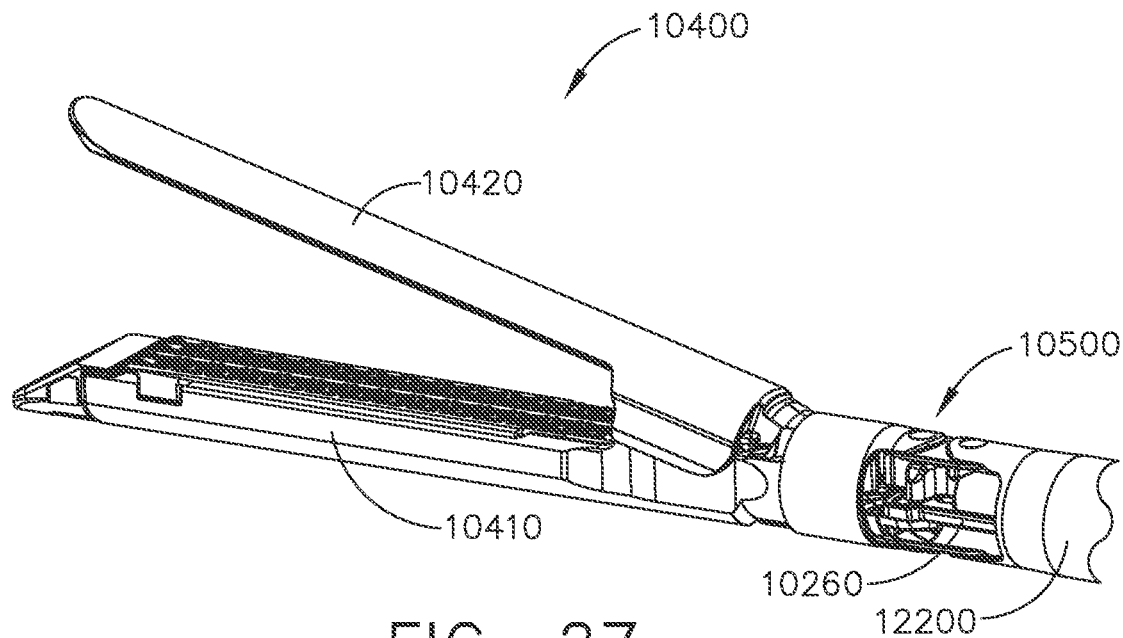
FIG. 27 illustrates a surgical instrument in accordance with at least one embodiment including an articulation joint, an end effector articulatable about the articulation joint, and a translatable articulation actuator configured to rotate the end effector about the articulation joint.
Figure 28:
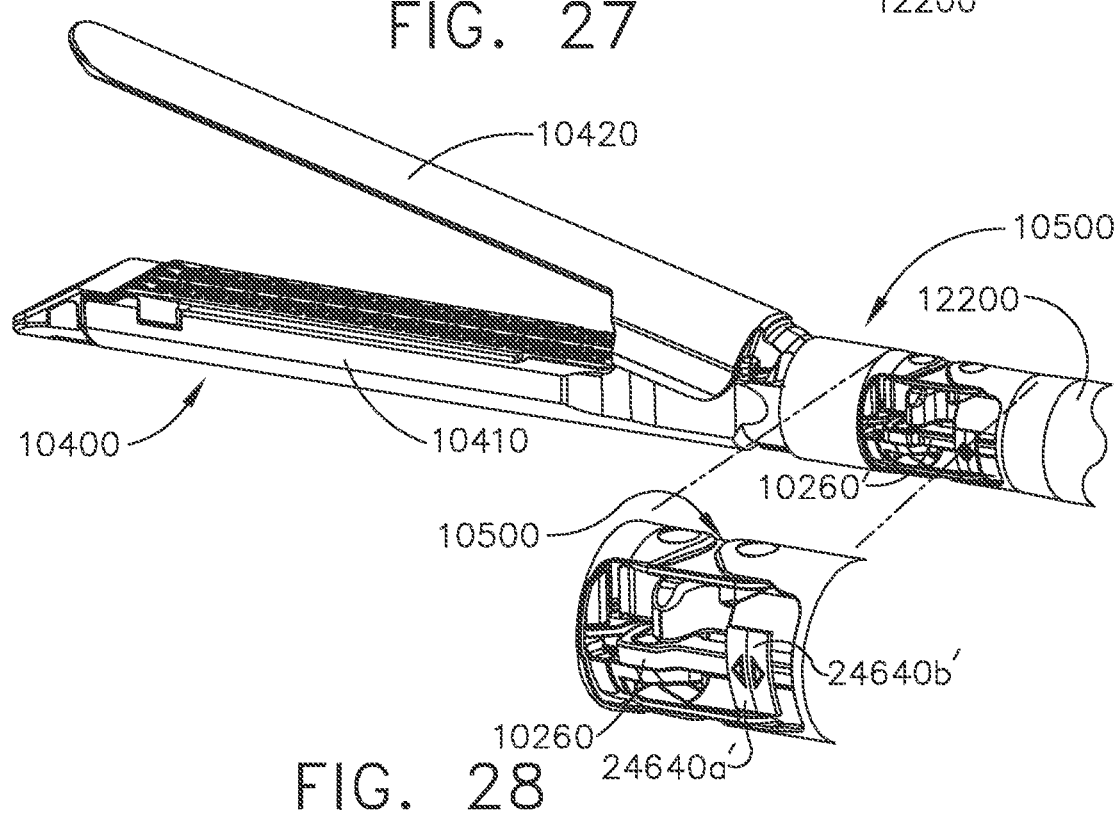
FIG. 28 is a partial perspective view of an articulatable end effector, an articulation actuator configured to rotate the end effector about an articulation joint, and demarcations on the articulation actuator which indicate the direction in which an end effector is articulated and/or is being articulated.

As discussed above, the articulation system of a surgical instrument can include an articulation driver which is movable proximally to articulate the end effector in a first direction and distally to articulate the end effector in a second direction. Referring to FIG. 27, a surgical instrument can comprise a handle 26100, a shaft 12200 extending from the handle 26100, and an end effector 10400 rotatably connected to the shaft 12200 about an articulation joint 10500. The shaft 12200 comprises an articulation driver 10260 comprising a proximal end operably coupled to an articulation drive system and a distal end coupled to the end effector 10400. To this end, the articulation driver 10260 extends distally past the articulation joint 10500 and, in this embodiment, is partially visible to a clinician holding the surgical instrument. The portion of the articulation driver 10260 visible to the clinician is also visible to the clinician through an endoscope monitor. In fact, a clinician may be able to observe the motion of the articulation driver 10260 through the endoscope monitor. The visible portion of the articulation driver 10260 comprises indicia, such as indicia 24640*a*' and 24640*b*', for example, thereon which correlates the movement of the articulation driver 10260 to the movement of the end effector 10400. In at least one instance, the indicia can comprise a first set of indicia which includes a distally-directed arrow 24640*a*' and a circular arrow indicating the direction that the end effector 10400 will be rotated if the articulation driver 10260 is moved distally. The indicia can also comprises a second set of indicia which includes a proximally-directed arrow 24640*b*' and a circular arrow in the opposite direction indicating the direction that the end effector 10400 will be rotated if the articulation driver 10260 is moved proximally. An alternative articulation driver 10260' is illustrated in FIG. 28 that comprises a laterally-extending portion which can be readily visible to the clinician. In such instances, the above-discussed indicia is positioned on the laterally-extending portion.

Figure 19:
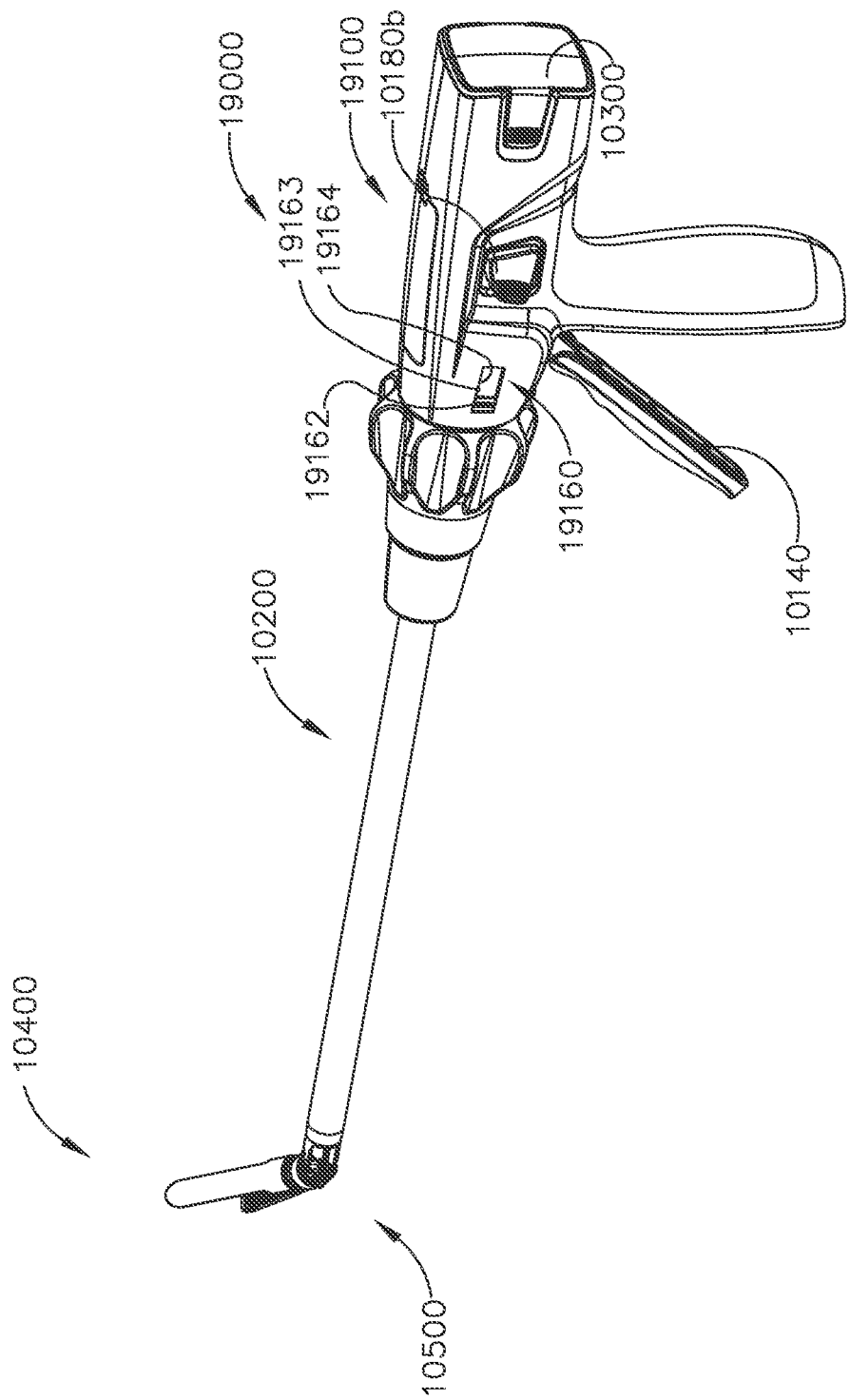
FIG. 19 is a perspective view of a surgical instrument in accordance with at least one embodiment including a slideable articulation switch including three positions—an articulate left position, an articulate right position, and a center, or home, position.

A surgical instrument 19000 is illustrated in FIG. 19. The surgical instrument 19000 is similar to the surgical instrument 15000 in many respects. The surgical instrument 19000 comprises a handle 19100 and a shaft 10200 extending from the handle 19100. The handle 19100 comprises an articulation actuator 19160 in communication with the control system of the surgical instrument 19000. As opposed to the articulation actuator 10160 which is arranged vertically, the articulation actuator 19160 is arranged horizontally. The articulation actuator 19160 comprises a slideable element 19162 which is slideable along an axis which is parallel to, or at least substantially parallel to, the longitudinal axis of the shaft 10200. In at least one instance, the axis of the articulation actuator 19160 is aligned with the longitudinal axis of the shaft 10200. The slideable element 19162 is positioned within a slot 19164 on the handle 19100 of the surgical instrument 19000. The slideable element 19162 is slideable distally to articulate the end effector 10400 to the right of the handle 19100 and proximally to articulate the end effector 10400 to the left of the handle 19100. This is true regardless of whether the end effector 10400 is rotated upwardly or downwardly owing to the control responsiveness flipping when the end effector 10400 is rotated past 90 degrees from its TDC position in either direction. That said, the controls of the articulation actuator 19160 can be reversed as outlined above.

The articulation actuator 19160 comprises a distal contact which is part of a first articulation control circuit and a proximal contact which is part of a second articulation control circuit. The slideable element 19162 engages the distal contact and closes the first articulation control circuit when the slideable element 19162 is in its distal position. The slideable element 19162 is not in contact with the proximal contact when the slideable element 19162 is in its distal position and, as such, the second articulation control circuit is open. Similarly, the slideable element 19162 engages the proximal contact and closes the second articulation control circuit when the slideable element 19162 is in its proximal position. Correspondingly, the slideable element 19162 is not in contact with the distal contact when the slideable element 19162 is in its proximal position and, as such, the first articulation control circuit is open. In any event, the articulation actuator 19160 comprises a detent 19163 in the middle of the range of motion of the slideable element 19162. The detent 19163 is configured to resist the motion of the slideable element 19162 as the slideable element 19162 moves from one side of the articulation actuator 19160 to the other. Such resistance to the motion of the slideable element 19162 can signal to the clinician that they will articulate the end effector 10400 in the opposite direction once they move the slideable element 19162 past that point. Moreover, such a detent 19163 provides a place to park the slideable element 19162 such that the end effector 10400 is not being articulated in either direction.

A surgical instrument 20000 is illustrated in FIG. 20. The surgical instrument 20000 is similar to the surgical instrument 10000 in many respects. The surgical instrument 20000 comprises a handle 20100 and a shaft 12200 extending from the handle 20100. The handle 20100 comprises an articulation actuator 20160 in communication with the control system of the surgical instrument 20000. The articulation actuator 20160 comprises a two-dimensional joystick movable within a plane which is aligned with, parallel to, or at least substantially parallel to, the longitudinal axis of the shaft 12200. The joystick is movable distally to articulate the end effector 10400 to the right of the handle 20100 and proximally to articulate the end effector 10400 to the left of the handle 20100. In at least one instance, the joystick comprises a handle having an inner end that is positioned in a sensor seat in communication with the control system of the surgical instrument 20000. The joystick is pivotable within the sensor seat by the clinician when the clinician manipulates the outer end of the joystick handle. Such movement of the joystick is detectable by the control system which operates the articulation system in response to the input from the sensor seat. The articulation actuator 20160 comprises one or more biasing mechanisms, such as springs, for example, configured to bias the joystick handle to a centered, or an at least substantially centered position, in the sensor seat in which the control system does not articulate the end effector 10400.

As discussed above, the end effector 10400 is articulatable within a plane. In alternative embodiments, a surgical instrument comprises a second articulation joint. In such embodiments, the end effector 10400 is rotatable within more than one plane. In various embodiments, a surgical instrument comprises an articulation joint which permits the end effector 10400 to be rotated within a three-dimensional spherical range of positions. Referring to FIG. 21, a surgical instrument 21000 comprises a shaft 21200 including an articulation joint 21500 which allows such articulation motion of the end effector 10400. The surgical instrument 21000 further comprises a handle 21100 including an articulation actuator 21160 in communication with a control system of the surgical instrument 21000. The articulation actuator 21160 comprises a three-dimensional joystick movable proximally, distally, upwardly, downwardly, and in compound directions. The joystick is movable distally to articulate the end effector to the right of the handle 20100 and proximally to articulate the end effector to the left of the handle 21100. The joystick is movable upwardly to articulate the end effector upwardly and downwardly to articulate the end effector downwardly, for example. The joystick is also movable in a direction which is both upward and distal to move the end effector in a direction which is both upward and to the right, for example. The joystick is also movable in a direction which is both downward and proximal to move the end effector in a direction which is both downward and to the left, for example. In at least one instance, the joystick comprises a handle having an inner end that is positioned in a sensor seat in communication with the control system of the surgical instrument 21000.

The joystick is orbitable within the sensor seat by the clinician when the clinician manipulates the outer end of the handle. Such movement of the joystick is detectable by the control system which operates the articulation system in response to the input from the sensor seat. The articulation actuator 21160 comprises one or more biasing mechanisms, such as springs, for example configured to bias the joystick handle to a centered, or an at least substantially centered position, in the sensor seat in which the control system does not articulate the end effector 10400.

A surgical instrument 22000 is illustrated in FIGS. 22A and 22B. The surgical instrument 22000 is similar to the surgical instrument 21000 in many respects. The surgical instrument 22000 comprises a handle 22100 and a shaft 21200 extending from the handle 22100. The handle 22100 comprises the articulation actuator 21160 positioned on the side of the handle 22100 and, in addition, an articulation actuator 22160 positioned on the front of the handle 22100. Similar to the articulation actuator 21160, the articulation actuator 22160 comprises a three-dimensional joystick in communication with the control system of the surgical instrument 21000 and is capable of articulating the end effector of the surgical instrument 21000 in a three-dimensional field. The front articulation actuator 22160 is readily accessible by the index finger of a clinician holding a pistol grip of the handle 22100. Alternative embodiments are envisioned which comprise the articulation actuator 22160, but not the articulation actuator 22160.

Figure 23:
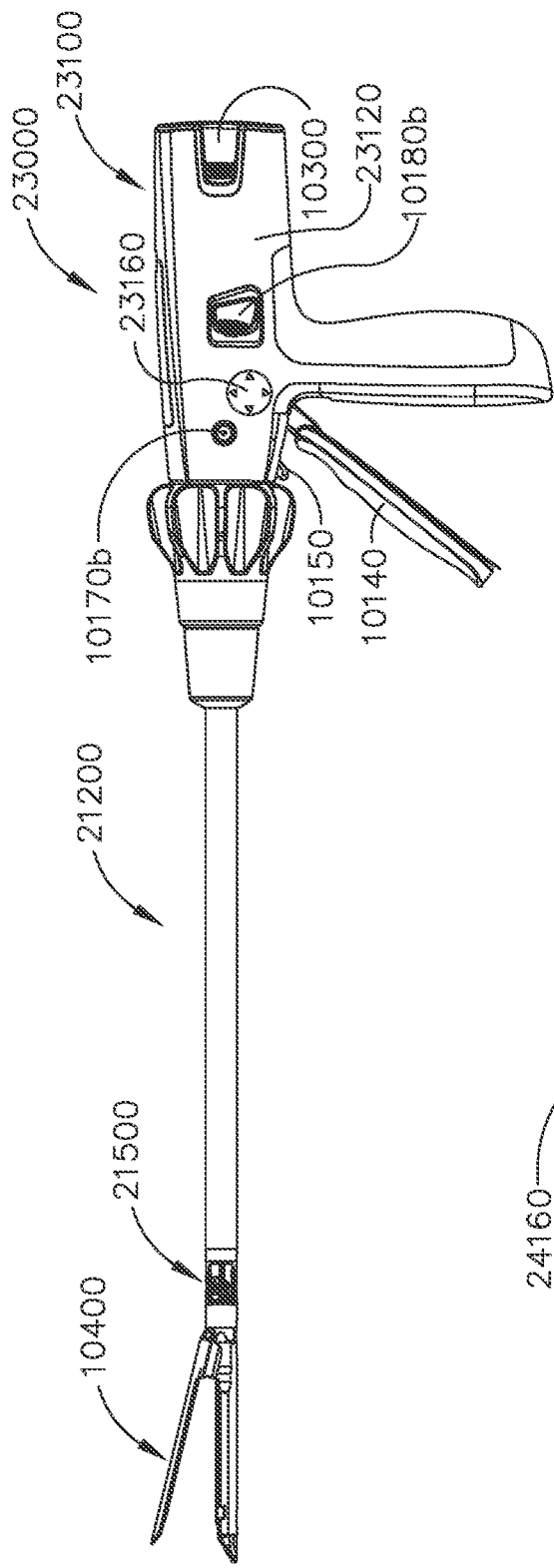
FIG. 23 is an elevational view of a surgical instrument in accordance with at least one embodiment including a 4-way tactile articulation control.

Referring to FIG. 23, a surgical instrument 23000 comprises a shaft 21200 including an articulation joint 21500 which allows for three-dimensional articulation motion of the end effector 10400. The surgical instrument 23000 further comprises a handle 23100 including a housing 23120 and, in addition, an articulation actuator 23160 in communication with a control system of the surgical instrument 23000. The articulation actuator 23160 comprises a four-way tactile control movable proximally, distally, upwardly, downwardly, and in compound directions. The four-way tactile control is movable distally to articulate the end effector to the right of the handle 23100 and proximally to articulate the end effector to the left of the handle 23100. The four-way tactile control is movable upwardly to articulate the end effector upwardly and downwardly to articulate the end effector downwardly. The four-way tactile control is also movable in a compound direction that is both upward and distal to move the end effector in a direction that is both upward and to the right, for example. The four-way tactile control is also movable in a compound direction that is both downward and proximal to move the end effector in a direction that is both downward and to the left, for example. In at least one instance, the four-way tactile control comprises four depressable actuators—one for each direction of right, left, up, and down—and each of which is part of a control circuit in communication with the control system of the surgical instrument 23000. The movement of the four-way tactile control is detectable by the control system which operates the articulation system in a three-dimensional range in response to the input from the articulation actuator 23160. The articulation actuator 23160 comprises one or more biasing mechanisms, such as springs, for example configured to bias the four-way tactile control to a centered, or an at least substantially centered position, in which the control system does not articulate the end effector 10400.

Figure 24:
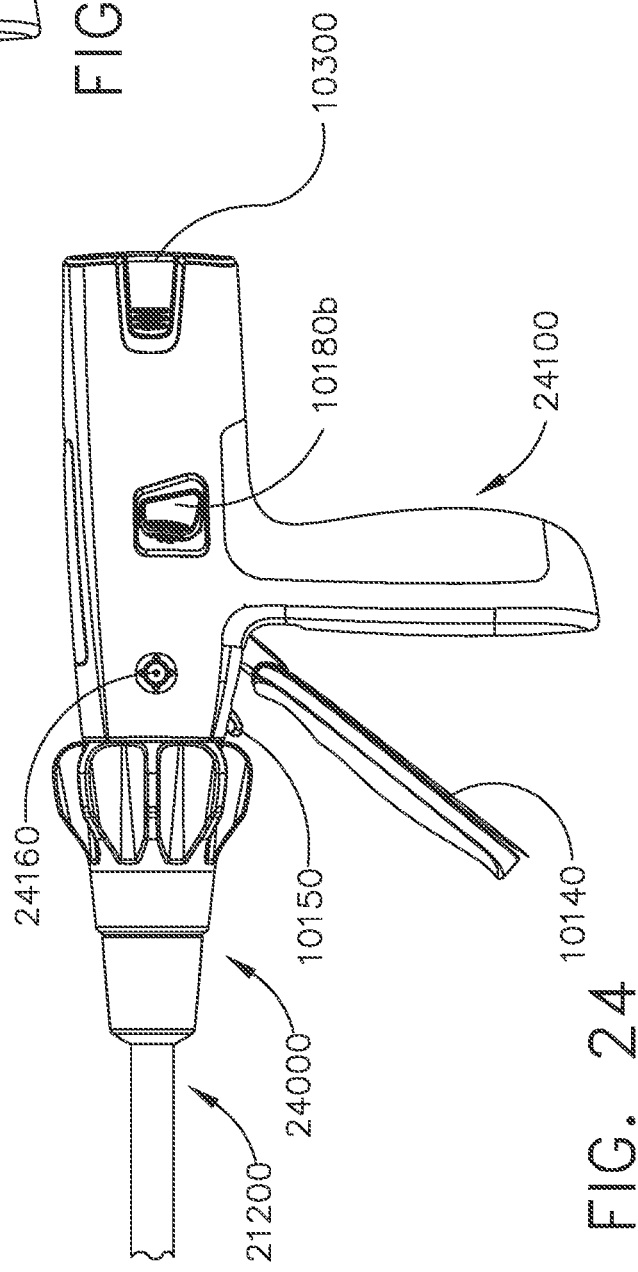
FIG. 24 is a partial elevational view of a surgical instrument in accordance with at least one embodiment including a 4-way tactile articulation control including a center, or home, actuator.

A surgical instrument 24000 is illustrated in FIG. 24. The surgical instrument 24000 is similar to the surgical instrument 23000 in many respects. The surgical instrument 24000 comprises a handle 24100 including an articulation actuator 24160. Similar to the articulation actuator 23160, the articulation actuator 24160 comprises a four-way tactile control. That said, the articulation actuator 24160 comprises an integral re-centering feature. More specifically, the articulation actuator 24160 comprises a depressable actuator positioned in the middle of the articulation actuator 24160 in communication with the control system of the surgical instrument 24000. When the center actuator is depressed, the control system operates to re-align the end effector 10400 with the longitudinal axis of the shaft 10200, much like the actuation of the actuator 10170 discussed above. As a result of the above, the re-centering actuator is positioned in the middle of the four directional actuators making for a compact and intuitive arrangement.

Figure 25:
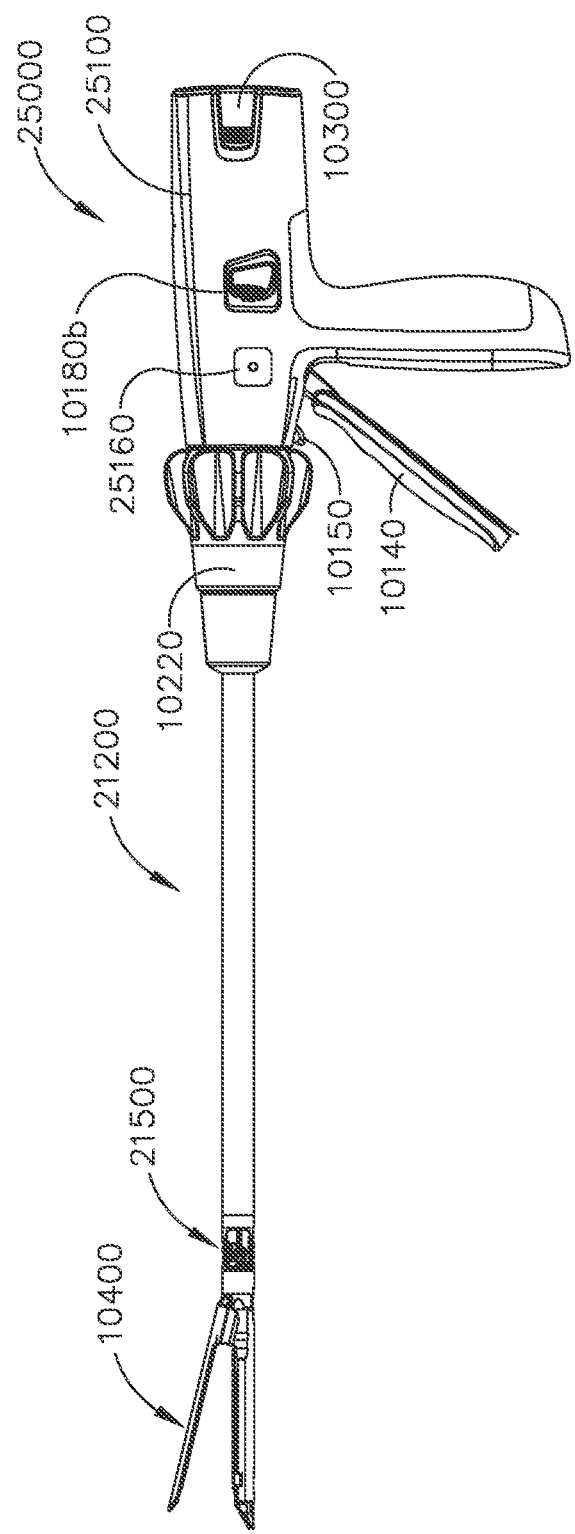
FIG. 25 is an elevational view of a surgical instrument in accordance with at least one embodiment including a 4-way capacitive surface.

A surgical instrument 25000 is illustrated in FIG. 25. The surgical instrument 25000 is similar to the surgical instrument 24000 in many respects. The surgical instrument 25000 comprises a handle 25100 including an articulation actuator 25160. Similar to the articulation actuator 23160, the articulation actuator 25160 comprises a four-way control in communication with a control system of the surgical instrument 25000. That said, the four-way control comprises a capacitive surface which allows a clinician to tap and/or drag their finger across the surface of the articulation actuator 25160 to control the articulation of the end effector in a three-dimensional range. In at least one instance, the articulation actuator comprises a touchscreen and an array of capacitive sensors positioned under the touchscreen configured to detect the presence and/or motion of the clinician's finger, for example. In use, tapping the top of the capacitive surface articulates the end effector 10400 upwardly, tapping the bottom of the capacitive surface articulates the end effector 10400 downwardly, tapping the distal end of the capacitive surface articulates the end effector 10400 to the right, and tapping the proximal end of the capacitive surface articulates the end effector 10400 to the left, for example.

Tapping the center of the articulation screen re-centers the end effector 10400 along the longitudinal axis of the shaft 21200. When a rotating motion is made on the surface of the articulation actuator 25160, the control system rotates the end effector 10400 in the direction and/or speed indicated by the rotating motion. In various instances, the control system of the surgical instrument 25000 comprises a pulse width modulation (PWM) control circuit for controlling the speed of the electric motor used to drive the articulation system of the surgical instrument 25000. In at least one embodiment, the control system comprises a frequency modulation (FM) control circuit in addition to or in lieu of the PWM control circuit for controlling the speed of the articulation motor.

As discussed above, an end effector of a surgical instrument can be rotatable in more than one direction and/or plane. To achieve this, in various embodiments, a surgical instrument comprises a first motor-driven system for moving the end effector in a left-to-right manner and a second motor-driven system for moving the end effector in an up-to-down manner. Both motor-driven systems are in communication with the control system of the surgical instrument and are drivable sequentially and/or concurrently by the control system to position the end effector in the direction indicated by the input from the articulation actuator, or articulation actuators.

Figure 29:
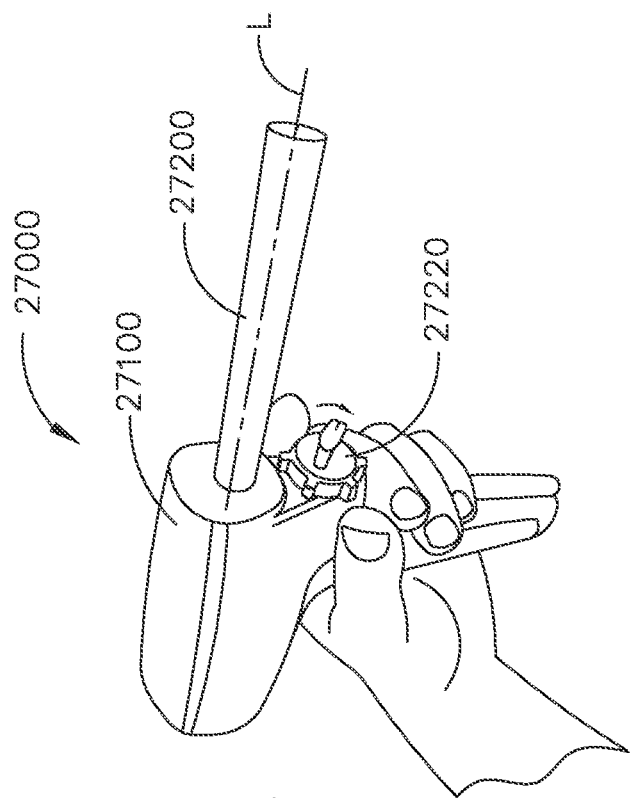
FIG. 29 is a perspective view of a surgical instrument in accordance with at least one embodiment comprising a handle, a rotatable shaft extending from the handle, and a rotatable actuator on the handle configured to rotate the shaft about a longitudinal axis.
Figure 30:
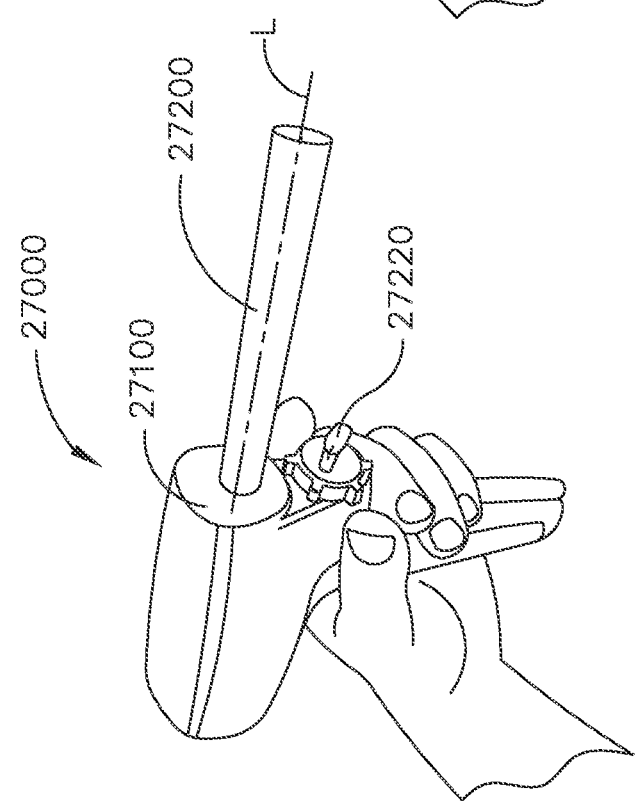
FIG. 30 is a perspective view of the surgical instrument of FIG. 29 illustrating the shaft in a rotated position.
Figure 31:
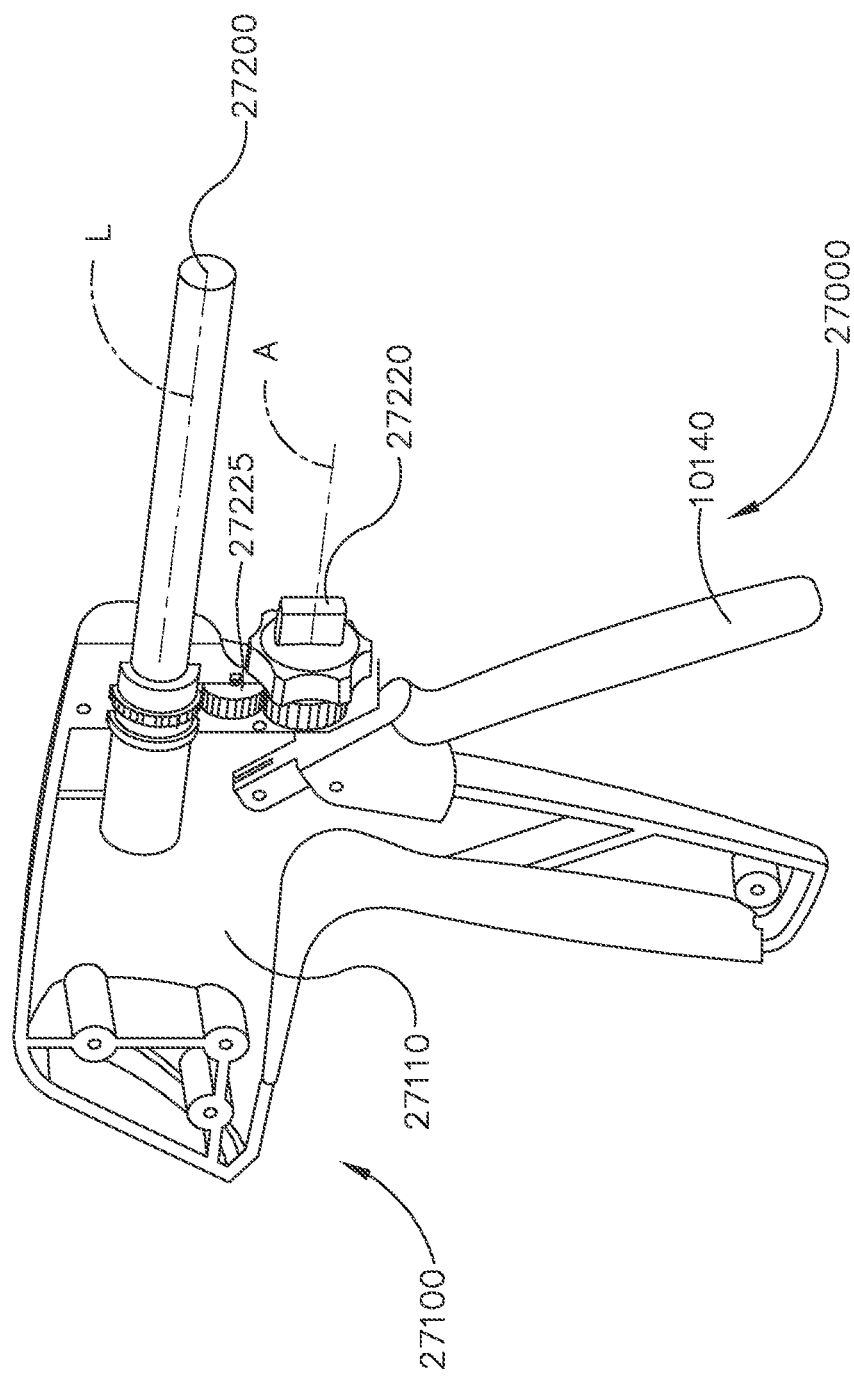
FIG. 31 is a perspective view of the surgical instrument of FIG. 29 illustrated with a portion of the handle housing removed.

Many of the surgical instruments described above comprise a grip configured to be grasped by a clinician to rotate the shaft about a longitudinal axis. In various instances, the clinician can hold the grip with one hand and can extend their index finger, for example, from that hand to grab the grip and rotate the shaft. Such an arrangement, however, requires the clinician to have a somewhat larger hand. While such a surgical instrument can be operated with one hand, a surgical instrument 27000 is illustrated in FIGS. 29 and 30 that may be easier to use. The surgical instrument 27000 comprises a handle 27100 and a shaft 27200 extending from the handle 27100 that is rotatable about a longitudinal axis. The handle 27100 comprises a handle frame 27110 and a housing that rotatably support the shaft 27200. The handle 27100 further comprises an actuator 27220 positioned on the front side of the handle housing 27110 which, when rotated by the clinician, rotates the shaft 27200 about its longitudinal axis L. The actuator 27220 is rotatably mounted to the handle housing 27110 and is rotatable about an axis A which is parallel to, or at least substantially parallel to, the longitudinal axis of the shaft 27200. The actuator 27220 comprises a ring of gear teeth extending around its perimeter which is operably engaged with a ring of gear teeth extending around the perimeter of the shaft 27200 via a transmission gear 27225 such that, when the actuator 27220 is rotated about its axis, the shaft 27200 is rotated about its longitudinal axis. That said, the gear teeth of the actuator 27220 are not directly engaged with the gear teeth of the shaft 27200; instead, the intermediate gear 27225—which is rotatably mounted in the handle 27100—is directly engaged with the gear teeth of the actuator 27220 and the shaft 27200. Such an arrangement synchronizes the motion of the actuator 27220 and the shaft 27200, i.e., rotating the actuator 27220 to the right rotates the shaft 27200 to the right and rotating the actuator 27220 to the left rotates the shaft 27200 to the left. Absent the introduction of the intermediate gear 27225, the shaft 27200 would rotate in an opposite direction, but such an arrangement may provide a torque balance that promotes the stability of the instrument.

Further to the above, embodiments are envisioned in which the rotation of the shaft 27200 is driven by an electric motor. In various embodiments, the actuator 27220, when rotated in the first direction, operates the electric motor to rotate the shaft 27200 in the first direction. Similarly, the electric motor rotates the shaft 27200 in the second direction when the actuator 27220 is rotated in the second direction. In at least one embodiment, the output shaft of the electric motor comprises a pinion gear operably intermeshed with the ring of gear teeth around the shaft 27200. Moreover, in at least one embodiment, the actuator 27220 comprises one or more sensors configured to detect the direction and degree of rotation of the actuator 27220 which are in communication with a control system of the surgical instrument. With this data, the control system is configured to control the direction and speed of the electric motor. In instances where the actuator 27220 is rotated a small amount in the first direction, for example, the shaft 27220 is rotated slowly in the first direction whereas the shaft 27220 is rotated quickly in the first direction when the actuator 27220 is rotated a larger amount in the first direction.

Further to the above, the actuator 27220 comprises a bar including a first end and a second end. The orientation of the bar is synchronized with the orientation of the shaft 27200. When the first end of the bar is directly above the second end, i.e., the first end is closest to the shaft 27200, the shaft 27200 is in its top-dead-center (TDC) position. Correspondingly, the shaft 27200 is in its bottom-dead-center (BDC) position when the second end of the bar is directly above the first end, i.e., the second end is closest to the shaft 27200. As a result of this arrangement, the user of the surgical instrument has an intuitive feel of the orientation of the shaft 27200 based on the orientation of the actuator 27220.

Figure 51:
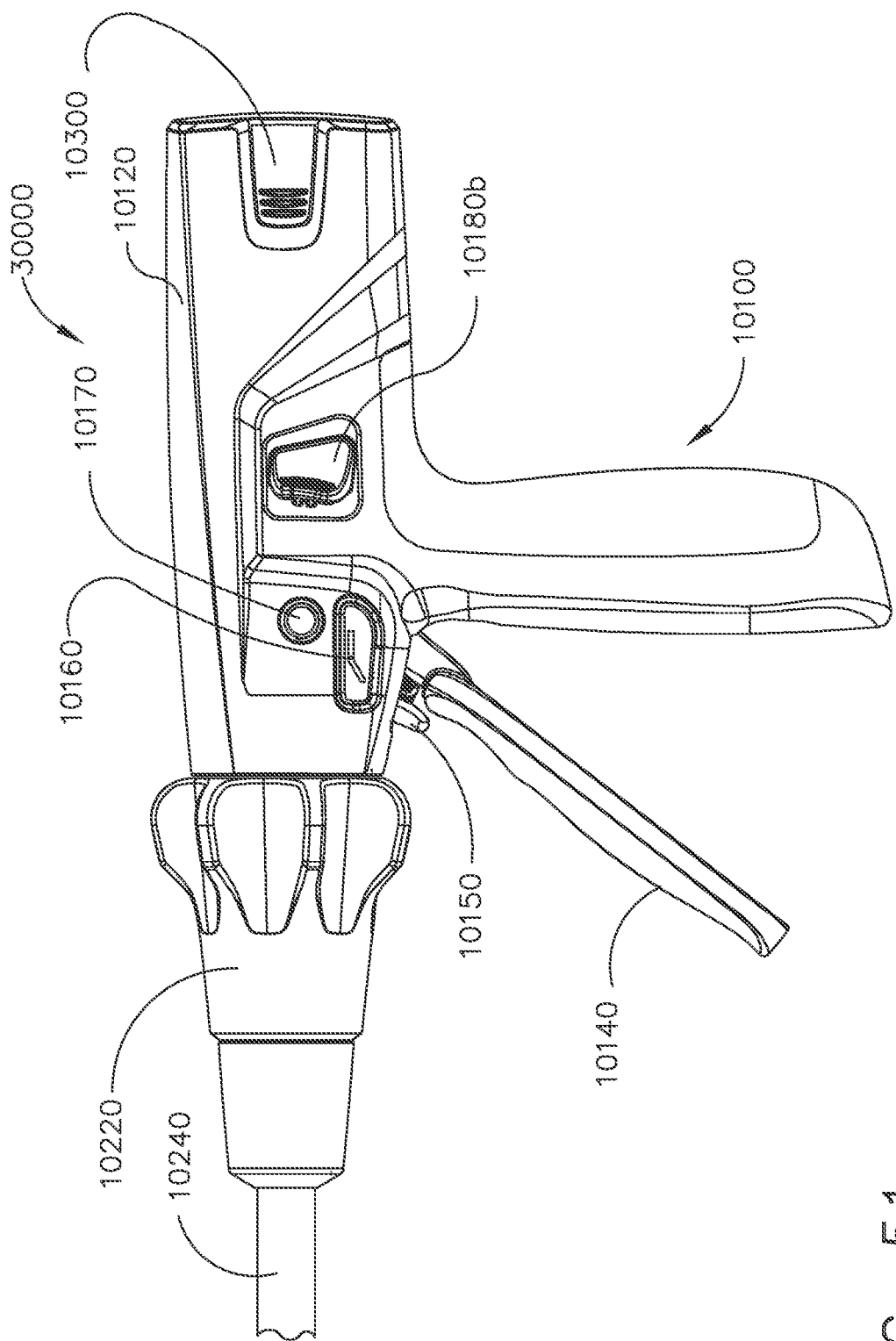
FIG. 51 is a partial elevational view of a surgical instrument in accordance with at least one embodiment.
Figure 52:
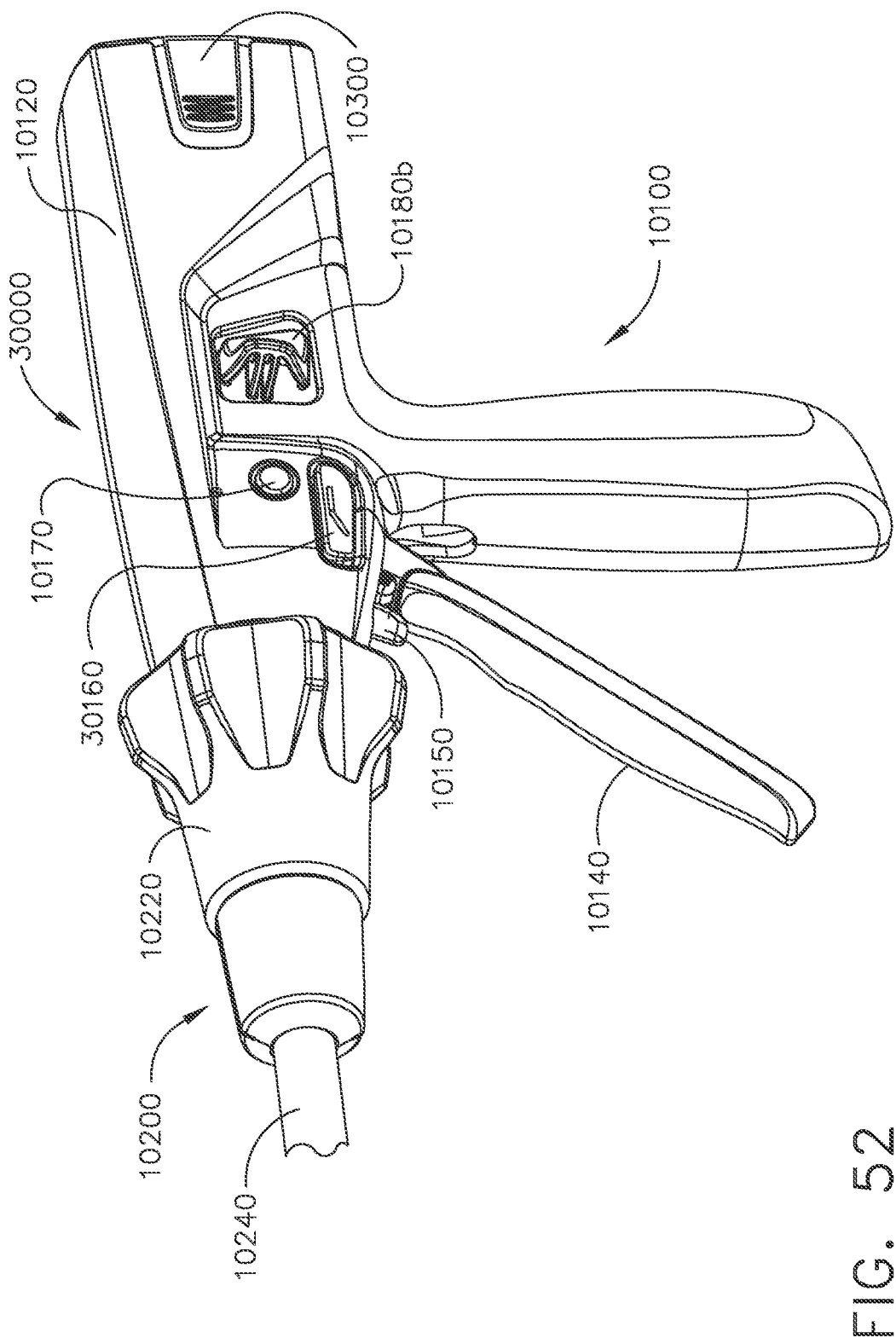
FIG. 52 is a partial perspective view of the surgical instrument of FIG. 51.
Figure 53:
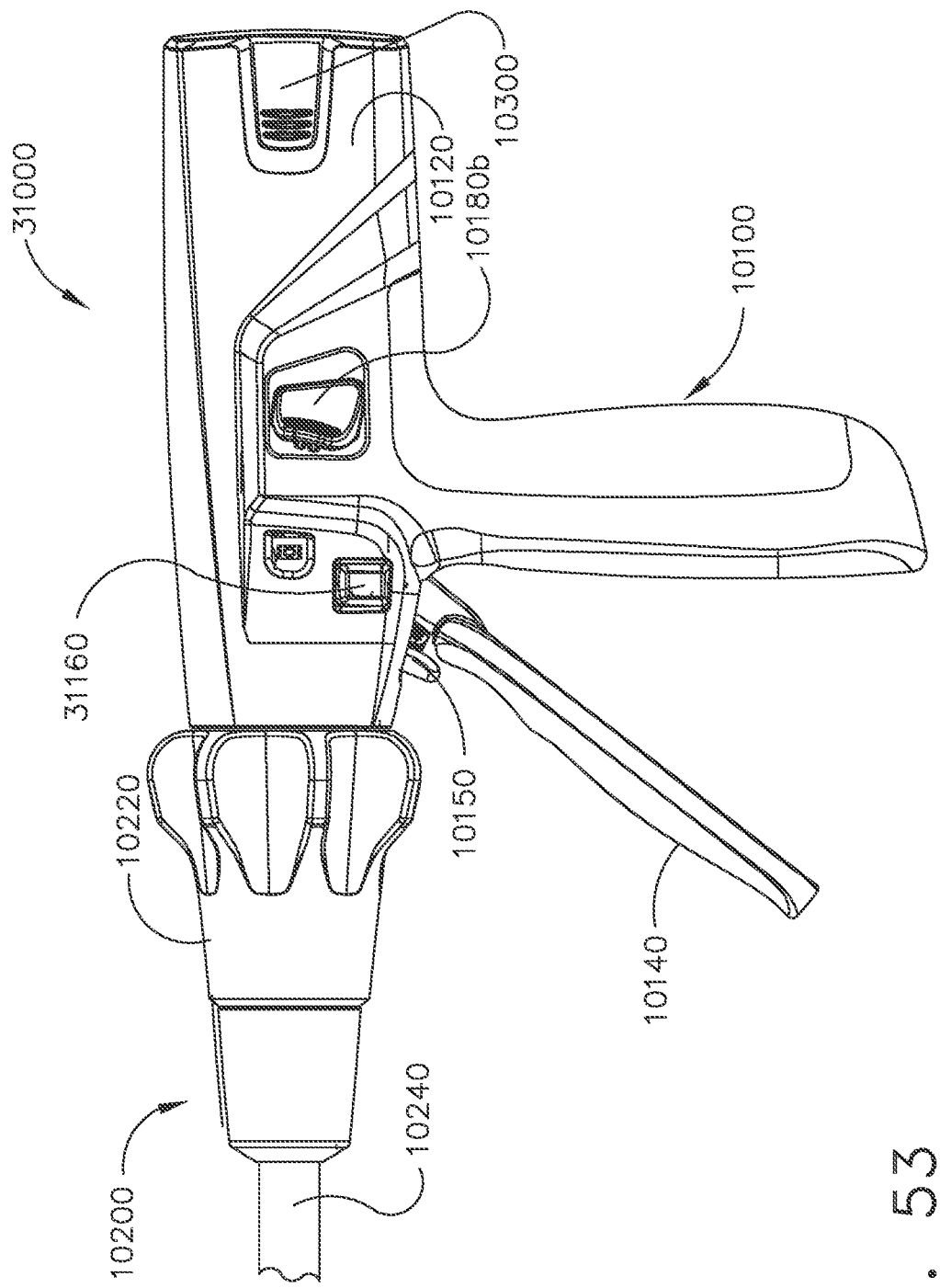
FIG. 53 is a partial elevational view of a surgical instrument in accordance with at least one embodiment.
Figure 54:
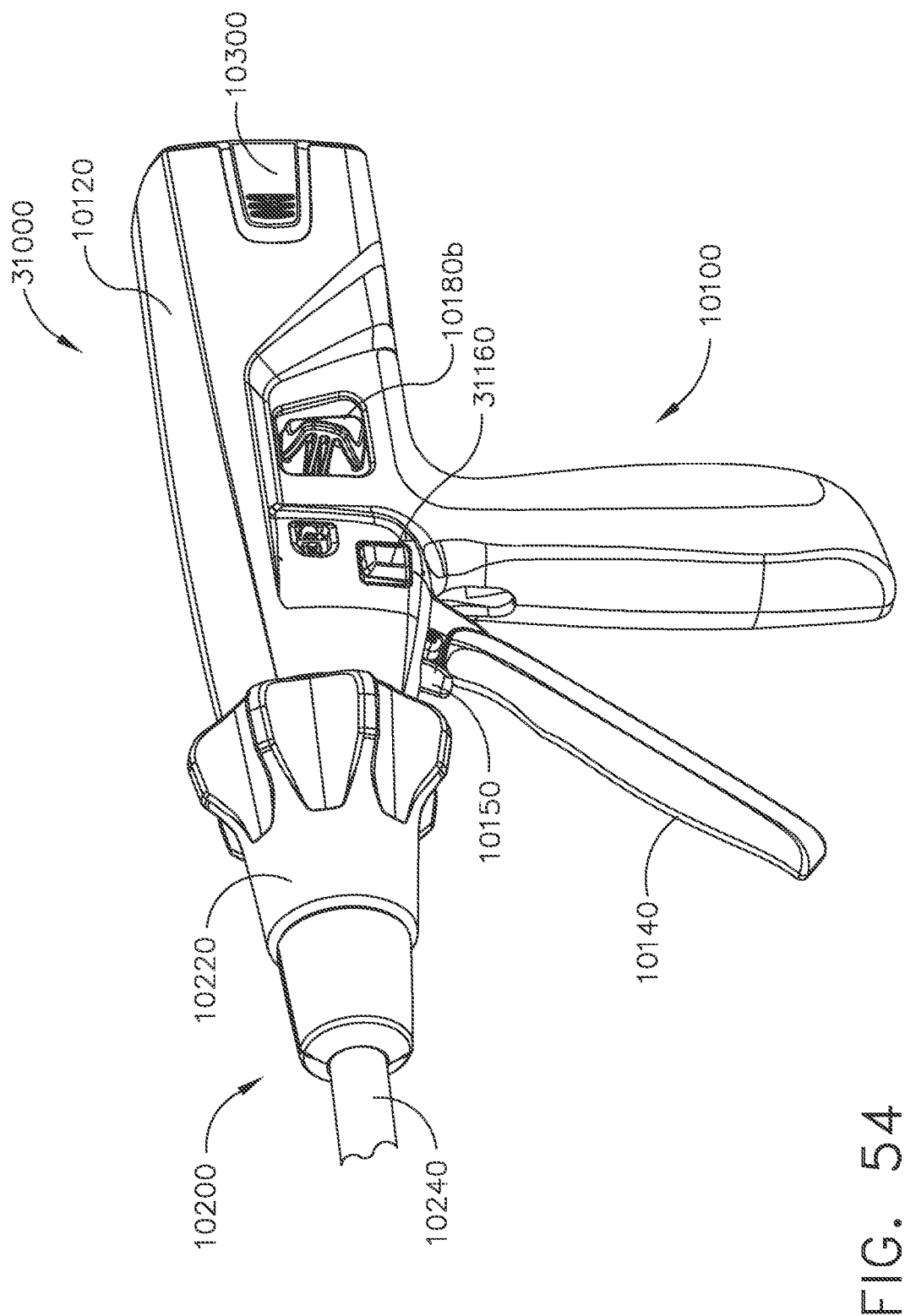
FIG. 54 is a partial perspective view of the surgical instrument of FIG. 53.

A surgical instrument 30000 is illustrated in FIGS. 51 and 52. The surgical instrument is similar to the surgical instrument 10000 in many respects. As opposed to the vertical articulation actuator 10160, the handle of the surgical instrument 30000 comprises a horizontal articulation actuator 30160. The horizontal articulation actuator 30160 comprises a rocker switch which can be rocked distally to rotate the end effector to the right and rocked proximally to rotate the end effector to the left. A surgical instrument 31000 is illustrated in FIGS. 53 and 54. The surgical instrument is similar to the surgical instrument 10000 in many respects. As opposed to the vertical articulation actuator 10160, the handle of the surgical instrument 31000 comprises an articulation actuator 31160. The articulation actuator 31160 comprises a multi-axis rocker switch that can be rocked proximal-to-distal to articulate the end effector in one plane and up-to-down to articulate the end effector in another plane. In various instances, the articulation planes are orthogonal to one another, but can be arranged in any suitable manner.

Figure 59:
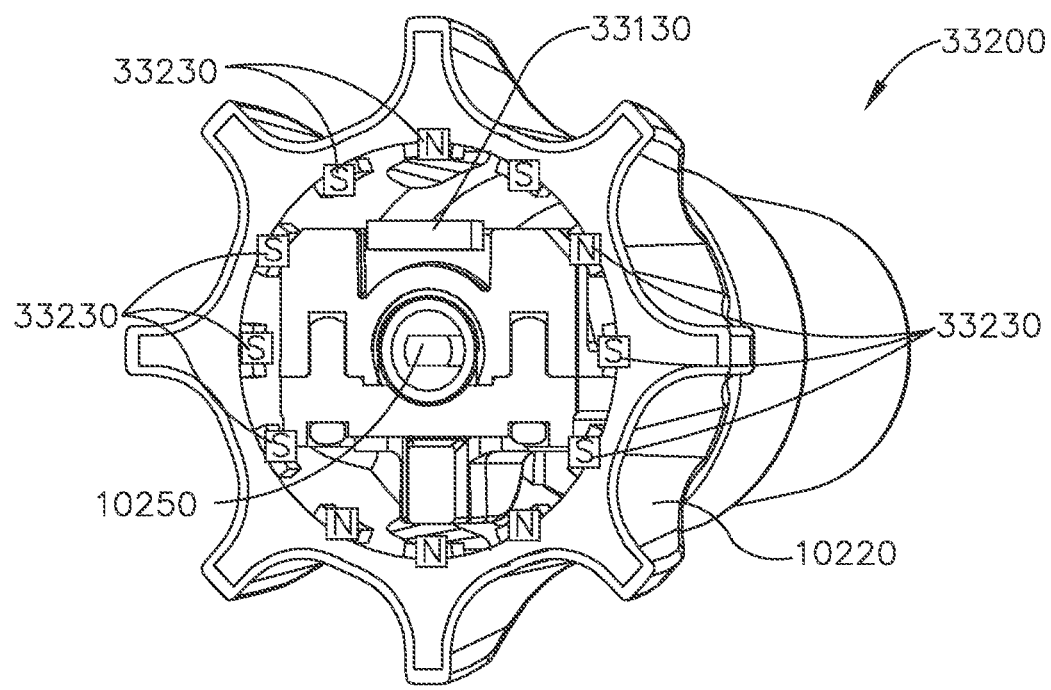
FIG. 59 is a partial perspective view of a shaft of a surgical instrument in accordance with at least one embodiment.

As discussed above, the control system of a surgical instrument can comprise an algorithm which, according to predetermined criteria, flips and/or otherwise re-orients the controls of the surgical instrument in certain instances. In various instances, as also discussed above, the algorithm can be configured to flip the articulation controls of the surgical instrument based on the rotation of the shaft relative to the handle. Referring to FIG. 59, a surgical instrument comprises a handle comprising a Hall Effect sensor 33130, and/or any other suitable sensor, in communication with the control system of the surgical instrument and, in addition, a shaft 33200 including an array of magnets 33230 arranged in a circular, or annular, pattern around the shroud, or grip, 10220 of the shaft 33200. Each magnet 33230 comprises a north pole (N) and a south pole (S) and the magnets 33230 are arranged in the manner indicated in FIG. 59—the N poles of some of the magnets 33230 are facing the handle while some S poles are facing toward the handle. When the shaft 33200 is rotated relative to the handle, this arrangement of the magnets 33230 allows the control system to track the position of the shaft 33200 and understand the orientation, or rotation, of the shaft 33200 relative to the handle. Within any three consecutive magnets 33230, for example, the pattern of magnets 33230 create a unique identifiable signature for a given rotation direction. That said, any suitable number and/or arrangement of discrete magnets could be used. Although twelve magnets 33230 are used, less than twelve magnets could be used—such as six magnets, for example. Moreover, more than twelve magnets could be used.

Figure 60:
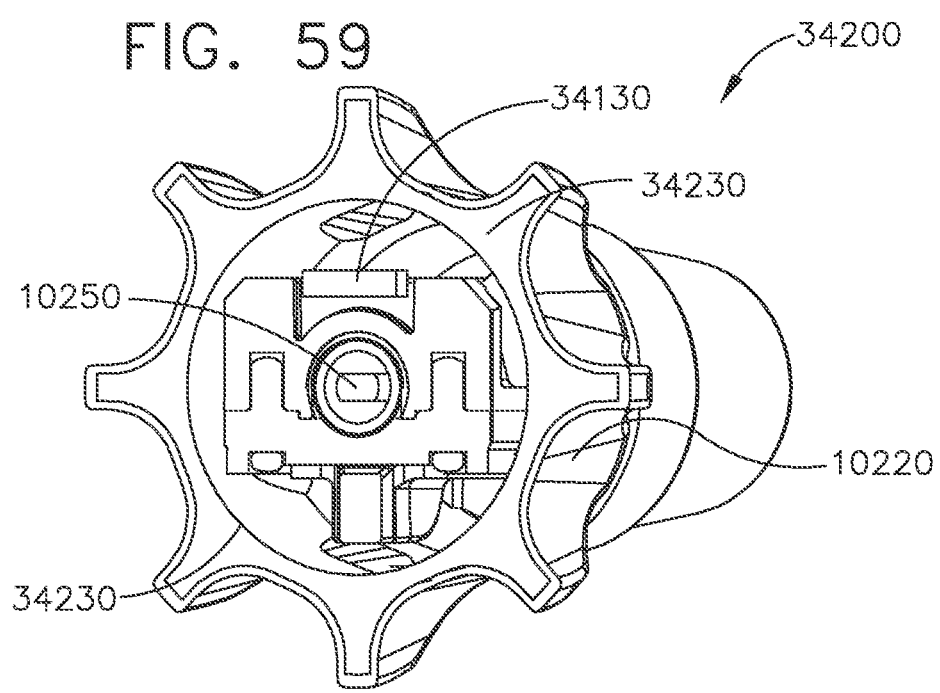
FIG. 60 is a partial perspective view of a shaft of a surgical instrument in accordance with at least one embodiment.

Referring to FIG. 60, a surgical instrument comprises a handle comprising a Hall Effect sensor 34130, and/or any other suitable sensor, in communication with the control system of the surgical instrument and, in addition, a shaft 34200 including a continuous annular magnet 34230 attached to the shroud, or grip, 10220 of the shaft 34200. In various instances, the annular magnet 34230 comprises a disc or ring embedded with magnetic microstructures which is detectable by the Hall Effect sensor. The annular magnet 34230 comprises a continuous, but varying, magnetic pattern around the perimeter thereof which provides a trackable pattern for the control system to assess the orientation, or rotation, of the shaft 34200. In other embodiments, the annular magnet 34230 comprises an intermittent magnetic pattern around the perimeter thereof that is trackable by the control system.

Figure 61:
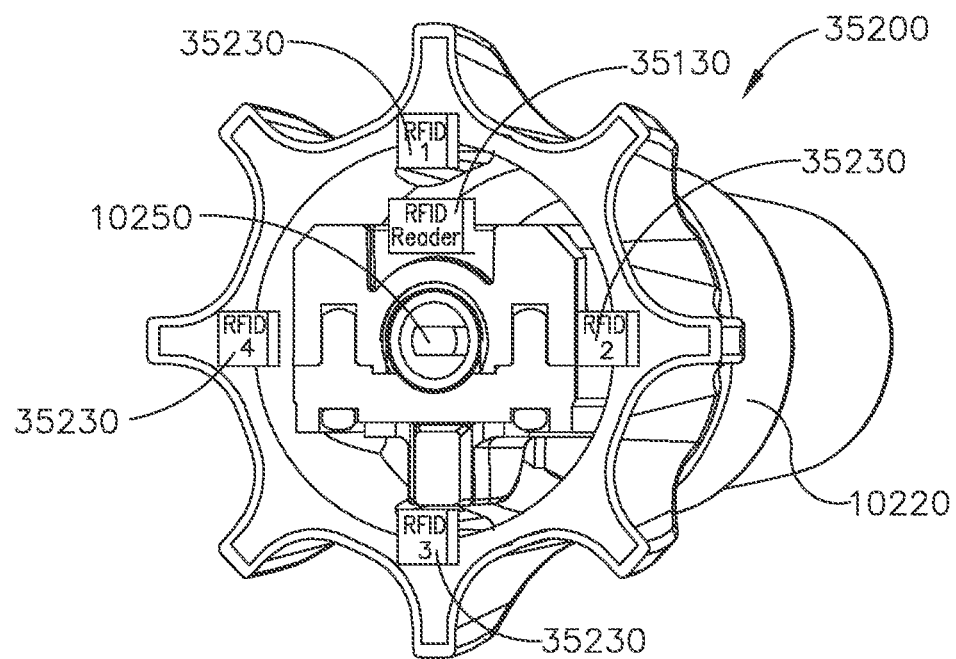
FIG. 61 is a partial perspective view of a shaft of a surgical instrument in accordance with at least one embodiment.

Referring to FIG. 61, a surgical instrument comprises a handle comprising a RFID reader 35130 in communication with the control system of the surgical instrument and, in addition, a shaft 35200 including a circular, or annular, array of RFID chips 35230 around the shroud, or grip, 10220 of the shaft 35200. Each RFID chip comprises a unique identification which is detectable by the RFID reader 35130 and, with this information, the control system is able to assess the orientation, or rotation, of the shaft 35200 relative to the handle. Notably, the RFID reader 35130 has a limited range to read the RFID chips 35230 and, thus, may be only able to read the most-adjacent RFID chip 35230. In some instances, the RFID reader 35130 can have sufficient range to read the two most-adjacent RFID chips 35230. The shaft 35200 comprises four RFID chips 35230, but can comprise any suitable number of RFID chips 35230. That said, the accuracy, or resolution, of the assessment made by the control system can be improved with more RFID chips in various instances.

Figure 62:
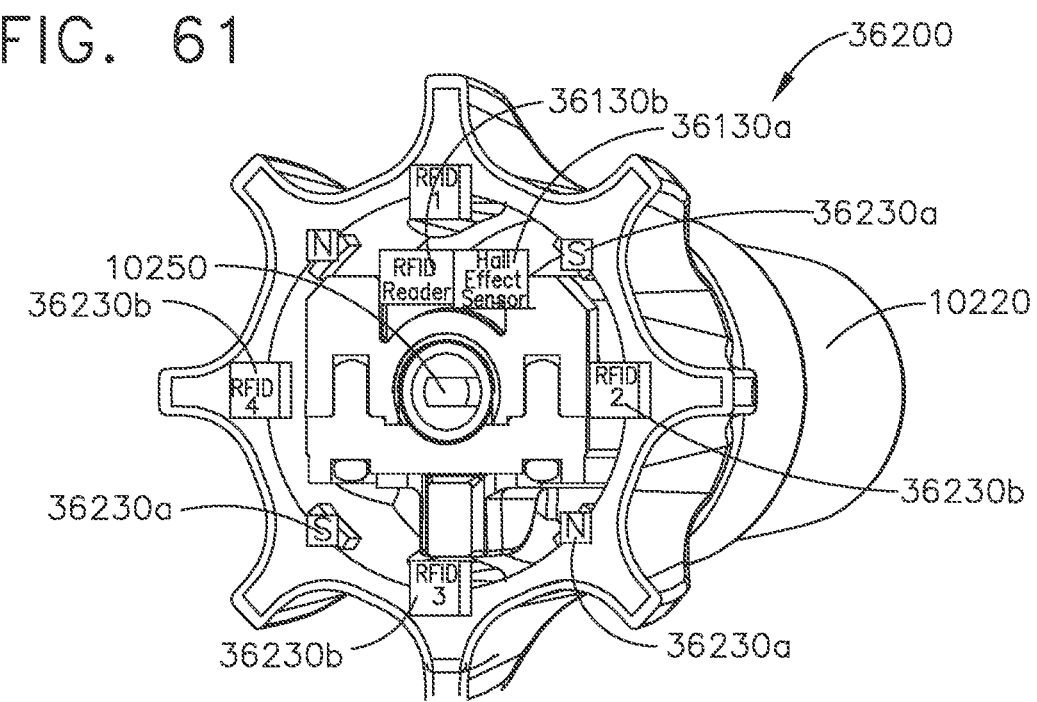
FIG. 62 is a partial perspective view of a shaft of a surgical instrument in accordance with at least one embodiment.

Referring to FIG. 62, a surgical instrument comprises a handle comprising a Hall Effect sensor 36130*a*, and/or any other suitable sensor, in communication with the control system of the surgical instrument and, in addition, a shaft 36200 including an array of magnets 36230*a* arranged in a circular, or annular, pattern around the shroud of the shaft 36200. The handle also comprises a RFID reader 36130*b* in communication with the control system of the surgical instrument and, in addition, a circular, or annular, array of RFID chips 36230*b* around the shroud of the shaft 36200. The control system is configured to use the data from the Hall Effect sensor 36130*a* and the RFID reader 36130*b* to assess the orientation of the shaft 36200 relative to the handle. Notably, the RFID chips 36230*b* are positioned intermediate the magnets 36230*a* which provides the control system with a detectable resolution between adjacent magnets 36230*a*. Similarly, the magnets 36230*a* are positioned intermediate the RFID chips 36230*b* which provides the control system with a detectable resolution between the RFID chips 36230*b*.

Figure 63:
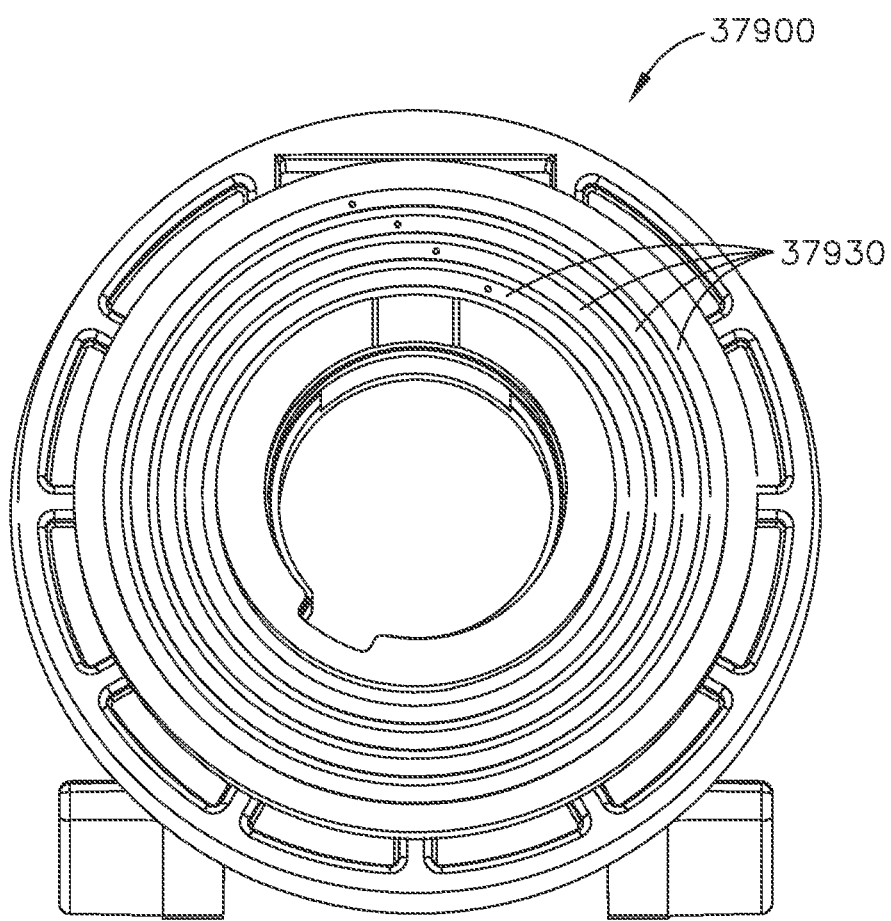
FIG. 63 is a perspective view of a slip ring assembly of a surgical instrument in accordance with at least one embodiment.
Figure 64:
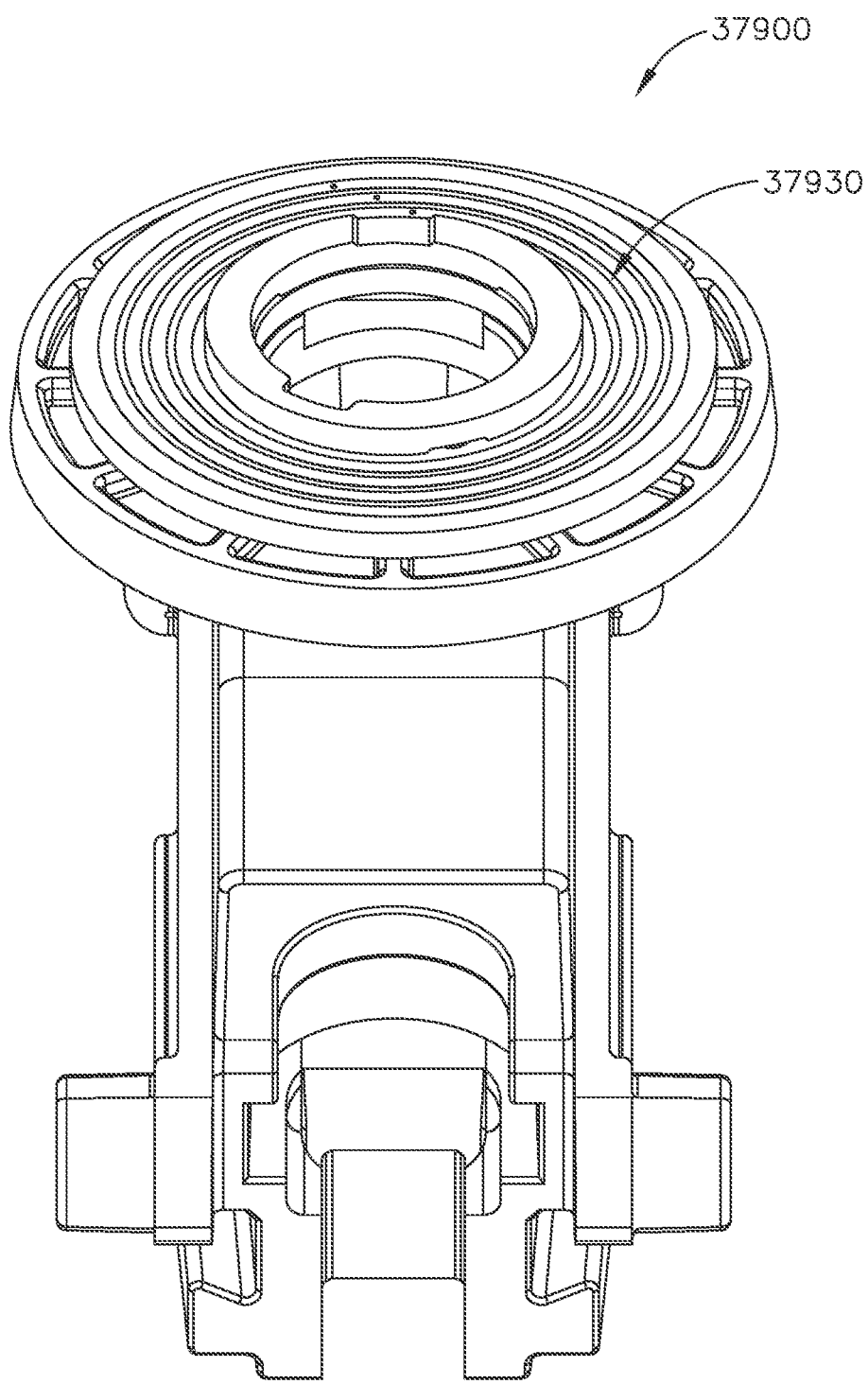
FIG. 64 is another perspective view of the slip ring assembly of FIG. 63.
Figure 65:
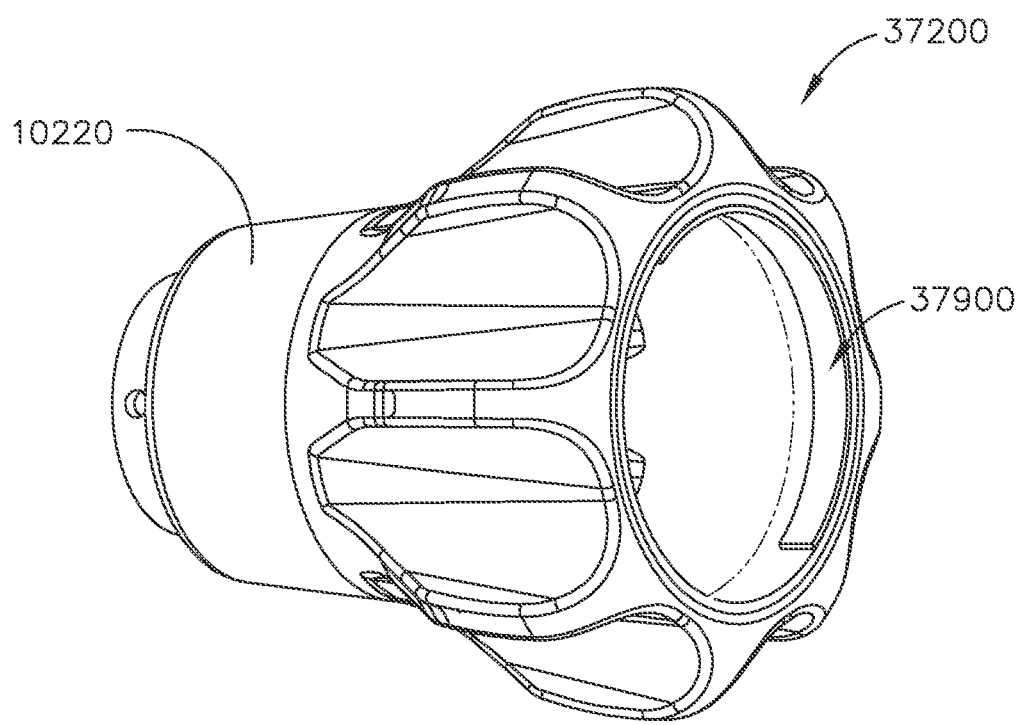
FIG. 65 is a perspective view of a shaft component of the surgical instrument of FIG. 63.
Figure 66:
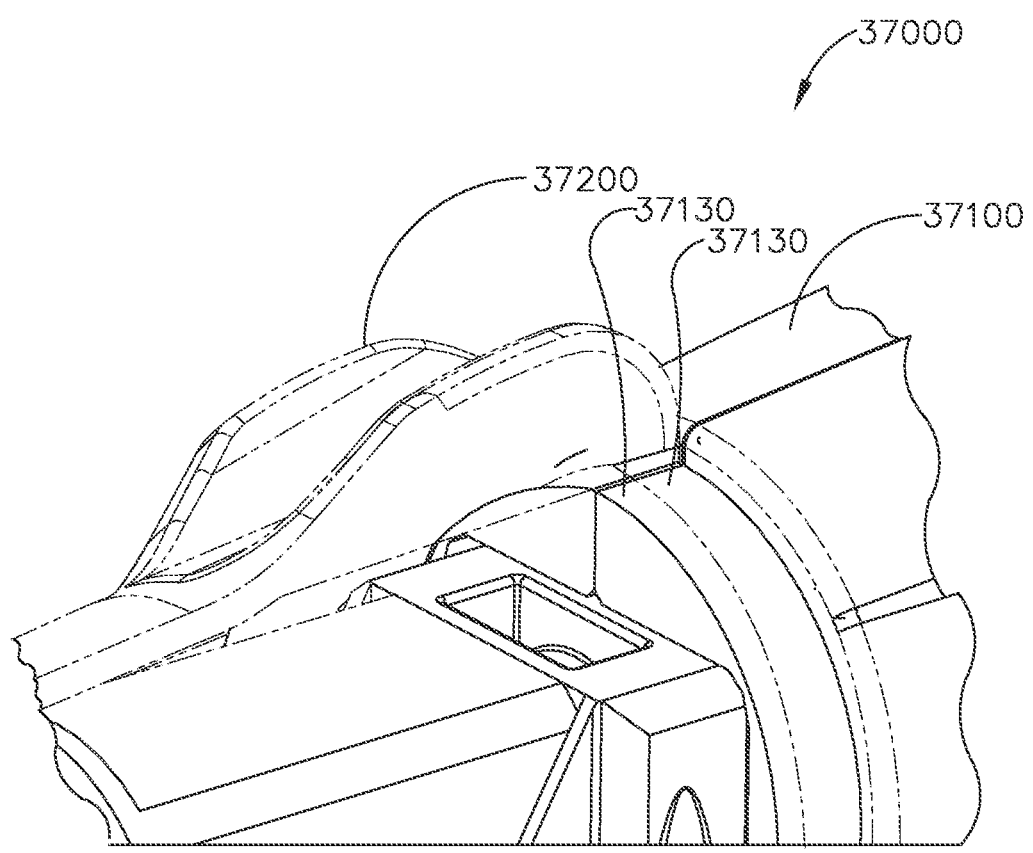
FIG. 66 is a partial perspective view of the surgical instrument of FIG. 63.

A surgical instrument 37000 is illustrated in FIGS. 63-66. The surgical instrument 37000 comprises a handle 37100 and a shaft 37200 extending from the handle 37100. The surgical instrument 37000 further comprises a slip joint 37900 between the handle 37100 and the shaft 37200. The slip joint 37900 comprises an electrical interface between the handle 37100 and the shaft 37200. The slip joint 37900 comprises annular rings 37930 mounted in the shaft 37200. Four annular rings 37930 are depicted in FIGS. 63 and 64, but a slip joint can comprise any suitable number of rings. The slip joint 37900 further comprises electrical contacts 37130 in the handle 37100. For instance, the slip joint 37900 comprises a first electrical contact 37130 engaged with a first annular ring 37930 and a second electrical contact 37130 engaged with a second annular ring 37930. That said, the slip joint 37900 can comprise any suitable number of electrical contacts to maintain power and/or signal communication between the handle and the shaft. Throughout the rotation of the shaft 37200, i.e., all 360 degrees, the electrical contacts 37130 remain in electrical contact with their respective annular rings 37930. In various instances, each electrical contact 37130 comprises a spring element configured to bias the electrical contact towards its respective annular ring 37930. The electrical contacts 37130 are in communication with the control system of the surgical instrument 37000—via separate circuits—such that the control system can assess the resistance of the circuits, and/or any other electrical properties of the circuits between the control system and the slip joint 37900. That said, the electrical contacts and rings of the slip joint 37900 can be part of any suitable circuit arrangement.

Further to the above, the slip joint 37900 can be used as an absolute position sensor for the shaft 37200 relative to the handle 37100. More specifically, an intermediate annular ring 37930, i.e., the annular ring 37930 between the first ring 37930 and the second ring 37930, can be used by the control system to assess the orientation of the shaft 37200. To this end, the slip joint 37900 comprises an intermediate electrical contact 37130 in electrical communication with the intermediate annular ring 37930 and the control system as part of an intermediate electrical circuit. The intermediate annular ring 37930 is comprised of a high-resistance material, as compared to the first and second annular rings 37930, and provides a 10,000 Ohm resistance, for example. The intermediate annular ring 37930 has a first portion which is electrically coupled to the first annular ring 37930, a second annular portion which is electrically coupled to the second annular ring 37930, and a small break therebetween. When the shaft 37200 is rotated relative to the handle 37100, the intermediate electrical contact 37130 slides along the intermediate annular ring 37930 and the resistance and voltage of the intermediate electrical circuit changes in a manner which is detectable by the control system owing to the closing and opening of the break by the intermediate contact 37130. The signal from the intermediate electrical circuit is digitized by an analog-digital converter of the control system, the data from which is usable by the control system to assess the orientation of the shaft 37200. In various instances, any suitable number of gaps in the intermediate annular ring 37930 and/or intermediate contacts 37130 can be used to provide a signal with sufficient resolution to determine the orientation, or rotation, of the shaft 37200 relative to the handle 37100.

In various embodiments, a resistive material is embedded in the shaft of a surgical instrument which is part of an electrical circuit that passes through a slip ring. As the shaft rotates, the resistance in the electrical circuit changes—which is detectable by the control system of the surgical instrument to assess the angular orientation of the shaft relative to the handle.

Figure 67:
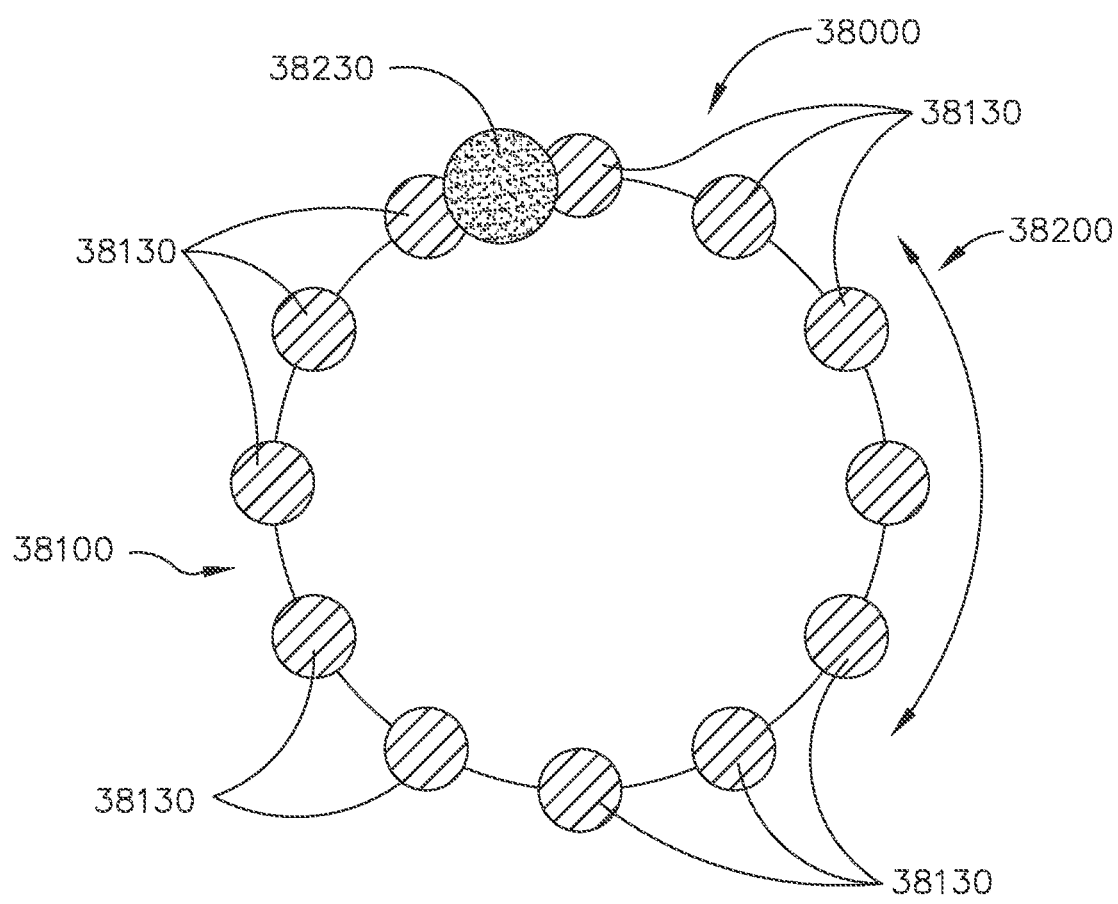
FIG. 67 is a diagram depicting a shaft orientation sensor array in accordance with at least one embodiment.

A representation of a surgical instrument 38000 is illustrated in FIG. 67. The surgical instrument 38000 comprises a handle 38100 and a shaft 38200 extending from the handle 38100. The handle 38100 comprises an annular array of Hall Effect sensors 38130 affixed to the frame and/or housing of the handle 38100. The Hall Effect sensors 38130 are positioned along a circumference in the handle 38100, as illustrated in FIG. 67. The Hall Effect sensors 38130 are in communication with the control system via electrical circuits. The shaft 38200 comprises a magnet 38230 mounted to the shroud of the shaft 38200 which is aligned, or at least substantially aligned, with the circumference of the Hall Effect sensors 38130. When the shaft 38200 is rotated about its longitudinal axis, the magnet 38230 moves along the sensor circumference. The sensors 38130 are positioned and arranged such that one or more of the sensors 38130 can detect the position of the magnet 38230 and, thus, the control system can determine the orientation of the shaft 38200 relative to the handle 38100 based on which Hall Effect sensors 38130 have detected the magnetic distortion, and the distortion intensity, created by the magnet 38230.

In various embodiments, a surgical instrument can include one or more optical sensors configured to detect the orientation of the shaft relative to the handle. In at least one embodiment, the handle of the surgical instrument comprises a light emitter and a light detector which are in communication with the control system of the surgical instrument. The shaft comprises a reflective surface that rotates with the shaft. The light emitter emits light onto the reflective surface and the light is reflected back into the light detector. The reflective surface comprises different portions with different reflectivities which creates patterns in the light reflected back to the light detector. With this information, the control system can assess the orientation of the shaft relative to the handle. In various instances, the reflective surface comprises openings and solid areas to create a binary off-on, or low-high, reflection response signal, for example.

In various embodiments, a surgical instrument comprises an electromechanical transducer, such as a linear variable differential transformer, for example, used in connection with a mechanical cam to measure the depth of the cam and relate it to the rotation angle of the shaft. In various embodiments, the handle of a surgical instrument comprises a magnetometer in communication with the control system and, in addition, and the shaft comprises a magnet which is detectable by the magnetometer.

In various embodiments, the shaft of a surgical instrument comprises a gyroscope sensor in the shaft which is used by the control system to assess the orientation of the shaft relative to the handle. In at least one such embodiment, the handle also comprises a gyroscope sensor in communication with the control system such that the relative orientation of the handle and the shaft can be assessed. In various embodiments, the shaft of a surgical instrument comprises a tilt sensor which is used by the control system to assess the orientation of the shaft relative to the handle. In at least one embodiment, a SQ-MIN-200 sensor can be used. A SQ-MIN-200 sensor acts like a normally-closed sensor which chatters open and closed as it is tilted or vibrated. That said, any suitable omnidirectional sensor, for example, could be used.

In various embodiments, a detectable element can be positioned on the clamp drive or closure tube of the shaft. When the shaft is rotated, the closure tube rotates with the shaft. Thus, the one or more sensors of the handle can detect the orientation of the shaft relative to the handle via the detectable element on the shaft. When the closure tube is translated to close the end effector, as described herein, the detectable element moves relative to the one or more sensors. Such translation of the detectable element can also be used to verify the closure of the end effector. In at least one instance, a Hall Effect sensor can be used to detect the rotation and translation of the detectable element. In various instances, the control system of a surgical instrument is configured to prevent the end effector from being articulated while the end effector is closed. This arrangement provides the feedback to the control system to determine not only the responsiveness of the articulation controls, but whether or not the control system should be responsive to the input from the articulation controls at all.

Figure 32:
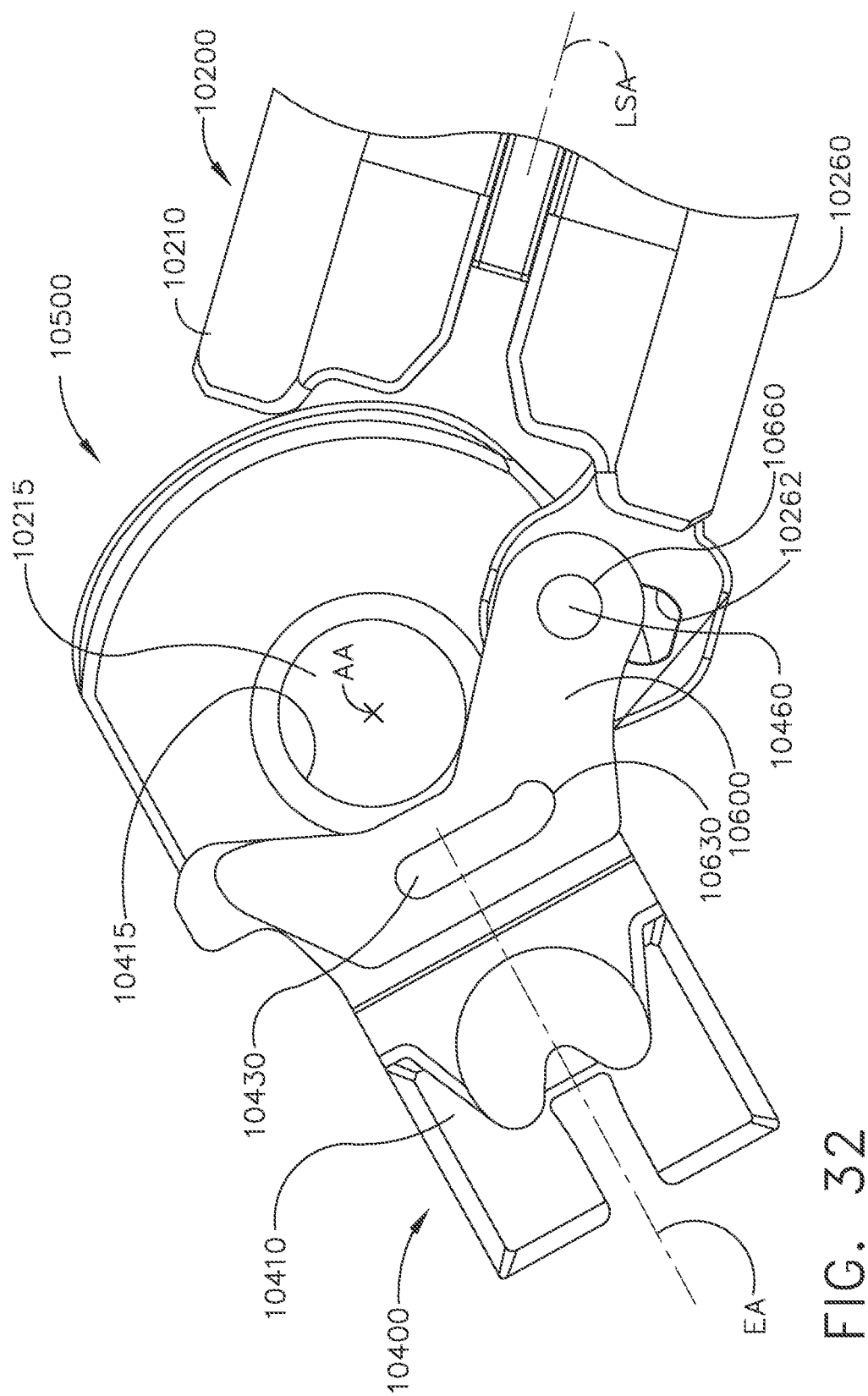
FIG. 32 is a partial detail view of the articulation joint of the surgical instrument of FIG. 1 illustrated with some components removed.

In various embodiments, referring again to FIGS. 27 and 28, the distal end of the articulation actuator 10260 of the surgical instrument 10000 is attached to the end effector 10400 such that the proximal and distal translation of the articulation actuator 10260 rotates the end effector 10400 about the articulation joint 10500. Referring to FIG. 32, the shaft 10200 of the surgical instrument 10000 comprises a shaft frame 10210 which slideably supports the articulation actuator 10260. Although not illustrated in FIG. 32, the shaft 10200 further comprises a pivot pin 10215 extending from the frame 10210. The pivot pin 10215 is closely received within a pivot aperture 10415 defined in the staple cartridge jaw 10410 of the end effector 10400 which defines an articulation axis AA of the articulation joint 10500. The articulation driver 10260 comprises a distal end including an aperture 10262 defined therein and the end effector 10400 further comprises an articulation pin 10460 extending from the proximal end of the staple cartridge jaw 10410 into the aperture 10262. When the articulation actuator 10260 is translated, as described above, the sidewalls of the aperture 10262 engage the articulation pin 10460 and either push or pull the articulation pin 10460—depending on the direction in which the articulation actuator 10260 is translated. The entire disclosure of U.S. Pat. No. 9,101,358, entitled ARTICULATABLE SURGICAL INSTRUMENT COMPRISING A FIRING DRIVE, which issued on Aug. 11, 2015, is incorporated by reference herein. The entire disclosure of U.S. Pat. No. 5,865,361, entitled SURGICAL STAPLING APPARATUS, which issued on Feb. 2, 2019, is incorporated by reference herein.

Further to the above, the end effector 10400 defines an end effector axis EA and the shaft 10200 defines a longitudinal shaft axis LSA. When the end effector 10400 is in an unarticulated position, the end effector axis EA is aligned, or at least substantially aligned, with the longitudinal shaft axis LSA. When the end effector 10400 is in an articulated position, as illustrated in FIG. 32, the end effector axis EA is transverse to the longitudinal shaft axis LSA. The aperture 10262 is elongate in order to accommodate relative movement between the articulation pin 10460 and the articulation driver 10260; however, for large articulation angles, the articulation driver 10260 may bind and/or flex which can, without more, result in the articulation driver 10260 decoupling from the articulation pin 10460. With that in mind, the end effector 10400 further comprises a retention plate 10600 configured to hold the articulation driver 10260 in engagement with the articulation pin 10460. The retention plate 10600 comprises a planar, or an at least substantially planar portion, which extends over the distal end of the articulation driver 10260 and comprises an aperture 10660 defined therein, the sidewalls of which are engaged with the articulation pin 10460. As a result, the articulation driver 10260 is trapped between the staple cartridge jaw 10410 and the retention plate 10600 such that the articulation driver 10260 does not unintentionally disengage from the staple cartridge jaw 10410. The retention plate 10600 is fixedly mounted to the staple cartridge jaw 10410 such that there is little, if any, relative movement between the retention plate 10600 and the staple cartridge jaw 10410. The staple cartridge jaw 10410 comprises a retention lug 10430 and the retention plate 10600 comprises an aperture 10630 defined therein, the sidewalls of which are engaged with the retention lug 10430 to hold the retention plate 10600 to the staple cartridge jaw 10410. In various instances, the retention plate 10600 can comprise a spring and/or biasing member.

Figure 33:
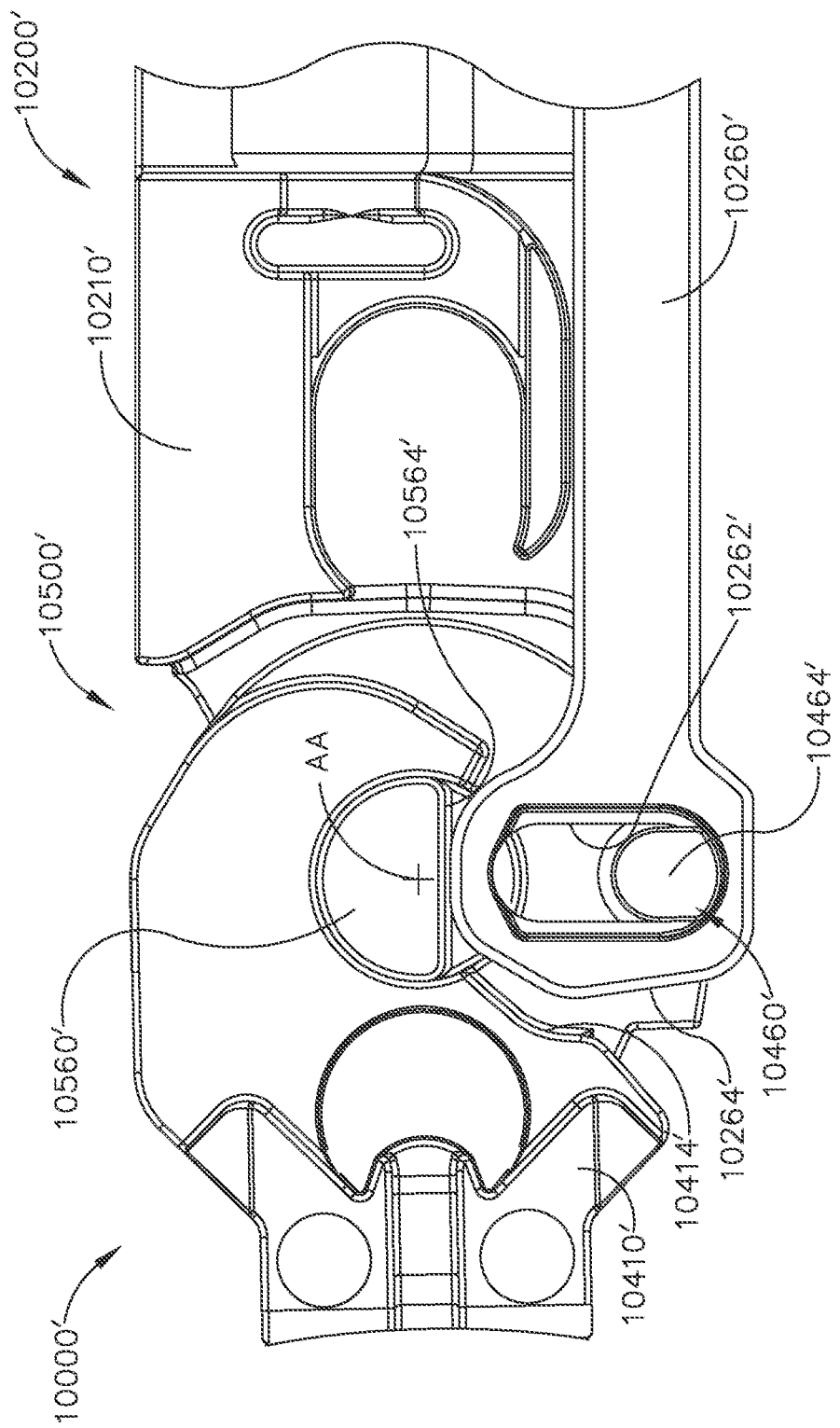
FIG. 33 is a partial detail view of an articulation joint in accordance with at least one alternative embodiment usable with the surgical instrument of FIG. 1.
Figure 34:
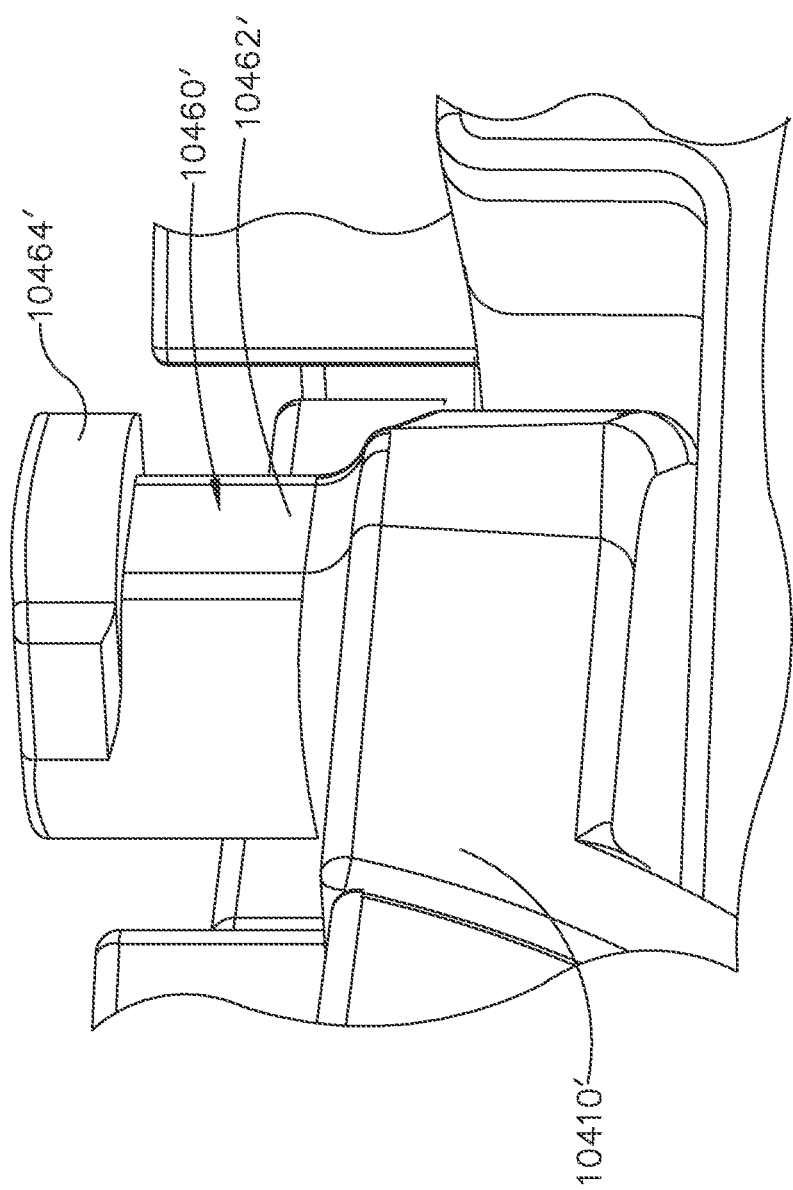
FIG. 34 is a partial perspective view of an articulation drive pin extending from a frame of the end effector of the embodiment of FIG. 33.
Figure 35:
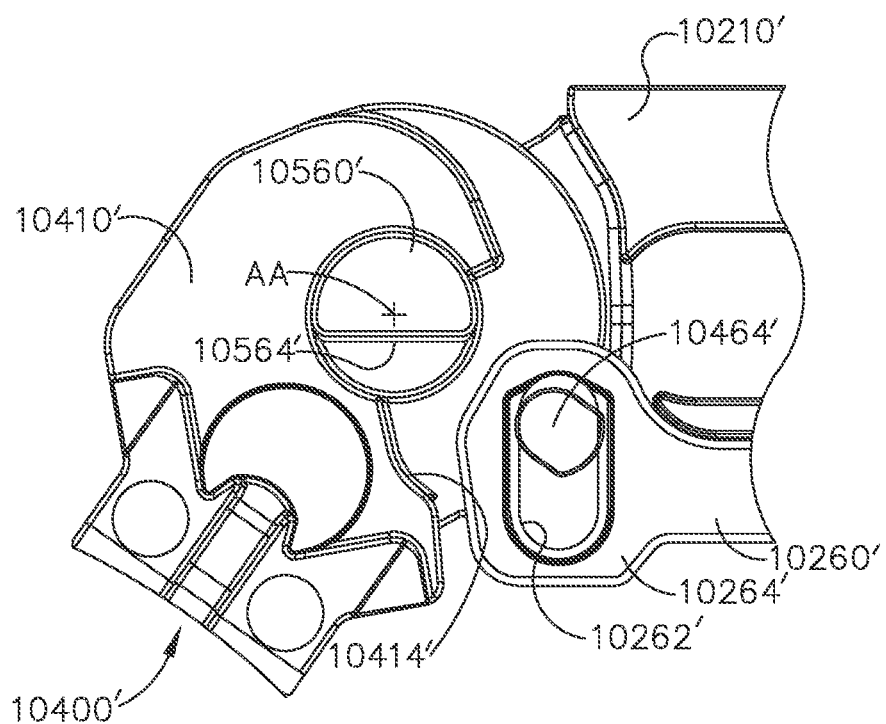
FIG. 35 is a partial detail view of the embodiment of FIG. 33 illustrating the end effector in an articulated position.
Figure 36:
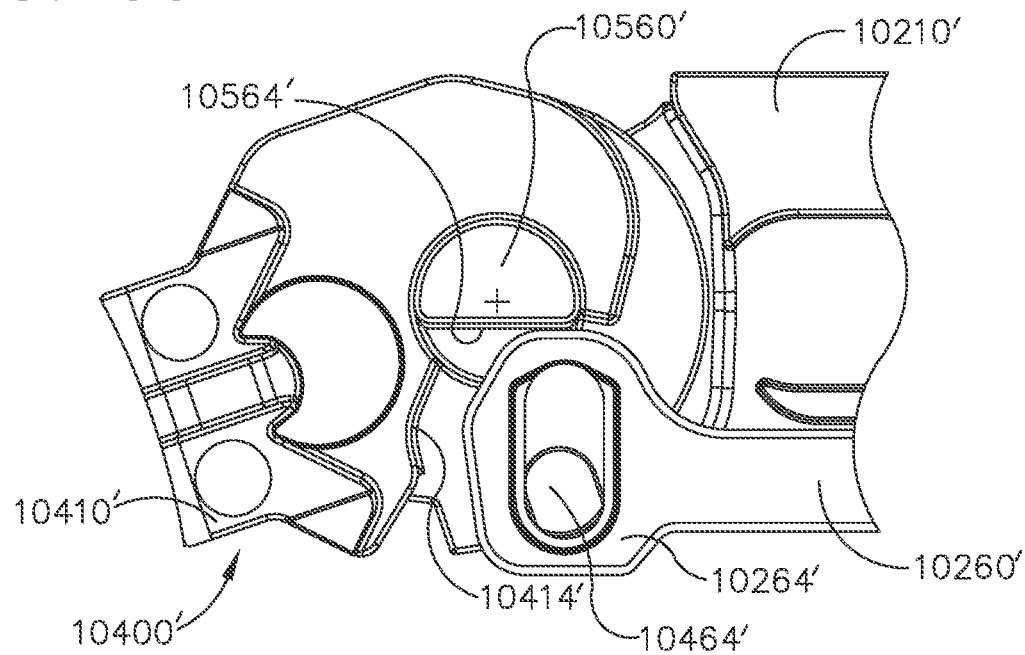
FIG. 36 is a partial detail view of the embodiment of FIG. 33 illustrating the end effector in another articulated position.
Figure 37:
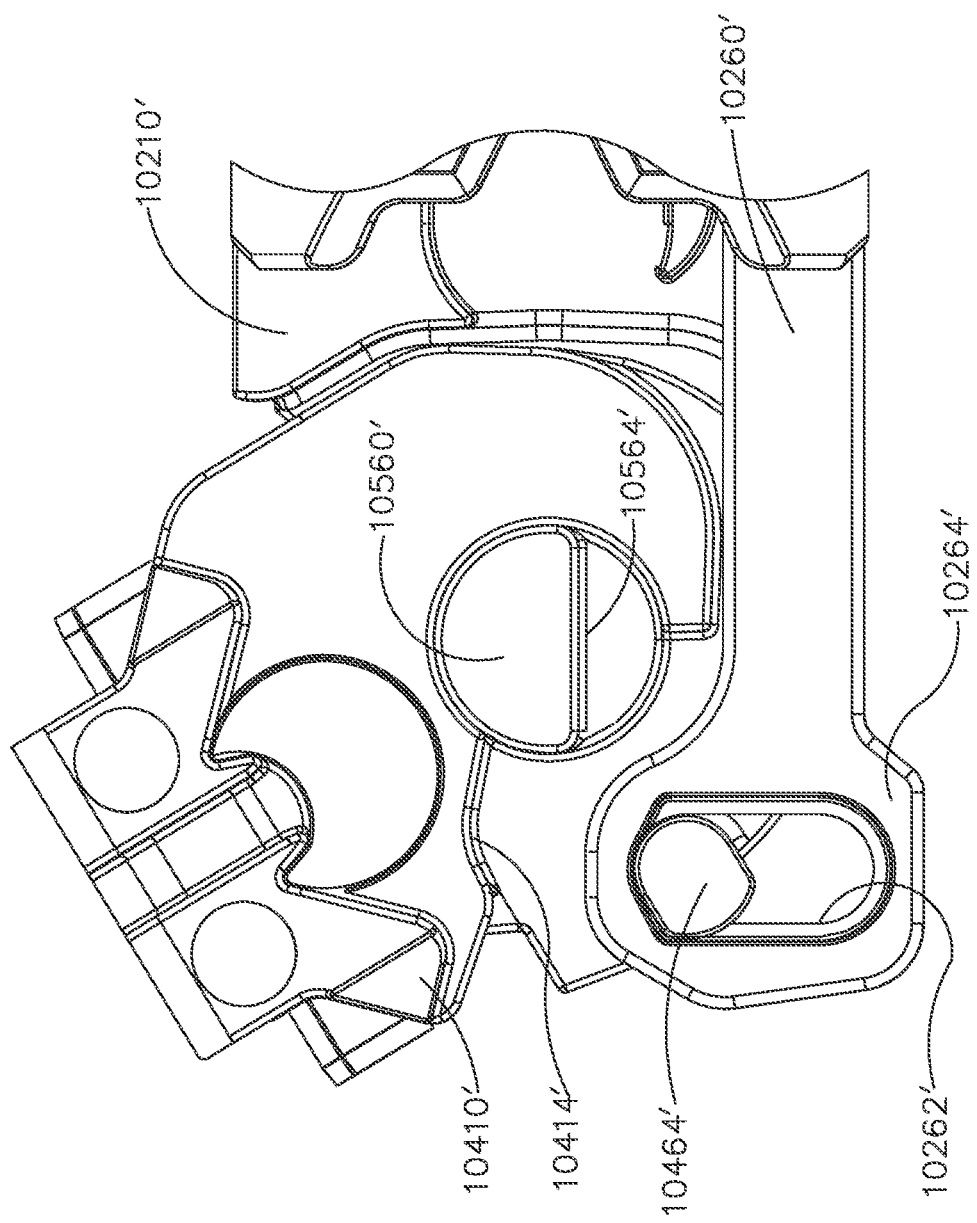
FIG. 37 is a partial detail view of the embodiment of FIG. 33 illustrating the end effector in another articulated position.
Figure 38:
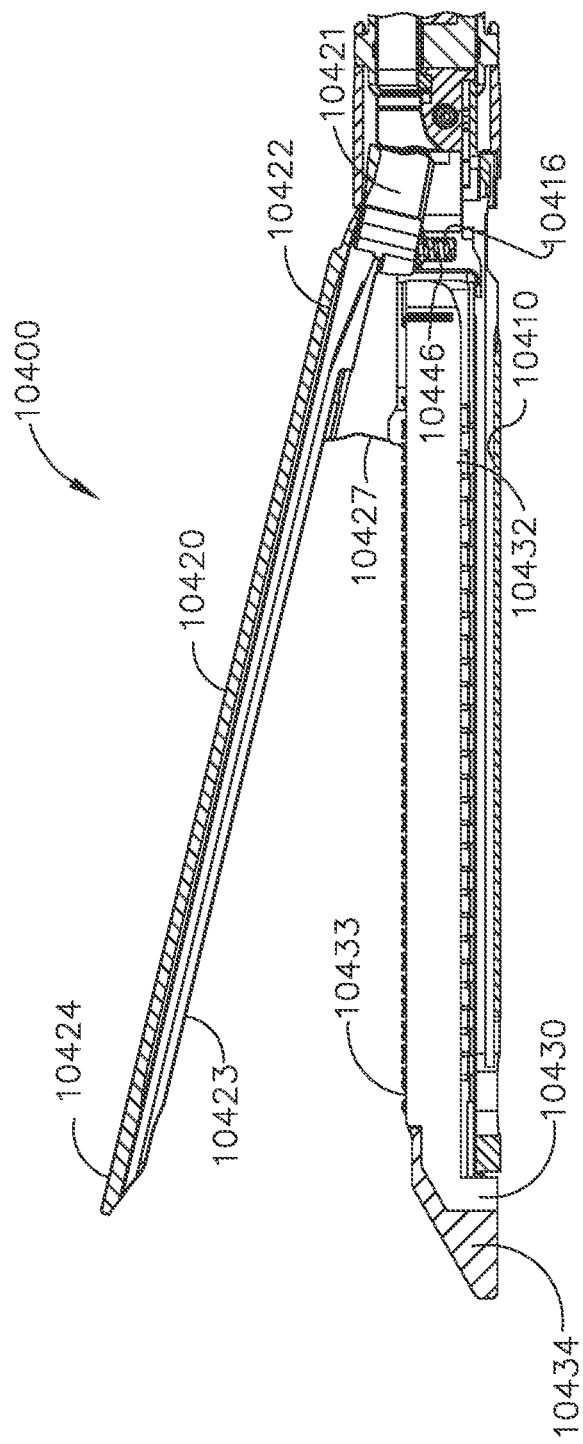
FIG. 38 is a cross-sectional view of the end effector of the surgical instrument of FIG. 1 illustrated in an open configuration.

In addition to or in lieu of the retention plate 10600, referring now to FIG. 33, a surgical instrument 10000' comprises an end effector 10400' and an articulation joint 10500' rotatably connecting the end effector to the shaft 10200'. Further to the above, the articulation joint 10500' comprises a pin 10560' extending from a shaft frame 10210' of the shaft 10200' that is closely received within an aperture defined in the staple cartridge jaw 10410' which defines the articulation axis AA for the articulation joint 10500'. The surgical instrument 10000' also comprises an articulation driver 10260' which comprises a distal end 10264' including a slot 10262' defined therein. Similar to the above, the staple cartridge jaw 10410' comprises an articulation pin 10460' extending from the staple cartridge jaw 10410' which extends into the slot 10262' of the distal end 10264' and the interaction between the sidewalls of the slot 10262' and the articulation pin 10460' drive the end effector 10400' about the articulation joint 10500'. Notably, the pin 10560' of the articulation joint 10500' comprises a clearance relief 10564' defined therein to provide clearance for the longitudinal movement of the articulation driver 10260'. The staple cartridge jaw 10410' also comprises a clearance relief 10414' defined therein to permit clearance for the rotation of the staple cartridge jaw 10410' about the articulation joint 10500'. In order to prevent the articulation driver 10260' from becoming decoupled from the staple cartridge jaw 10410', referring to FIGS. 34-37, the articulation pin 10460' comprises a retention shoulder 10464' extending from a cylindrical portion 10462'. The retention shoulder 10464' extends over a portion of the distal end 10264' of the articulation driver 10260' throughout the articulation of the end effector 10400'. Thus, regardless of whether the end effector 10400' is articulated all the way to the left (FIG. 35) or all the way to the right (FIG. 37), or anywhere in between, the retention shoulder 10464' prevents, or at least limits the possibility of, the articulation driver 10260' disengaging from the staple cartridge jaw 10410'.

In various embodiments, further to the above, the clearance relief 10414' comprises a retention shoulder or lip which prevents the articulation driver 10260' from decoupling from the articulation pin 10460'. The retention shoulder 10464' of the articulation pin 10460' is sized and configured such that the width of the retention shoulder 10464' is wider than the width of the slot 10262'. That said, the slot 10262' comprises a length which is larger than its width which permits the retention shoulder 10464' to be interested through the slot 10262' such that the articulation driver 10260' can be assembled to the articulation pin 10460'. The width of the slot 10262' is defined along an axis that is parallel to the longitudinal axis of the shaft while the length of the slot 10262' is defined along an axis that is orthogonal to the longitudinal axis of the shaft. Such an arrangement permits the end effector to articulate relative to the shaft while minimizing binding between the end effector and the articulation driver 10260'. That said, the articulation driver 10260' is comprised of a flexible material that permits the articulation driver 10260' to resiliently flex to accommodate the end articulation of the end effector.

Figure 44:
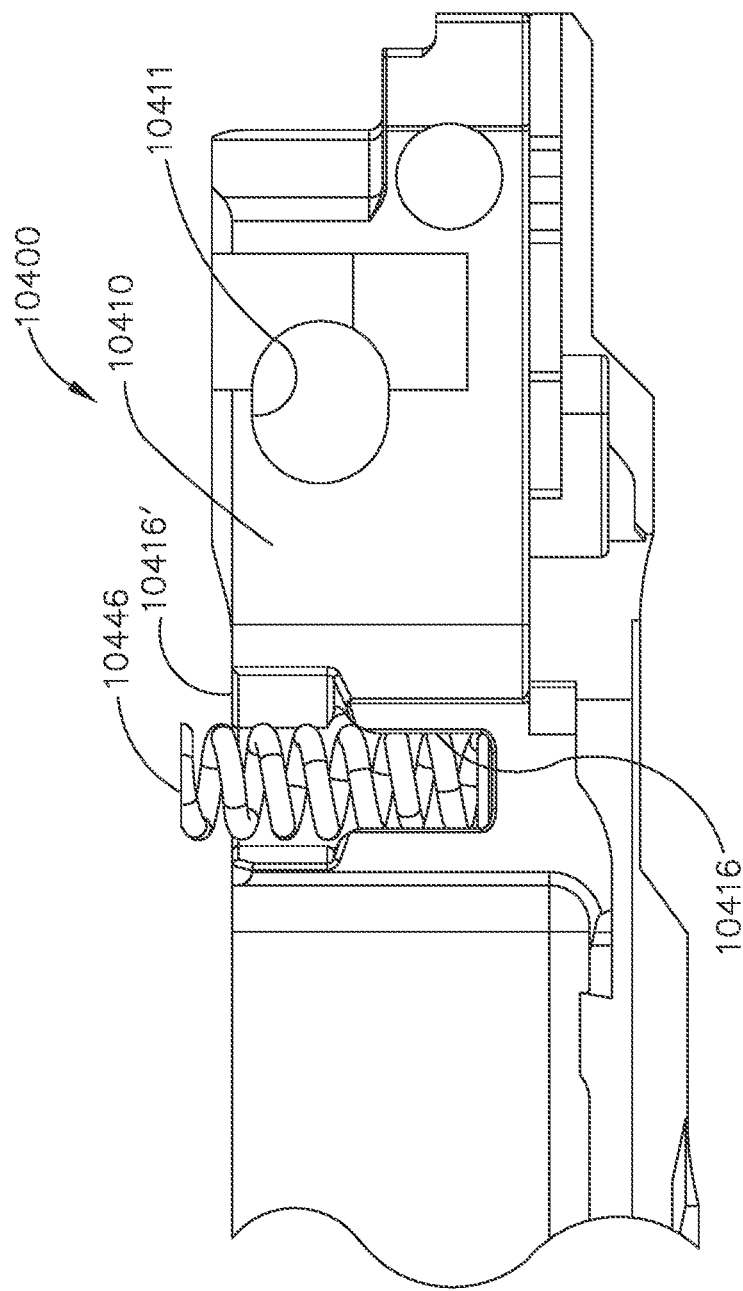
FIG. 44 is a partial cross-sectional view of a staple cartridge jaw of an end effector in accordance with at least one embodiment illustrated without a staple cartridge in the staple cartridge jaw.

As discussed above, the end effector 10400 comprises a staple cartridge jaw 10410 configured to receive a replaceable staple cartridge, such as staple cartridge 10430, for example, and an anvil jaw 10420 configured to deform the staples ejected from the staple cartridge 10430. The staple cartridge jaw 10410 comprises a channel including a bottom support and two lateral sidewalls extending upwardly configured to receive the staple cartridge 10430. The staple cartridge 10430 comprises a proximal end 10432, a distal end 10434, and a deck 10433 extending between the proximal end 10432 and the distal end 10434. When the staple cartridge 10430 is inserted into the staple cartridge jaw 10410, the proximal end 10432 is guided into position between the staple cartridge jaw 10410 and the anvil jaw 10420 and then seated into the staple cartridge jaw 10410. The anvil jaw 10420 comprises a proximal end 10422, a distal end 10424, a tissue compression surface 10423 extending between the proximal end 10422 and the distal end 10424, and a pivot rotatably connecting the anvil jaw 10420 to the staple cartridge jaw 10410. Referring to FIG. 44, the anvil jaw 10420 comprises lateral pins that extend into apertures 10411 defined in the staple cartridge jaw 10410. As discussed above, the anvil jaw 10420 is rotatable into a closed, or clamped, position by the closure drive of the stapling instrument 10000. When the closure drive is retracted, the anvil jaw 10420 is opened. Referring to FIGS. 38-43, the stapling instrument 10000 further comprises one or more biasing members, or springs, 10446 configured to open the anvil jaw 10420 when the closure drive is retracted. The surgical instrument 10000 comprises two opening springs 10446, but could comprise any suitable number of biasing members. In any event, each spring 10446 is positioned in a recess 10416 defined in the staple cartridge jaw 10410. The recesses 10416 closely receive the springs 10446 such that the springs 10446 do not buckle under a compressive load; however, the recesses 10416 are sized and configured to accommodate any lateral expansion of the springs 10446 as the anvil jaw 10420 is being closed.

Figure 42:
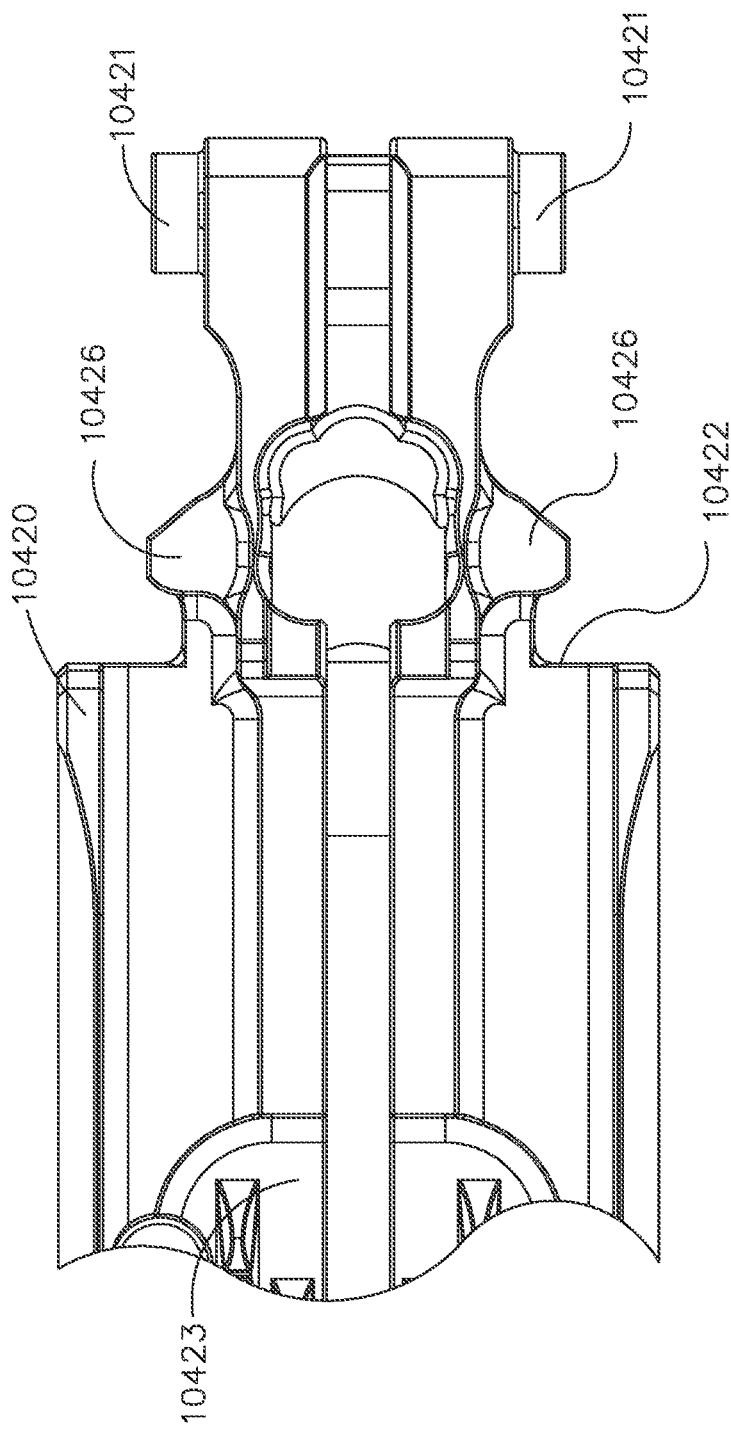
FIG. 42 is a partial perspective view of the anvil jaw of FIG. 40.
Figure 43:
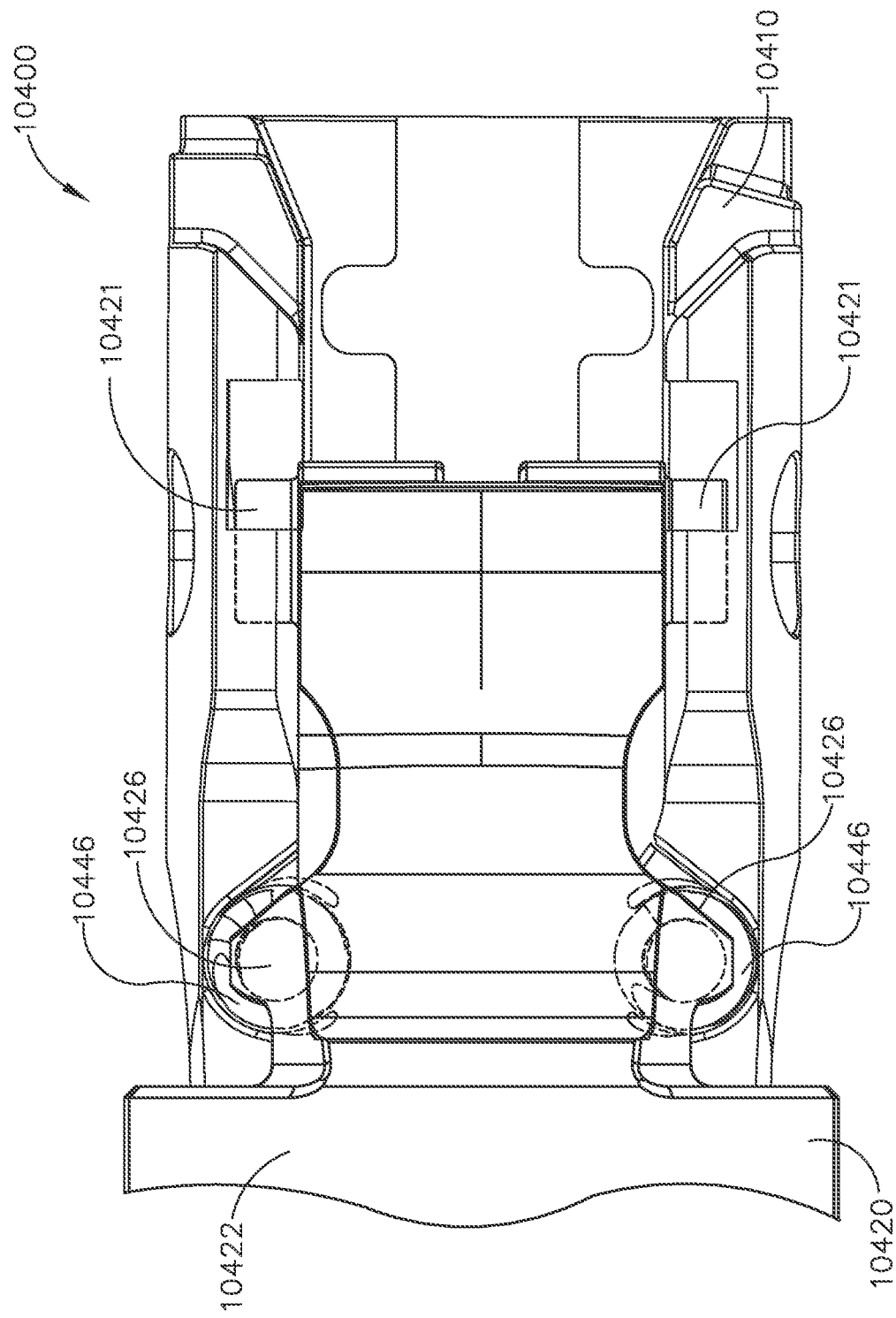
FIG. 43 is a partial top view of the pivot joint of FIG. 40.

Referring primarily to FIG. 42, the anvil jaw 10420 comprises lateral tabs 10426 adjacent the proximal end 10422 of the anvil 10420 which are in contact with the springs 10446. When the anvil jaw 10420 is closed, the springs 10446 are compressed between the lateral tabs 10426 and the bottom of the recesses 10416. When the closure system is retracted, the springs 10446 resiliently re-expand and push upwardly on the lateral tabs 10426 to rotate the anvil jaw 10420 into its open, or unclamped, position. Notably, referring primarily to FIG. 40, the staple cartridge jaw 10410 has a stop portion 10419 defined thereon which is contacted by the proximal end 10422 of the anvil 10420 when the anvil 10420 reaches its fully-open position. The anvil 10420 comprises a proximal stop surface 10429 which contacts the stop portion 10419 of the staple cartridge jaw 10410. In such instances, the anvil jaw 10420 cannot be opened any further. As a result of the above, the springs 10446 hold the anvil jaw 10420 against the stop portion 10419 of the staple cartridge jaw 10410 until the anvil jaw 10420 is closed once again.

Figure 39:
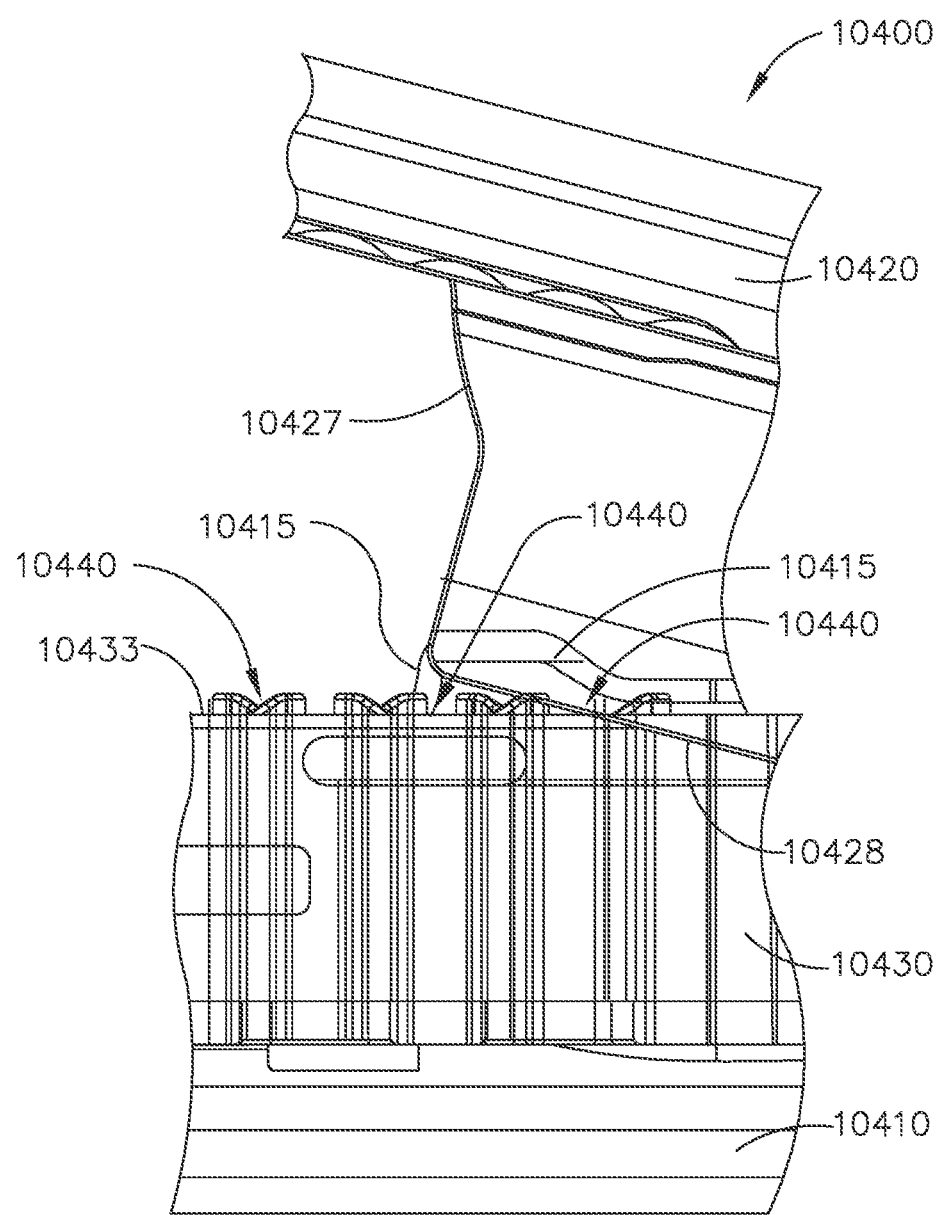
FIG. 39 is a partial cross-sectional view of the end effector of the surgical instrument of FIG. 1 illustrating tissue stops of the end effector.
Figure 40:
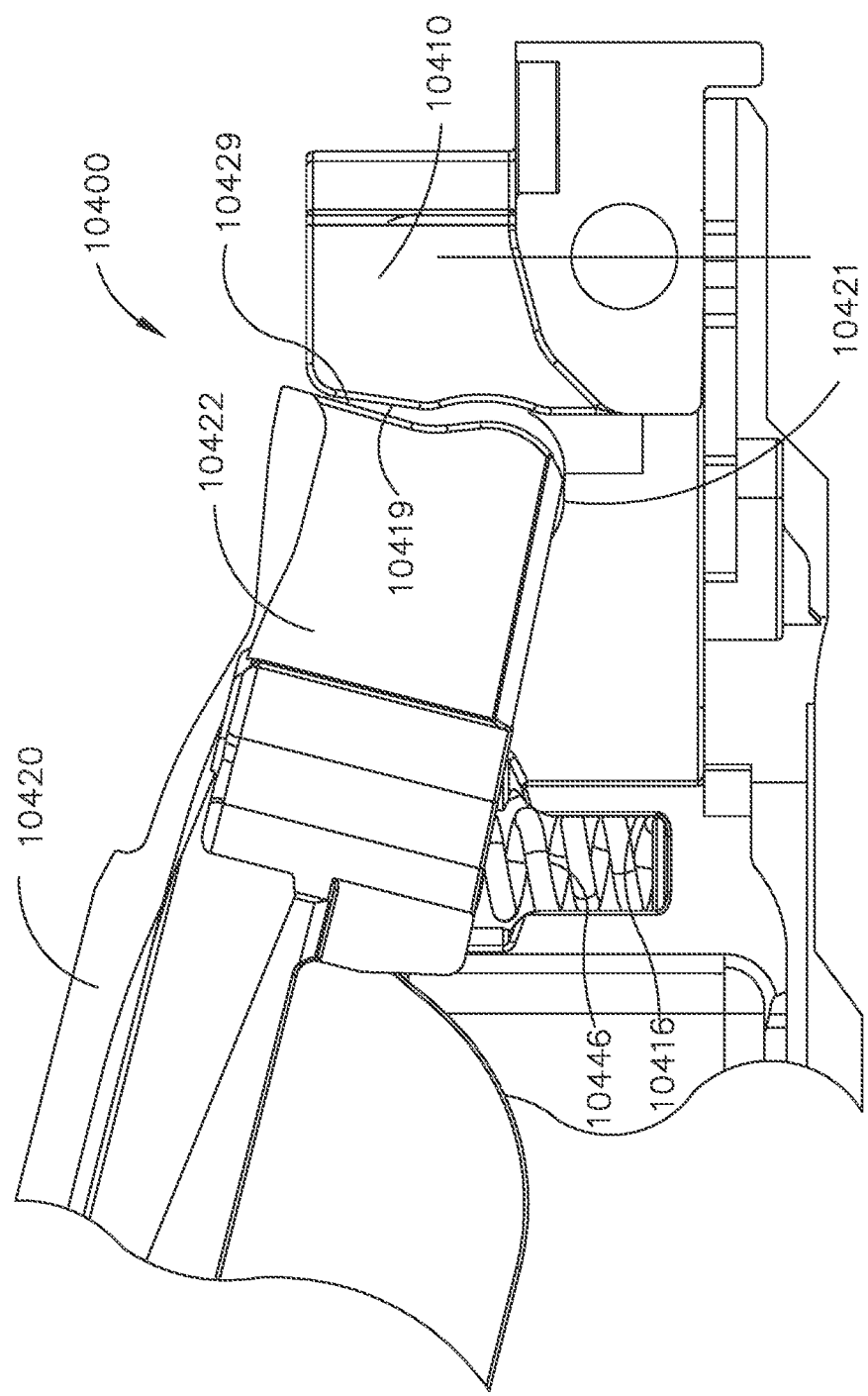
FIG. 40 is a partial cross-sectional view of the end effector of the surgical instrument of FIG. 1 illustrating a pivot joint between a staple cartridge jaw and an anvil jaw of the end effector.

When the anvil jaw 10420 is in its open position, the staple cartridge jaw 10410 is positioned on one side of the tissue that is to be stapled and the anvil jaw 10420 is positioned on the opposite side. In such instances, the end effector 10400 is moved relative to the tissue until the tissue is suitably positioned between the staple cartridge jaw 10410 and the anvil jaw 10420. The anvil jaw 10420 comprises lateral tissue stops 10427 which extend downwardly alongside the staple cartridge jaw 10410 which are configured to make sure that the tissue positioned within the end effector 10400 is positioned over the staple cavities in the staple cartridge 10430. Referring primarily to FIG. 39, the tissue stops 10427 extend distally with respect to the proximal-most staple cavities 10440. In at least one instance, the tissue stops 10427 extend distally with respect to at least one staple cavity 10440 in each longitudinal row of staple cavities 10440. As a result, the tissue stops 10427 make sure that the tissue captured in the end effector 10400 is not cut by the tissue cutting knife without being stapled. When the anvil jaw 10420 is closed, the tissue stops 10427 move relative to the staple cartridge jaw 10410. The tissue stops 10427 are sized and configured such that tissue does not become accidentally pinched between the tissue stops 10427 and the lateral sides of the staple cartridge jaw 10410. More specifically, the bottom edges 10428 of the tissue stops 10427 are configured such that they extend alongside the lateral sides of the staple cartridge jaw 10410 even when the anvil jaw 10420 is in its fully-open position, as illustrated in FIG. 39. Notably, the lateral sides 10415 of the staple cartridge jaw 10410 extend upwardly above the deck 10433 to make sure that there is overlap between the tissue stops 10427 and the lateral sides 10415 of the staple cartridge jaw 10410—when viewed from the side—throughout the entire range of motion of the anvil jaw 10420.

In various embodiments, further to the above, the distal edges of the tissue stops 10427 extend below the deck 10433 throughout the entire range of motion of the anvil jaw 10420. Thus, the distal edges of the tissue stops 10427 extend below the top surface of the deck 10433 when the anvil jaw 10420 is in its fully-open position and its fully-clamped position. Such an arrangement reduces the possibility of the tissue being pinched when the anvil jaw 10420 is moved. In certain embodiments, the staple cartridge comprises tissue stops that extend upwardly from the deck 10433 alongside the tissue stops 10427. Similar to the above, the distal edges of the tissue stops 10427 extend below the cartridge tissue stops through the entire range of motion of the anvil jaw 10420. Such an arrangement also reduces the possibility of the tissue being pinched when the anvil jaw 10420 is moved. Moreover, these arrangements would be useful in embodiments where the staple cartridge jaw 10410 moves relative to the anvil jaw 10420.

Figure 45A:
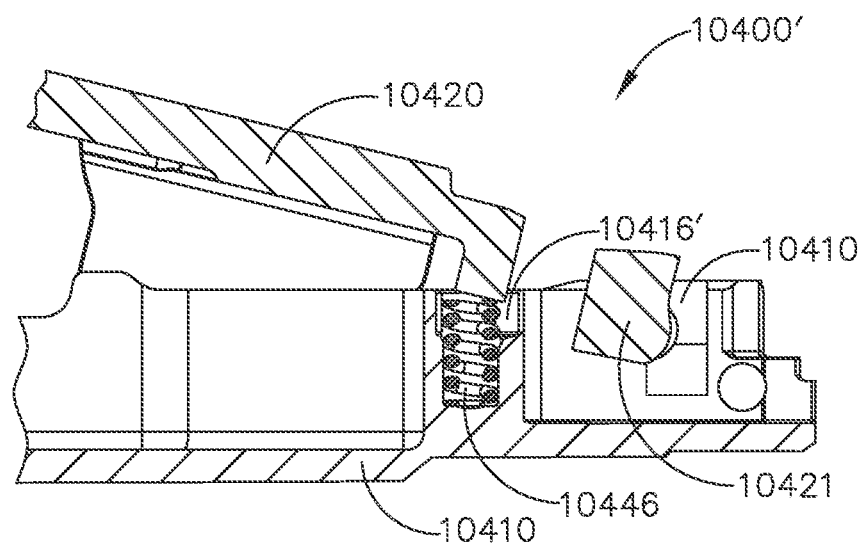
FIG. 45A is a partial cross-sectional view of the end effector of FIG. 44 in an open configuration.
Figure 45B:
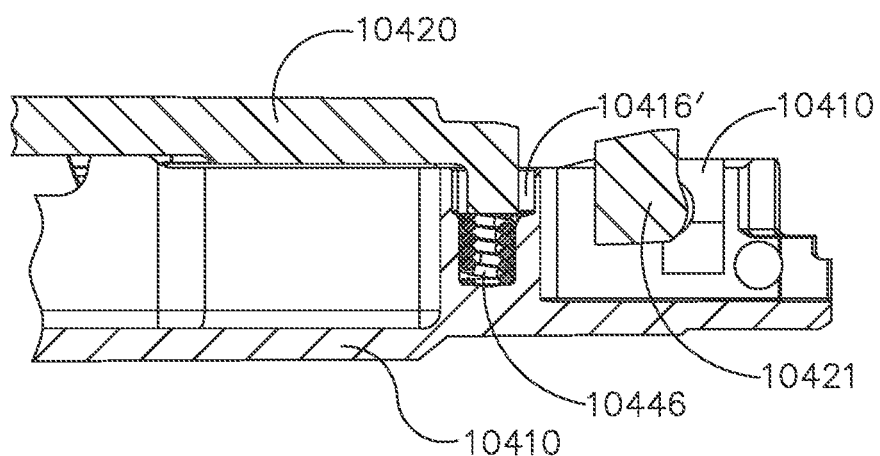
FIG. 45B is a partial cross-sectional view of the end effector of FIG. 44 in a closed configuration.

As discussed above and referring primarily to FIGS. 44, 45A, and 45B the end effector 10400 comprises a staple cartridge jaw 10410 that includes spring recesses 10416 defined therein which comprise wider top openings 10416'. The spring recesses 10416 still support the springs 10446 and keep them from buckling, but the wider top openings 10416' of the spring recesses 10416 provide clearance for the lateral tabs 10426 when the anvil jaw 10420 is in its closed position. In such an arrangement, the lateral tabs 10426 can move into the staple cartridge jaw 10410 to compress the springs 10446. In such instances, the springs 10446 can be highly compressed by the anvil jaw 10420, thereby assuring a strong opening force from the springs 10446 when the anvil jaw 10420 is released by the closure drive. The above being said, embodiments are envisioned without the wider top openings 10416'. In such embodiments, the springs are closely received by the spring recesses 10416 along the length of the springs 10446.

Figure 46:
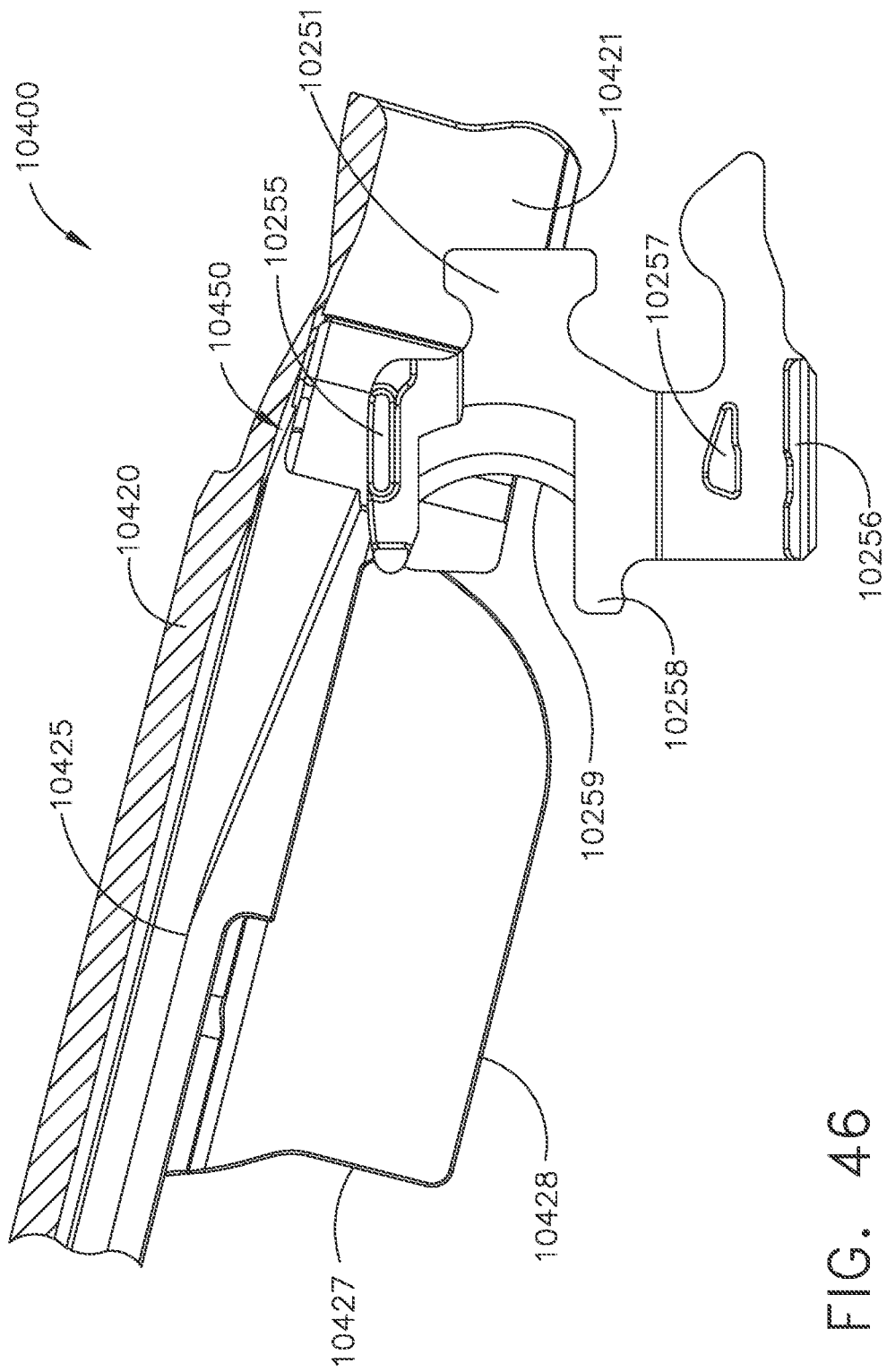
FIG. 46 is a partial cross-sectional view of the end effector of the surgical instrument of FIG. 1 illustrating a firing member in an unfired position.
Figure 47:
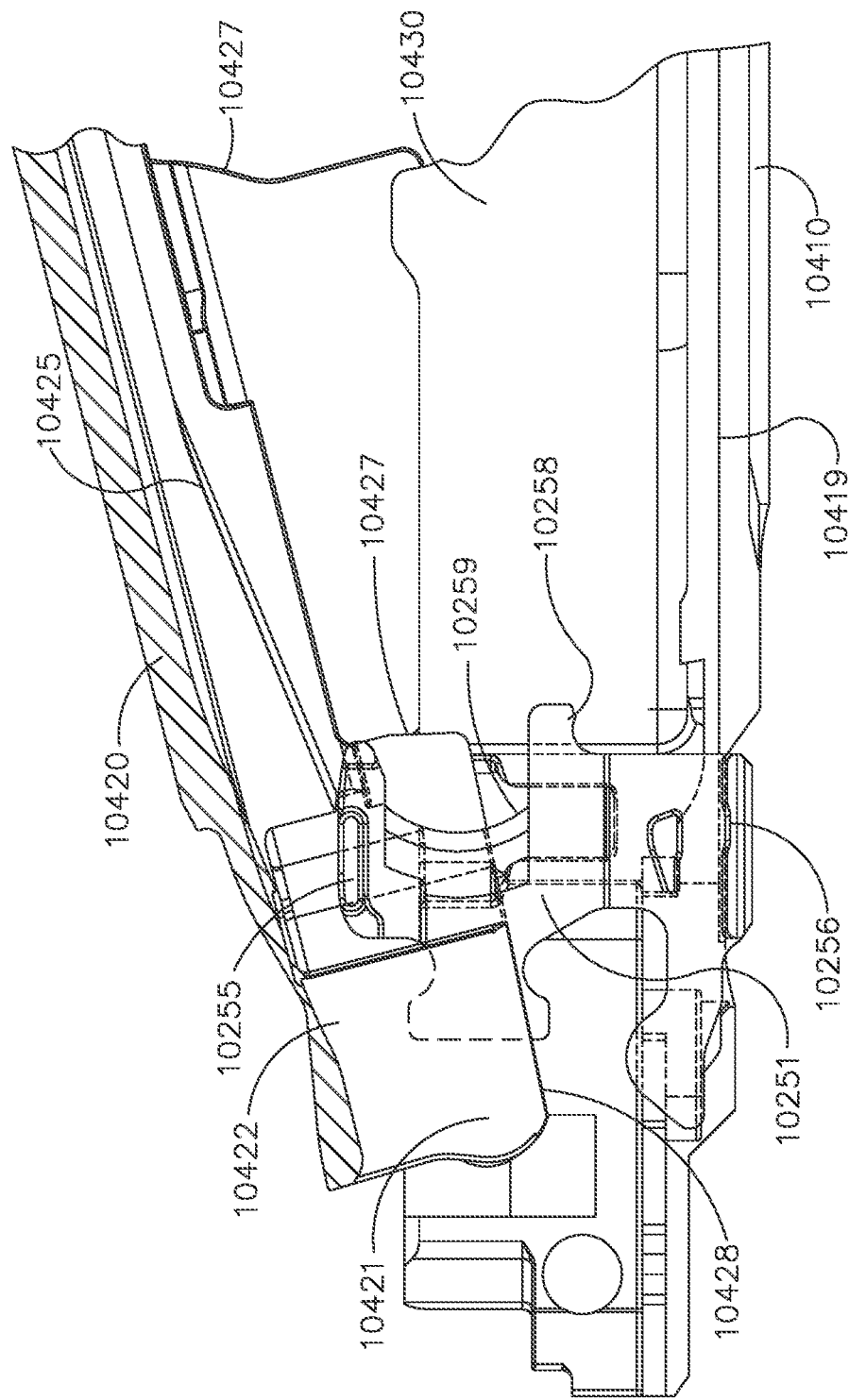
FIG. 47 is a partial cross-sectional view of the end effector of the surgical instrument of FIG. 1 illustrating a cartridge stop on the anvil jaw configured to stop the proximal insertion of a staple cartridge into the staple cartridge jaw.

The tissue cutting member 10251 of the firing drive of the stapling instrument 10000 is illustrated in FIGS. 46 and 47, the tissue cutting member comprises a body including a distal nose 10258 and a tissue cutting edge 10259 which pass through the end effector 10400 during a staple firing stroke. The tissue cutting member 10251 further comprises a top cam member 10255 configured to engage the anvil jaw 10420 and a bottom cam member 10256 configured to engage the staple cartridge jaw 10410 during the staple firing stroke. A longitudinal cam surface 10425 in a longitudinal slot of the anvil jaw 10420 can be seen in FIG. 46 which is engaged by the top cam member 10255 during the staple firing stroke. The staple cartridge jaw 10410 also has a longitudinal cam surface 10419 which is engaged by the bottom cam member 10256. The cam members 10255 and 10256 position the jaws 10410 and 10420 relative to one another during the staple firing stroke and hold the jaws 10410 and 10420 in their closed configuration throughout the staple firing stroke. The cam members 10255 and 10256 also set the staple forming gap between the staple drivers in the staple cartridge and the forming pockets defined in the anvil jaw 10420.

Notably, FIGS. 46 and 47 illustrate the anvil jaw 10420 in its open position and the tissue cutting member 10251 in its unfired position, i.e., its position before the staple firing stroke has begun. The anvil jaw 10420 comprises a clearance pocket 10450 defined therein which is aligned with the top cam member 10255 of the tissue cutting member 10251 when the tissue cutting member 10251 is in its unfired position. Such an arrangement allows the tissue cutting member 10251 to be parked just proximal to the longitudinal cam surface 10425 in the anvil jaw 10420, and the corresponding cam surface in the staple cartridge jaw 10410, when the tissue cutting member 10251 is in its unfired position. Such an arrangement provides for a shorter, and more maneuverable, end effector for a given staple line length. Moreover, the tissue cutting member 10251 comprises a tissue cutting edge 10259 that is positioned proximally with respect to the staple cavities defined in the staple cartridge and proximally with respect to the distal edges of the tissue stops when the tissue cutting member is in its unfired position. As a result, the tissue being inserted into the end effector is unlikely to be cut by the tissue cutting edge 10259 until the tissue cutting member 10251 is advanced distally from its unfired position during a firing stroke.

Figure 41:
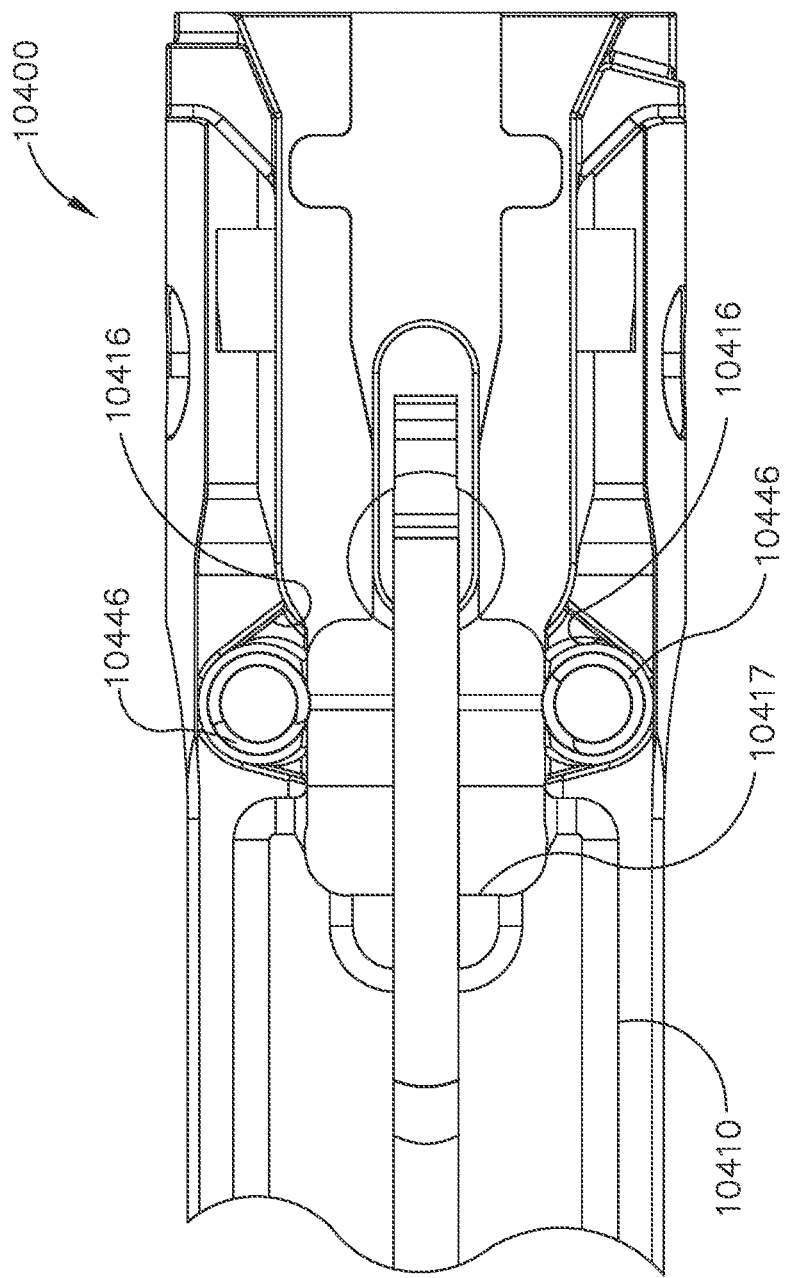
FIG. 41 is a partial plan view of the staple cartridge jaw of FIG. 40 without a staple cartridge positioned in the staple cartridge jaw.

Further to the above, it is desirable for the tissue cutting member 10251 to be in its unfired position at the beginning of the staple firing stroke. If the tissue cutting member 10251 is not in its unfired position at the outset of the staple firing stroke, a missing cartridge/spent cartridge lockout of the stapling instrument 10000 may be accidentally bypassed. Referring to FIG. 41, the lockout of the stapling instrument 10000 comprises a shoulder 10417 defined in the bottom of the staple cartridge jaw 10410. If a proper unspent staple cartridge is seated in the staple cartridge jaw 10410 at the outset of the staple firing stroke, and the tissue cutting member 10251 is in its unfired position at the outset of the staple firing stroke, the tissue cutting member 10251 will be lifted over the lockout shoulder 10417. More specifically, referring to FIG. 46, the nose 10258 of the tissue cutting member 10251 will be supported by a staple driving sled in the staple cartridge such that lockout tabs 10257 of the firing member 10251 (of which the tissue cutting member is a part), and/or any other portion of the firing member 10251, do not contact the lockout shoulder 10417. If, however, a staple cartridge is not seated in the staple cartridge jaw 10410, a staple cartridge is seated the staple cartridge jaw 10410 but has been previously spent, or an incorrect staple cartridge is seated in the staple cartridge jaw 10410, the sled will not support the nose 10258 of the tissue cutting member 10251 and the lockout tabs 10257 will contact the lockout shoulder 10417 at the outset of the staple firing stroke—thereby preventing the staple firing stroke. If the tissue cutting member 10251 is somehow positioned distally with respect to the lockout shoulder 10417 at the outset of the staple firing stroke, however, the advantages provided by the lockout of the surgical instrument 10000 are lost.

The entire disclosures of U.S. Pat. No. 7,143,923, entitled SURGICAL STAPLING INSTRUMENT HAVING A FIRING LOCKOUT FOR AN UNCLOSED ANVIL, which issued on Dec. 5, 2006; U.S. Pat. No. 7,044,352, SURGICAL STAPLING INSTRUMENT HAVING A SINGLE LOCKOUT MECHANISM FOR PREVENTION OF FIRING, which issued on May 16, 2006; U.S. Pat. No. 7,000,818, SURGICAL STAPLING INSTRUMENT HAVING SEPARATE DISTINCT CLOSING AND FIRING SYSTEMS, which issued on Feb. 21, 2006; U.S. Pat. No. 6,988,649, SURGICAL STAPLING INSTRUMENT HAVING A SPENT CARTRIDGE LOCKOUT, which issued on Jan. 24, 2006; and U.S. Pat. No. 6,978,921, SURGICAL STAPLING INSTRUMENT INCORPORATING AN E-BEAM FIRING MECHANISM, which issued on Dec. 27, 2005, are incorporated by reference herein.

Figure 48:
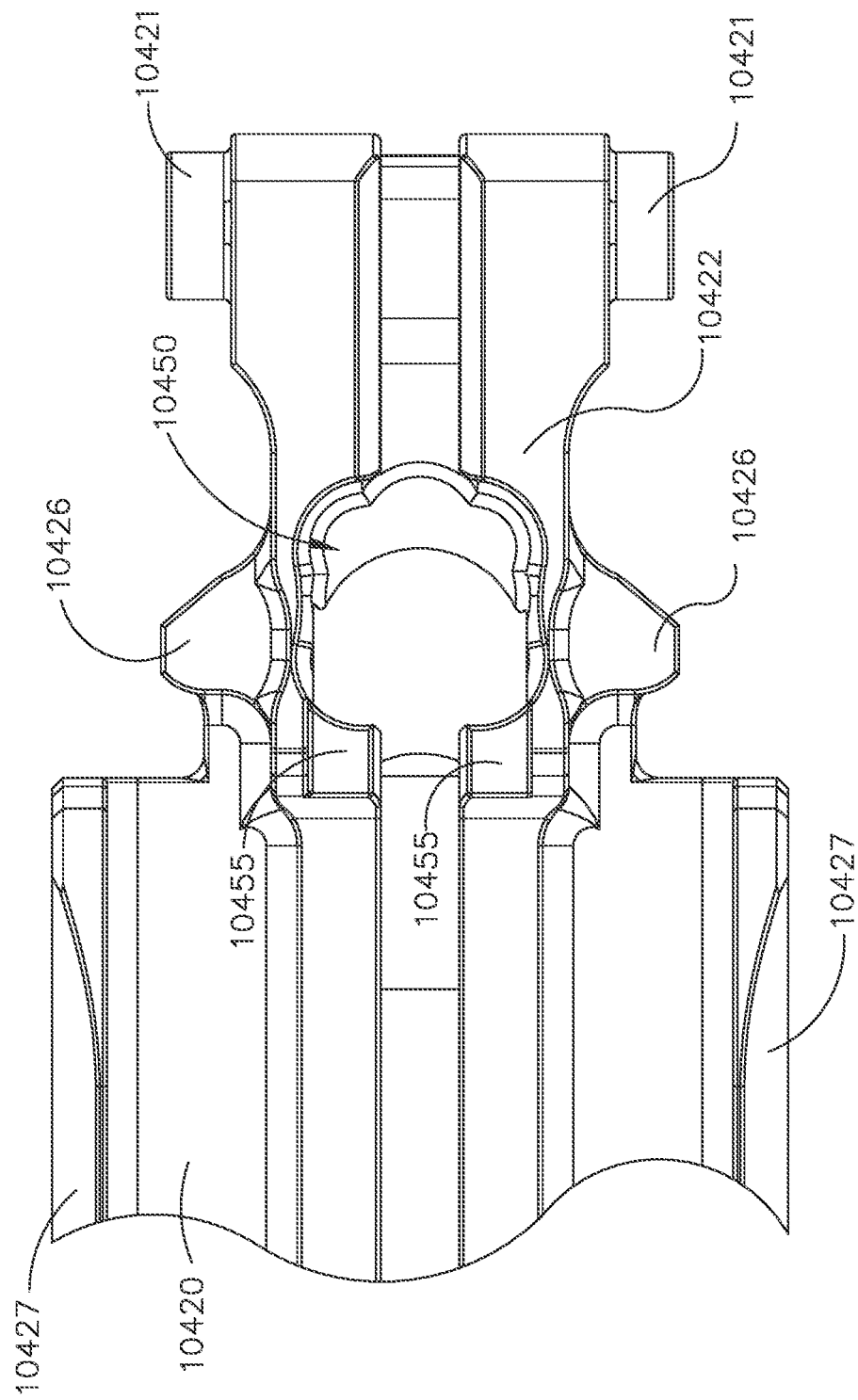
FIG. 48 is a partial perspective view of the anvil jaw of the surgical instrument of FIG. 1 illustrating surfaces configured to control the position of the firing member of FIG. 46 in its unfired position while the end effector is in an open configuration.
Figure 49:
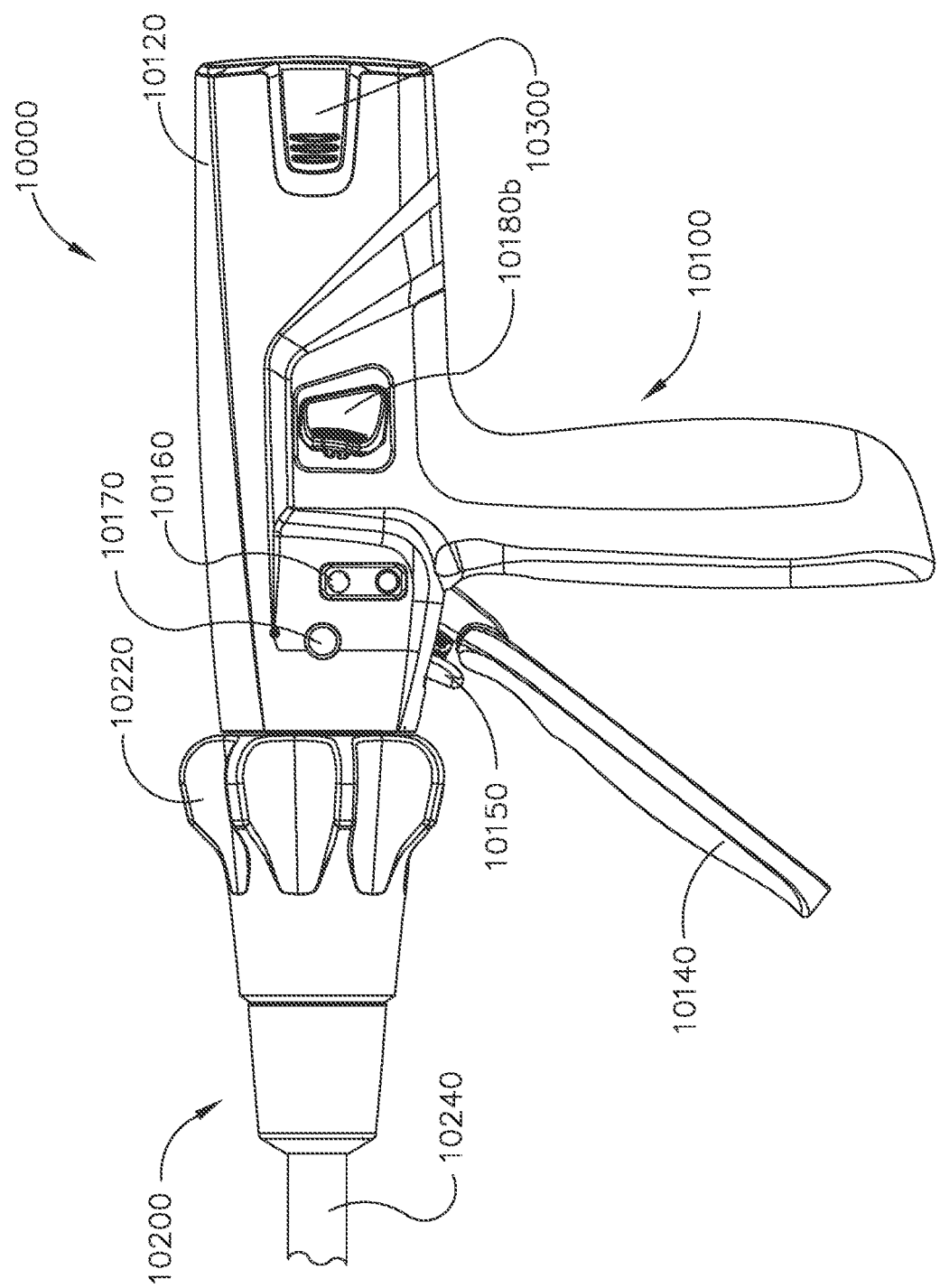
FIG. 49 is a partial elevational view of the surgical instrument of FIG. 1.
Figure 50:
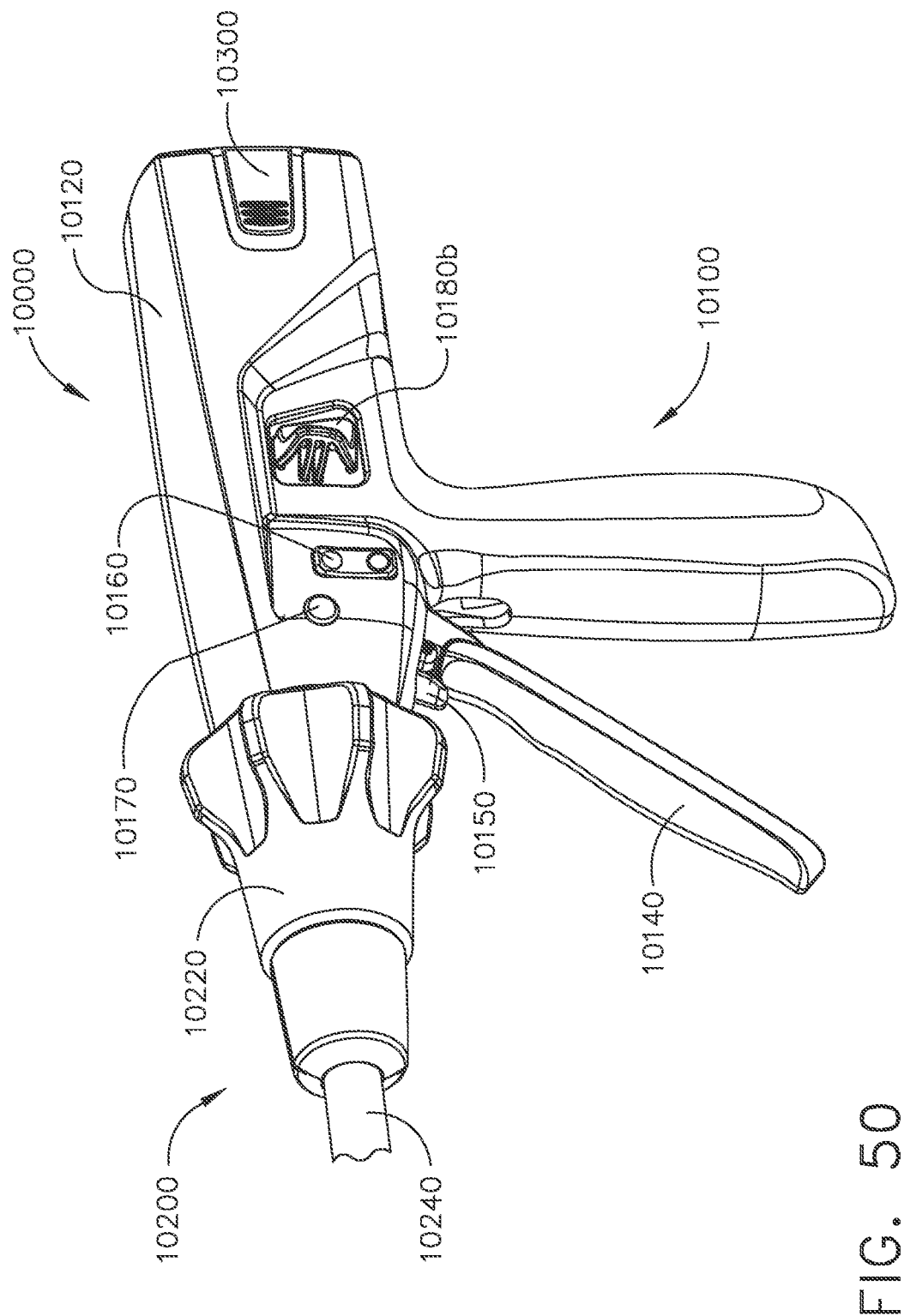
FIG. 50 is a partial perspective view of the surgical instrument of FIG. 1.

The above being said, referring to FIG. 48, the anvil jaw 10420 comprises shoulders, or stops, 10455 defined thereon which are configured to contact the top cam member 10255 of the tissue cutting member 10251 when the anvil jaw 10420 is moved into its open position. In such instances, the anvil jaw 10420 positions the tissue cutting member 10251 in its unfired position even if the tissue cutting member 10251 has been accidentally moved or positioned too far distally. Such an arrangement is particularly useful after the surgical instrument 10000 has already been used at least once and the staple firing system has been reset, or retracted as, in some instances, the tissue cutting member 10251 may not have been fully returned to its unfired position after the last staple firing stroke. As a result of the above, the possibility of the lockout of the surgical instrument 10000 being accidentally bypassed is reduced. Notably, the shoulders 10455 and the clearance pocket 10450 are positioned proximally with respect to the distal edges of the tissue stops 10427 which assures that the tissue cutting member 10251 is positioned proximally relative to the tissue captured within the end effector such that the tissue is not accidentally incised against the tissue cutting member 10251.

As discussed above, the articulation driver 10260 is translatable proximally and distally to articulate the end effector 10400 about the articulation joint 10500. That said, the articulation driver 10260 is actually a distal articulation driver of the articulation drive system. Referring to FIGS. 72 and 74-76, the articulation drive system further comprises a translatable proximal articulation driver 10270 which moves the distal articulation driver 10260. The articulation drive system also comprises an articulation lock 10280 positioned intermediate the proximal articulation driver 10270 and the distal articulation driver 10260, as described in greater detail below. The proximal articulation driver 10270 comprises an articulation rod 10272, a proximal push projection 10274 extending from the articulation rod 10272, and a distal pull projection 10276 extending from the articulation rod 10272. When the proximal articulation driver 10270 is pushed distally, the proximal push projection 10274 contacts the articulation lock 10280, unlocks the articulation lock 10280, and drives the distal articulation driver 10260 distally to articulate the end effector 10400. When the proximal articulation driver 10270 is stopped, the articulation lock 10280 automatically re-locks and holds the end effector 10400 in position. When the proximal articulation driver 10270 is pulled proximally, the distal pull projection 10276 contacts the articulation lock 10280, unlocks the articulation lock 10280, and pulls the distal articulation driver 10260 proximally to articulate the end effector 10400. Similar to the above, the articulation lock 10280 automatically re-locks when the proximal articulation driver 10270 stops. When the articulation lock 10280 is locked, the end effector 10400 is prevented from being back-driven or unintentionally moved out of its position. When the articulation lock 10280 is unlocked, the end effector 10400 can be articulated into a new position.

Figure 72:
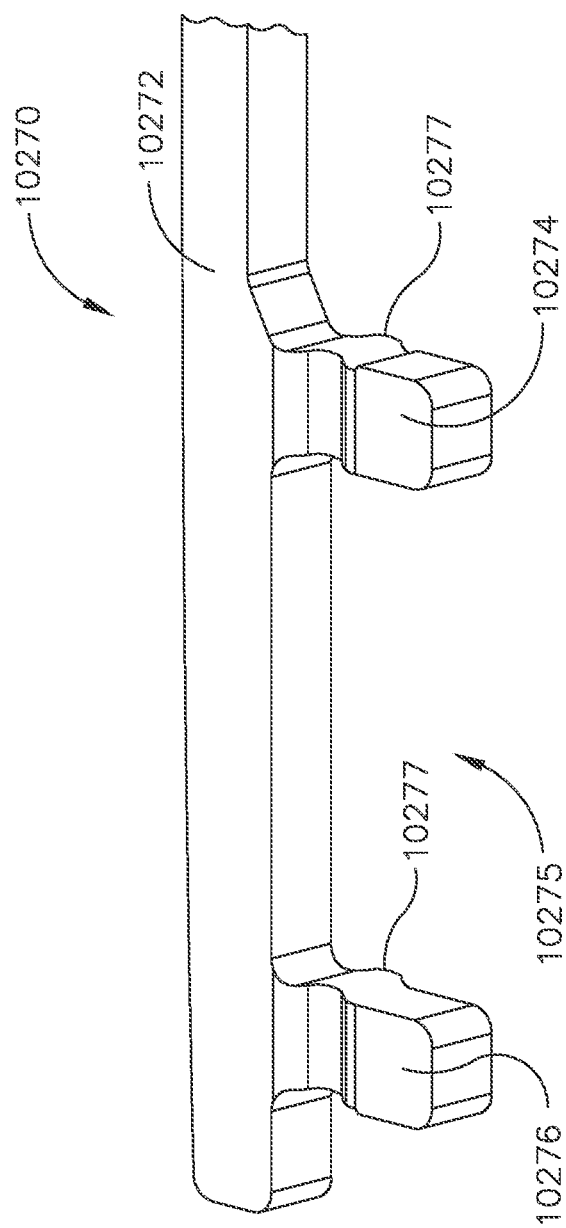
FIG. 72 is a perspective view of the distal end of a proximal articulation rod in accordance with at least one embodiment.

Further to the above, referring to FIG. 72, a space 10275 is defined between the projections 10274 and 10276 of the proximal articulation driver 10270. The distal articulation driver 10260 comprises a similar arrangement. More specifically, the distal articulation driver 10260 comprises a proximal projection 10269 and a distal projection 10267 with a space defined between them. The projections 10274 and 10276 of the proximal articulation driver 10270 are positioned within, and move within, this space defined between the projections 10267 and 10269 of the distal articulation driver 10260. The articulation lock 10280 comprises a stationary rod 10282 extending through the distal articulation driver 10260 and lock members 10284 rotatably and slideably mounted to the stationary rod 10282. The lock members 10284 are biased into a locked position by a spring 10286 positioned between two sets of lock members 10284 which causes the lock members 10284 to bite into the stationary rod 10282. When the proximal articulation rod 10270 is translated, however, the proximal articulation rod 10270 pushes on the lock members 10284 to rotate them out of their locked position so that the end effector 10400 can be articulated.

Figure 73:
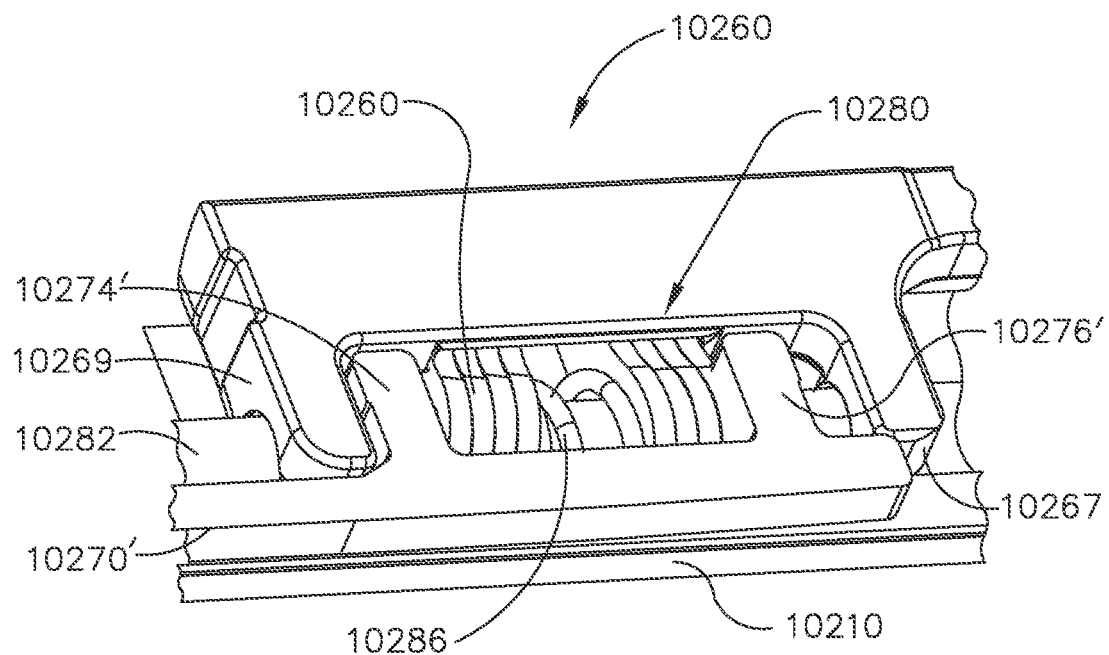
FIG. 73 is a perspective view of the interface between a proximal articulation rod and a distal articulation rod of an articulation drive in accordance with at least one embodiment.
Figure 73A:
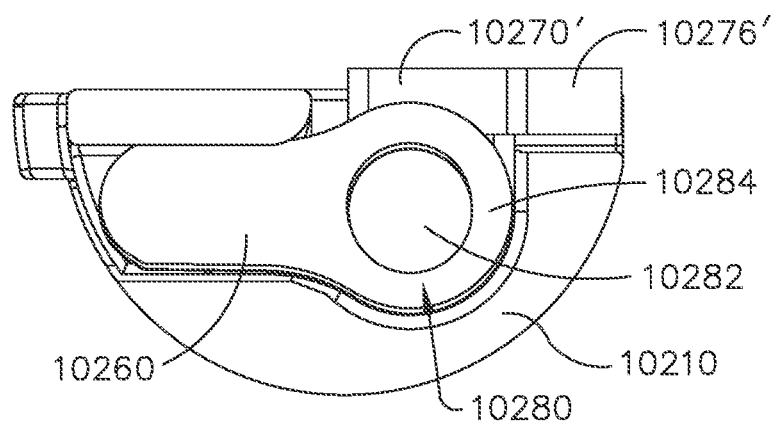
FIG. 73A is a detail view of the interface between the proximal articulation rod of FIG. 73 and an articulation lock.
Figure 74:
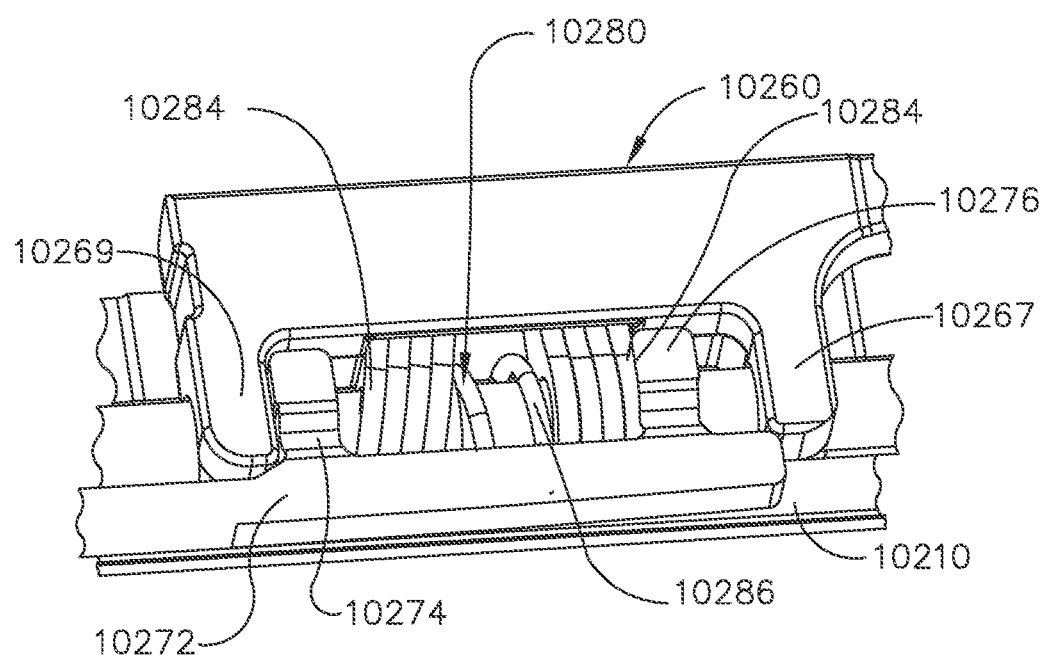
FIG. 74 is a perspective view of the interface between the proximal articulation rod of FIG. 72 with the distal articulation rod of FIG. 73.
Figure 74A:
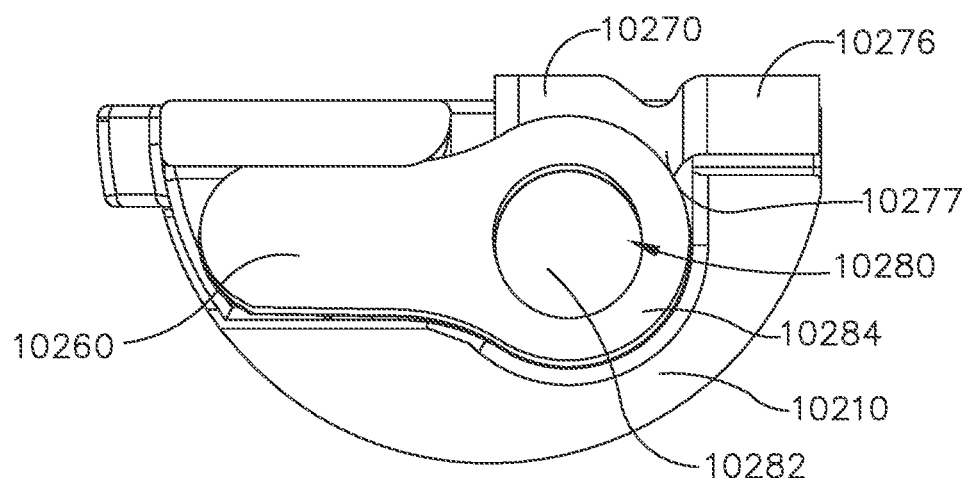
FIG. 74A is a detail view of the interface between the proximal articulation rod of FIG. 72 with the articulation lock of FIG. 73A.
Figure 75:
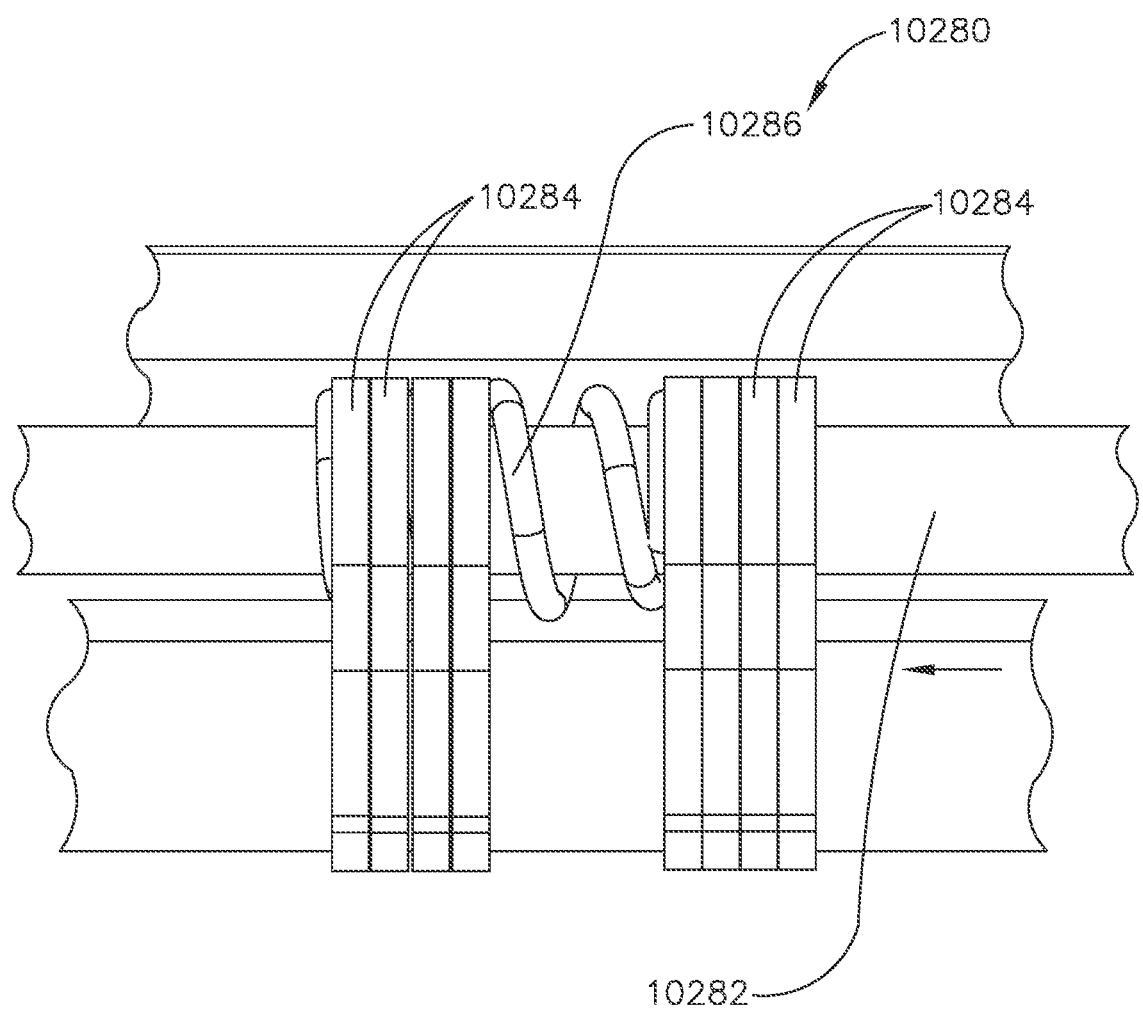
FIG. 75 is a perspective view of the articulation lock of FIG. 73A.
Figure 76:
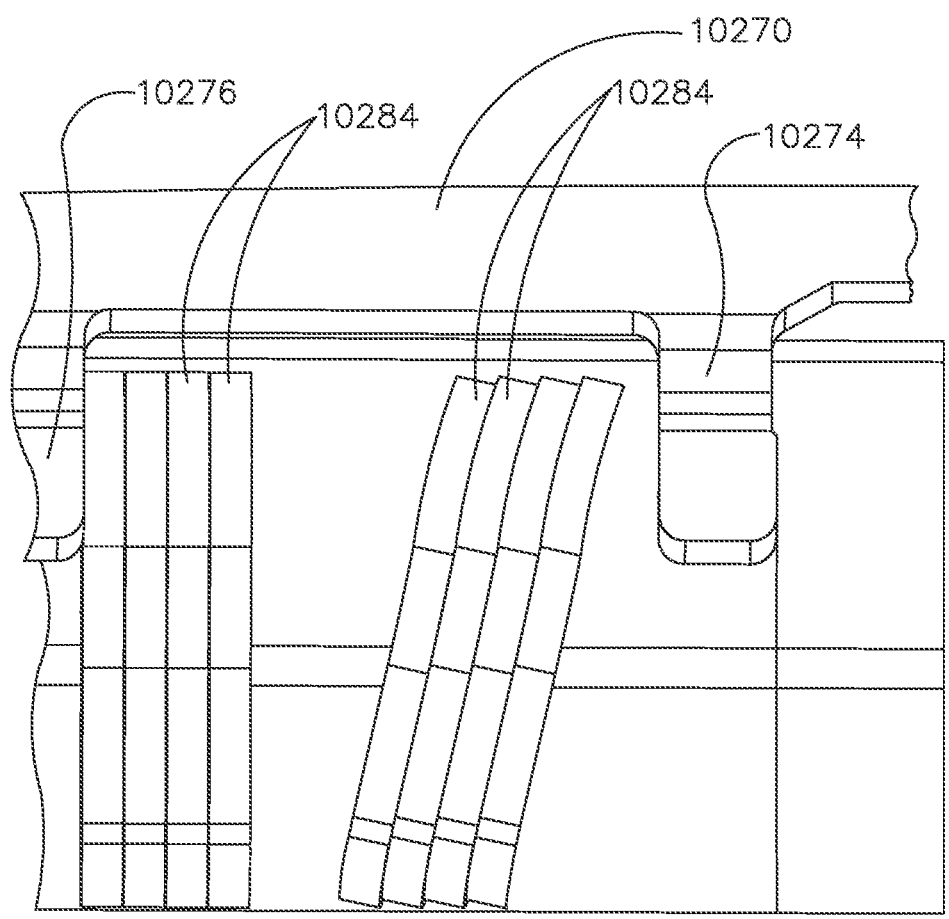
FIG. 76 is another perspective view of the articulation lock of FIG. 73A.

Further to the above, the projections 10274 and 10276 of the proximal articulation driver 10270 directly contact the lock members 10284. Referring to FIG. 74A, the projections 10274 and 10276 each comprises a projection, or bump, 10277 extending therefrom which engages the lock members 10284. The bumps 10277 provide a large pushing area for the proximal articulation driver 10270 to push against the lock members 10284. By way of comparison, a proximal articulation driver 10270' is illustrated in FIGS. 73 and 73A which does not have the bumps 10277 on its projections 10274' and 10276'. The arrangement of FIGS. 73 and 73A is still useful, but the contact area between the proximal articulation driver 10270' and lock members 10284 is smaller than the contact area between the proximal articulation driver 10270 and the lock members 10284. As a result of the larger contact area with the lock members 10284, the stress and strain in the proximal articulation driver 10270 is smaller than that of the proximal articulation driver 10270'. Moreover, the arrangement of the bumps 10277 can increase the torque arm between the proximal articulation driver 10270 and the lock members 10284 thereby lowering the force needed to unlock the articulation lock 10280.

Figure 77:
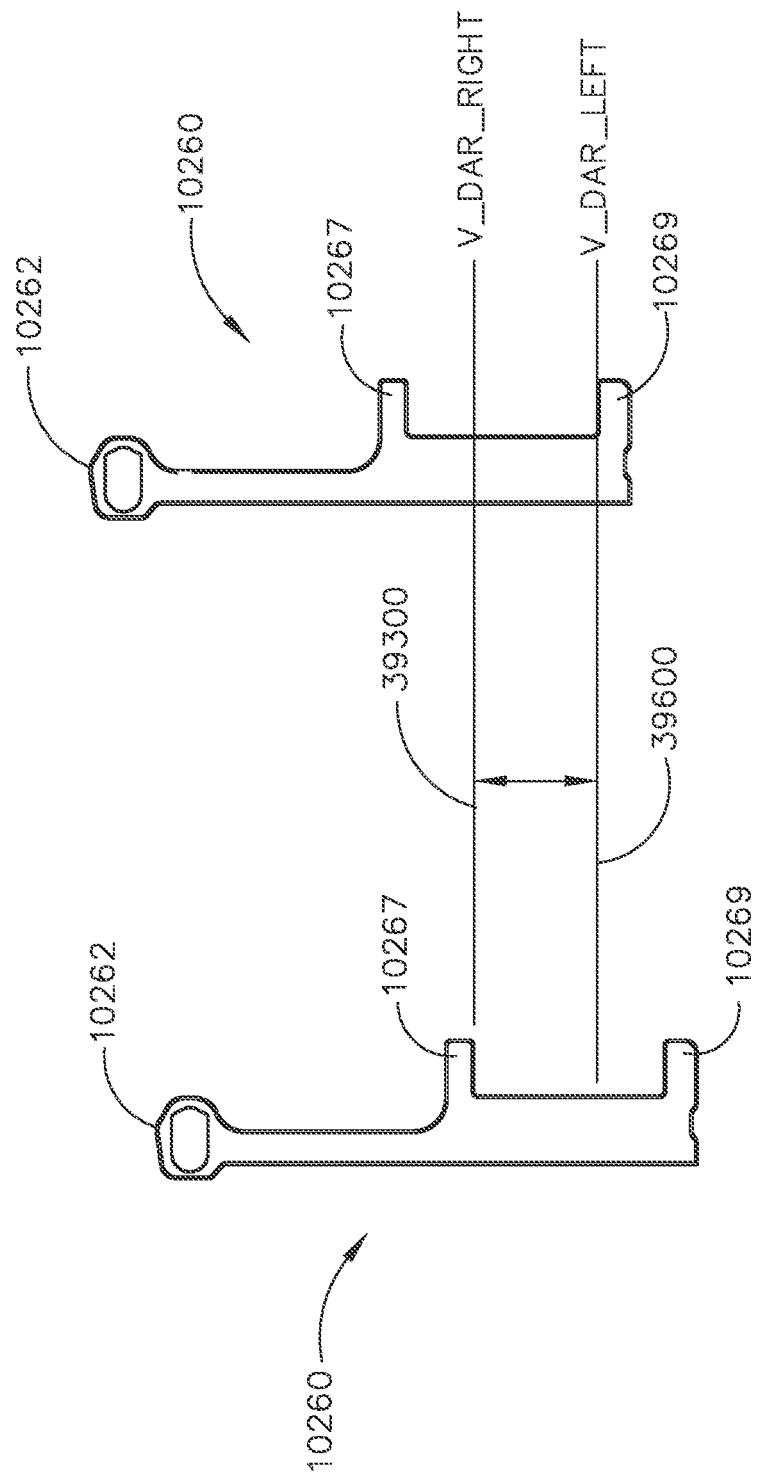
FIG. 77 illustrates the range of motion for the distal articulation rod of FIG. 73.
Figure 78:
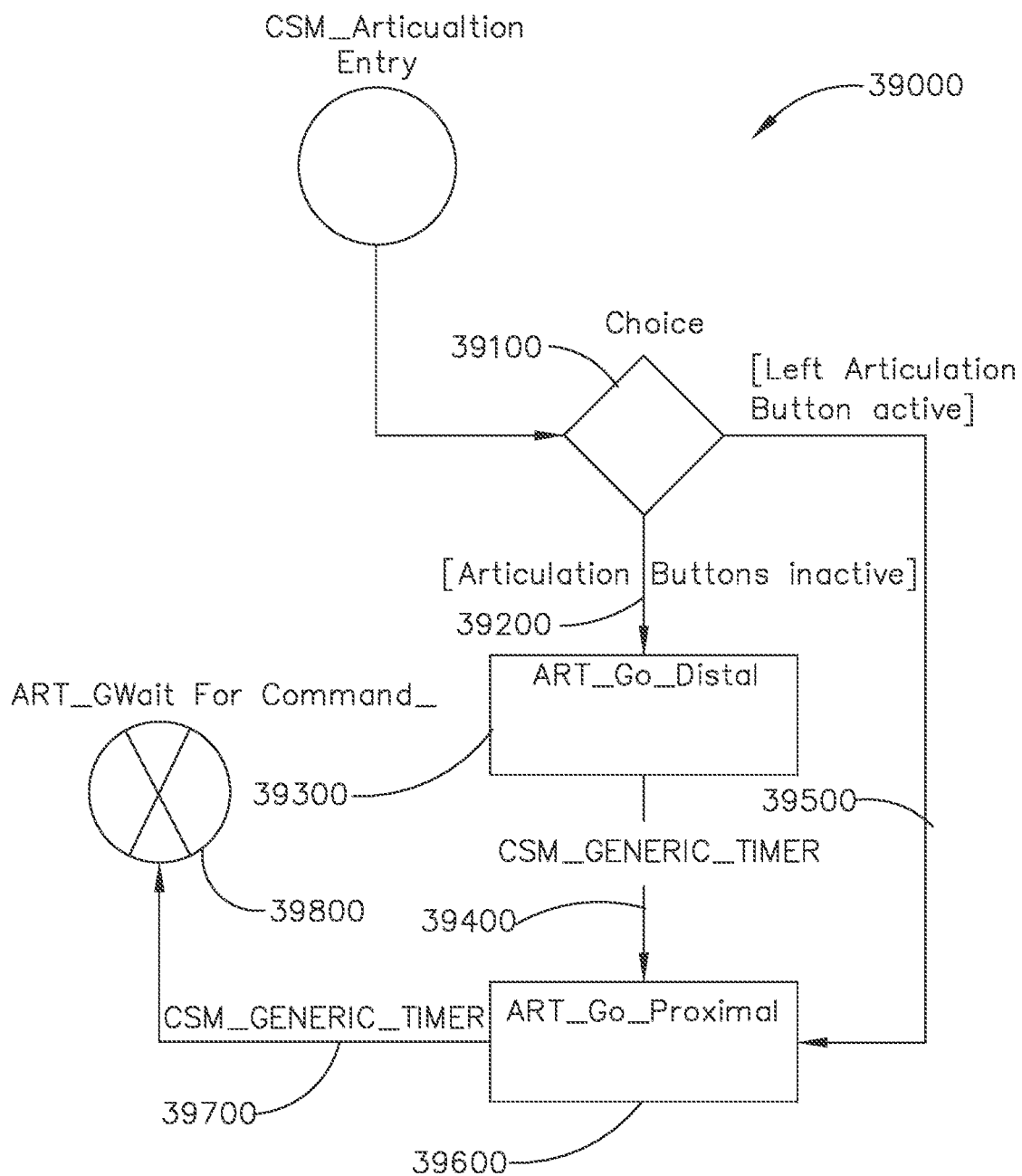
FIG. 78 is an algorithm for a control system to assess and acquire the position of an articulation system.

Described herein are various mechanisms and methods for determining the orientation of the shaft relative to the handle. Many of these mechanisms are able to evaluate the orientation of the shaft in real time and without regard to the previous orientation, or orientations, of the shaft. Such arrangements are particularly useful when the surgical instrument loses power, for example. When the surgical instrument re-powers, the control system can immediately assess the orientation of the shaft and the proper responsiveness of the articulation controls, for example. Moreover, the surgical instruments disclosed herein can be configured to immediately assess the articulation angle of the end effector when the surgical instrument is re-powered. Upon re-powering, the control system will evaluate whether the end effector is in a closed configuration or an open configuration. If the end effector is in a closed configuration upon re-powering, the control system will determine that the surgical instrument lost power during the staple firing mode and prompt the clinician to retract the staple firing system. If the end effector is in an open configuration upon re-powering, or once the end effector is in an open position upon re-powering, the control system will seek to make sure that the articulation drive system is coupled to the staple firing system such that the end effector can be straightened, or otherwise suitably oriented by the clinician, to remove the surgical instrument from the patient. FIG. 78 depicts an algorithm 39000 for the control system to assure that the articulation system is engaged with the staple firing drive. In this algorithm, the control system sweeps the staple firing drive between the positions associated with the furthest-right end effector position and its furthest-left end effector position such that, if the articulation drive was not already coupled to the firing drive, it would become so. These far-right and far-left orientations of the end effector correspond to the distal-most and proximal-most positions of the articulation driver 10260, as illustrated in FIG. 77. These positions are also the distal-most and the proximal-most positions, respectively, of the articulation driver 10270. The control system comprises one or more non-volatile device memories for storing information regarding the distal-most (far-right orientation) and proximal-most (far-left orientation) positions of the articulation drive system. As such, this information is available to the control system upon re-powering and the control system can limit its assessment to this range. In various embodiments, the surgical instrument can comprise a sensor configured to assess whether or not the articulation drive is mechanically coupled to the staple firing drive.

Further to the above, the algorithm 39000 comprises a step 39100 in which the control system assess whether or not an articulation button is depressed at the start-up, or initialization, of the surgical instrument. If it is determined at step 39100 that an articulation button is not depressed, the algorithm follows logic path 39200. In logic path 39200, the control system actuates the electric motor that drives the articulation system at step 39300 to push the articulation driver 10260 distally to articulate the end effector to the right. The control system then waits a predetermined amount of time at step 39400 before proceeding to step 39600 in which the control system actuates the motor in an opposite direction to pull the articulation driver 10260 proximally and articulate the end effector to the left. The control system then waits again for a predetermined amount of time at step 39700 and, after this time, waits for an input command at step 39800. In various embodiments, the control system comprises a timer circuit for counting the appropriate amount of time. If, on the other hand, the control system detects that the left articulation control is actuated at step 39100, the algorithm 39000 follows logic path 39500 and articulates the end effector to the left. If the control system detects that the right articulation control is actuated at step 39100, the algorithm 39000 follows a logic path that articulates the end effector to the right.

During a staple firing stroke, further to the above, the staples of a staple cartridge are progressively ejected by a firing member. The firing member ejects the proximal staples of the staple cartridge at the beginning of the staple firing stroke and the distal staples at the end of the staple firing stroke. In instances where all of the staples of a staple cartridge properly contact their staple forming pockets in the anvil positioned opposite to the staple cartridge, the staples will properly form and the staple firing force will be low. In instances where some of the staples miss their staple forming pockets, such staples may malform thereby increasing the force required to perform the staple firing stroke. Slowing the staple firing stroke may improve staple formation and lower the force required to perform the staple firing stroke. In various instances, detecting the force being applied by the staple firing system can be directly detected through one or more force sensors and/or strain gauges, for example. In other instances, detecting the force can be achieved by a current sensor or ammeter circuit, for example, which measures the current to the electric motor of the staple firing drive. The entire disclosure of U.S. patent application Ser. No. 16/361,793, entitled SURGICAL INSTRUMENT COMPRISING AN ADAPTIVE CONTROL SYSTEM, filed on Mar. 22, 2019 is incorporated by reference herein. These approaches may be suitable in various instances, but described below are embodiments and methods which assess the duty cycle of the staple firing system during the staple firing stroke.

Further to the above, the control system of the surgical instrument 10000 comprises a pulse width modulation (PWM) control circuit configured to control the speed of the firing drive electric motor. The PWM control circuit applies voltage pulses to the firing drive electric motor to perform the staple firing stroke. In various instances, the PWM control circuit increases the duration of the voltage pulses it applies to the firing drive electric motor in order to increase the speed of the firing drive electric motor and, correspondingly, the speed of the staple firing stroke. In other instances, the PWM control circuit decreases the duration of the voltage pulses it applies to the firing drive electric motor in order to decrease the speed of the firing drive electric motor and, correspondingly, the speed of the staple firing stroke. In either event, the PWM control circuit can make these pulse length adjustments without substantially increasing or decreasing the magnitude of the voltage pulses being applied to the motor. That said, embodiments are envisioned in which the magnitude of the voltage pulses, or certain voltage pulses, could be changed. In any event, as described in greater detail below, the control system is configured to drive the staple firing drive at a constant, or near constant, speed by adjusting the duration of the pulses via the PWM circuit. The entire disclosure of U.S. Pat. No. 8,499,992, entitled DEVICE AND METHOD FOR CONTROLLING COMPRESSION OF TISSUE, which issued on Aug. 6, 2013, is incorporated by reference herein.

The ratio of the time in which the voltage is applied to the electric motor (ON time) by the PWM circuit divided by the total time (ON time+OFF time) is the duty cycle of the staple firing drive motor. Thus, the duty cycle can range between 0% (completely OFF) and 100% (completely ON), i.e., a constant voltage without periodic interruptions. The terms ON and OFF suggest a non-zero voltage and a zero voltage; however, the terms ON and OFF are inclusive of HIGH and LOW voltages, respectively. The terms LOW or OFF include zero voltage and non-zero voltages that have a magnitude which is less than the HIGH or ON voltage. In view of the above, another way of expressing the duty cycle of the firing drive electric motor is the ratio of the time in which the voltage is applied to the electric motor (HIGH time) by the PWM circuit divided by the total time (HIGH time+LOW time).

The PWM control circuit applies the voltage pulses to the firing drive electric motor at regular intervals; however, the control system can comprise a frequency modulation (FM) control circuit to change the frequency of the voltage pulse intervals. In various instances, the FM control circuit decreases the interval between the voltage pulses to increase the speed of the firing drive electric motor and the staple firing stroke. Correspondingly, the FM control circuit increases the interval between the voltage pulses to decrease the speed of the firing drive electric motor and the staple firing stroke. In addition to or in lieu of the above, the control system can increase the magnitude of the voltage it applies to the firing drive electric motor to increase the speed of the firing drive electric motor and the staple firing stroke and/or decrease the magnitude of the voltage it applies to the firing drive electric motor to decrease the speed of the firing drive electric motor and the staple firing stroke.

Figure 79:
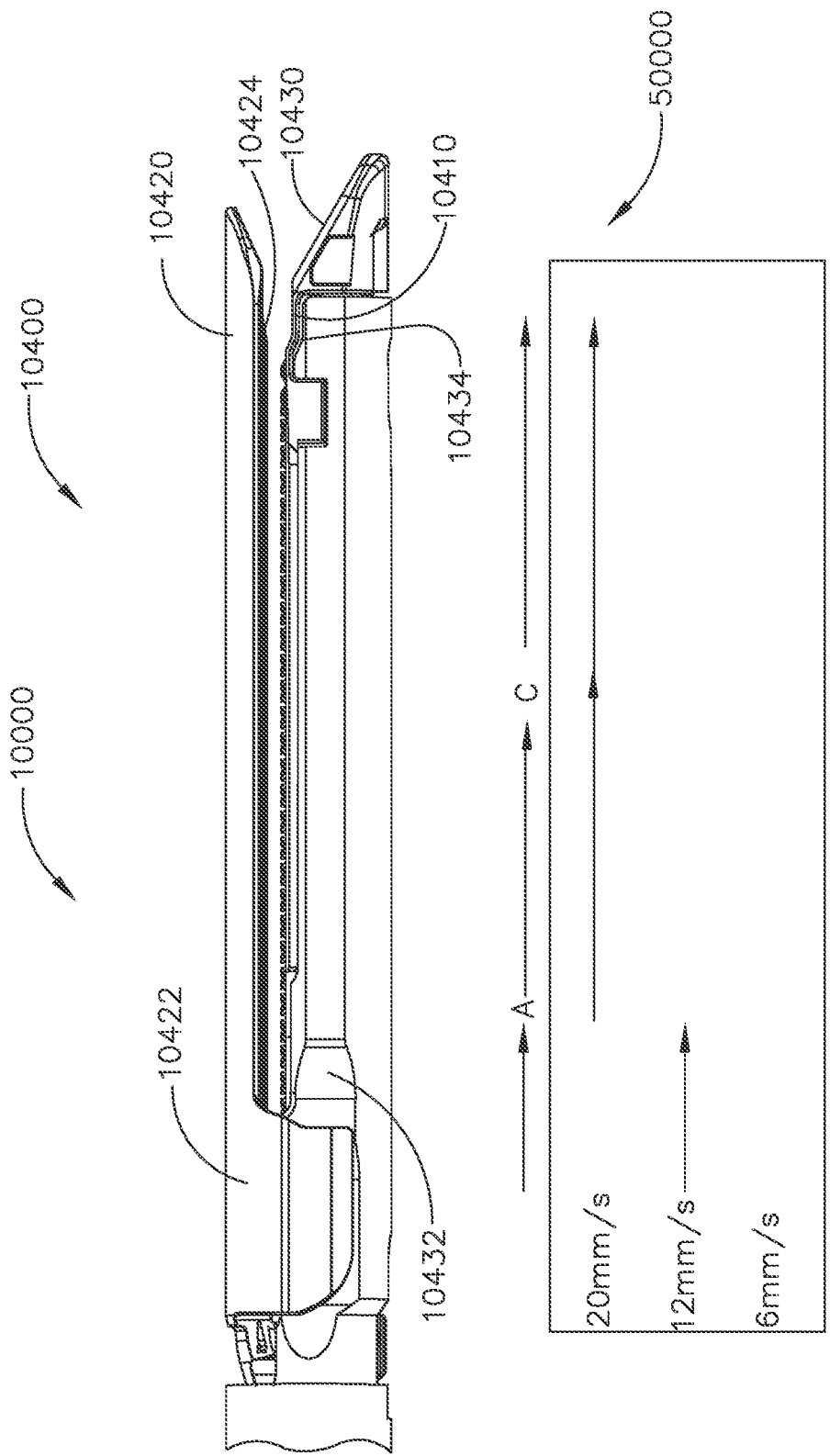
FIG. 79 depicts the end effector of the surgical instrument of FIG. 1 and a speed chart algorithm of the staple firing system during a staple firing stroke.

The control system of the surgical instrument 10000 comprises an algorithm for controlling the speed of the staple firing member. Referring to FIG. 79, the control system includes an algorithm 50000 configured to drive the staple firing member at a low speed, an intermediate speed, and a high speed. The low speed is 6 mm/s, or approximately 6 mm/s. The intermediate speed is 12 mm/s, or approximately 12 mm/s. The high speed is 20 mm/s, or approximately 20 mm/s. That said, a control system can be configured to operate the staple firing drive at any suitable number of speeds and/or at any suitable speed. The control system is configured to monitor the speed of the staple firing drive, via a motor speed sensor, and adjust the length of the voltage pulses applied to the electric motor of the staple firing drive to bring the speed of the staple firing drive to the target speed. For instance, if the target speed of the staple firing drive at a given point in the staple firing stroke is 12 mm/s and the actual speed is 11 mm/s, the control system increases the length of the voltage pulses it is applying to the electric motor to increase the speed of the staple firing drive. Stated another way, the control system increases the duty cycle of the firing drive electric motor to increase the speed of the staple firing drive. Correspondingly, the control system is configured to shorten the length of the voltage pulses it is applying to the firing drive electric motor if the speed of the staple firing drive exceeds the target speed until the speed of the staple firing drive reaches the target speed. Stated another way, the control system is configured to lower the duty cycle of the firing drive electric motor to decrease the speed of the staple firing drive. Notably, the target speed for the staple firing drive can change during the staple firing stroke, as described in greater detail below.

As discussed above, the firing member of the staple firing drive is moved distally during the staple firing stroke. Referring to FIGS. 47 and 79, the firing member is advanced distally from its proximal, unfired position to move the top cam member 10255 of the firing member up the ramp of the internal slot 10425 defined in the anvil 10420. The distance between the proximal, unfired position and the distal end of the internal slot ramp is 15 mm, or approximately 15 mm, for example. This initial 15 mm motion of the firing member can be used to close the end effector and/or pass over the firing lockout described above if a proper unspent staple cartridge is seated in the end effector. That being said, during this range of motion, the control system moves the firing member distally at the intermediate speed of 12 mm/s and evaluates the duty cycle needed to drive the staple firing member at this speed. If the duty cycle is between 40% and 60% in this initial range, the control system continues to drive the staple firing drive at the intermediate speed of 12 mm/s. If the duty cycle is above 60%, the control system lowers the target speed of the staple firing drive to the low speed of 6 mm/s. Such instances can arise when thick tissue is present between the anvil 10420 and the staple cartridge 10430. On the other hand, if the duty cycle is below 40% during this initial range, the control system increases the target speed to the high speed of 20 mm/s. Such instances can arise when thin tissue is present between the anvil 10420 and the staple cartridge 10430. In FIG. 79, the end of this initial range is demarcated by point A and, notably, staples are not deployed, or fired, during this initial range. After point A, the firing member fires the staples as the firing member is advanced distally until the firing member reaches the end of the staple firing stroke and/or the clinician stops the staple firing stroke by releasing the firing trigger.

Referring to the algorithm 50000 in FIG. 79, it can be seen that the staple firing member was driven at the intermediate speed, 12 mm/s, for the first 15 mm and then at the high speed, 20 mm/s, for the rest of the staple firing stroke. As described above, this shift in speed occurred because the control system measured that the duty cycle was below 40% during the first 15 mm of the staple firing stroke. Had the firing member been blocked by the lockout in the first 15 mm, however, the duty cycle would have spiked immediately to 100% and the control system is configured to immediately stop the staple firing stroke in response to such asymptotic duty cycle spikes. Once the firing member has passed this initial 15 mm distance, in various instances, the remainder of the staple firing stroke comprises approximately 30 mm, approximately 45 mm, or approximately 60 mm, for example. These lengths represent the different staple pattern lengths that are currently desirable in many staple cartridges, but any suitable staple pattern lengths could be used. In some embodiments, the control system does not re-evaluate the duty cycle of the staple firing drive to adjust the target speed of the firing member after an initial evaluation of the firing drive duty cycle. The control system of embodiment of FIG. 79, however, continues to evaluate the duty cycle of the staple firing drive throughout the staple firing stroke. At point C in the staple firing stroke, the control system makes another adjustment to the target speed or maintains the target speed according to the criteria set forth above. As depicted in FIG. 79, the duty cycle of the staple firing drive was determined to be between 40% and 60% at point C and, thus, the control system maintained the target speed of 20 mm/s. Point C is half way between point A and the end of the staple firing stroke, i.e., half way into the staple pattern. That said, point C can be at any suitable location. Moreover, the control system can be configured to adjust the target speed of the staple firing drive at any suitable number of points during the staple firing stroke. In at least one instance, the control system can make a target speed adjustment at every 15 mm during the staple firing stroke, for example. For a 30 mm staple cartridge, the control system could make a total of two target speed adjustments, as illustrated in FIG. 79. For a 45 mm staple cartridge, the control system could make a total of three target speed adjustments at 15 mm intervals and, for a 60 mm staple cartridge, the control system could make a total of four target speed adjustments at 15 mm intervals, for example.

Figure 80:
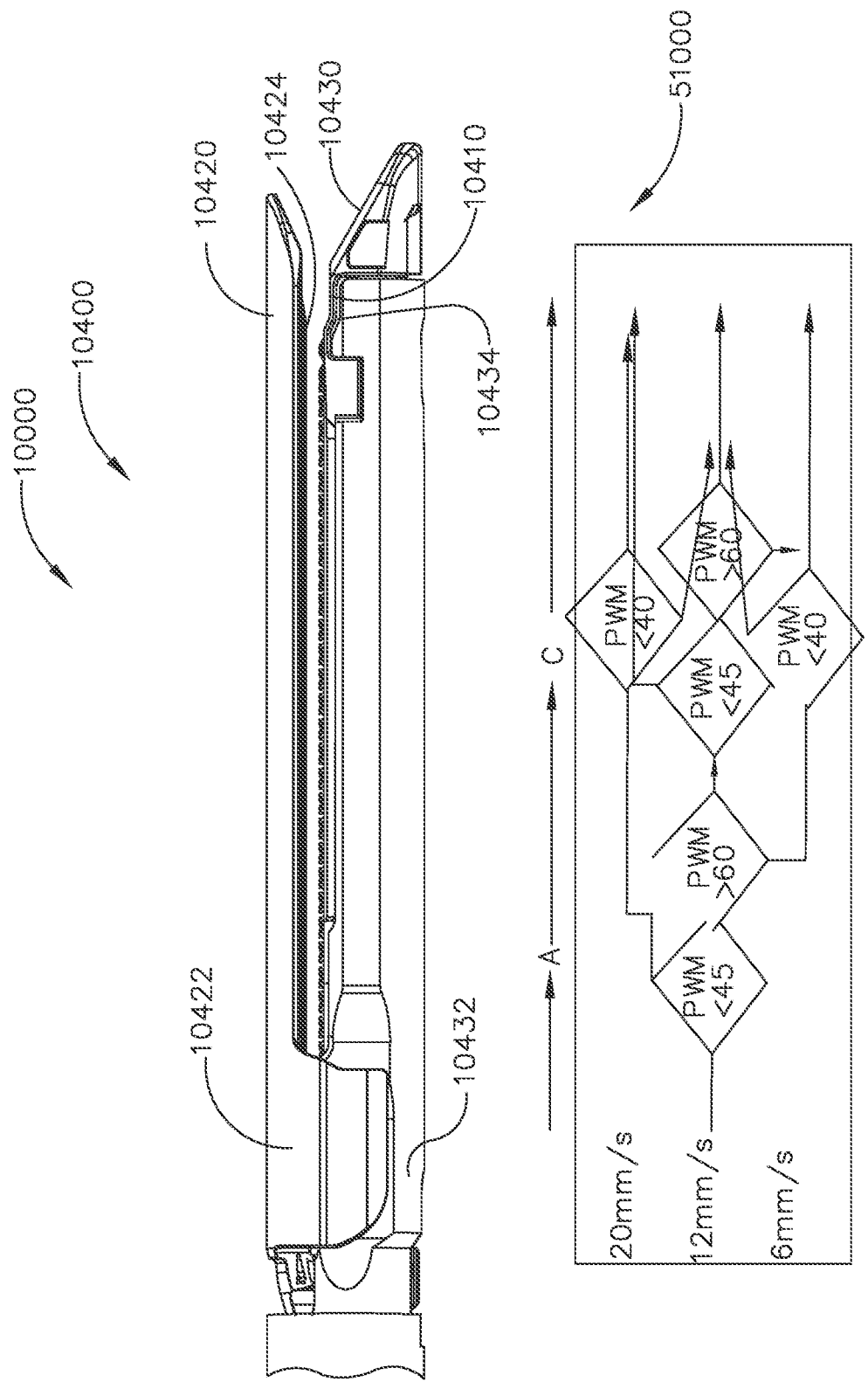
FIG. 80 depicts the end effector of the surgical instrument of FIG. 1 and a speed chart algorithm of the staple firing system in accordance with at least one embodiment.

For the examples given above, the control system used the same set of criteria for evaluating the duty cycle at every target speed adjustment point. That said, referring to FIG. 80, embodiments are envisioned in which the control system uses different sets of duty cycle criteria at different target speed adjustment points. For instance, the control system can use a first set of duty cycle criteria at the first target speed adjustment point and a second set of duty cycle criteria at the second target speed adjustment point. In at least one instance, referring to the algorithm 51000 in FIG. 80, the control system increases the target speed of the staple firing drive if the duty cycle is below 45% at the first target speed adjustment point. That said, the control system increases the target speed of the staple firing drive at the second target speed adjustment point if the duty cycle is below 40%. Any suitable threshold, or thresholds, could be used. In the embodiment illustrated in FIG. 80, the upper duty cycle threshold of 60% is the same at both the first and second target speed adjustment points in the algorithm 51000. If the duty cycle is in excess of 60%, the control system shortens the voltage pulses to slow the staple firing system. In other embodiments, the upper duty cycle threshold can be different at the first and second target speed adjustment points.

Figure 81:
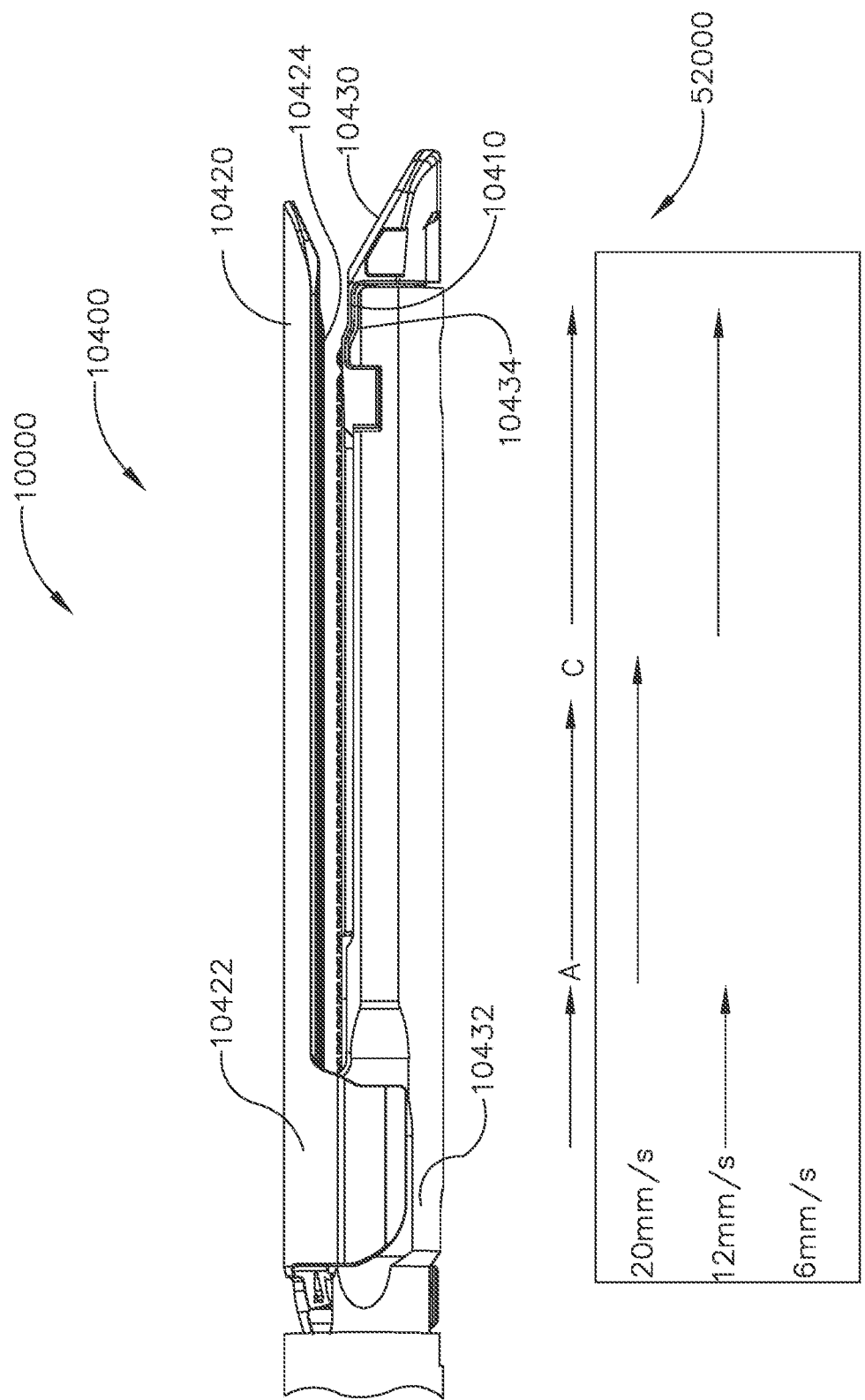
FIG. 81 depicts the end effector of the surgical instrument of FIG. 1 and a speed chart algorithm of the staple firing system during a staple firing stroke.

Further to the above, referring to FIG. 81, the algorithm of the control system increased the target speed at point A from the intermediate speed to the high speed but then lowered the target speed at point C from the high speed to the intermediate speed. At point C, the control system determined that the duty cycle of the firing drive electric motor was above 60% and lowered the target speed one level, i.e., from the high speed to the intermediate speed. Notably, the control system did not lower the target speed from the high speed to the low speed at point C as the control system is configured to only raise or lower the target speed one level at each check point. In order for the target speed of the staple firing drive to be lowered from the high speed to the low speed, the duty cycle would have to exceed the upper duty cycle threshold at two checkpoints. These checkpoints can be consecutive checkpoints, or non-consecutive checkpoints. That said, embodiments are envisioned in which the control system comprises a safety duty cycle threshold that, if exceeded, would cause the control system to drop the target speed of the staple firing drive to the low speed regardless of the speed of the staple firing drive prior to that checkpoint.

Figure 82A:
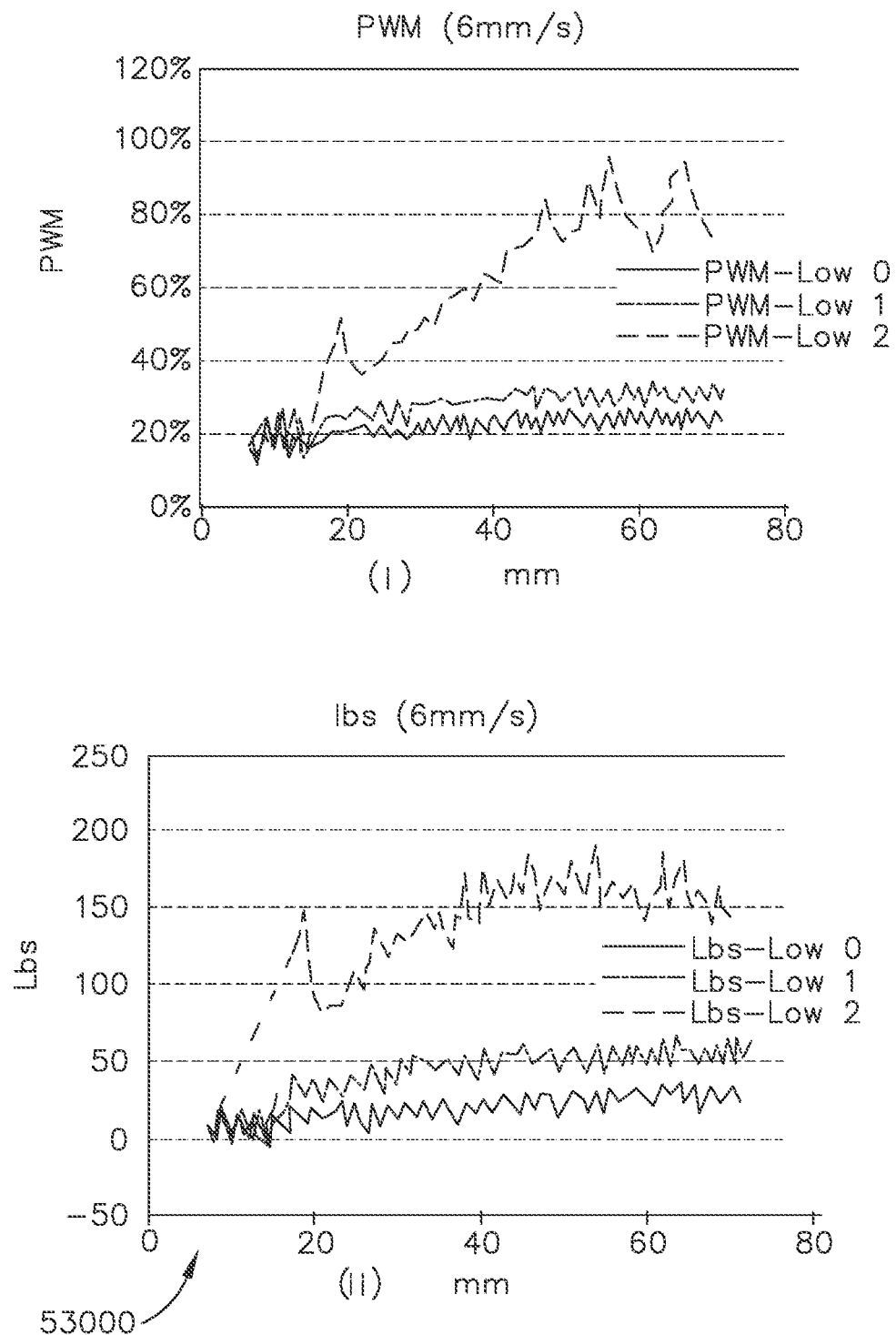
FIG. 82A depicts a graph of the duty cycle of and firing force experienced by the staple firing system of the surgical instrument of FIG. 1 during three staple firing strokes.

FIG. 82A depicts two graphs—a duty cycle graph (i) and a firing force graph (ii) of the staple firing drive. The duty cycle graph (i) and the firing force graph (ii) are correlated to demonstrate three different staple firing strokes. Two of the staple firing strokes in FIG. 82A stay below the 40% duty cycle threshold as the firing force is low. In such staple firing strokes, the control system increases the target speed of the staple firing system at each check point according to the current algorithm, although other algorithms are possible. One of the staple firing strokes in FIG. 82A reaches a 100% duty cycle because the firing force is high. When the duty cycle is in excess of 60% at a target speed adjustment point, the control system decreases the target speed of the staple firing system according to the current algorithm, although other algorithms are possible. Notably, the duty cycle of this staple firing isn't above the 60% threshold at the beginning of the staple firing stroke and, as a result, the control system may not actually lower the target speed if the duty cycle didn't exceed the upper threshold of 60% until after the check point, or check points.

Figure 82B:
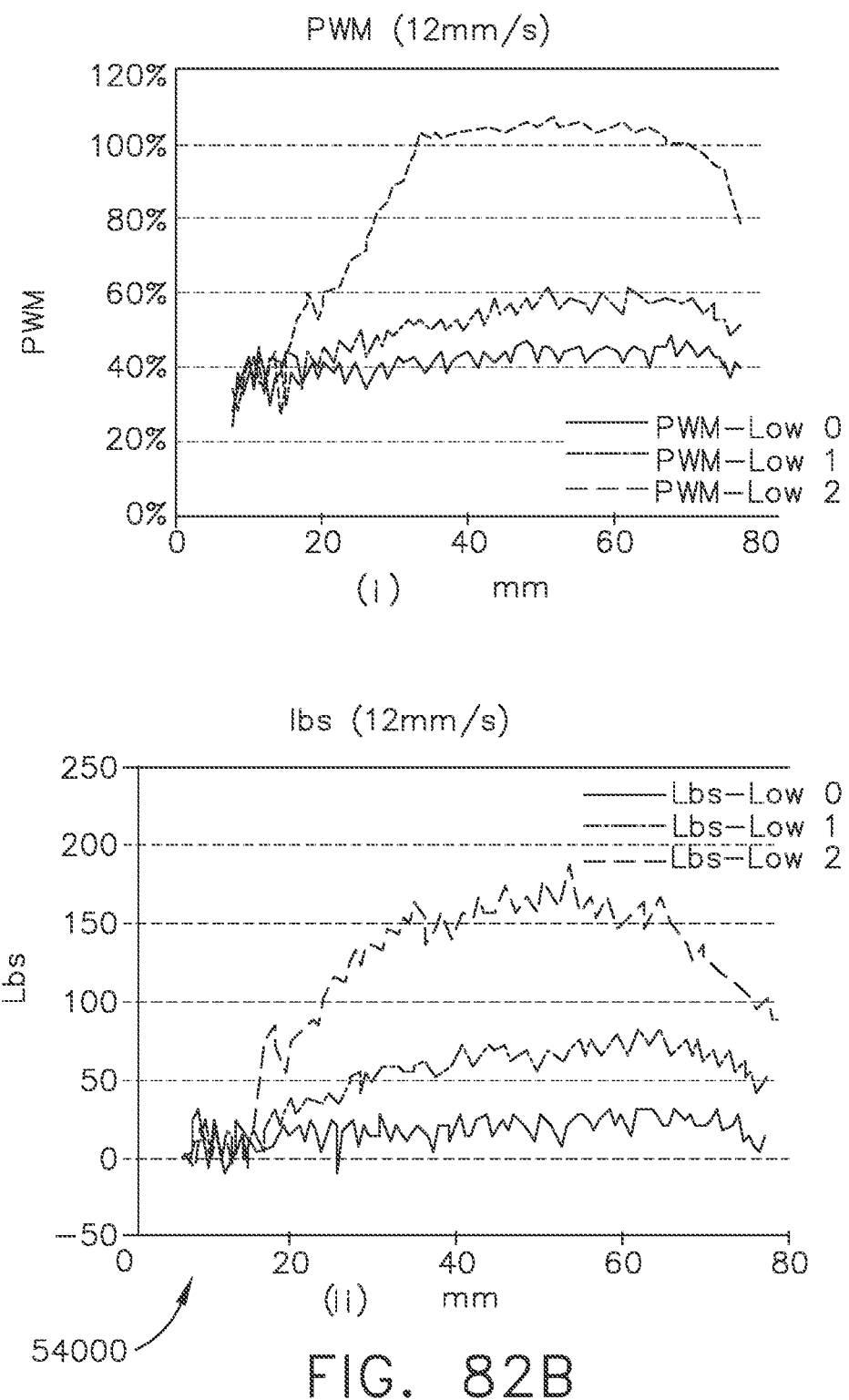
FIG. 82B depicts a graph of the duty cycle of and firing force experienced by the staple firing system of the surgical instrument of FIG. 1 during three staple firing strokes at a higher firing speed than that of FIG. 82A.

FIG. 82B depicts two graphs—a duty cycle graph (i) and a firing force graph (ii) of the staple firing drive. The duty cycle graph (i) and the firing force graph (ii) are correlated to demonstrate three different staple firing strokes. Two of the staple firing strokes in FIG. 82B stay between the 40% duty cycle threshold and the 60% duty cycle threshold as the firing force is relatively low. In such staple firing strokes, the control system does not change the target speed of the staple firing system according to the current algorithm, although other algorithms are possible. One of the staple firing strokes in FIG. 82B reaches a 100% duty cycle, however, because the firing force is high. When the duty cycle is in excess of 60% at a target speed adjustment point, the control system decreases the target speed of the staple firing system according to the current algorithm, although other algorithms are possible. In this instance, the duty cycle exceeded the upper duty cycle threshold at about 20 mm distal to the proximal, unfired starting position of the staple firing member. Stated another way, the duty cycle jumped above 60% as soon as the staple firing drive started to fire the staples, i.e., at 5 mm past the 15 mm initial range discussed above. As a result, the control system may not react to the elevated duty cycle until after a 30 mm checkpoint, for example.

Notably, further to the above, the graphs of FIGS. 82A and 82B, and several other graphs, depict a stream of dots along the staple firing stroke. These dots represent the data samples taken by the control system. The closeness of the dots represents a fairly high data sample rate, although lower or higher data sample rates could be used. As can be seen in these figures, the data is subject to a certain amount of jitter or chatter which can cause the control system to react to outlying data, especially when the duty cycle data is near the upper or lower duty cycle thresholds. In various instances, the control system can utilize a data smoothing algorithm which uses averages, and/or other statistical evaluations, of the data over a number of collected data points to determine the duty cycle at the target speed evaluation points. In at least one such instance, the control system uses the average of three consecutive duty cycle measurements, for example, to determine the duty cycle value used for assessing the algorithm criteria.

Figure 83A:
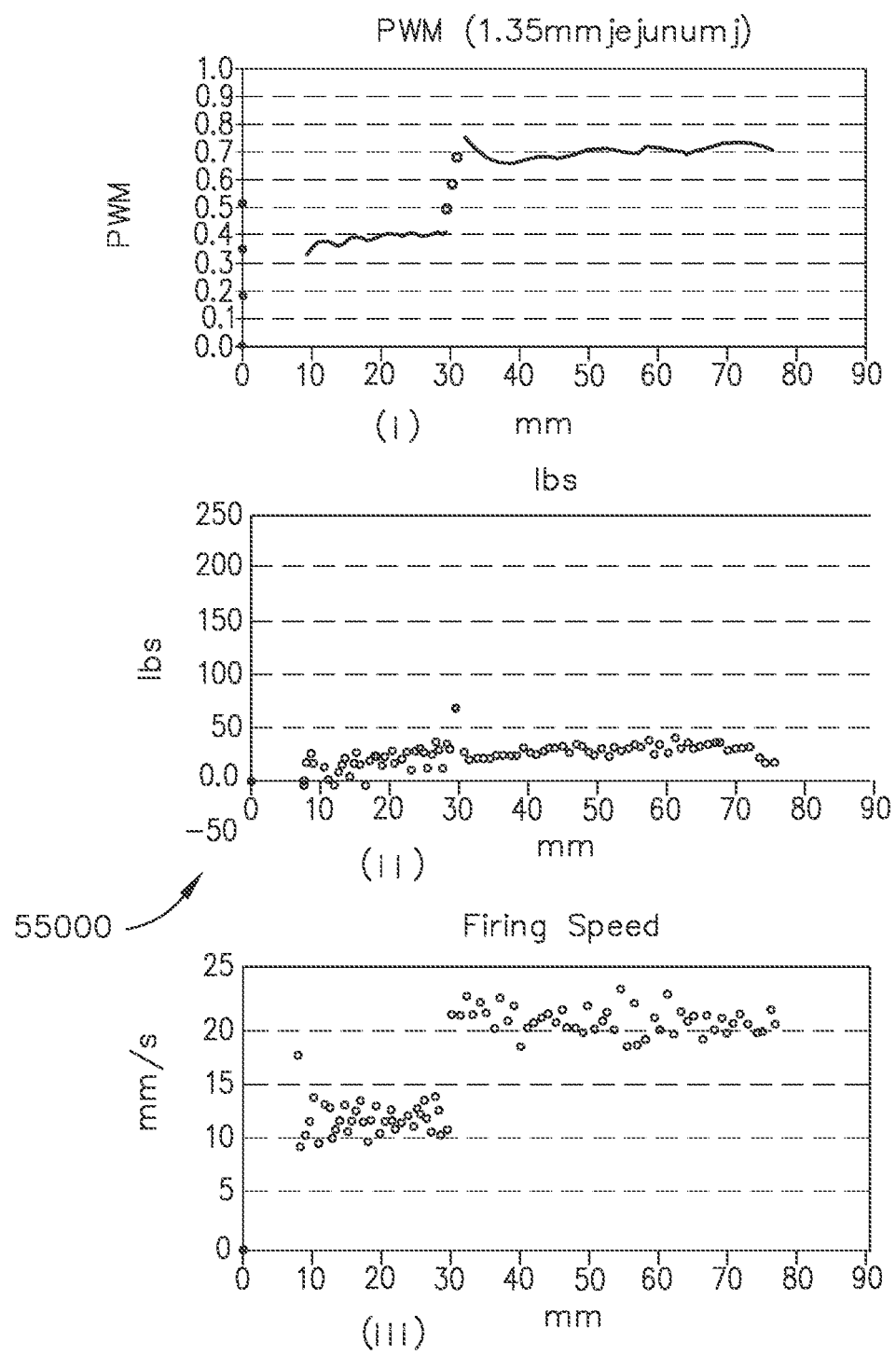
FIG. 83A depicts a graph of the duty cycle, firing force, and firing speed experienced by the staple firing system of the surgical instrument of FIG. 1 during a staple firing stroke through 1.35 mm thick jejunum tissue.
Figure 83B:
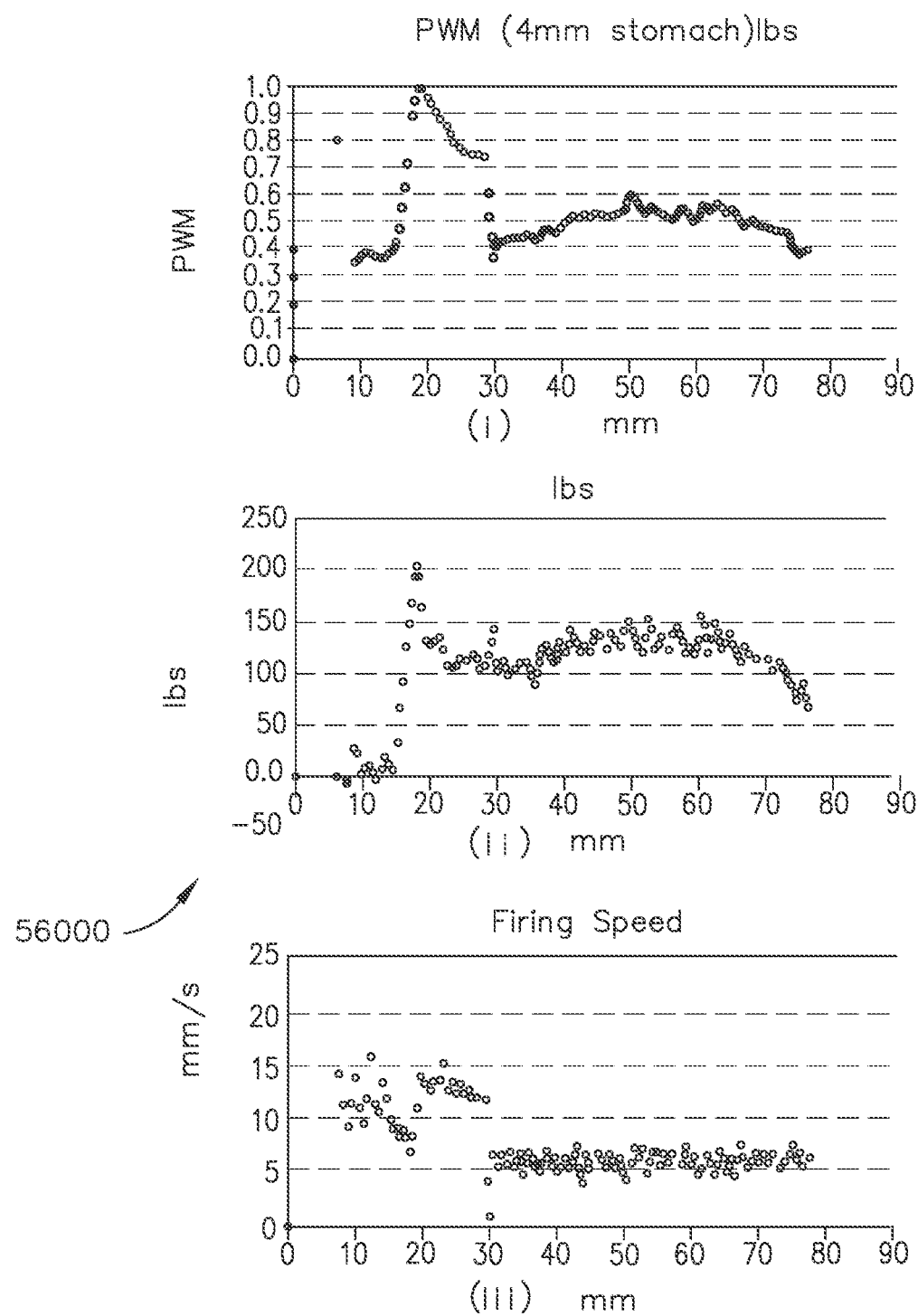
FIG. 83B depicts a graph of the duty cycle, firing force, and firing speed experienced by the staple firing system of the surgical instrument of FIG. 1 during a staple firing stroke through 4 mm thick stomach tissue.

FIG. 83A depicts three graphs—a duty cycle graph (i), a firing force graph (ii), and a firing speed graph (iii) of the staple firing drive. The duty cycle graph (i), the firing force graph (ii), and the firing speed graph (iii) are correlated to demonstrate a staple firing stroke. The duty cycle of the staple firing stroke jumps from below the lower duty cycle threshold of 40% to above the upper duty cycle threshold of 60% at about the 30 mm mark, which is about 15 mm into deforming the staples. This jump in duty cycle was not because the firing force increased; rather the jump in duty cycle occurred because the control system increased the duty cycle to increase the speed of the staple firing drive in accordance with its target speed selection criteria. FIG. 83B depicts a similar jump in the duty cycle at about 20 mm; however, this jump in duty cycle occurred because the staple firing member encountered an elevated resistance while deforming the staples and the control system responded by increasing the length of the voltage pulses it was applying to the electric motor in order to maintain the staple firing speed at its target speed. Stated another way, the control system spiked the duty cycle because the control system was struggling to maintain the intermediate speed, i.e., 12 mm/s, of the staple firing system. This situation did not last long as the control system re-lowered the duty cycle at the 30 mm target speed check point while lowering the speed of the staple firing stroke to its low, i.e., 6 mm/s, target speed.

Figure 84A:
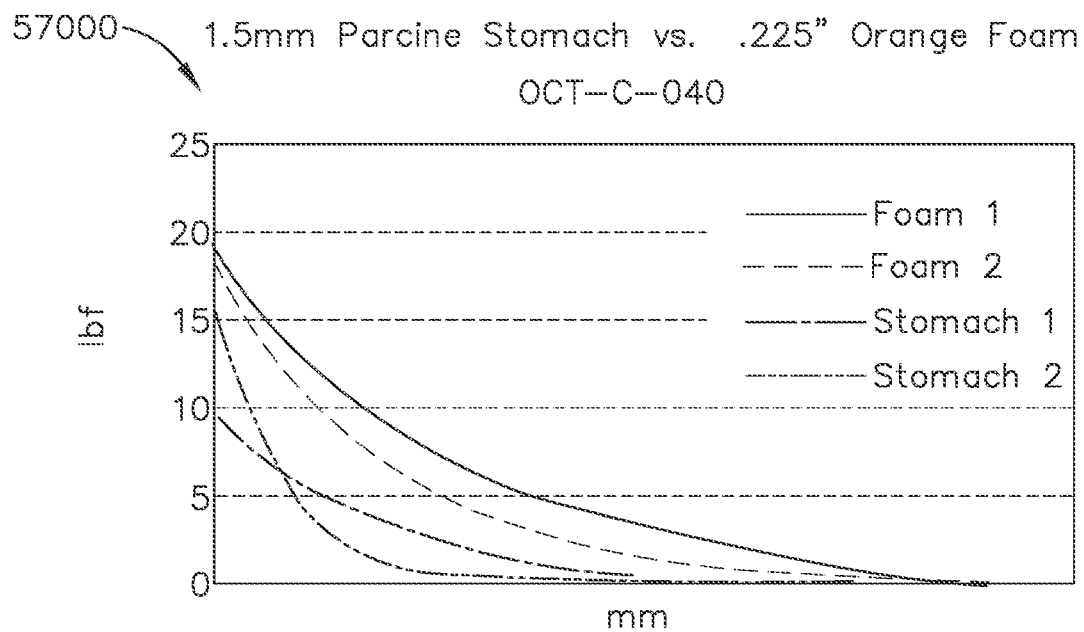
FIGS. 84A and 84B depict graphs comparing the firing force through tissue as compared to a tissue analogue.
Figure 84B:
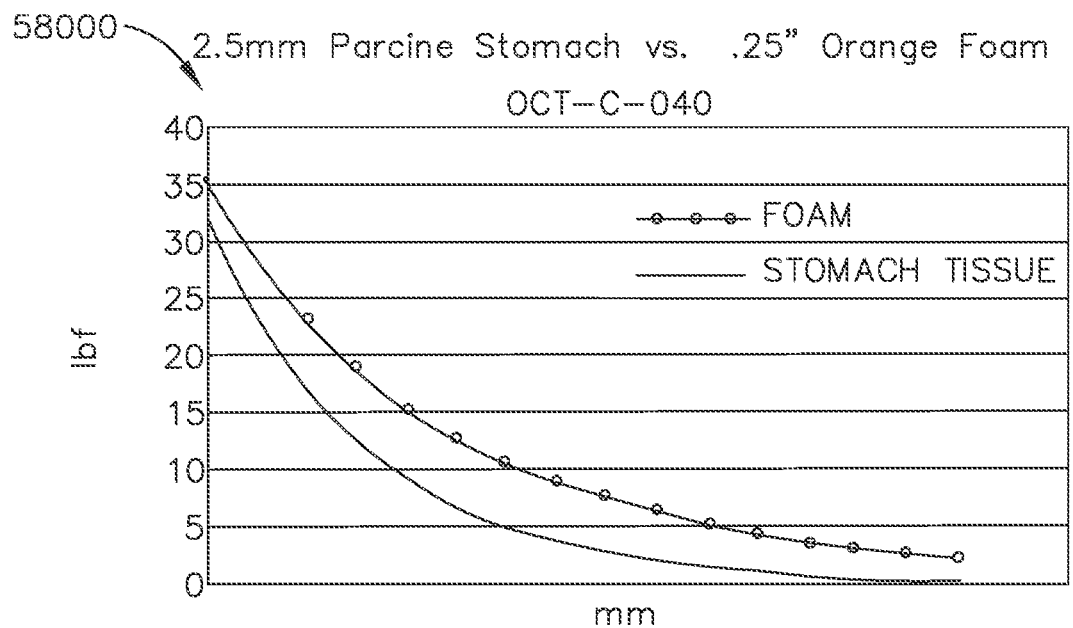

FIGS. 84A and 84B depict graphs which demonstrate that the firing force of the staple firing drive for stapling and cutting actual tissue tracks that of the firing force for stapling and cutting a tissue analogue, such as foam, for example.

Figure 85A:
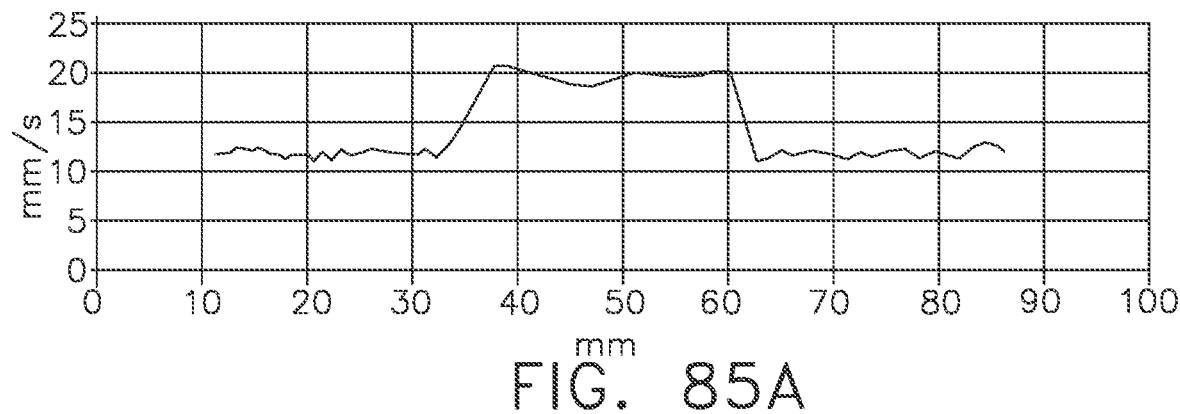
FIGS. 85A and 85B depict graphs demonstrating the duty cycle and the firing speed experienced by the staple firing system of the surgical instrument of FIG. 1 during several staple firing strokes.
Figure 85B:
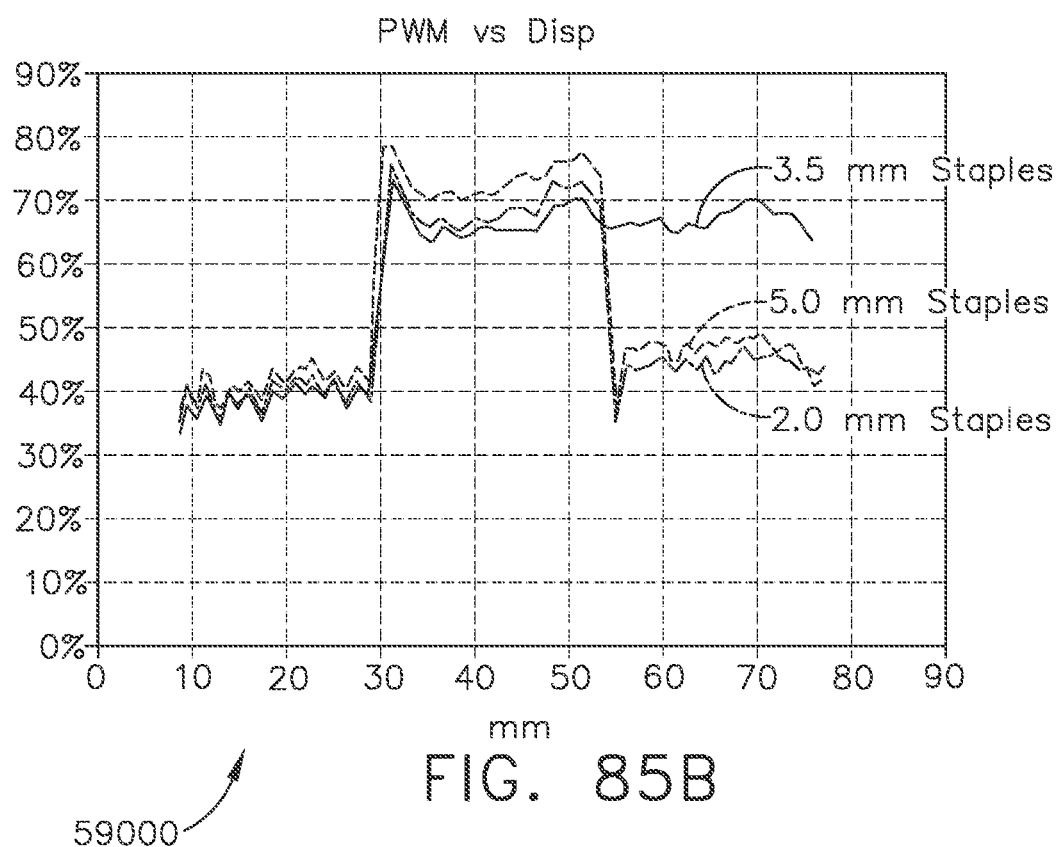

FIGS. 85A and 85B depict several staple firing stroke examples that occurred when stapling and cutting stomach tissue. The staple firing strokes followed a very similar duty cycle pattern. For instance, all of the staple firing strokes started below the lower duty cycle threshold and, in response, the control system increased the speed of the staple firing stroke from the intermediate speed to the high speed. To do so, the control system increased the duration of the voltage pulses being applied to the electric motor of the staple drive system at a first check point. In doing so, however, the duty cycle jumped above the upper duty cycle threshold and, at the next check point, the control system shortened the voltage pulses to lower the duty cycle and slow the staple firing stroke back to its intermediate speed. Notably, in one example, the speed of the staple firing drive was maintained at the high speed. In this example, the staples being deformed were smaller as compared to the staples used during the other staple firing strokes and they duty cycle stayed just under the threshold.

FIG. 86A depicts the duty cycle of two staple firing strokes while stapling thin jejunum tissue—one that occurred when the end effector was articulated and one that occurred when the end effector was not articulated. As can be seen in FIG. 86A, the two duty cycle curves are very similar and are, notably, between about 60% and about 80% of the duty cycle. FIG. 86B depicts the duty cycle of two staple firing strokes while stapling thick jejunum tissue—one that occurred when the end effector was articulated and one that occurred when the end effector was not articulated. As can be seen in FIG. 86B, the two duty cycle curves are very similar and are, notably, between about 60% and about 80% of the duty cycle. Also, notably, the duty cycle is somewhat higher for the thick jejunum tissue (FIG. 86B) as compared to the thin jejunum tissue (FIG. 86A). FIG. 86C depicts the duty cycle of two staple firing strokes while stapling stomach tissue—one that occurred when the end effector was articulated and one that occurred when the end effector was not articulated. As can be seen in FIG. 86C, the two duty cycle curves are very similar and, notably, reach the maximum duty cycle once the staple firing drive starts deforming staples at about 15 mm from the proximal, unfired position of the firing member.

Figure 87:
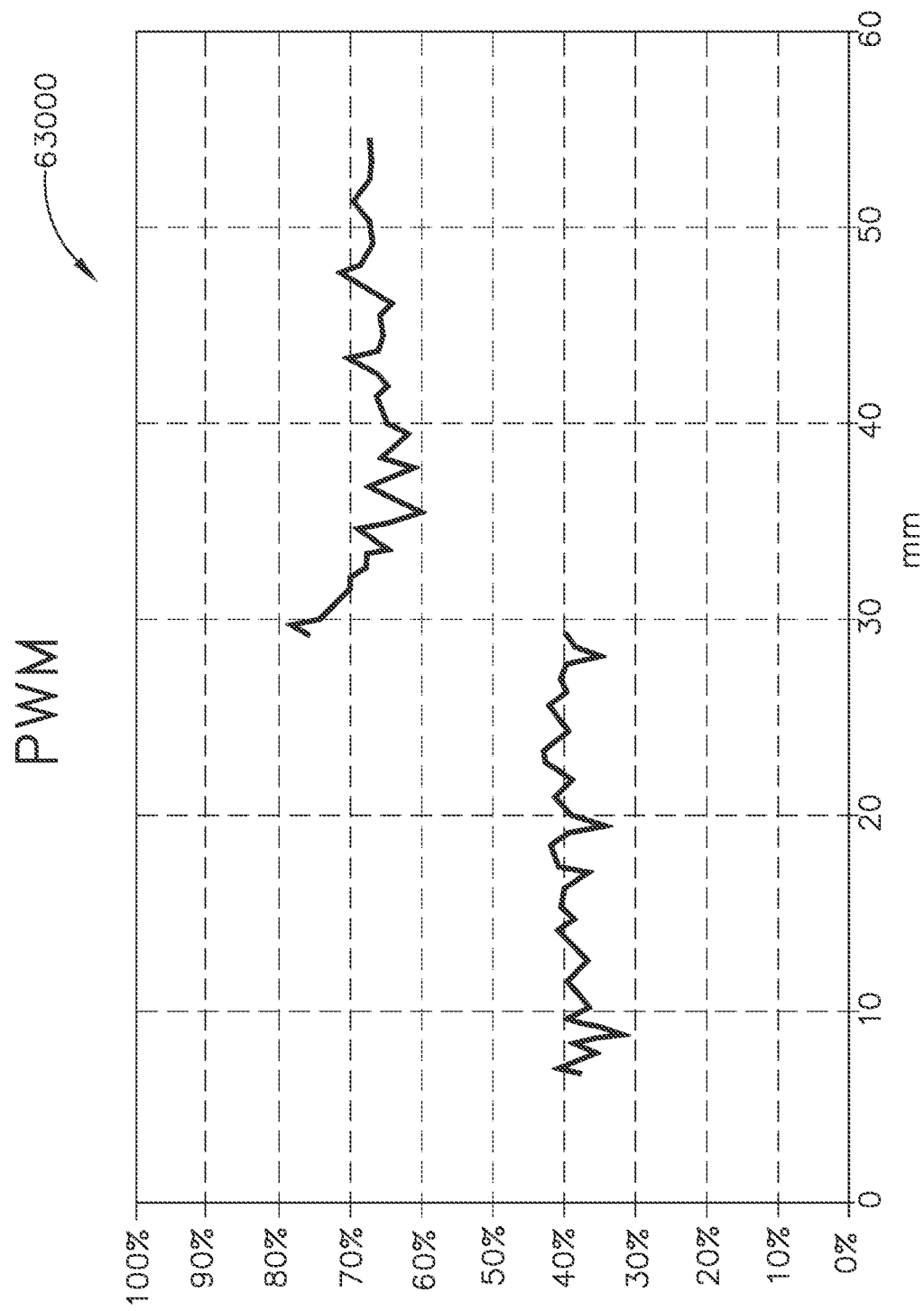
FIG. 87 depicts a graph of the duty cycle of the staple firing system of the surgical instrument of FIG. 1 during a staple firing stroke in which the control system increased the speed of the staple firing stroke.

FIG. 87 comprises a graph 63000 depicting the duty cycle of a staple firing stroke. As illustrated in the graph 63000, the duty cycle is just at or just below 40% for the first 30 mm of the staple firing stroke (15 mm of the initial travel and 15 mm of staple firing) and is then raised by the control system to increase the speed of the staple firing drive. Similar to the above, increasing the duty cycle in this instance overshot the duty cycle above the top duty cycle threshold of 60% where it remained for the rest of the staple firing stroke, i.e., the last 30 mm.

Figure 88:
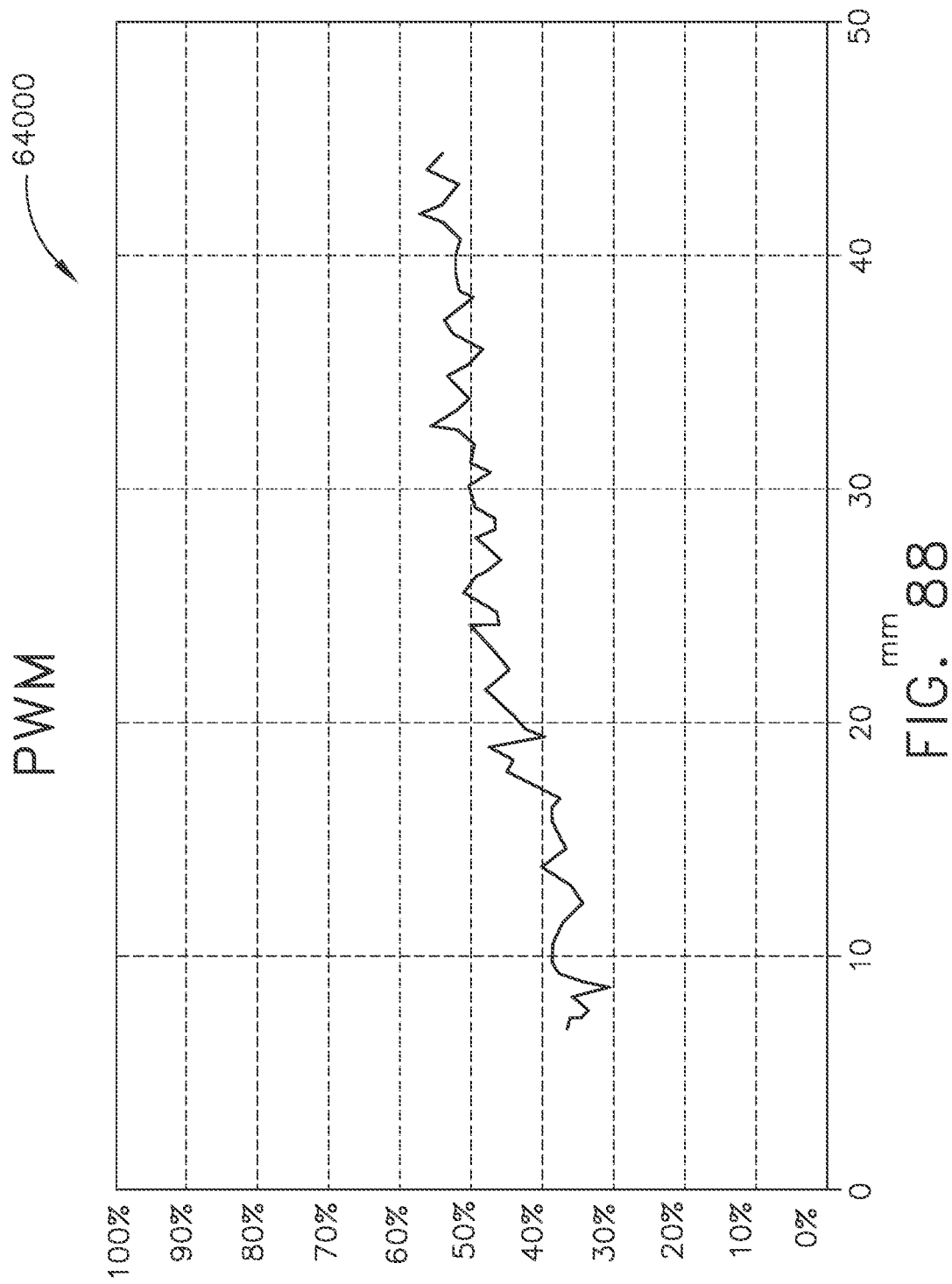
FIG. 88 depicts a graph of the duty cycle of the staple firing system of the surgical instrument of FIG. 1 during a staple firing stroke in which the control system substantially maintained the same speed throughout the staple firing stroke.

FIG. 88 comprises a graph 64000 depicting the duty cycle of a staple firing stroke. As illustrated in the graph 64000, the duty cycle begins below the 40% duty cycle threshold but then gradually increases into the zone between the upper and lower duty cycle thresholds. In such a zone, the control system does not increase or decrease the speed of the staple firing system and/or otherwise adjust the duty cycle of the firing drive electric motor other than to maintain the speed of the staple firing system at the intermediate target speed. As such, a smooth duty cycle curve is seen without abrupt changes.

Figure 89:
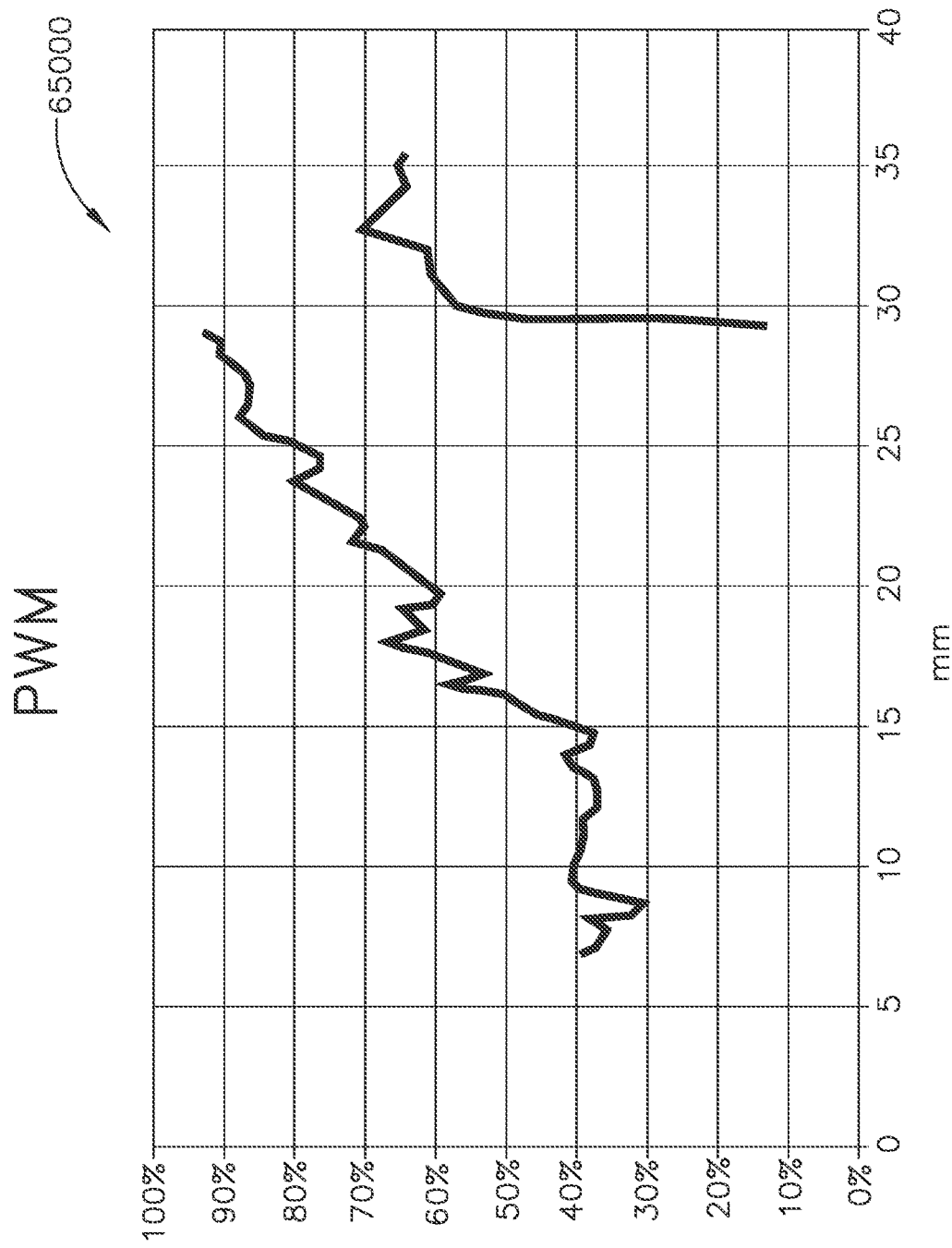
FIG. 89 depicts a graph of the duty cycle of the staple firing system of the surgical instrument of FIG. 1 during a staple firing stroke in which the control system decreased the speed of the staple firing stroke.

FIG. 89 comprises a graph 65000 depicting the duty cycle of a staple firing stroke. As illustrated in the graph 65000, the duty cycle begins at about the 40% lower duty cycle threshold and then proceeds upwardly quickly once the firing member starts deforming staples at the 15 mm point. In fact, the duty cycle increases to almost 100% until the next check point is reached at 30 mm where, as described above, the control system lowered the duty cycle to slow the staple firing drive. FIG. 89 depicts a drastic drop in the duty cycle at this point but returns to an elevated state just above the upper duty cycle threshold for the remainder of the staple firing stroke.

The lower duty cycle threshold is described as being 40% in many instances, and 45% in other instances. That said, the lower duty cycle threshold can be any suitable value, such as 30%, 33%, 35%, or 50%, for example. Similarly, the upper duty cycle threshold is described as being 60%. That said, the upper duty cycle threshold can be any suitable value, such as 50%, 55%, 65%, 67%, 70%, or 75%, for example.

As mentioned above, the staple firing stroke stops when the clinician releases the firing trigger. When the clinician actuates the firing trigger once again, the staple firing stroke resumes. In such instances, the control system returns the speed of the staple firing stroke to the speed just before the staple firing stroke was stopped. The control system comprises one or more memory devices for storing the speed of the staple firing stroke during the staple firing stroke such that the control system can access the stored speed to re-start the staple firing stroke. If the control system does not have access to this data, the control system can re-start the staple firing stroke in its intermediate speed, for example.

As described herein, the surgical instrument 10000 is configured to evaluate the speed of the staple firing stroke and compare the measured speed of the staple firing stroke to a target speed. The surgical instrument 10000 comprises an encoder in communication with the control system which is configured to measure the speed of the staple firing stroke. In at least one instance, a gear in the staple firing drive is observed by the encoder to evaluate the speed of the staple firing stroke. The gear comprises teeth which pass in front of the encoder as the gear is rotated during the staple firing stroke. The rate in which the teeth pass the encoder is used by the control system to assess the speed of the staple firing drive. In at least one instance, the gear makes one full rotation during the entire staple firing stroke. In addition to or in lieu of the above, the gear is comprised of metal and the control system comprises a Hall Effect sensor configured to sense the rate in which the metal gear teeth pass by the Hall Effect sensor. In various embodiments, the control system is configured to evaluate the speed of a translating component of the staple firing drive.

As described herein, an algorithm of a control system uses the duty cycle of the firing drive electric motor to assess whether the speed of the staple firing drive should be adapted, and in which direction, i.e., slower or faster. Various other algorithms use data in addition to the duty cycle of the firing drive electric motor to adapt the speed of the staple firing stroke. For instance, a speed adaptation algorithm can utilize the articulation angle of the end effector, the initial battery voltage, the operative battery voltage, the current through the motor, PID error, and/or any characterization of the PWM circuit made during the manufacturing process of the surgical instrument, for example. These parameters, among others, can be used in a mathematical operation, or evaluation equation, to determine whether or not to adapt the speed of the staple firing stroke, the direction in which the speed is to be adapted, and/or the amount of the adaptation. The parameters used can be instantaneous measurements and/or measurements averaged over several readings. The parameters used can include the rate of change, or change in slope, of the measurements. The values of the parameters can be added, subtracted, multiplied, and/or divided according to the evaluation equation.

FIGS. 68-71 depict an end effector 40000 comprising an anvil jaw 40420 and a cartridge jaw 10410. The anvil jaw 40420 comprises a proximal portion 40100 and a distal portion, or tip, 40200 attached to the proximal portion 40100. The distal portion 40200 is rotatable between a first operational orientation (FIG. 68) and a second operational orientation (FIG. 70 and FIG. 71) to provide a clinician with the ability to choose between a straight anvil tip and an angled anvil tip before using the end effector 40000.

The proximal portion 40100 comprises an angled distal end that can be characterized by a first angle 40120 and a second angle 40130. The first angle 40120 is measured with reference to a top plane defined by the top of the proximal portion 40100 while the second angle 40130 is measured with reference to a bottom plane defined by the bottom of the proximal portion 40100. In various instances, the first angle 40120 and the second angle 40130 are supplementary angles. In at least one instance, the first angle 40120 and the second angle 40130 are substantially supplementary. The distal portion 40200 comprises an angled proximal end which is attached to the distal end of the proximal portion 40100. The angled proximal end of the distal portion 40200 can be characterized by a first angle 40220 and a second angle 40230. In various instances, the first angle 40220 and the second angle 40230 are supplementary angles. In at least one instance, the first angle 40220 and the second angle 40230 are substantially supplementary. In various instances, the first angle 40120 and the first angle 40220 are supplementary angles and the second angle 40130 and the second angle 40230 are supplementary angles. This configuration permits the proximal portion 40100 and the distal portion 40200 of the anvil jaw 40420 to have a complimentary, angled attachment plane where a distal face 40110 of the proximal portion 40100 and a proximal face 40210 of the distal portion 40200 abut each other in both the first orientation and the second orientation.

Figure 68:
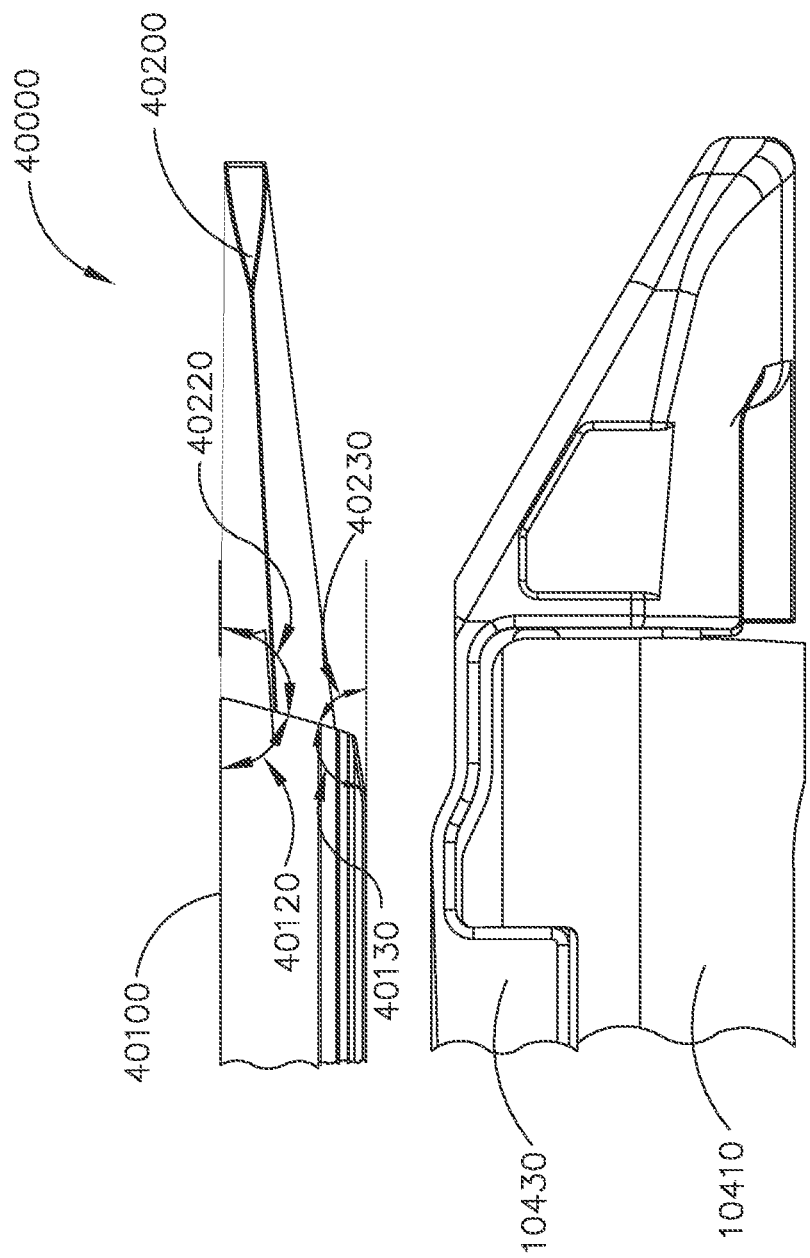
FIG. 68 is a partial elevational view of an end effector comprising an anvil jaw and a cartridge jaw, wherein the anvil jaw comprises a distal portion that rotatable between a first operational orientation and a second operational orientation which is different than the first operational orientation, and wherein the distal portion of the anvil jaw is illustrated in the first operational orientation.
Figure 69:
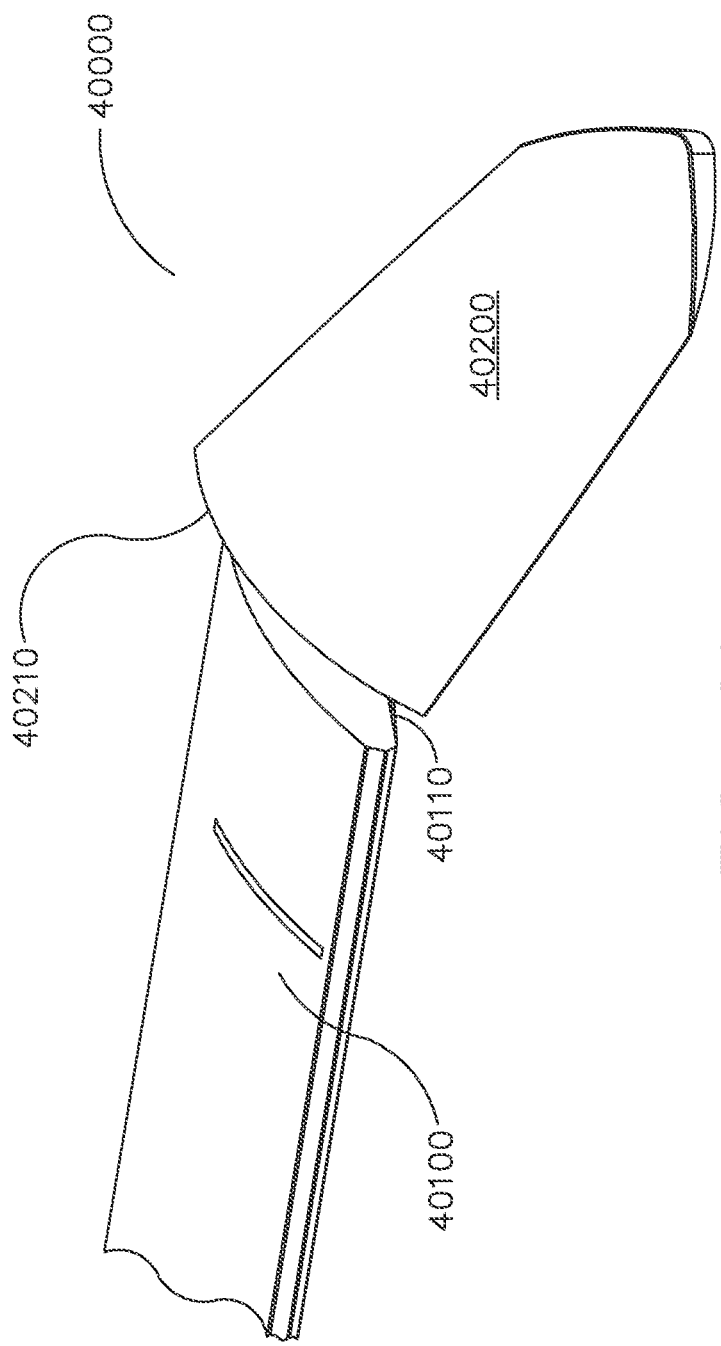
FIG. 69 is a partial perspective view of the anvil jaw of FIG. 68, wherein the distal portion of the anvil jaw is illustrated in a partially rotated orientation.
Figure 69A:
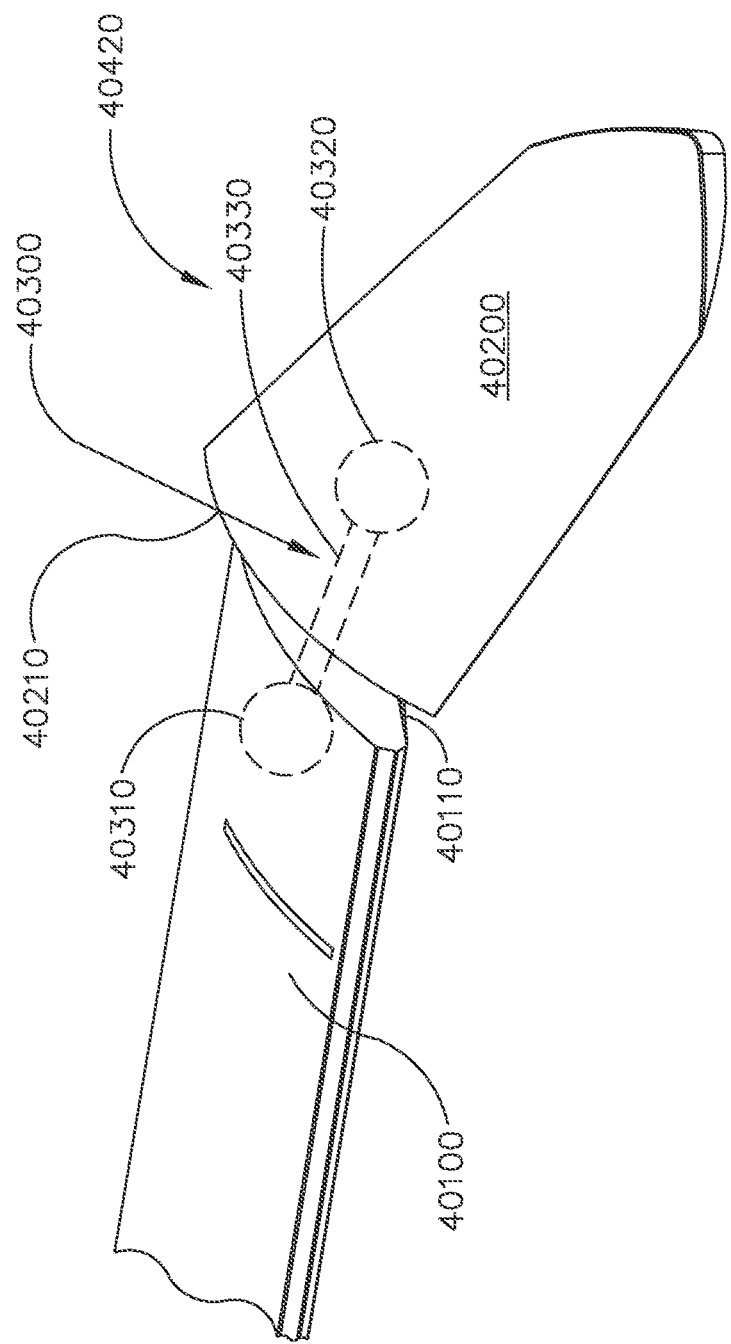
FIG. 69A depicts a connector holding the distal portion to the anvil jaw of FIG. 68.
Figure 70:
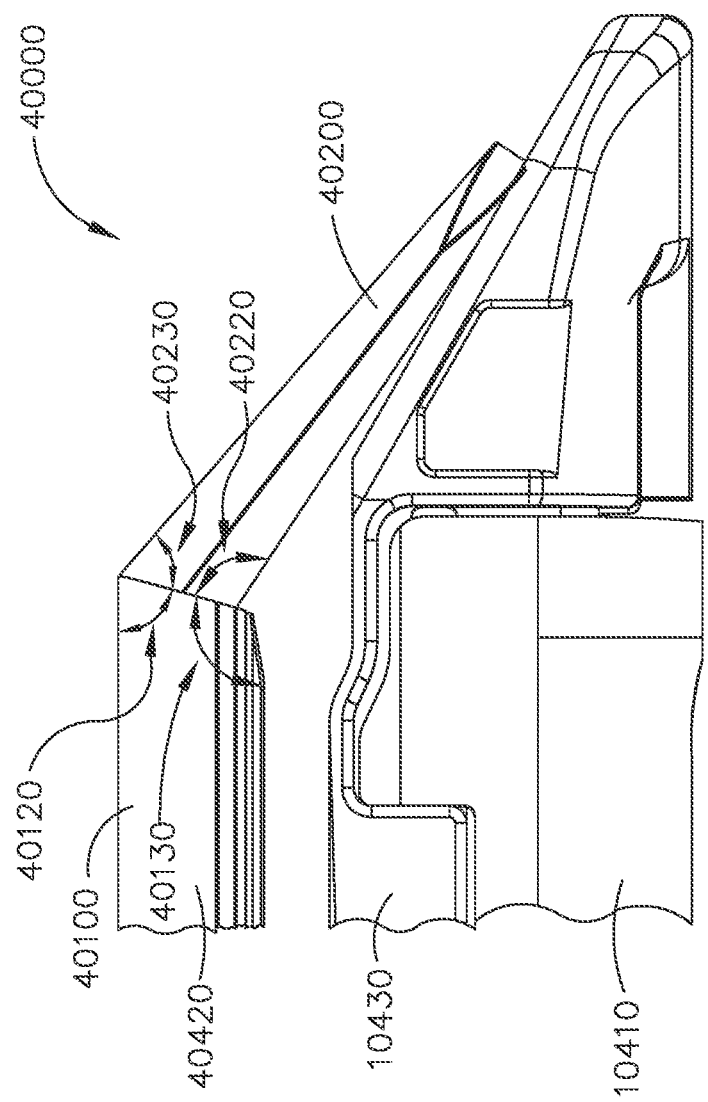
FIG. 70 is a partial elevational view of the end effector of FIG. 68, wherein the distal portion of the anvil jaw is illustrated in the second operational orientation.
Figure 71:
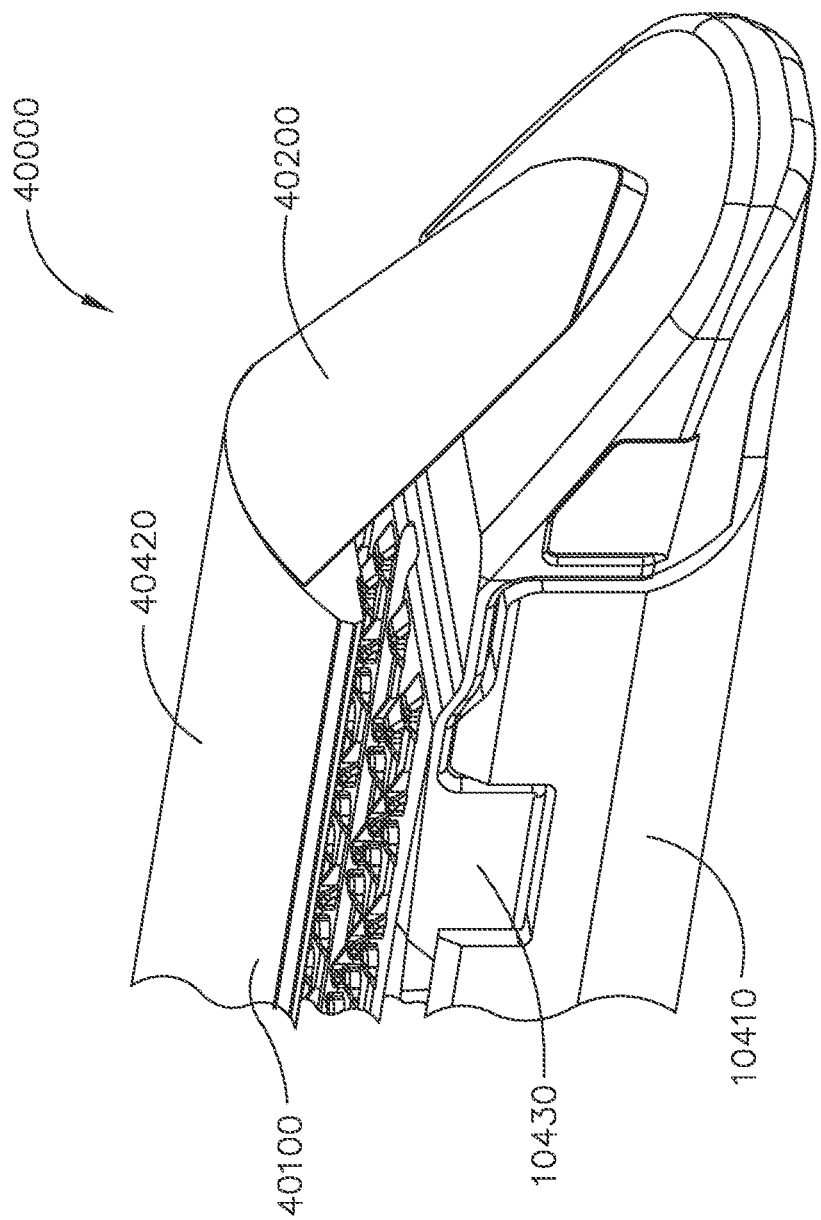
FIG. 71 is a partial perspective view of the end effector of FIG. 68, wherein the distal portion of the anvil jaw is illustrated in the second operational orientation.

Utilizing an attachment mechanism, referring to FIGS. 69 and 69A, the distal portion 40200 is rotatable relative to the proximal portion 40100 such that the distal portion 40200 can be rotated into different orientations. To move the distal portion 40200 into the second orientation shown in FIG. 70, the distal portion 40200 is rotated 180 degrees from the first orientation show in FIG. 68. This configuration allows a user to change the anvil jaw 40420 between a straight-tipped anvil jaw and an angle-tipped anvil jaw. In the second orientation shown in FIGS. 70 and 71, the first angle 40120 and the second angle 40230 abut each other and, correspondingly, the first angle 40220 and the second angle 40130 abut each other. The angles at the attachment interface in the second orientation (FIG. 70) are not supplementary as they were in the first orientation (FIG. 68).

The attachment mechanism used can be any suitable attachment mechanism. In at least one instance, referring to FIG. 69A, the attachment mechanism comprises a flexible rotatable pin 40300 anchored to the proximal portion 40100 and the distal portion 40200. Such a mechanism allows rotation of the rotatable portion between different orientations while keeping the proximal portion 40100 and the distal portion 40200 attached to each other. One or more spring members and/or detents may be used in conjunction with the pin to hold the portions in either the first operational orientation or the second operational orientation. The attachment mechanism may be embedded in either the proximal portion 40100 and/or the distal portion 40200. The attachment mechanism may comprise a bi-stable compliance mechanism configured to bias the portion 40200 into either orientation to prevent the inadvertent partial rotation of the rotatable distal portion 40200. The attachment mechanism may comprise spring-loaded detents, a living hinge, sliding members, and/or various other locking members. The attachment mechanisms may also comprise interference and/or friction-fit interfaces between the proximal portion 40100 and the distal portion 40200.

Further to the above, and referring again to FIG. 69A, the flexible pin 40300 comprises a spherical first end 40310 mounted in a chamber defined in the proximal anvil portion 40100, a spherical second end 40320 mounted in a chamber defined in the distal anvil portion 40200, and a flexible connector 40330 connecting the first end 40310 and the second end 40320. The spherical first end 40310 and the spherical second end 40320 can rotate within their respective chambers such that the flexible pin 40300 can rotate relative to the proximal portion 40100 and/or such that the distal portion 40200 can rotate relative to the flexible pin 40300. In either event, such relative rotation permits the rotation of the distal portion 40200 as described above. The length of the flexible connector 40330 is selected such that the flexible connector 40330 is in a resiliently stretched state for every orientation of the distal portion 40200. As a result, the flexible connector 40330 acts to pull the distal portion 40200 against the first anvil portion 40100. Given that the proximal portion 40100 includes the staple forming pockets and the distal portion 40200 does not comprise staple forming pockets, the retention force provided by the pin 40300 does not need to withstand staple forming forces and is sufficient to hold the distal portion 40200 in place while the end effector 40000 is being positioned in the patient. The pin can be spring loaded in the socket such that the spring pulls the head proximally in the chamber thus holding the proximal portion 40100 and the distal portion 40200 together. To rotate the distal portion 40200 between orientations, the distal portion 40200 can be pulled distally to overcome the biasing force, twisted into another orientation, and released so that the spring may pull the distal portion 40200 against the proximal portion 40100. The interface between the distal portion 40200 and the proximal portion may further comprise interlocking features extending therefrom to prevent inadvertent movement relative to each other. For example, teeth may extend from one portion and into corresponding slots defined in the other portion when the distal portion 40200 is in its first and second orientations, but not when the distal portion 40200 is pulled away from the proximal portion 40100.

In at least one instance, the distal portion 40200 comprises two halves, for example, which are assembled around the attachment mechanism. The two halves may utilize an elastomer to hold the halves together around the pin, for example. In at least one instance, a snap-fit mechanism can be used to assemble the two halves together around the attachment mechanism.

In various instances, the proximal portion 40100 and the distal portion 40200 are comprised of one or more materials. For example, the proximal portion 40100 may be comprised of one or more materials and the distal portion 40200 may be comprised of one or more materials. In at least one instance, the distal portion 40200 is comprised of metal toward the attachment interface and is comprised of an over-molded soft tip extending distally from the metal portion. The soft tip may be comprised of rubber and/or plastic, for example. The anvil jaw 40410 may further comprise an intermediate component positioned between the proximal portion 40100 and the distal portion 40200. The intermediate component can house one or more parts of the attachment mechanism. The intermediate component may also provide an atheistically pleasing and/or functional transition piece between the proximal portion 40100 and the distal portion 40200 which may be useful in a scenario where the proximal portion 40100 and the distal portion 40200 comprise more than one material.

In at least one instance, the first portion 40100 and the second portion 40200 comprise edges designed to eliminate any sharp edges presented by rotation of the second portion 40200 relative to the first portion 40100.

As discussed above, the surgical instruments disclosed herein may comprise control systems. Each of the control systems can comprise a circuit board having one or more processors and/or memory devices. Among other things, the control systems are configured to store sensor data, for example. They are also configured to store data which identifies the type of staple cartridge attached to a stapling instrument, for example. More specifically, the type of staple cartridge can be identified when attached to the stapling instrument by the sensors and the sensor data can be stored in the control system. This information can be obtained by the control system to assess whether or not the staple cartridge is suitable for use.

The surgical instrument systems described herein are motivated by an electric motor; however, the surgical instrument systems described herein can be motivated in any suitable manner. In certain instances, the motors disclosed herein may comprise a portion or portions of a robotically controlled system. U.S. patent application Ser. No. 13/118, 241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail, the entire disclosure of which is incorporated by reference herein. The disclosures of International Patent Publication No. WO 2017/083125, entitled STAPLER WITH COMPOSITE CARDAN AND SCREW DRIVE, published May 18, 2017, International Patent Publication No. WO 2017/083126, entitled STAPLE PUSHER WITH LOST MOTION BETWEEN RAMPS, published May 18, 2017, International Patent Publication No. WO 2015/153642, entitled SURGICAL INSTRUMENT WITH SHIFTABLE TRANSMISSION, published Oct. 8, 2015, U.S. Patent Application Publication No. 2017/0265954, filed Mar. 17, 2017, entitled STAPLER WITH CABLE-DRIVEN ADVANCEABLE CLAMPING ELEMENT AND DUAL DISTAL PULLEYS, U.S. Patent Application Publication No. 2017/0265865, filed Feb. 15, 2017, entitled STAPLER WITH CABLE-DRIVEN ADVANCEABLE CLAMPING ELEMENT AND DISTAL PULLEY, and U.S. Patent Publication No. 2017/0290586, entitled STAPLING CARTRIDGE, filed on Mar. 29, 2017, are incorporated herein by reference in their entireties.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:
- U.S. Pat. No. 5,403,312, entitled ELECTROSURGICAL HEMOSTATIC DEVICE, which issued on Apr. 4, 1995;
- U.S. Pat. No. 7,000,818, entitled SURGICAL STAPLING INSTRUMENT HAVING SEPARATE DISTINCT CLOSING AND FIRING SYSTEMS, which issued on Feb. 21, 2006;
- U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;
- U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;
- U.S. Pat. No. 7,670,334, entitled SURGICAL INSTRUMENT HAVING AN ARTICULATING END EFFECTOR, which issued on Mar. 2, 2010;
- U.S. Pat. No. 7,753,245, entitled SURGICAL STAPLING INSTRUMENTS, which issued on Jul. 13, 2010;
- U.S. Pat. No. 8,393,514, entitled SELECTIVELY ORIENTABLE IMPLANTABLE FASTENER CARTRIDGE, which issued on Mar. 12, 2013;
- U.S. patent application Ser. No. 11/343,803, entitled SURGICAL INSTRUMENT HAVING RECORDING CAPABILITIES, now U.S. Pat. No. 7,845,537;
- U.S. patent application Ser. No. 12/031,573, entitled SURGICAL CUTTING AND FASTENING INSTRUMENT HAVING RF ELECTRODES, filed Feb. 14, 2008;
- U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;
- U.S. patent application Ser. No. 12/235,782, entitled MOTOR-DRIVEN SURGICAL CUTTING INSTRUMENT, now U.S. Pat. No. 8,210,411;
- U.S. patent application Ser. No. 12/235,972, entitled MOTORIZED SURGICAL INSTRUMENT, now U.S. Pat. No. 9,050,083.
- U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;
- U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;
- U.S. patent application Ser. No. 12/893,461, entitled STAPLE CARTRIDGE, filed Sep. 29, 2012, now U.S. Pat. No. 8,733,613;
- U.S. patent application Ser. No. 13/036,647, entitled SURGICAL STAPLING INSTRUMENT, filed Feb. 28, 2011, now U.S. Pat. No. 8,561,870;
- U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;
- U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;
- U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;
- U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;
- U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and
- U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

The invention claimed is:

1. A surgical instrument, comprising:
a shaft;
an end effector extending distally from the shaft;
a firing system, comprising:
an electric motor;
a first jaw;
a second jaw movable relative to the first jaw; and
a firing member configured to be translated by the electric motor through a firing stroke from a proximal starting position to a distal end position; and
a control system, comprising:
a pulse width modulation circuit in communication with the electric motor, wherein the pulse width modulation circuit is configured to adjust a duty cycle of voltage pulses to achieve a target speed; and
a control circuit in communication with the pulse width modulation circuit, wherein the control circuit is configured to:
evaluate the duty cycle when the firing member is at a plurality of adjustment points, wherein each adjustment point of the plurality of adjustment points is a respective predetermined position between the starting proximal position and distal end position within the firing stroke, and wherein each adjustment point is associated with one or more respective predetermined thresholds; and
set the target speed of the firing member, when the firing member is at each adjustment point, based at least in part on a comparison of the duty cycle to the one or more respective predetermined thresholds at each adjustment point.

2. The surgical instrument of claim 1,
wherein the end effector further comprises a staple cartridge including staples removably stored therein, and wherein the firing member is configured to drive the staples from the staple cartridge during the firing stroke, and
wherein the predetermined position is distal of a half way point of a staple pattern length of the staples.

3. The surgical instrument of claim 1, wherein the firing member comprises a tissue cutting knife configured to cut patient tissue captured between the first jaw and the second jaw.

4. The surgical instrument of claim 1, wherein the firing member comprises a first cam configured to engage the first jaw during the firing stroke and a second cam configured to engage the second jaw during the firing stroke, and wherein the firing member holds the second jaw relative to the first jaw during the firing stroke.

5. The surgical instrument of claim 1,
wherein the control system further comprises a speed sensor configured to detect a translation speed of the firing member, and
wherein the speed sensor comprises a motor speed sensor, and wherein the speed sensor detects the translation speed of the firing member by sensing a speed of the electric motor.

6. The surgical instrument of claim 5, wherein the pulse width modulation circuit is configured to increase the duty cycle of voltage pulses when the translation speed is below the target speed.

7. The surgical instrument of claim 5, wherein the pulse width modulation circuit is configured to decrease the duty cycle of voltage pulses when the translation speed is above the target speed.

8. The surgical instrument of claim 1, wherein the control circuit is configured to increase the target speed when the firing member is at the adjustment point and the duty cycle is below the predetermined threshold.

9. The surgical instrument of claim 1, wherein the control circuit is configured to lower the target speed when the firing member is at the adjustment point and the duty cycle is above the predetermined threshold.

10. A surgical instrument, comprising:
a shaft;
an end effector extending distally from the shaft;
a firing system, comprising:
an electric motor;
a first jaw;
a second jaw movable relative to the first jaw; and
a firing member translatable from a proximal position toward a distal position by the electric motor during a firing stroke; and
a control system, comprising:
a pulse width modulation circuit in communication with the electric motor, wherein the pulse width modulation circuit is configured to adjust a duty cycle of voltage pulses to achieve a target speed of the firing member; and
a control circuit in communication with the pulse width modulation circuit, wherein the control circuit is configured to:
compare the duty cycle to one or more first predetermined thresholds during the firing stroke at a first adjustment point, wherein the first adjustment point is a predetermined distance distally from a proximal unfired starting position;
compare the duty cycle to one or more second predetermined threshold during the firing stroke at a second adjustment point, wherein the second adjustment point is a predetermined distance distally from the first adjustment point; and
change the target speed based on the comparison of the duty cycle to the one or more first predetermined thresholds at the first adjustment point and/or based on the comparison of the duty cycle to the one or more second predetermined thresholds at the second adjustment point.

11. The surgical instrument of claim 10,
wherein the firing member is configured to be translated by the electric motor through a firing stroke from a proximal starting position to a distal end position, and
wherein the first adjustment point and/or the second adjustment point is more than half way between the starting proximal position and distal end position.

12. The surgical instrument of claim 10, wherein the end effector further comprises a staple cartridge including staples removably stored therein, and wherein the firing member drives the staples from the staple cartridge during the firing stroke.

13. The surgical instrument of claim 10, wherein the firing member comprises a tissue cutting knife configured to cut patient tissue captured between the first jaw and the second jaw.

14. The surgical instrument of claim 10, wherein the firing member comprises a first cam configured to engage the first jaw during the firing stroke and a second cam configured to engage the second jaw during the firing stroke, and wherein the firing member holds the second jaw relative to the first jaw during the firing stroke.

15. The surgical instrument of claim 10,
wherein the control system further comprises a speed sensor configured to detect a translation speed of the firing member, and
wherein the speed sensor comprises a motor speed sensor, and wherein the speed sensor detects the translation speed of the firing member by sensing a speed of the electric motor.

16. The surgical instrument of claim 10, wherein the control circuit is configured to increase the target speed of the firing member at the first adjustment point and/or the second adjustment point when the duty cycle is below a lower predetermined threshold of the one or more first predetermined thresholds at the first adjustment point and/or when the duty cycle is below a lower predetermined threshold of the one or more second predetermined thresholds at the second adjustment point.

17. The surgical instrument of claim 10, wherein the control circuit is configured to decrease the target speed of the firing member at the first adjustment point and/or the second adjustment point when the duty cycle is above an upper predetermined threshold of the one or more first predetermined thresholds at the first adjustment point and/or when the duty cycle is above an upper predetermined threshold of the one or more second predetermined thresholds at the second adjustment point.

18. The surgical instrument of claim 10, wherein the control system is configured to evaluate the duty cycle at a beginning of the firing stroke.

19. The surgical instrument of claim 10, wherein the control system is configured to evaluate the duty cycle throughout the firing stroke.

* * * * *